(12) United States Patent
Setti et al.

(10) Patent No.: US 11,566,030 B2
(45) Date of Patent: Jan. 31, 2023

(54) SUBSTITUTED 2,6-DIHYDROPYRROLO[3,4-C]PYRAZOLES AS PYRUVATE KINASE ACTIVATORS

(71) Applicant: Global Blood Therapeutics, Inc., South San Francisco, CA (US)

(72) Inventors: Lina Q. Setti, Fremont, CA (US); Shahul Nilar, Foster City, CA (US); Zhe Li, San Diego, CA (US); Ming Yu, Foster City, CA (US); Manuel Zancanella, San Mateo, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 17/665,942

(22) Filed: Feb. 7, 2022

(65) Prior Publication Data

US 2022/0267337 A1 Aug. 25, 2022

Related U.S. Application Data

(60) Provisional application No. 63/147,058, filed on Feb. 8, 2021, provisional application No. 63/156,614, filed on Mar. 4, 2021, provisional application No. 63/252,891, filed on Oct. 6, 2021.

(51) Int. Cl.
*A61K 31/4162* (2006.01)
*C07D 487/04* (2006.01)

(52) U.S. Cl.
CPC .................. *C07D 487/04* (2013.01)

(58) Field of Classification Search
CPC .......................... A61K 31/4162; C07D 487/04
USPC ........................................ 514/403; 548/360.5
See application file for complete search history.

(56) References Cited

FOREIGN PATENT DOCUMENTS

| WO | WO 2010/118063 A2 | 10/2010 |
|---|---|---|
| WO | WO 2010/129596 A1 | 11/2010 |
| WO | WO 2011/002816 A1 | 1/2011 |
| WO | WO 2012/083246 A1 | 6/2012 |
| WO | WO 2012/088314 A1 | 6/2012 |
| WO | WO 2012/092442 A1 | 7/2012 |
| WO | WO 2014/074848 A1 | 5/2014 |
| WO | WO 2014/139144 A1 | 9/2014 |
| WO | WO 2018/075474 A1 | 9/2018 |
| WO | WO 2019/035863 A1 | 2/2019 |
| WO | WO 2019/035864 A1 | 2/2019 |
| WO | WO 2019/035865 A1 | 2/2019 |
| WO | WO 2020/061255 A1 | 3/2020 |
| WO | WO 2020/061261 A1 | 3/2020 |
| WO | WO 2020/061378 A1 | 3/2020 |
| WO | WO 2020/167976 A1 | 8/2020 |
| WO | WO-2021202796 A1 * | 10/2021 |

OTHER PUBLICATIONS

Jordan, V. C. Nature Reviews: Drug Discovery, 2, 2003, 205.*
Hackam, et al. JAMA, 296(14), 2006, 1731-1732.*
WIPO Application No. PCT/US2022/015505, PCT International Search Report and Written Opinion of the International Searching Authority dated Apr. 25, 2022.

\* cited by examiner

*Primary Examiner* — Douglas M Willis
(74) *Attorney, Agent, or Firm* — Alston & Bird LLP

(57) ABSTRACT

The subject matter described herein is directed to pyruvate kinase activating compounds of Formula I:

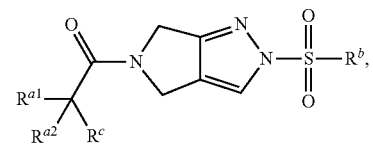

and pharmaceutical salts thereof, methods of preparing the compounds, pharmaceutical compositions comprising the compounds and methods of administering the compounds for the treatment of diseases associated with PKR and/or PKM2, such as pyruvate kinase deficiency, sickle cell disease, and beta-thalassemia.

31 Claims, No Drawings

SUBSTITUTED 2,6-DIHYDROPYRROLO[3,4-C]PYRAZOLES AS PYRUVATE KINASE ACTIVATORS

CROSS-REFERENCE TO RELATED APPLICATIONS

This application claims priority to U.S. Provisional Patent Application No. 63/252,891, filed Oct. 6, 2021; U.S. Provisional Patent Application No. 63/156,614, filed Mar. 4, 2021; and U.S. Provisional Patent Application No. 63/147,058, filed Feb. 8, 2021, each of which is incorporated herein by reference in its entirety.

FIELD

The subject matter described herein is directed to pyruvate kinase activating compounds, methods of making the compounds, pharmaceutical compositions, and their use in the treatment of diseases associated with PKR and/or PKM2.

BACKGROUND

Pyruvate kinase (PK) is an essential component of cellular metabolism, converting ADP and phosphoenolpyruvate (PEP) to pyruvate in the final step of glycolysis. There are four unique isoforms of pyruvate kinase that vary in concentration by different tissue types (Dayton et al., *EMBO Rep.* 2016 17(12):1721-1730; Israelsen and Vander Heiden, *Semin. Cell Dev. Biol.* 2015 July; 43:43-51; Mazurek, *Int. J. Biochem. Cell Biol.* 2011 July; 43(7):969-80). Each isomer is responsible for catalyzing the production of pyruvate and ATP, while being regulated in a manner respective to each tissue type.

Pyruvate kinase in the liver (PKL) and pyruvate kinase from erythrocytes/red blood cells (PKR) are tetrameric enzymes that depend on an endogenous activator called fructose-1,6-bisphosphate (FBP) for activation (Koler and Vanbellinghen, *Adv. Enzyme Regul.* 1968 6:127-42; Taylor and Bailey, *Biochem J.* 1967 967 February; 102(2):32C-33C). The PKM1 isoform is found in the brain, heart, and skeletal muscle where it functions as a stable and constitutively active tetrameric protein. PKM1 therefore does not require FBP for activation. The PKM2 isomer is expressed in most tissue types, including cancers, developing embryos, and all proliferative tissues. Similar to PKR and PKL, PKM2 requires FBP for allosteric activation via stabilization of the enzyme in a tetrameric and most active form (Cardenas and Dyson, *J. Exp. Zool.* 1978 June; 204(3):361-7; Imamura and Tanaka, *J. Biochem.* 1972 June; 71(6):1043-51; Strandholm et al., *Arch. Biochem. Biophys.* 1976 March; 173(1):125-31).

Mature red blood cells (RBCs) rely on glycolysis for energy production. All tumor cells exclusively express the PKM2 isoform, suggesting that PKM2 would be a good target for cancer therapy. PKM2 is also expressed in adipose tissue and activated T-cells. Thus, controlling the regulation of PKM2 activity may be effective for treatment of obesity and diabetes in addition to cancer.

Genetic mutations in all glycolytic enzymes result in hemolytic anemia (Van Wijk and Van Solinge, *Blood* 2005 106 (13): 4034-4042). Mutations in PKL and PKR that result in a loss of function are known to cause PK deficiency (PKD) and the clinical manifestation of these mutations appear confined to RBCs.

There are greater than 200 known and reported mutations associated with PKD reported worldwide (Zanella et al., *J. Haematol.* 2005 July; 130(1):11-25). Some mutations directly disrupt catalytic activity of the PK enzyme while other mutations disrupt the interactions between monomers that stabilize the active tetrameric enzyme. The mutation of Arginine residue 510 to Glutamine is one of the most common mutations found in North American and European patients, ~40% of patients, and is known to disrupt stability of the PKR tetramer (Kedar et al., *Clin. Genet.* 2009 February; 75(2):157-62; Wang et al., *Blood* 2001 Nov. 15; 98(10):3113-20).

Patients with PKD suffer from chronic hemolytic anemia in addition to multiple co-morbidities. Blood transfusions and splenectomy are common treatments and it has been suggested that gene therapies could be used for treatment of PKD in the near future (Garcia-Gomez et al., *Molecular Therapy* 2016 Aug. 1; 24(7); Grace et al., *Am. J. Hematol.* 2015 September; 90(9):825-30).

The number of PKD patients worldwide is unknown; however, the prevalence in the general Caucasian population is estimated to be around 1:20,000 people with 51 cases per million people in North America (Beutler and Gelbart, *Blood* 2000 Jun. 1; 95(11):3585-8).

There are no approved drugs for the treatment of PKD. Clinically, hereditary PKR deficiency disorder manifests as a non-spherocytic hemolytic anemia. The clinical severity of this disorder ranges from no observable symptoms in fully-compensated hemolysis to potentially fatal severe anemia requiring chronic transfusions and/or splenectomy at early development or during physiological stress. For some of the most severe cases, while extremely rare population-wise with estimated frequency of 1 in 20,000 patients, there is no disease modifying treatment besides transfusions. These hereditary non-spherocytic hemolytic anemia patients present a clear unmet medical need. RBCs from patients with either sickle cell anemia or with beta-thalassemia suffer from increased ATP demand to maintain overall RBC health. The activation of PKR in both sickle cell disease patients and beta-thalassemia patients could lead to improved cell fitness and survival.

What is therefore needed and not effectively addressed by the art are compounds that act as pyruvate kinase activators that have desired efficacy and therapeutic potential. This problem as well as others stemming from pyruvate kinase deficiency are addressed by the subject matter described herein.

BRIEF SUMMARY

In certain embodiments, the subject matter described herein is directed to a compound of Formula I (which includes Formulae I-Ia, I-Ib, II, III, IA, and IB) or a pharmaceutically acceptable salt thereof.

In certain embodiments, the subject matter described herein is directed to a pharmaceutical composition comprising a compound of Formula I or a pharmaceutically acceptable salt thereof.

In certain embodiments, the subject matter described herein is directed to a method of treating a disease or disorder associated with modulation of pyruvate kinase (PKR) and/or PKM2 in a subject, comprising administering to the subject an effective amount of a compound of Formula I, a pharmaceutically acceptable salt thereof, or a pharmaceutical composition comprising a compound of Formula I.

In certain embodiments, the subject matter described herein is directed to a method of activating PKR and/or PKM2 in a subject, comprising administering to the subject an effective amount of a compound of Formula I, a pharmaceutically acceptable salt thereof, or a pharmaceutical composition comprising a compound of Formula I.

In certain embodiments, the subject matter described herein is directed to a method of treating a subject afflicted with a disease associated with decreased activity of PKR and/or PKM2, comprising administering to the subject an effective amount of a compound of Formula I, a pharmaceutically acceptable salt thereof, or a pharmaceutical composition comprising a compound of Formula I.

Other embodiments are also described.

DETAILED DESCRIPTION

Described herein are pyruvate kinase activators of Formula I, methods of making the compounds, pharmaceutical compositions comprising the compounds, and their use in the treatment of diseases associated with decreased pyruvate kinase activity.

PKR activating compounds could be used to treat patients with beta-thalassemia and sickle cell anemia (Alli et al., *Hematology* 2008 December; 13(6):369-72; Kung et al., *Blood* 2017 Sep. 14; 130(11):1347-135). As shown in a mouse model of beta-thalassemia, the PKR activator in clinical trials, AG-348, increased PK activity and ATP levels, as well as improved RBC parameters. Similar results were obtained from treating human beta-thalassemia RBCs ex vivo (Kuo et al., *Mitapivat (AG-348), an oral PK-R activator, in adults with non-transfusion-dependent thalassemia: A phase 2, open-label, multicenter study in progress;* 61$^{st}$ Am. Soc. Hematol. Annual Meeting, December 2019).

The compounds of Formula I described herein are useful in the treatment of diseases or disorders associated with pyruvate kinase function. As demonstrated by the biochemical assays described herein, the compounds of Formula I activate PKR and/or PKM2. In certain embodiments, the compounds described herein are more effective at activating PKR and/or PKM2 than AG-348. The compounds of Formula I are useful in the treatment of diseases including, but not limited to, pyruvate kinase deficiency and sickle cell disease, such as sickle cell anemia, and beta-thalassemia. Also, the compounds are methods described herein are useful in treating cancer.

Pyruvate kinase activators are needed that also possess additional beneficial properties such as improved solubility, stability, and/or potency. An advantage of the pyruvate kinase activator compounds of Formula I described herein is their preparation in sufficient yields by the synthetic routes disclosed herein.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. Unless otherwise defined, all technical and scientific terms used herein have the same meaning as commonly understood by one of ordinary skill in this field. All publications, patent applications, patents, and other references mentioned herein are incorporated by reference in their entirety. In the event that one or more of the incorporated literature, patents, and similar materials differs from or contradicts this application, including but not limited to defined terms, term usage, described techniques, or the like, this application controls.

I. Definitions

As used in the present specification, the following words, phrases and symbols are generally intended to have the meanings as set forth below, except to the extent that the context in which they are used indicates otherwise.

A dash ("—") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through or perpendicular across the end of a line in a structure indicates a specified point of attachment of a group. Unless chemically or structurally required, no directionality or stereochemistry is indicated or implied by the order in which a chemical group is written or named.

The prefix "$C_u$-$C_v$" indicates that the following group has from u to v carbon atoms. For example, "$C_1$-$C_6$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±50%. In certain other embodiments, the term "about" includes the indicated amount ±20%. In certain other embodiments, the term "about" includes the indicated amount ±10%. In other embodiments, the term "about" includes the indicated amount ±5%. In certain other embodiments, the term "about" includes the indicated amount ±1%. In certain other embodiments, the term "about" includes the indicated amount ±0.5% and in certain other embodiments, 0.1%. Such variations are appropriate to perform the disclosed methods or employ the disclosed compositions. Also, to the term "about x" includes description of "x". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_1$-$C_{20}$ alkyl), 1 to 12 carbon atoms (i.e., $C_1$-$C_{12}$ alkyl), 1 to 8 carbon atoms (i.e., $C_1$-$C_8$ alkyl), 1 to 6 carbon atoms (i.e., $C_1$-$C_6$ alkyl), 1 to 4 carbon atoms (i.e., $C_1$-$C_4$ alkyl), or 1 to 3 carbon atoms (i.e., $C_1$-$C_3$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

The term "alkylene" by itself or as part of another substituent means a divalent radical derived from an alkane, such as, methylene —CH$_2$—, ethylene —CH$_2$CH$_2$—, and the like. As an example, a "hydroxy-methylene" refers to HO—CH$_2$—*, where * is the attachment point to the molecule.

Unless indicated explicitly otherwise, where combinations of groups are referred to herein as one moiety, e.g., arylalkyl or aralkyl, the last mentioned group contains the atom by which the moiety is attached to the rest of the molecule.

"Alkoxy" refers to the group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy and 1,2-dimethylbutoxy.

"Amino" refers to the group —NR$^y$R$^z$ wherein R$^y$ and R$^z$ are independently hydrogen, alkyl, cycloalkyl, heterocyclyl, aryl, or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., C$_6$-C$_{20}$ aryl), 6 to 12 carbon ring atoms (i.e., C$_6$-C$_{12}$ aryl), or 6 to 10 carbon ring atoms (i.e., C$_6$-C$_{10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one sp$^3$ carbon atom (i.e., at least one non-aromatic ring). As used herein, cycloalkyl has from 3 to 20 ring carbon atoms (i.e., C$_3$-C$_{20}$ cycloalkyl), 3 to 12 ring carbon atoms (i.e., C$_3$-C$_{12}$ cycloalkyl), 3 to 10 ring carbon atoms (i.e., C$_3$-C$_{10}$ cycloalkyl), 3 to 8 ring carbon atoms (i.e., C$_3$-C$_8$ cycloalkyl), 3 to 7 ring carbon atoms (i.e., C$_3$-C$_7$ cycloalkyl), or 3 to 6 ring carbon atoms (i.e., C$_3$-C$_6$ cycloalkyl). Monocyclic groups include, for example, cyclopropyl, cyclobutyl, cyclopentyl, cyclohexyl, cycloheptyl and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl and the like. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Halogen" or "halo" refers to atoms occupying group VIIA of the periodic table, such as fluoro, chloro, bromo or iodo.

"Haloalkyl" refers to an unbranched or branched alkyl group as defined above, wherein one or more (e.g., 1 to 6, or 1 to 3) hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like. "C$_1$-C$_3$ haloalkyl" and "halo-C$_1$-C$_3$ alkyl" are used interchangeably herein and refer to an alkyl chain having 1 to 3 carbon atoms, wherein one or more of the hydrogen atoms in the alkyl chain are replaced by a halogen. Further, C$_1$-C$_3$ fluoroalkyl (or fluoro-C$_1$-C$_3$ alkyl) refers to an alkyl chain having 1 to 3 carbon atoms, wherein one or more of the hydrogen atoms in the alkyl chain are replaced by fluoro. Non-limiting examples of haloalkyl groups include —CH$_2$CH$_2$CF$_3$, —CHF$_2$, —CF$_3$, —CH$_2$CHF$_2$, and —CH$_2$CF$_3$.

"Haloalkoxy" refers to an alkoxy group as defined above, wherein one or more (e.g., 1 to 6, or 1 to 3) hydrogen atoms are replaced by a halogen. "C$_1$-C$_3$ haloalkoxy" and "halo-C$_1$-C$_3$ alkoxyl" are used interchangeably herein and refer to an alkoxy group having 1 to 3 carbon atoms in the alkyl unit of the alkoxy group, wherein one or more of the hydrogen atoms in the alkyl chain are replaced by a halogen. Non-limiting examples of haloalkoxy groups include —OCH$_2$CHF$_2$, —OCH$_2$CF$_3$, and —OCF$_3$.

"Hydroxyalkyl" or "hydroxyalkylene" and the like refers to an alkyl or alkylene group as defined above, wherein one or more (e.g., 1 to 6, or 1 to 3) hydrogen atoms are replaced by a hydroxy group. By way of example, the term "hydroxy-C$_1$-C$_3$ alkyl," "C$_1$-C$_3$ hydroxyalkyl", or "hydroxy-C$_1$-C$_3$ alkylene" refers to a one to three carbon alkyl chain where one or more hydrogens on any carbon is replaced by a hydroxy group, in particular, one hydrogen on one carbon of the chain is replaced by a hydroxy group.

"Heteroaryl" refers to an aromatic group having a single ring, multiple rings or multiple fused rings, with one or more ring heteroatoms independently selected from nitrogen, oxygen, and sulfur. As used herein, heteroaryl includes 1 to 20 ring carbon atoms (i.e., C$_1$-C$_{20}$ heteroaryl), 3 to 12 ring carbon atoms (i.e., C$_3$-C$_{12}$ heteroaryl), or 3 to 8 carbon ring atoms (i.e., C$_3$-C$_8$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 9-10 membered ring systems (9- to 10-membered heteroaryl), 6-10 membered ring systems (6- to 10-membered heteroaryl), 5-10 membered ring systems (5- to 10-membered heteroaryl), 5-7 membered ring systems (5- to 7-membered heteroaryl), or 5-6 membered ring systems (5- to 6-membered heteroaryl), each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or partially unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more (e.g., 1 to 3) oxo (=O) or N-oxide (—O⁻) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_2$-$C_{20}$ heterocyclyl), 2 to 12 ring carbon atoms (i.e., $C_2$-$C_{12}$ heterocyclyl), 2 to 10 ring carbon atoms (i.e., $C_2$-$C_{10}$ heterocyclyl), 2 to 8 ring carbon atoms (i.e., $C_2$-$C_8$ heterocyclyl), 3 to 12 ring carbon atoms (i.e., $C_3$-$C_{12}$ heterocyclyl), 3 to 8 ring carbon atoms (i.e., $C_3$-$C_8$ heterocyclyl), or 3 to 6 ring carbon atoms (i.e., $C_3$-$C_6$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. When the heterocyclyl ring contains 4- or 6-ring atoms, it is also referred to herein as a 4- or 6-membered heterocyclyl. When the heterocyclyl ring contains 5- to 7-ring atoms, it is also referred to herein as a 5- to 7-membered heterocyclyl. When the heterocyclyl ring contains 5- to 10-ring atoms, it is also referred to herein as a 5- to 10-membered heterocyclyl. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl" when there are two positions for substitution on the same carbon atom. Examples of the spiro-heterocyclyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

"($C_1$-$C_3$ alkoxy)-$C_1$-$C_3$ alkyl" refers to an -alkyl-alkoxy group, wherein both the alkoxy unit and the alkyl unit each individually contain an alkyl chain having 1 to 3 carbon atoms.

"($C_1$-$C_3$-alkoxy)-$C_1$-$C_3$ alkoxy" refers to an -alkoxy-alkoxy group, wherein both alkoxy units each individually contain an alkyl chain having 1 to 3 carbon atoms.

The terms "optional" or "optionally" means that the subsequently described event or circumstance may or may not occur and that the description includes instances where said event or circumstance occurs and instances in which it does not. Also, the term "optionally substituted" refers to any one or more (e.g., 1 to 5, 1 to 4, or 1 to 3) hydrogen atoms on the designated atom or group may or may not be replaced by a moiety other than hydrogen.

The term "substituted" used herein means any of the above groups (i.e., alkyl, alkylene, alkoxy, haloalkyl, haloalkoxy, cycloalkyl, aryl, heterocyclyl, and/or heteroaryl) wherein at least one (e.g., 1 to 5, 1 to 4, or 1 to 3) hydrogen atom is replaced by a bond to a non-hydrogen atom such as, but not limited to alkyl, alkoxy, amino, aryl, aralkyl, carboxyl, carboxyl ester, cyano, cycloalkyl, halo, haloalkyl, haloalkoxy, hydroxyalkyl, heteroaryl, heterocyclyl, —NHNH$_2$, hydroxy, oxo, nitro, —S(O)OH, —S(O)$_2$OH, N-oxide or —Si($R^y$)$_3$, wherein each $R^y$ is independently hydrogen, alkyl, alkenyl, alkynyl, heteroalkyl, cycloalkyl, aryl, heteroaryl or heterocyclyl.

In certain embodiments, "substituted" includes any of the above alkyl, alkenyl, alkynyl, cycloalkyl, heterocyclyl, aryl or heteroaryl groups in which one or more (e.g., 1 to 5, 1 to 4, or 1 to 3) hydrogen atoms are independently replaced with deuterium, halo, cyano, nitro, oxo, alkyl, haloalkyl, cycloalkyl, heterocyclyl, aryl, heteroaryl, —NR$^g$R$^h$, —NR$^g$C(=O)R$^h$, —NR$^g$C(=O)NR$^g$R$^h$, —NR$^g$C(=O)OR$^h$, —NR$^g$S(=O)$_{1-2}$R$^h$, —C(=O)R$^g$, —C(=O)OR$^g$, —OC(=O)OR$^g$, —OC(=O)R$^g$, —C(=O)NR$^g$R$^h$, —OC(=O)NR$^g$R$^h$, —OR$^g$, —SR$^g$, —S(=O)R$^g$, —S(=O)$_2$R$^g$, —OS(=O)$_{1-2}$R$^g$, —S(=O)$_{1-2}$OR$^g$, —NR$^g$S(=O)$_{1-2}$NR$^g$R$^h$, =NSO$_2$R$^g$, =NOR$^g$, —S(=O)$_{1-2}$NR$^g$R$^h$, —SF$_5$, —SCF$_3$ or —OCF$_3$. In certain embodiments, "substituted" also means any of the above groups in which one or more (e.g., 1 to 5, 1 to 4, or 1 to 3) hydrogen atoms are replaced with —C(=O)R$^g$, —C(=O)OR$^g$, —C(=O)NR$^g$R$^h$, —CH$_2$SO$_2$R$^g$, or —CH$_2$SO$_2$NR$^g$R$^h$. In the foregoing, R$^g$ and R$^h$ are the same or different and independently hydrogen, alkyl, alkoxy, aryl, cycloalkyl, haloalkyl, heterocyclyl, and/or heteroaryl. In certain embodiments, "substituted" also means any of the above groups in which one or more (e.g., 1 to 5, 1 to 4, or 1 to 3) hydrogen atoms are replaced by a bond to an amino, cyano, hydroxyl, nitro, oxo, halo, alkyl, alkoxy, alkylamino, aryl, cycloalkyl, haloalkyl, heterocyclyl, N-heterocyclyl, heteroaryl, or two of R$^g$ and R$^h$ and R$^i$ are taken together with the atoms to which they are attached to form a heterocyclyl ring optionally substituted with oxo, halo or alkyl optionally substituted with oxo, halo, amino, hydroxyl, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to four. In certain embodiments, as used herein, the phrase "one or more" refers to one to three.

Any compound or structure given herein, is intended to represent unlabeled forms as well as isotopically labeled forms (isotopologues) of the compounds. These forms of compounds may also be referred to as and include "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S $^{18}$F, $^{36}$Cl, $^{123}$I and $^{125}$I, respectively. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F, $^3$H, $^{11}$C labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium. Further, in some embodiments, the corresponding deuterated analog is provided.

In many cases, the compounds of this disclosure are capable of forming acid and/or base salts by virtue of the presence of amino and/or carboxyl groups or groups similar thereto.

Provided also are a pharmaceutically acceptable salt, isotopically enriched analog, deuterated analog, isomer (such as a stereoisomer), mixture of isomers (such as a mixture of stereoisomers), prodrug, and metabolite of the compounds described herein.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include, e.g., hydrochloric acid, hydrobromic acid, sulfuric acid, nitric acid, phosphoric acid and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., NH$_2$(alkyl)), dialkyl amines (i.e., HN(alkyl)$_2$), trialkyl amines (i.e., N(alkyl)$_3$), substituted alkyl amines (i.e., NH$_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., NH$_2$(alkenyl)), dialkenyl amines (i.e., HN(alkenyl)$_2$), trialkenyl amines (i.e., N(alkenyl)$_3$), substituted alkenyl amines (i.e., NH$_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., NH$_2$(cycloalkyl), HN(cycloalkyl)$_2$, N(cycloalkyl)$_3$), mono-, di- or tri-arylamines (i.e., NH$_2$(aryl), HN(aryl)$_2$, N(aryl)$_3$) or mixed amines, etc. Specific examples of suitable amines include, by way of example only, isopropylamine, trimethyl amine, diethyl amine, tri (iso-propyl) amine, tri(n-propyl) amine, ethanolamine, 2-dimethylaminoethanol, piperazine, piperidine, morpholine, N-ethylpiperidine and the like.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid and ethanolamine.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The present compounds, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The present subject matter is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present subject matter contemplates various stereoisomers and mixtures thereof and includes "enantiomers," which refers to two stereoisomers whose molecules are nonsuperimposeable mirror images of one another.

"Diastereomers" are stereoisomers that have at least two asymmetric atoms, but which are not mirror-images of each other.

Relative centers of the compounds as depicted herein are indicated graphically using the "thick bond" style (bold or parallel lines) and absolute stereochemistry is depicted using wedge bonds (bold or parallel lines).

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The term, "metabolite," as used herein refers to a resulting product formed when a compound disclosed herein is metabolized. As used herein, the term "metabolized" refers to the sum of processes (including but not limited to hydrolysis reactions and reactions catalyzed by enzymes) by which a particular substance, such as a compound disclosed herein, is changed by an organism. For example, an aldehyde moiety (—C(O)H) of the compounds of the present subject matter may be reduced in vivo to a —CH$_2$OH moiety.

As used herein, the term "activator" refers to a compound of Formula I or a pharmaceutically acceptable salt thereof that increases the activity of pyruvate kinase R (PKR) or pyruvate kinase M2 (PKM2), unless specified otherwise. By "activate" herein is meant to increase the activity of PKR or PKM2 activity to a level that is greater than the basal levels of activity for PKR or PKM2 in the presence of the compound. In some embodiments, the term "activate" means an increase in the activity of PKR or PKM2 of at least about 5%, at least about 10%, at least about 20%, at least about 25%, at least about 50%, at least about 60%, at least about 70%, at least about 80%, at least about 90%, or at least about 95%. In other embodiments, activate means an increase in PKR or PKM2 activity of about 5% to about 25%, about 25% to about 50%, about 50% to about 75%, or about 75% to 100%. In some embodiments, activate means an increase in PKR or PKM2 activity of about 95% to 100%, e.g., an increase in activity of 95%, 96%, 97%, 98%, 99%, or 100%. Such increases can be measured using a variety of techniques that would be recognizable by one of skill in the art, including in vitro assays.

As used herein, the term "pyruvate kinase activator" and the like refers to a compound that activates, increases, or modulates one or more of the biological activities of pyruvate kinase. The activity could increase, for example, at least about 5%, 10%, 15%, 20%, 25%, 30%, 35%, 40%, 45%, 50%, 55%, 60%, 65%, 70%, 75%, 80%, 85%, 95% or 100% of the activity of pyruvate kinase compared to an appropriate control. The increase can be a statistically significant increase.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a pyrukate kinase deficiency (PKD). The therapeutically effective amount may vary depending on the subject, and disease or condition being treated, the weight and age of the subject, the severity of the disease or condition, and the manner of administering, which can readily be determined by one of ordinary skill in the art.

Additional definitions may also be provided below as appropriate.

II. Compounds

In certain embodiments, the subject matter described herein is directed to compounds of Formula I, and pharmaceutically acceptable salts thereof:

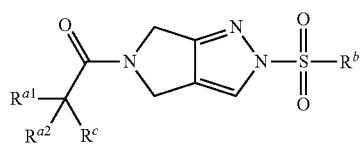

I wherein,
$R^{a1}$ is hydroxy, $C_1$-$C_3$ alkoxy, hydroxy-$C_1$-$C_3$ alkoxy, or hydroxy-$C_1$-$C_3$ alkyl;
$R^{a2}$ is hydrogen or $C_1$-$C_3$ alkyl;
or $R^{a1}$ and $R^{a2}$, together with the carbon atom to which they are each attached, form a 4- to 5-membered heterocyclyl;
$R^c$ is phenyl or pyridinyl, each optionally substituted with one or two substituents independently selected in each instance from the group consisting of halo, $C_1$-$C_3$ alkyl, $C_1$-$C_3$ alkoxy, hydroxy-$C_1$-$C_3$ alkoxy, ($C_1$-$C_3$ alkoxy)-$C_1$-$C_3$ alkoxy, hydroxy-$C_1$-$C_3$ alkyl, and ($C_1$-$C_3$ alkoxy)-$C_1$-$C_3$ alkyl; and
$R^b$ is a thiazol-2(3H)-one or a 5-membered heteroaryl ring, each optionally substituted with one, two, or three substituents independently selected in each instance from the group consisting of $C_1$-$C_3$ alkyl, halo-$C_1$-$C_3$ alkyl, halo-$C_1$-$C_3$ alkoxy, halo, $C_1$-$C_3$ alkoxy, ($C_1$-$C_3$ alkoxy)-$C_1$-$C_3$ alkyl, ($C_1$-$C_3$-alkoxy)-$C_1$-$C_3$ alkoxy, 3- to 6-membered cycloalkyl, 4- to 6-membered heterocyclyl, phenyl, and 5- or 6-membered heteroaryl; or a pharmaceutically acceptable salt thereof.

Useful compounds include all those having variables as described above.

In certain embodiments, useful compounds of Formula I include those where $R^{a1}$ is $C_1$-$C_3$ hydroxyalkyl. In certain embodiments, useful compounds of Formula I include those where $R^{a1}$ is —OH, —CH$_2$OH, —CH(OH)CH$_3$, —OCH$_3$, or —OCH$_2$CH$_2$OH. In certain embodiments, useful compounds of Formula I include those where $R^{a1}$ is —OH, —CH$_2$OH, or —CH(OH)CH$_3$. In certain embodiments, useful compounds of Formula I include those where $R^{a1}$ is —CH$_2$OH.

In certain embodiments, useful compounds of Formula I include those where $R^{a2}$ is hydrogen or —CH$_3$. In certain embodiments, useful compounds of Formula I include those where $R^2$ is hydrogen.

In certain embodiments, useful compounds of Formula I include those where $R^{a1}$ and $R^{a2}$, together with the carbon atom to which they are each attached, form an oxetanyl ring.

In certain embodiments, useful compounds of Formula I include those where $R^c$ is phenyl or pyridinyl, each optionally substituted with one or two halos. In certain embodiments, useful compounds of Formula I include those where $R^c$ is phenyl or pyridinyl, each optionally substituted with one halo. In certain embodiments, useful compounds of Formula I include those where $R^c$ is phenyl or pyridinyl, each optionally substituted with fluoro or chloro. In certain embodiments, useful compounds of Formula I include those where $R^c$ is phenyl or pyridinyl, each optionally substituted with fluoro. In certain embodiments, useful compounds of Formula I include those where $R^c$ is phenyl, 2-fluorophenyl, 2-chlorophenyl, or pyridin-2-yl. In certain embodiments, useful compounds of Formula I include those where $R^c$ is phenyl, 2-fluorophenyl, or pyridin-2-yl. In certain embodiments, useful compounds of Formula I include those where $R^c$ is 2-fluorophenyl. In certain embodiments, useful compounds of Formula I include those where $R^c$ is

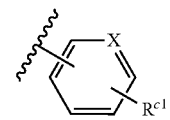

wherein, X is CH or N; and $R^{c1}$ is hydrogen, fluoro, or chloro. In certain embodiments, useful compounds of Formula I include those where $R^c$ is

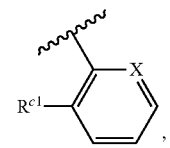

wherein X is CH or N; and $R^{c1}$ is hydrogen, fluoro, or chloro. In certain embodiments, useful compounds of Formula I include those where $R^c$ is phenyl. In certain embodiments, useful compounds of Formula I include those where $R^c$ is phenyl substituted ortho (i.e.

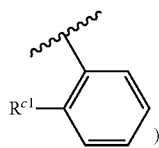

with $C_1$-$C_3$ alkyl, ($C_1$-$C_3$-alkoxy)-$C_1$-$C_3$ alkoxy, $C_1$-$C_3$ alkoxy, or hydroxy-$C_1$-$C_3$ alkoxy, where $R^{c1}$ in

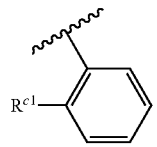

is $C_1$-$C_3$ alkyl, ($C_1$-$C_3$-alkoxy)-$C_1$-$C_3$ alkoxy, $C_1$-$C_3$ alkoxy, or hydroxy-$C_1$-$C_3$ alkoxy. In certain embodiments, useful compounds of Formula I include those where $R^c$ is phenyl substituted ortho with —$CH_3$, —$CH_2CH_3$, —$CH_2CH_2CH_3$, —$OCH_3$, —$OCH_2CH_3$, methoxy-$C_1$-$C_3$ alkoxy, —$OCH_2CH_2OH$, or —$OCH_2CH_2OH$. In certain embodiments, useful compounds of Formula I include those where $R^c$ is phenyl substituted ortho with —$CH_2CH_3$, —$OCH_3$, —$OCH_2CH_2OH$, or —$OCH_2CH_2OCH_3$.

In certain embodiments, useful compounds of Formula I include those where $R^b$ is a thiazol-2(3H)-one or a 5-membered heteroaryl ring substituted with one or two substituents, each independently selected from the group consisting of $C_1$-$C_3$ alkyl, halo-$C_1$-$C_3$ alkoxy, halo-$C_1$-$C_3$ alkyl, ($C_1$-$C_3$ alkoxy)-$C_1$-$C_3$ alkyl, $C_1$-$C_3$ alkoxy, phenyl, and 4- to 6-membered heterocyclyl. In certain embodiments, useful compounds of Formula I include those where $R^b$ is a thiazol-2(3H)-one or a 5-membered heteroaryl ring substituted with one or two substituents, each independently selected from the group consisting of —$CH_3$, —$CH_2CH_3$, —$CH_2CH_2CH_3$, —$CH(CH_3)_2$, fluoro-$C_1$-$C_3$ alkyl, fluoro-$C_1$-$C_3$ alkoxy, phenyl, 5-membered heterocyclyl, methoxy-$C_1$-$C_3$ alkyl, —$OCH_2CH_3$, and —$OCH_3$. In certain embodiments, useful compounds of Formula I include those where $R^b$ is a thiazol-2(3H)-one or a 5-membered heteroaryl ring substituted with one or two substituents, each independently selected from the group consisting of —$CH_3$, —$CH_2CH_3$, —$CF_3$, —$CH_2CHF_2$, —$CH_2CH_2CF_3$, —$CHF_2$, —$OCH_2CHF_2$, phenyl, —$OCH_2CF_3$, —$CH_2CF_3$, —$CH_2CH_2F$, —$CH_2CH_2OCH_3$, —$OCH_2CH_3$, —$OCH_3$, and tetrahydrofuranyl. In certain embodiments, useful compounds of Formula I include those where $R^b$ is a 5-membered heteroaryl ring substituted with one $C_1$-$C_3$ haloalkyl and optionally further substituted with one $C_1$-$C_3$ alkyl. In certain embodiments, useful compounds of Formula I include those where $R^b$ is a 5-membered heteroaryl ring substituted with one substituent selected from the group consisting of $C_1$-$C_3$ alkyl and $C_1$-$C_3$ haloalkyl. In certain embodiments, useful compounds of Formula I include those where $R^b$ is a 5-membered heteroaryl ring substituted with one $C_1$-$C_3$ haloalkyl. In certain embodiments, useful compounds of Formula I include those where $R^b$ is a 5-membered heteroaryl ring substituted with two substituents, each independently selected from the group consisting of $C_1$-$C_3$ alkyl and $C_1$-$C_3$ haloalkyl. In certain embodiments, useful compounds of Formula I include those where $R^b$ is a 5-membered heteroaryl ring substituted with one $C_1$-$C_3$ alkyl and one $C_1$-$C_3$ haloalkyl. In certain embodiments, useful compounds of Formula I include those where the 5-membered heteroaryl ring of $R^b$ contains one, two, or three nitrogen ring atoms. In certain embodiments, useful compounds of Formula I include those where the 5-membered heteroaryl ring of $R^b$ is pyrazolyl, imidazolyl, pyrrolyl, oxazolyl, triazolyl, or thiazolyl. In certain embodiments, useful compounds of Formula I include those where the 5-membered heteroaryl ring of $R^b$ is pyrazolyl. In certain embodiments, useful compounds of Formula I include those where $R^b$ is

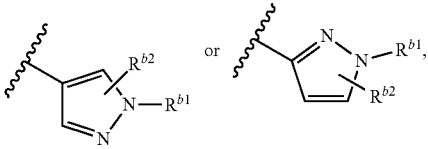

where, $R^{b1}$ is halo-$C_1$-$C_3$ alkyl, methoxy-$C_1$-$C_3$ alkyl, $C_1$-$C_3$ alkyl, hydrogen, or tetrahydrofuranyl; and $R^{b2}$ is hydrogen, halo-$C_1$-$C_3$ alkyl, or $C_1$-$C_3$ alkyl. In certain embodiments, useful compounds of Formula I include those where $R^b$ is

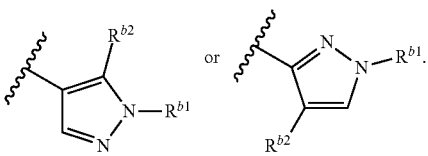

In certain embodiments, useful compounds of Formula I include those where $R^b$ is

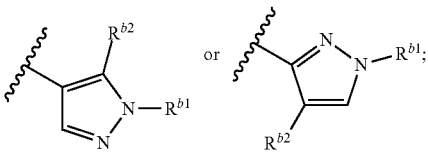

wherein $R^{b1}$ is halo-$C_1$-$C_3$ alkyl; and $R^{b2}$ is hydrogen or $C_1$-$C_3$ alkyl. In certain embodiments, useful compounds of Formula I include those where $R^{b2}$ is hydrogen. In certain embodiments, useful compounds of Formula I include those where $R^{b2}$ is $C_1$-$C_3$ alkyl. In certain embodiments, useful compounds of Formula I include those where $R^{b2}$ is —$CH_3$. In certain embodiments, useful compounds of Formula I include those where $R^{b1}$ is fluoro-$C_1$-$C_3$ alkyl. In certain embodiments, useful compounds of Formula I include those where $R^{b1}$ is —$CHF_2$, —$CH_2CH_2CF_3$, —$CH_2CH_2F$, —$CH_2CHF_2$, or —$CH_2CF_3$. In certain embodiments, useful compounds of Formula I include those where $R^{b1}$ is —$CH_2CH_2F$, —$CH_2CHF_2$, or —$CH_2CF_3$. In certain embodiments, useful compounds of Formula I include those where $R^{b1}$ is —$CH_2CH_2F$. In certain embodiments, useful compounds of Formula I include those where $R^{b1}$ is —$CH_2CHF_2$. In certain embodiments, useful compounds of Formula I include those where $R^{b1}$ is —$CH_2CF_3$. In certain embodiments, useful compounds of Formula I include those where $R^{b1}$ is $C_1$-$C_3$ alkyl; and $R^{b2}$ is fluoro-$C_1$-$C_3$ alkyl. In certain embodiments, useful compounds of Formula I include those where $R^{b1}$ is —$CH_2CH_3$; and $R^{b2}$ is —$CF_3$. In certain embodiments, useful compounds of Formula I include those where $R^b$ is

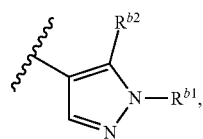

wherein $R^{b2}$ is hydrogen and $R^{b1}$ is —CH$_2$CH$_2$F, —CH$_2$CHF$_2$, or —CH$_2$CF$_3$. In certain embodiments, useful compounds of Formula I include those where $R^b$ is

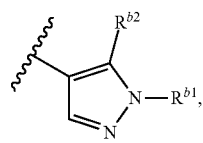

wherein $R^{b2}$ is —CH$_3$ and $R^{b1}$ is —CH$_2$CHF$_2$. In certain embodiments, useful compounds of Formula I include those where $R^b$ is

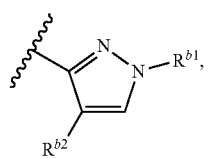

wherein $R^{b2}$ is hydrogen and $R^{b1}$ is —CH$_2$CHF$_2$. In certain embodiments, useful compounds of Formula I include those where $R^{b1}$ is —CH$_2$CH$_2$OCH$_3$ or tetrahydrofuranyl; and $R^{b2}$ is hydrogen. In certain embodiments, useful compounds of Formula I include those where the 5-membered heteroaryl ring of $R^b$ is thiazolyl. In certain embodiments, useful compounds of Formula I include those where $R^b$ is

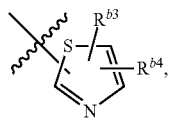

where, $R^{b3}$ is halo-C$_1$-C$_3$ alkoxy, C$_1$-C$_3$ alkyl, halo-C$_1$-C$_3$ alkyl, or C$_1$-C$_3$ alkoxy; and $R^{b4}$ is hydrogen or C$_1$-C$_3$ alkyl. In certain embodiments, useful compounds of Formula I include those where R$_b$ is

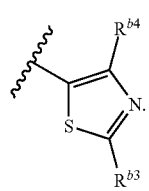

In certain embodiments, useful compounds of Formula I include those where $R^b$ is

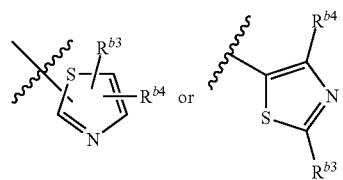

and $R^{b3}$ is —CH$_3$, —CH$_2$CH$_2$CF$_3$, —OCH$_2$CHF$_2$, —OCH$_2$CHF$_3$, —OCH$_3$, or —OCH$_2$CH$_3$; and $R^{b4}$ is —CH$_3$. In certain embodiments, useful compounds of Formula I include those where $R^b$ is a thiazol-2(3H)-one. In certain embodiments, useful compounds of Formula I include those where the thiazol-2(3H)-one of $R^b$ is

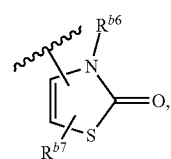

where $R^{b6}$ is selected from the group consisting of hydrogen, C$_1$-C$_3$ alkyl, and halo-C$_1$-C$_3$ alkyl; and $R^{b7}$ is selected from the group consisting of hydrogen and C$_1$-C$_3$ alkyl. In certain embodiments, useful compounds of Formula I include those where the thiazol-2(3H)-one of $R^b$ is

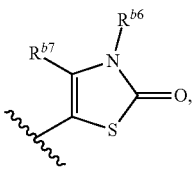

wherein $R^{b6}$ is selected from the group consisting of methyl, ethyl, and —CH$_2$CHF$_2$; and $R^{b7}$ is methyl. In certain embodiments, useful compounds of Formula I include those where $R^b$ is a 5-membered heteroaryl ring, where the 5-membered heteroaryl ring of $R^b$ is thiophenyl. In certain embodiments, useful compounds of Formula I include those where $R^b$ is

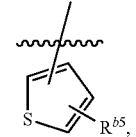

wherein, $R^{b5}$ is halo, C$_1$-C$_3$ alkyl, phenyl, or halo-C$_1$-C$_3$ alkyl. In certain embodiments, useful compounds of Formula I include those where $R^b$ is

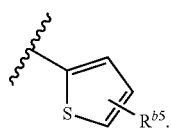

In certain embodiments, useful compounds of Formula I include those where $R^b$ is

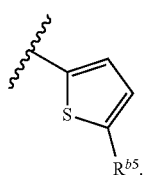

In certain embodiments, useful compounds of Formula I include those where $R^{b5}$ is phenyl, —CH$_2$CH$_3$, —CF$_3$, bromo, or —CH$_2$CH$_2$CF$_3$. In certain embodiments, useful compounds of Formula I include those where $R^b$ is an imidazolyl. In certain embodiments, useful compounds of Formula I include those where $R^b$ is

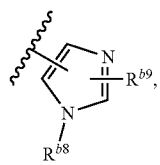

where $R^{b8}$ and $R^{b9}$ are each independently selected from the group consisting of hydrogen, $C_1$-$C_3$ alkyl, and halo-$C_1$-$C_3$ alkyl. In certain embodiments, useful compounds of Formula I include those where $R^b$ is

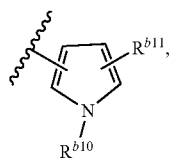

where $R^{b8}$ is halo-$C_1$-$C_3$ alkyl and $R^{b9}$ is hydrogen. In certain embodiments, useful compounds of Formula I include those where $R^{b8}$ is —CH$_2$CF$_2$H. In certain embodiments, useful compounds of Formula I include those where $R^b$ is a pyrrolyl. In certain embodiments, useful compounds of Formula I include those where $R^b$ is

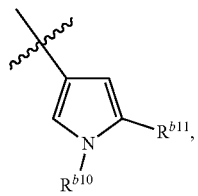

where $R^{b10}$ and $R^{b11}$ are each independently selected from the group consisting of hydrogen, $C_1$-$C_3$ alkyl, and halo-$C_1$-$C_3$ alkyl. In certain embodiments, useful compounds of Formula I include those where $R^b$ is

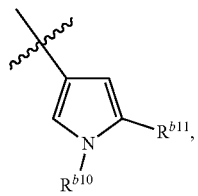

where $R^{10}$ is hydrogen and $R^{b11}$ is halo-$C_1$-$C_3$ alkyl. In certain embodiments, useful compounds of Formula I include those where $R^{b11}$ is —CF$_3$. In certain embodiments, useful compounds of Formula I include those where $R^b$ is a triazolyl. In certain embodiments, useful compounds of Formula I include those where $R^b$ is

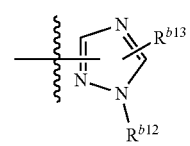

$R^{b12}$ and $R^{13}$ are each independently selected from the group consisting of hydrogen, $C_1$-$C_3$ alkyl, and halo-$C_1$-$C_3$ alkyl. In certain embodiments, useful compounds of Formula I include those where $R^b$ is

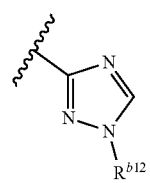

where $R^{b13}$ is hydrogen and $R^{b12}$ is halo-$C_1$-$C_3$ alkyl. In certain embodiments, useful compounds of Formula I include those where $R^{12}$ is —CH$_2$CHF$_2$. In certain embodiments, useful compounds of Formula I include those where R is an oxazolyl. In certain embodiments, useful compounds of Formula I include those where $R^b$ is

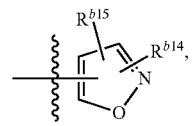

where $R^{14}$ and $R^{15}$ are each independently selected from the group consisting of hydrogen, $C_1$-$C_3$ alkyl, and halo-$C_1$-$C_3$ alkyl. In certain embodiments, useful compounds of Formula I include those where $R^b$ is

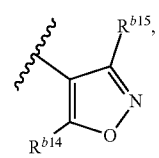

where $R^{b14}$ and $R^{15}$ are each $C_1$-$C_3$ alkyl. In certain embodiments, useful compounds of Formula I include those where $R^{14}$ and $R^{15}$ are each methyl.

In certain embodiments, useful compounds of Formula I include those where the compound is of Formula I-Ia

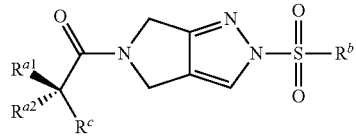

I-Ia or pharmaceutically acceptable salts thereof, where, $R^{a1}$, $R^{a2}$, $R^c$ and $R^b$ are as described above.

In certain embodiments, useful compounds of Formula I include those where the compound is of Formula I-Ib

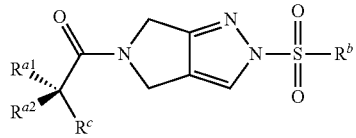

I-Ib or pharmaceutically acceptable salts thereof, where, $R^{a1}$, $R^{a2}$, $R^c$ and $R^b$ are as described above.

In certain embodiments, useful compounds of Formula I include those where the compound is of Formula II

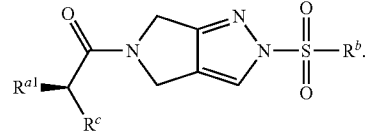

II or pharmaceutically acceptable salts thereof, where, $R^{a1}$, $R^c$ and $R^b$ are as described above.

In certain embodiments, useful compounds of Formula I include those where the compound is of Formula III

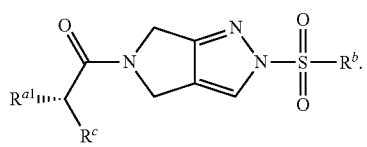

III or pharmaceutically acceptable salts thereof, where, $R^{a1}$, $R^c$ and $R^b$ are as described above.

In certain embodiments, useful compounds of Formula I include those where the compound is of Formula IA

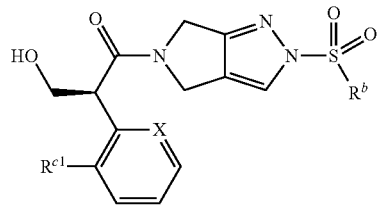

IA or pharmaceutically acceptable salts thereof, where, X, $R^{C1}$ and $R^b$ are as described above.

In certain embodiments, useful compounds of Formula I include those where the compound is of Formula IB

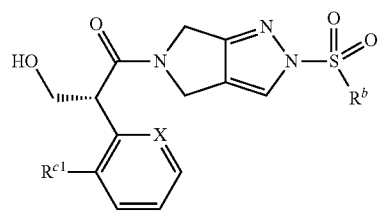

IB or pharmaceutically acceptable salts thereof, where, X, $R^{C1}$ and $R^b$ are as described above.

In certain embodiments, useful compounds include those of Formula IA

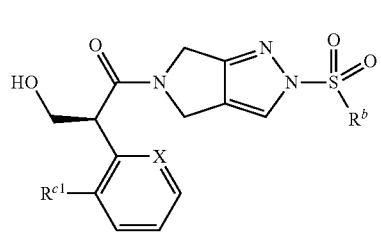

IA or pharmaceutically acceptable salts thereof, where X is CH; $R^{c1}$ is fluoro or hydrogen; $R^b$ is

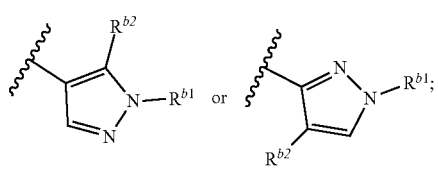

where $R^{b1}$ is halo-$C_1$-$C_3$ alkyl; and $R^{b2}$ is hydrogen or $C_1$-$C_3$ alkyl. In certain embodiments, useful compounds include those of Formula IA, where $R^{b1}$ is —$CH_2CH_2F$, —$CH_2CHF_2$, or —$CH_2CF_3$; and $R^{b2}$ is hydrogen or methyl. In certain other embodiments, useful compounds include those of Formula IA, where $R^{b1}$ is —$CH_2CH_2F$, —$CH_2CHF_2$, or —$CH_2CF_3$; and $R^{b2}$ is hydrogen. The subject matter described herein includes the following compounds in Table 1, or pharmaceutically acceptable salts thereof:

TABLE 1

| Compd No. | Structure | IUPAC Name | Mass Found (M + 1) |
|---|---|---|---|
| 1 | 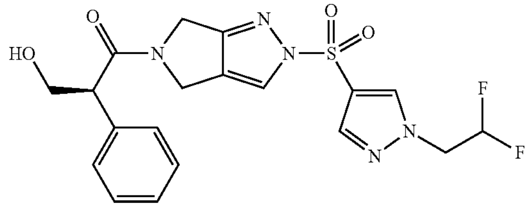 [SMILES: O=C([C@H](CO)c1ccccc1)N1Cc2cn(S(=O)(=O)c3cnn(CC(F)F)c3)nc2C1] | (2S)-1-(2-{[1-(2,2-difluoroethyl)-1H-pyrazol-4-yl]sulfonyl}-2H,4H,5H,6H-pyrrolo[3,4-c]pyrazol-5-yl)-3-hydroxy-2-phenylpropan-1-one | 452 |
| 2 | 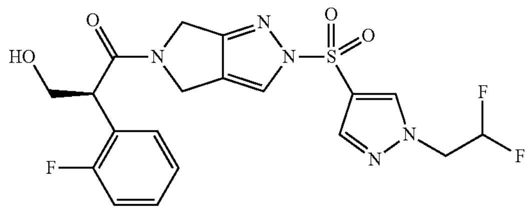 [SMILES: O=C([C@H](CO)c1ccccc1F)N1Cc2cn(S(=O)(=O)c3cnn(CC(F)F)c3)nc2C1] | (2S)-1-(2-{[1-(2,2-difluoroethyl)-1H-pyrazol-4-yl]sulfonyl}-2H,4H,5H,6H-pyrrolo[3,4-c]pyrazol-5-yl)-2-(2-fluorophenyl)-3-hydroxypropan-1-one | 470 |
| 3 | 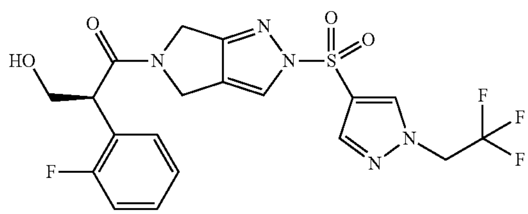 [SMILES: O=C([C@H](CO)c1ccccc1F)N1Cc2cn(S(=O)(=O)c3cnn(CC(F)(F)F)c3)nc2C1] | (2S)-2-(2-fluorophenyl)-3-hydroxy-1-(2-{[1-(2,2,2-trifluoroethyl)-1H-pyrazol-4-yl]sulfonyl}-2H,4H,5H,6H-pyrrolo[3,4-c]pyrazol-5-yl)propan-1-one | 488 |
| 4 | 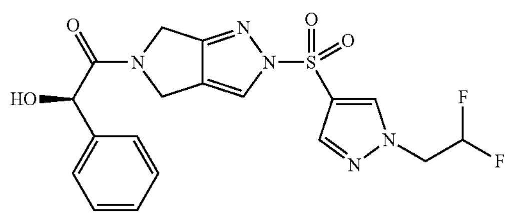 [SMILES: O=C([C@H](O)c1ccccc1)N1Cc2cn(S(=O)(=O)c3cnn(CC(F)F)c3)nc2C1] | (2R)-1-(2-{[1-(2,2-difluoroethyl)-1H-pyrazol-4-yl]sulfonyl}-2H,4H,5H,6H-pyrrolo[3,4-c]pyrazol-5-yl)-2-hydroxy-2-phenylethan-1-one | 438 |
| 5 | 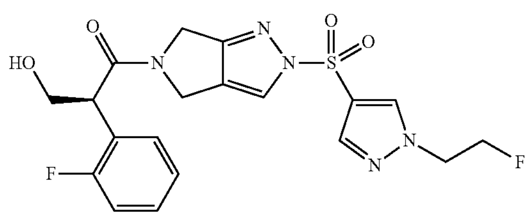 [SMILES: O=C([C@H](CO)c1ccccc1F)N1Cc2cn(S(=O)(=O)c3cnn(CCF)c3)nc2C1] | (2S)-1-(2-{[1-(2-fluoroethyl)-1H-pyrazol-4-yl]sulfonyl}-2H,4H,5H,6H-pyrrolo[3,4-c]pyrazol-5-yl)-2-(2-fluorophenyl)-3-hydroxypropan-1-one | 452 |
| 6 | 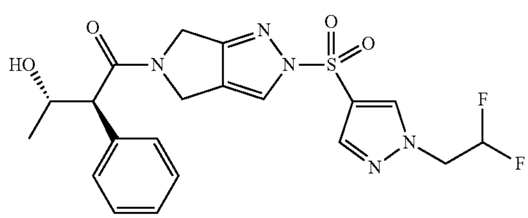 [SMILES: C[C@H](O)[C@@H](C(=O)N1Cc2cn(S(=O)(=O)c3cnn(CC(F)F)c3)nc2C1)c1ccccc1] | (2S,3S)-1-(2-{[1-(2,2-difluoroethyl)-1H-pyrazol-4-yl]sulfonyl}-2H,4H,5H,6H-pyrrolo[3,4-c]pyrazol-5-yl)-3-hydroxy-2-phenylbutan-1-one | 466 |
| 7 | 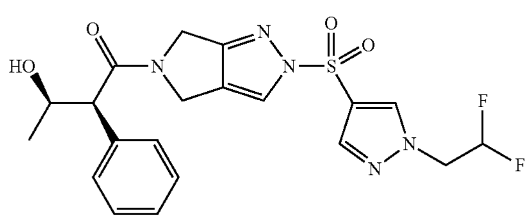 [SMILES: C[C@@H](O)[C@@H](C(=O)N1Cc2cn(S(=O)(=O)c3cnn(CC(F)F)c3)nc2C1)c1ccccc1] | (2S,3R)-1-(2-{[1-(2,2-difluoroethyl)-1H-pyrazol-4-yl]sulfonyl}-2H,4H,5H,6H-pyrrolo[3,4-c]pyrazol-5-yl)-3-hydroxy-2-phenylbutan-1-one | 466 |

TABLE 1-continued

| Compd No. | Structure | IUPAC Name | Mass Found (M + 1) |
|---|---|---|---|
| 8 | 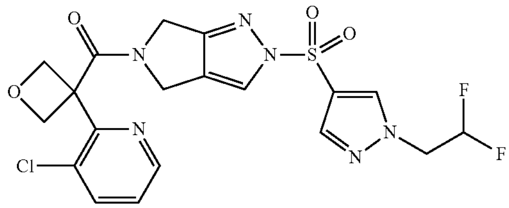 [SMILES: O=C(N1Cc2cn(S(=O)(=O)c3cnn(CC(F)F)c3)nc2C1)C1(c2ncccc2Cl)COC1] | 3-chloro-2-[3-(2-{[1-(2,2-difluoroethyl)-1H-pyrazol-4-yl]sulfonyl}-2H,4H,5H,6H-pyrrolo[3,4-c]pyrazole-5-carbonyl)oxetan-3-yl]pyridine | 499 |
| 9 | 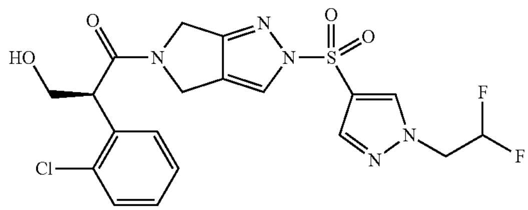 [SMILES: O=C([C@H](CO)c1ccccc1Cl)N1Cc2cn(S(=O)(=O)c3cnn(CC(F)F)c3)nc2C1] | (2S)-2-(2-chlorophenyl)-1-(2-{[1-(2,2-difluoroethyl)-1H-pyrazol-4-yl]sulfonyl}-2H,4H,5H,6H-pyrrolo[3,4-c]pyrazol-5-yl)-3-hydroxypropan-1-one | 486 |
| 10* | 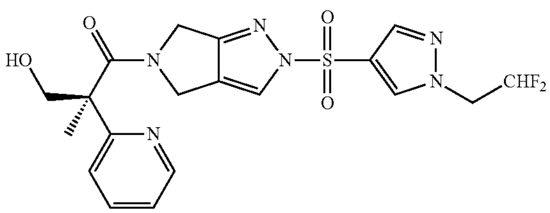 [SMILES: C[C@](CO)(C(=O)N1Cc2cn(S(=O)(=O)c3cnn(CC(F)F)c3)nc2C1)c1ccccn1] | (2S)-1-(2-{[1-(2,2-difluoroethyl)-1H-pyrazol-4-yl]sulfonyl}-2H,4H,5H,6H-pyrrolo[3,4-c]pyrazol-5-yl)-3-hydroxy-2-methyl-2-(pyridin-2-yl)propan-1-one | 467 |
| | OR | OR | |
| | | (2R)-1-(2-{[1-(2,2-difluoroethyl)-1H-pyrazol-4-yl]sulfonyl}-2H,4H,5H,6H-pyrrolo[3,4-c]pyrazol-5-yl)-3-hydroxy-2-methyl-2-(pyridin-2-yl)propan-1-one | |
| 11 | 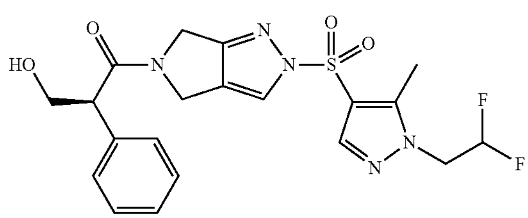 [SMILES: Cc1c(S(=O)(=O)n2cc3c(n2)CN(C(=O)[C@H](CO)c2ccccc2)C3)cnn1CC(F)F] | (2S)-1-(2-{[1-(2,2-difluoroethyl)-5-methyl-1H-pyrazol-4-yl]sulfonyl}-2H,4H,5H,6H-pyrrolo[3,4-c]pyrazol-5-yl)-3-hydroxy-2-phenylpropan-1-one | 466 |
| 12 | 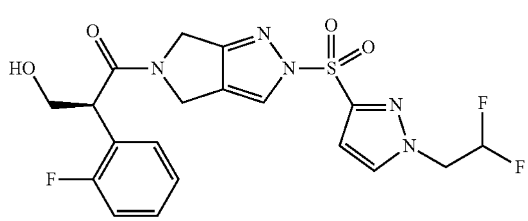 [SMILES: O=C([C@H](CO)c1ccccc1F)N1Cc2cn(S(=O)(=O)c3ccn(CC(F)F)n3)nc2C1] | (2S)-1-(2-{[1-(2,2-difluoroethyl)-1H-pyrazol-3-yl]sulfonyl}-2H,4H,5H,6H-pyrrolo[3,4-c]pyrazol-5-yl)-2-(2-fluorophenyl)-3-hydroxypropan-1-one | 470.1 |
| 13 | 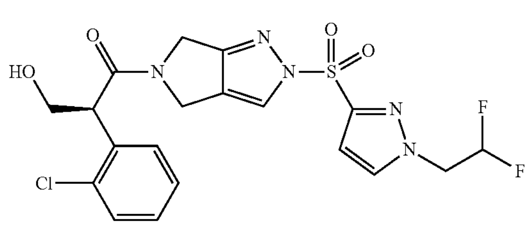 [SMILES: O=C([C@H](CO)c1ccccc1Cl)N1Cc2cn(S(=O)(=O)c3ccn(CC(F)F)n3)nc2C1] | (2S)-2-(2-chlorophenyl)-1-(2-{[1-(2,2-difluoroethyl)-1H-pyrazol-3-yl]sulfonyl}-2H,4H,5H,6H-pyrrolo[3,4-c]pyrazol-5-yl)-3-hydroxypropan-1-one | 486 |

TABLE 1-continued

| Compd No. | Structure | IUPAC Name | Mass Found (M + 1) |
|---|---|---|---|
| 14 | 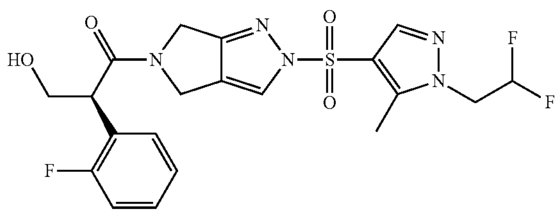 [SMILES: Cc1c(S(=O)(=O)n2cc3c(n2)CN(C(=O)[C@H](CO)c2ccccc2F)C3)cnn1CC(F)F] | (2S)-1-(2-{[1-(2,2-difluoroethyl)-5-methyl-1H-pyrazol-4-yl]sulfonyl}-2H,4H,5H,6H-pyrrolo[3,4-c]pyrazol-5-yl)-2-(2-fluorophenyl)-3-hydroxypropan-1-one | 484 |
| 15 | 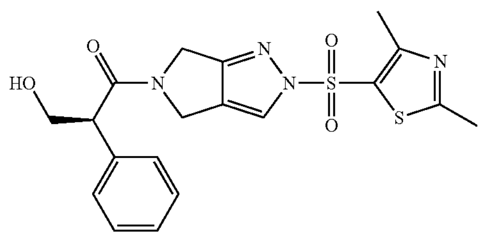 [SMILES: Cc1nc(C)c(S(=O)(=O)n2cc3c(n2)CN(C(=O)[C@H](CO)c2ccccc2)C3)s1] | (2S)-1-{2-[(2,4-dimethyl-1,3-thiazol-5-yl)sulfonyl]-2H,4H,5H,6H-pyrrolo[3,4-c]pyrazol-5-yl}-3-hydroxy-2-phenylpropan-1-one | 433.04 |
| 16 | 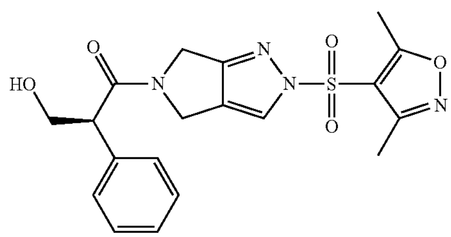 [SMILES: Cc1noc(C)c1S(=O)(=O)n1cc2c(n1)CN(C(=O)[C@H](CO)c1ccccc1)C2] | (2S)-1-{2-[(3,5-dimethyl-1,2-oxazol-4-yl)sulfonyl]-2H,4H,5H,6H-pyrrolo[3,4-c]pyrazol-5-yl}-3-hydroxy-2-phenylpropan-1-one | 417.03 |
| 17 | 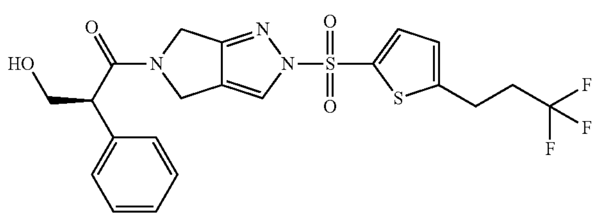 [SMILES: O=C([C@H](CO)c1ccccc1)N1Cc2cn(S(=O)(=O)c3ccc(CCC(F)(F)F)s3)nc2C1] | (2S)-3-hydroxy-2-phenyl-1-(2-{[5-(3,3,3-trifluoropropyl)thiophen-2-yl]sulfonyl}-2H,4H,5H,6H-pyrrolo[3,4-c]pyrazol-5-yl)propan-1-one | 499.89 |
| 18 | 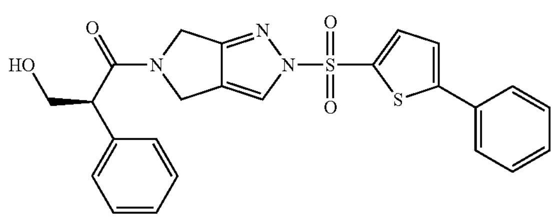 [SMILES: O=C([C@H](CO)c1ccccc1)N1Cc2cn(S(=O)(=O)c3ccc(-c4ccccc4)s3)nc2C1] | (2S)-3-hydroxy-2-phenyl-1-{2-[(5-phenylthiophen-2-yl)sulfonyl]-2H,4H,5H,6H-pyrrolo[3,4-c]pyrazol-5-yl}propan-1-one | 479.92 |
| 19 | 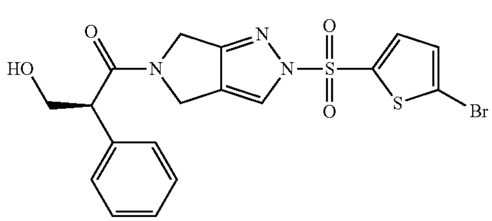 [SMILES: O=C([C@H](CO)c1ccccc1)N1Cc2cn(S(=O)(=O)c3ccc(Br)s3)nc2C1] | (2S)-1-{2-[(5-bromothiophen-2-yl)sulfonyl]-2H,4H,5H,6H-pyrrolo[3,4-c]pyrazol-5-yl}-3-hydroxy-2-phenylpropan-1-one | 481.83/ 483.74 |

TABLE 1-continued

| Compd No. | Structure | IUPAC Name | Mass Found (M + 1) |
|---|---|---|---|
| 20 | 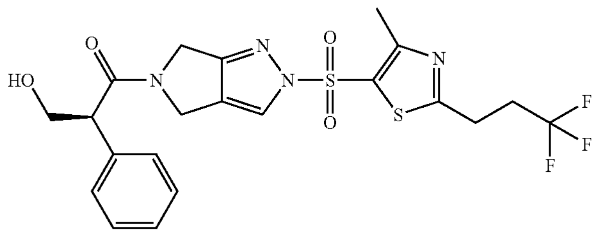 [SMILES: Cc1nc(CCC(F)(F)F)sc1S(=O)(=O)n1cc2c(n1)CN(C(=O)[C@H](CO)c1ccccc1)C2] | (2S)-3-hydroxy-1-(2-{[4-methyl-2-(3,3,3-trifluoropropyl)-1,3-thiazol-5-yl]sulfonyl}-2H,4H,5H,6H-pyrrolo[3,4-c]pyrazol-5-yl)-2-phenylpropan-1-one | 515.04 |
| 21 | 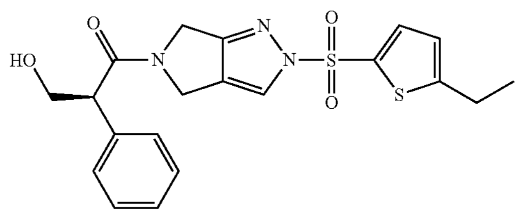 [SMILES: CCc1ccc(S(=O)(=O)n2cc3c(n2)CN(C(=O)[C@H](CO)c2ccccc2)C3)s1] | (2S)-1-{2-[(5-ethylthiophen-2-yl)sulfonyl]-2H,4H,5H,6H-pyrrolo[3,4-c]pyrazol-5-yl}-3-hydroxy-2-phenylpropan-1-one | 432.04 |
| 22 | 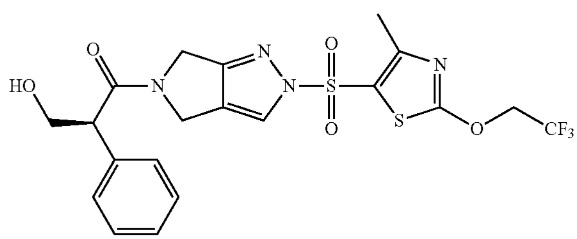 [SMILES: Cc1nc(OCC(F)(F)F)sc1S(=O)(=O)n1cc2c(n1)CN(C(=O)[C@H](CO)c1ccccc1)C2] | (2S)-3-hydroxy-1-(2-{[4-methyl-2-(2,2,2-trifluoroethoxy)-1,3-thiazol-5-yl]sulfonyl}-2H,4H,5H,6H-pyrrolo[3,4-c]pyrazol-5-yl)-2-phenylpropan-1-one | 516.95 |
| 23 | 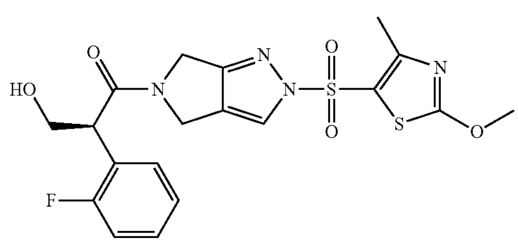 [SMILES: COc1nc(C)c(S(=O)(=O)n2cc3c(n2)CN(C(=O)[C@H](CO)c2ccccc2F)C3)s1] | (2S)-2-(2-fluorophenyl)-3-hydroxy-1-{2-[(2-methoxy-4-methyl-1,3-thiazol-5-yl)sulfonyl]-2H,4H,5H,6H-pyrrolo[3,4-c]pyrazol-5-yl}propan-1-one | 466.96 |
| 24 | 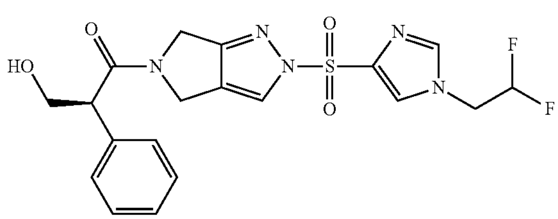 [SMILES: O=C([C@H](CO)c1ccccc1)N1Cc2cn(S(=O)(=O)c3cn(CC(F)F)cn3)nc2C1] | (2S)-1-(2-{[1-(2,2-difluoroethyl)-1H-imidazol-4-yl]sulfonyl}-2H,4H,5H,6H-pyrrolo[3,4-c]pyrazol-5-yl)-3-hydroxy-2-phenylpropan-1-one | 452.05 |

TABLE 1-continued

| Compd No. | Structure | IUPAC Name | Mass Found (M + 1) |
|---|---|---|---|
| 25 | 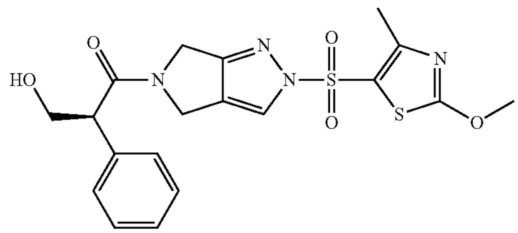 [SMILES: COc1nc(C)c(S(=O)(=O)n2cc3c(n2)CN(C(=O)[C@H](CO)c2ccccc2)C3)s1] | (2S)-3-hydroxy-1-{2-[(2-methoxy-4-methyl-1,3-thiazol-5-yl)sulfonyl]-2H,4H,5H,6H-pyrrolo[3,4-c]pyrazol-5-yl}-2-phenylpropan-1-one | 449.11 |
| | OR | OR | |
| | | 5-({5-[(2S)-3-hydroxy-2-phenylpropanoyl]-2H,4H,5H,6H-pyrrolo[3,4-c]pyrazol-2-yl}sulfonyl)-3,4-dimethyl-2,3-dihydro-1,3-thiazol-2-one | |
| 26 | 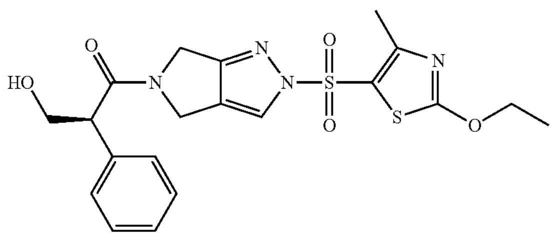 [SMILES: CCOc1nc(C)c(S(=O)(=O)n2cc3c(n2)CN(C(=O)[C@H](CO)c2ccccc2)C3)s1] | (2S)-3-hydroxy-1-{2-[(2-ethoxy-4-methyl-1,3-thiazol-5-yl)sulfonyl]-2H,4H,5H,6H-pyrrolo[3,4-c]pyrazol-5-yl}-2-phenylpropan-1-one | 462.92 |
| | OR | OR | |
| | | 3-ethyl-5-({5-[(2S)-hydroxy-2-phenylpropanoyl]-2H,4H,5H,6H-pyrrolo[3,4-c]pyrazol-2-yl}sulfonyl)-4-methyl-2,3-dihydro-1,3-thiazol-2-one | |
| 27 | 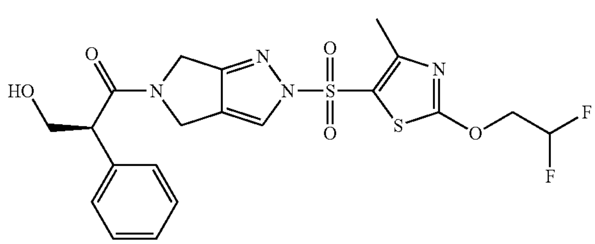 [SMILES: Cc1nc(OCC(F)F)sc1S(=O)(=O)n1cc2c(n1)CN(C(=O)[C@H](CO)c1ccccc1)C2] | (2S)-1-(2-{[2-(2,2-difluoroethoxy)-4-methyl-1,3-thiazol-5-yl]sulfonyl]-2H,4H,5H,6H-pyrrolo[3,4-c]pyrazol-5-yl)-3-hydroxy-2-phenylpropan-1-one | 498.96 |
| | OR | OR | |
| | | 3-(2,2-difluoroethyl)-5-({5-[(2S)-3-hydroxy-2-phenylpropanoyl]-2H,4H,5H,6H-pyrrolo[3,4-c]pyrazol-2-yl}sulfonyl)-4-methyl-2,3-dihydro-1,3-thiazol-2-one | |

TABLE 1-continued

| Compd No. | Structure | IUPAC Name | Mass Found (M + 1) |
|---|---|---|---|
| 28* | 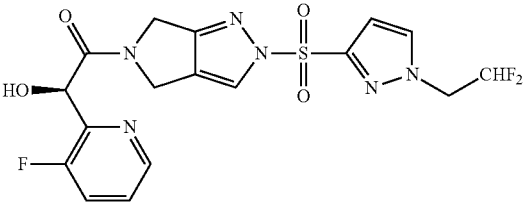 OR 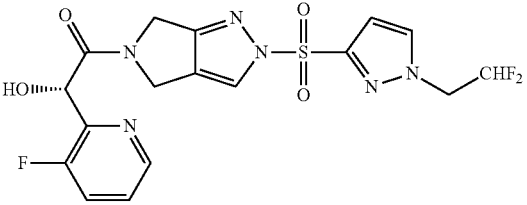 | (R)-1-(2-((1-(2,2-difluoroethyl)-1H-pyrazol-3-yl)sulfonyl)-2,6-dihydropyrrolo[3,4-c]pyrazol-5(4H)-yl)-2-(3-fluoropyridin-2-yl)-2-hydroxyethan-1-one OR (S)-1-(2-((1-(2,2-difluoroethyl)-1H-pyrazol-3-yl)sulfonyl)-2,6-dihydropyrrolo[3,4-c]pyrazol-5(4H)-yl)-2-(3-fluoropyridin-2-yl)-2-hydroxyethan-1-one | 457 |
| 29* | 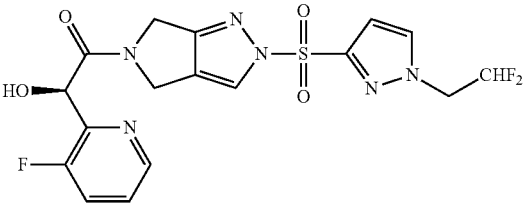 OR 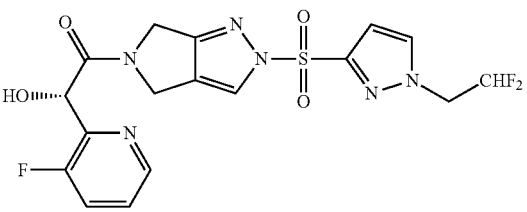 | (R)-1-(2-((1-(2,2-difluoroethyl)-1H-pyrazol-3-yl)sulfonyl)-2,6-dihydropyrrolo[3,4-c]pyrazol-5(4H)-yl)-2-(3-fluoropyridin-2-yl)-2-hydroxyethan-1-one OR (S)-1-(2-((1-(2,2-difluoroethyl)-1H-pyrazol-3-yl)sulfonyl)-2,6-dihydropyrrolo[3,4-c]pyrazol-5(4H)-yl)-2-(3-fluoropyridin-2-yl)-2-hydroxyethan-1-one | 457 |
| 30 | 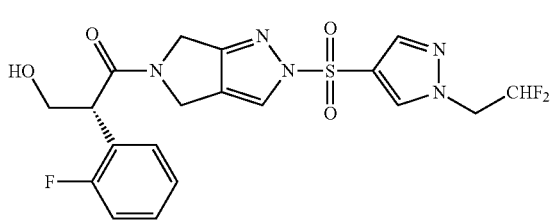 | (R)-1-(2-((1-(2,2-difluoroethyl)-1H-pyrazol-3-yl)sulfonyl)-2,6-dihydropyrrolo[3,4-c]pyrazol-5(4H)-yl)-2-(2-fluorophenyl)-3-hydroxypropan-1-one | 470 |

TABLE 1-continued

| Compd No. | Structure | IUPAC Name | Mass Found (M + 1) |
|---|---|---|---|
| 31* | 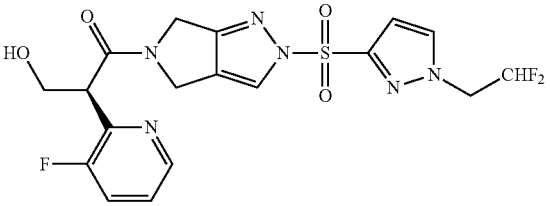 OR 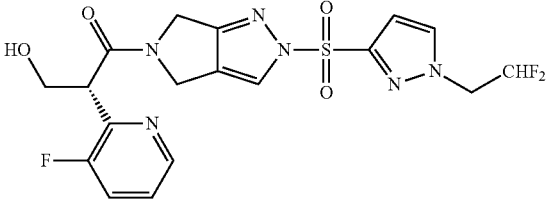 | (S)-1-(2-((1-(2,2-difluoroethyl)-1H-pyrazol-3-yl)sulfonyl)-2,6-dihydropyrrolo[3,4-c]pyrazol-5(4H)-yl)-2-(3-fluoropyridin-2-yl)-3-hydroxypropan-1-one OR (R)-1-(2-((1-(2,2-difluoroethyl)-1H-pyrazol-3-yl)sulfonyl)-2,6-dihydropyrrolo[3,4-c]pyrazol-5(4H)-yl)-2-(3-fluoropyridin-2-yl)-3-hydroxypropan-1-one | 471 |
| 32* | 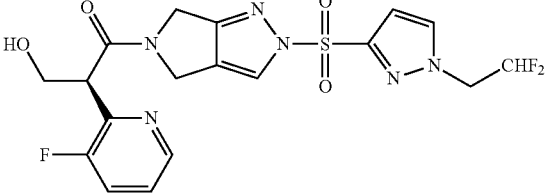 OR 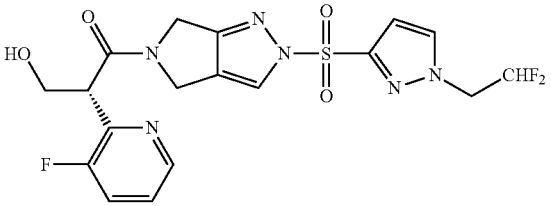 | (S)-1-(2-((1-(2,2-difluoroethyl)-1H-pyrazol-3-yl)sulfonyl)-2,6-dihydropyrrolo[3,4-c]pyrazol-5(4H)-yl)-2-(3-fluoropyridin-2-yl)-3-hydroxypropan-1-one OR (R)-1-(2-((1-(2,2-difluoroethyl)-1H-pyrazol-3-yl)sulfonyl)-2,6-dihydropyrrolo[3,4-c]pyrazol-5(4H)-yl)-2-(3-fluoropyridin-2-yl)-3-hydroxypropan-1-one | 471 |
| 33 | 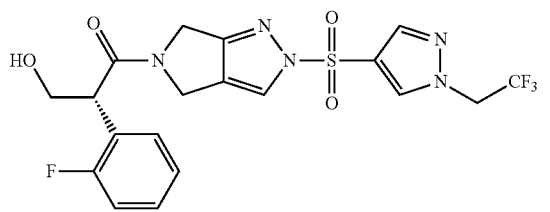 | (2R)-2-(2-fluorophenyl)-3-hydroxy-1-[2-[1-(2,2,2-trifluoroethyl)pyrazol-4-ylsulfonyl]-4H,6H-pyrrolo[3,4-c]pyrazol-5-yl]propan-1-one | 488 |
| 34 | 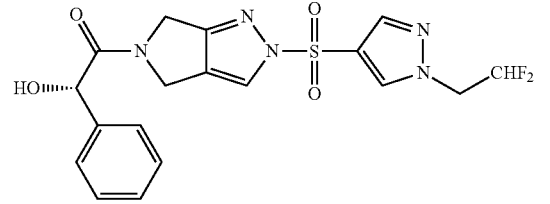 | (2S)-1-[2-[1-(2,2-difluoroethyl)pyrazol-4-ylsulfonyl]-4H,6H-pyrrolo[3,4-c]pyrazol-5-yl]-2-hydroxy-2-phenylethanone | 438 |

TABLE 1-continued

| Compd No. | Structure | IUPAC Name | Mass Found (M + 1) |
|---|---|---|---|
| 35 | 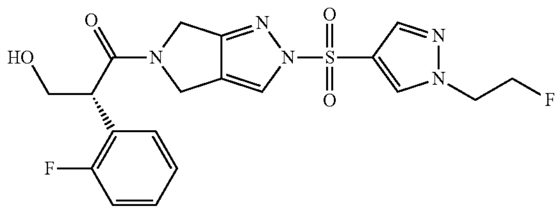 [SMILES: O=C([C@@H](CO)c1ccccc1F)N1Cc2cn(S(=O)(=O)c3cnn(CCF)c3)nc2C1] | (2R)-1-[2-[1-(2-fluoroethyl)pyrazol-4-ylsulfonyl]-4H,6H-pyrrolo[3,4c]pyrazol-5-yl]-2-(2-fluorophenyl)-3-hydroxypropan-1-one | 452 |
| 36 | 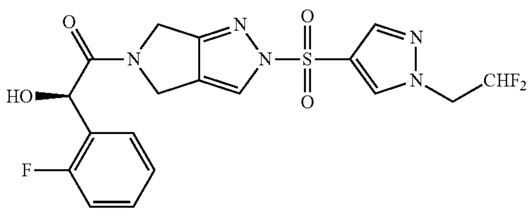 [SMILES: O=C([C@H](O)c1ccccc1F)N1Cc2cn(S(=O)(=O)c3cnn(CC(F)F)c3)nc2C1] | (2R)-1-[2-[1-(2,2-difluoroethyl)pyrazol-4-ylsulfonyl]-4H,6H-pyrrolo[3,4-c]pyrazol-5-yl]-2-(2-fluorophenyl)-2-hydroxyethanone | 456 |
| 37 | 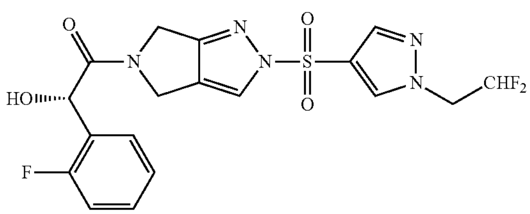 [SMILES: O=C([C@@H](O)c1ccccc1F)N1Cc2cn(S(=O)(=O)c3cnn(CC(F)F)c3)nc2C1] | (2S)-1-[2-[1-(2,2-difluoroethyl)pyrazol-4-ylsulfonyl]-4H,6H-pyrrolo[3,4-c]pyrazol-5-yl]-2-(2-fluorophenyl)-2-hydroxyethanone | 456 |
| 38* | | (2R)-1-[2-[1-(2,2-difluoroethyl)pyrazol-4-ylsulfonyl]-4H,6H-pyrrolo[3,4-c]pyrazol-5-yl]-2-(3-fluoropyridin-2-yl)-2-hydroxyethanone | 457 |
| | OR | OR | |
| | | (2S)-1-[2-[1-(2,2-difluoroethyl)pyrazol-4-ylsulfonyl]-4H,6H-pyrrolo[3,4-c]pyrazol-5-yl]-2-(3-fluoropyridin-2-yl)-2-hydroxyethanone | |

TABLE 1-continued

| Compd No. | Structure | IUPAC Name | Mass Found (M + 1) |
|---|---|---|---|
| 39* | 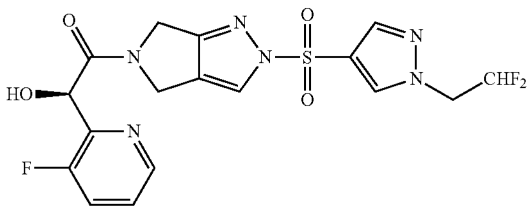 [SMILES: O=C([C@H](O)c1ncccc1F)N1Cc2cn(S(=O)(=O)c3cnn(CC(F)F)c3)nc2C1] | (2R)-1-[2-[1-(2,2-difluoroethyl)pyrazol-4-ylsulfonyl]-4H,6H-pyrrolo[3,4-c]pyrazol-5-yl]-2-(3-fluoropyridin-2-yl)-2-hydroxyethanone | 457 |
| | OR | OR | |
| | | (2S)-1-[2-[1-(2,2-difluoroethyl)pyrazol-4-ylsulfonyl]-4H,6H-pyrrolo[3,4-c]pyrazol-5-yl]-2-(3-fluoropyridin-2-yl)-2-hydroxyethanone | |
| 40* | 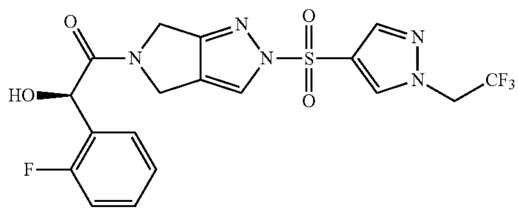 [SMILES: O=C([C@H](O)c1ccccc1F)N1Cc2cn(S(=O)(=O)c3cnn(CC(F)(F)F)c3)nc2C1] | (2R)-2-(2-fluorophenyl)-2-hydroxy-1-{2-[1-(2,2,2-trifluoroethyl)pyrazol-4-ylsulfonyl]-4H,6H-pyrrolo[3,4-c]pyrazol-5-yl}ethanone | 474 |
| | OR | OR | |
| | | (2S)-2-(2-fluorophenyl)-2-hydroxy-1-{2-[1-(2,2,2-trifluoroethyl)pyrazol-4-ylsulfonyl]-4H,6H-pyrrolo[3,4-c]pyrazol-5-yl}ethenone | |
| 41* | 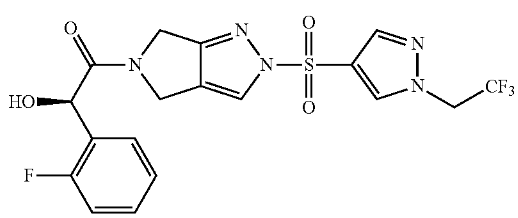 [SMILES: O=C([C@H](O)c1ccccc1F)N1Cc2cn(S(=O)(=O)c3cnn(CC(F)(F)F)c3)nc2C1] | (2R)-2-(2-fluorophenyl)-2-hydroxy-1-{2-[1-(2,2,2-trifluoroethyl)pyrazol-4-ylsulfonyl]-4H,6H-pyrrolo[3,4-c]pyrazol-5-yl}ethenone | 474 |
| | OR | OR | |
| | | (2S)-2-(2-fluorophenyl)-2-hydroxy-1-{2-[1-(2,2,2-trifluoroethyl)pyrazol-4-ylsulfonyl]-4H,6H-pyrrolo[3,4-c]pyrazol-5-yl}ethenone | |

TABLE 1-continued

| Compd No. | Structure | IUPAC Name | Mass Found (M + 1) |
|---|---|---|---|
| 42* | 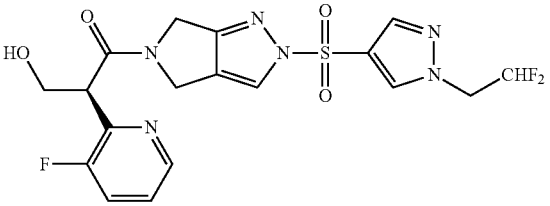 OR 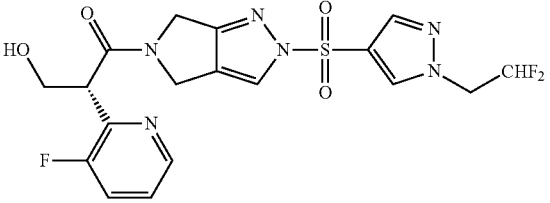 | S)-1-(2-((1-(2,2-difluoroethyl)-1H-pyrazol-4-yl)sulfonyl)-2,6-dihydropyrrolo[3,4-c]pyrazol-5(4H)-yl)-2-(3-fluoropyridin-2-yl)-3-hydroxypropan-1-one OR (R)-1-(2-((1-(2,2-difluoroethyl)-1H-pyrazol-4-yl)sulfonyl)-2,6-dihydropyrrolo[3,4-c]pyrazol-5(4H)-yl)-2-(3-fluoropyridin-2-yl)-3-hydroxypropan-1-one | 471 |
| 43* | 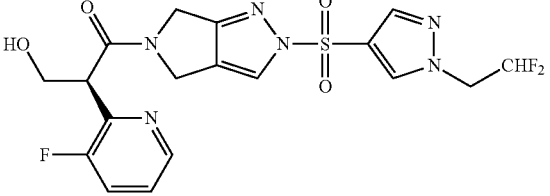 OR 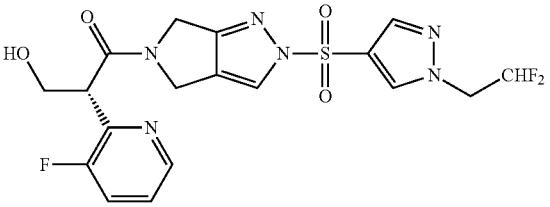 | S)-1-(2-((1-(2,2-difluoroethyl)-1H-pyrazol-4-yl)sulfonyl)-2,6-dihydropyrrolo[3,4-c]pyrazol-5(4H)-yl)-2-(3-fluoropyridin-2-yl)-3-hydroxypropan-1-one OR (R)-1-(2-((1-(2,2-difluoroethyl)-1H-pyrazol-4-yl)sulfonyl)-2,6-dihydropyrrolo[3,4-c]pyrazol-5(4H)-yl)-2-(3-fluoropyridin-2-yl)-3-hydroxypropan-1-one | 471 |
| 44 | 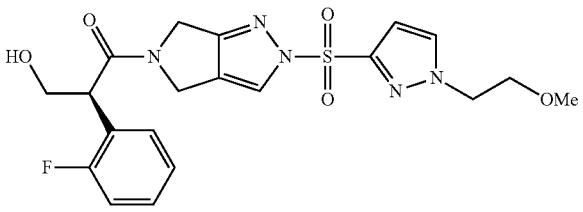 | (2S)-2-(2-fluorophenyl)-3-hydroxy-1-[2-[1-(2-methoxyethyl)pyrazol-3-yl]sulfonyl]-4H,6H-pyrrolo[3,4-c]pyrazol-5-yl]propan-1-one | 464.2 |
| 45 | 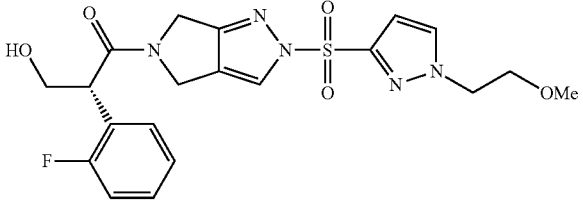 | (2R)-2-(2-fluorophenyl)-3-hydroxy-1-[2-[1-(2-methoxyethyl)pyrazol-3-yl]sulfonyl]-4H,6H-pyrrolo[3,4-c]pyrazol-5-yl]propan-1-one | 464.2 |

TABLE 1-continued

| Compd No. | Structure | IUPAC Name | Mass Found (M + 1) |
|---|---|---|---|
| 46 | 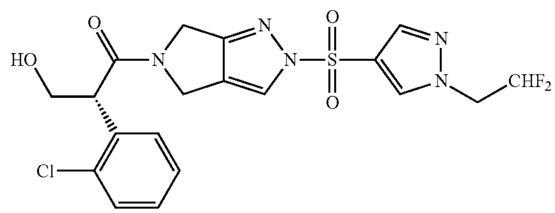 | (R)-2-(2-chlorophenyl)-1-(2-((1-(2,2-difluoroethyl)-1H-pyrazol-4-yl)sulfonyl)-2,6-dihydropyrrolo[3,4-c]pyrazol-5(4H)-yl)-3-hydroxypropan-1-one | 486 |
| 47 | 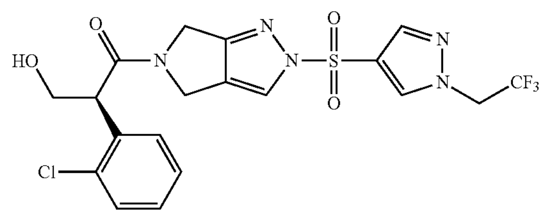 [SMILES: O=C([C@H](CO)c1ccccc1Cl)N1Cc2cn(S(=O)(=O)c3cnn(CC(F)(F)F)c3)nc2C1] | (2S)-2-(2-chlorophenyl)-3-hydroxy-1-[2-[1-(2,2,2-trifluoroethyl)pyrazol-4-ylsulfonyl]-4H,6H-pyrrolo[3,4-c]pyrazol-5-yl]propan-1-one | 504 |
| 48 | 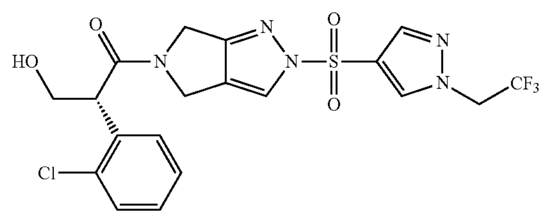 [SMILES: O=C([C@@H](CO)c1ccccc1Cl)N1Cc2cn(S(=O)(=O)c3cnn(CC(F)(F)F)c3)nc2C1] | (2R)-2-(2-chlorophenyl)-3-hydroxy-1-[2-[1-(2,2,2-trifluoroethyl)pyrazol-4-ylsulfonyl]-4H,6H-pyrrolo[3,4-c]pyrazol-5-yl]propan-1-one | 504 |
| 49 | 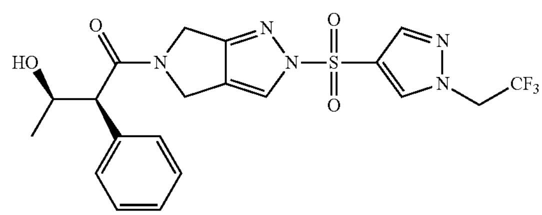 [SMILES: C[C@@H](O)[C@@H](C(=O)N1Cc2cn(S(=O)(=O)c3cnn(CC(F)(F)F)c3)nc2C1)c1ccccc1] | (2S,3R)-3-hydroxy-2-phenyl-1-{2-[1-(2,2,2-trifluoroethyl)pyrazol-4-ylsulfonyl]-4H,6H-pyrrolo[3,4-c]pyrazol-5-yl}butan-1-one | 484 |
| 50 | 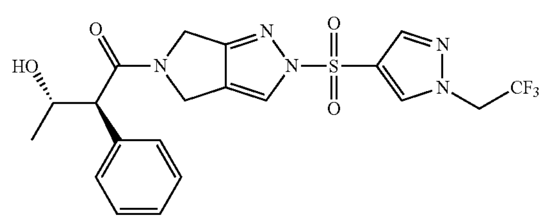 [SMILES: C[C@H](O)[C@@H](C(=O)N1Cc2cn(S(=O)(=O)c3cnn(CC(F)(F)F)c3)nc2C1)c1ccccc1] | (2S,3S)-3-hydroxy-2-phenyl-1-{2-[1-(2,2,2-trifluoroethyl)pyrazol-4-ylsulfonyl]-4H,6H-pyrrolo[3,4-c]pyrazol-5-yl}butan-1-one | 484 |
| 51 | 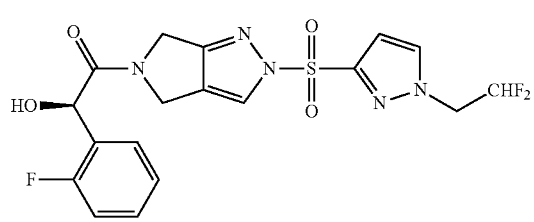 [SMILES: O=C([C@H](O)c1ccccc1F)N1Cc2cn(S(=O)(=O)c3ccn(CC(F)F)n3)nc2C1] | (2R)-1-{2-[1-(2,2-difluoroethyl)pyrazol-3-ylsulfonyl]-4H,6H-pyrrolo[3,4-c]pyrazol-5-yl}-2-(2-fluorophenyl)-2-hydroxyethanone | 456 |
| 52 | 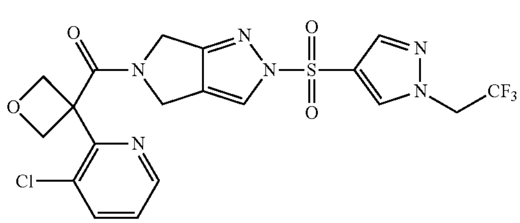 [SMILES: O=C(N1Cc2cn(S(=O)(=O)c3cnn(CC(F)(F)F)c3)nc2C1)C1(c2ncccc2Cl)COC1] | (3-(3-chloropyridin-2-yl)oxetan-3-yl)(2-((1-(2,2,2-trifluoroethyl)-1H-pyrazol-4-yl)sulfonyl)-2,6-dihydropyrrolo[3,4-c]pyrazol-5(4H)-yl)methanone | 517 |

TABLE 1-continued

| Compd No. | Structure | IUPAC Name | Mass Found (M + 1) |
|---|---|---|---|
| 53 | 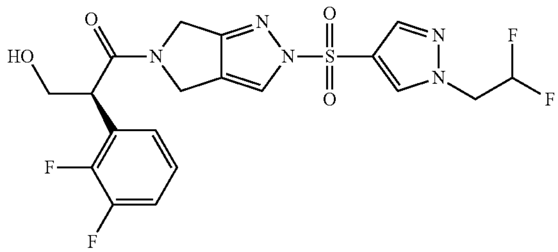 [SMILES: O=C([C@H](CO)c1cccc(F)c1F)N1Cc2cn(S(=O)(=O)c3cnn(CC(F)F)c3)nc2C1] | (2S)-1-{2-[1-(2,2-difluoroethyl)pyrazol-4-ylsulfonyl]-4H,6H-pyrrolo[3,4-c]pyrazol-5-yl}-2-(2,3-difluorophenyl)-3-hydroxypropan-1-one | 488 |
| 54 | 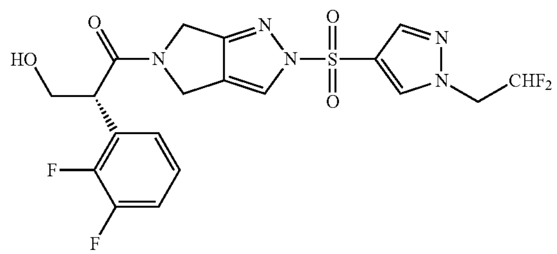 | (2R)-1-{2-[1-(2,2-difluoroethyl)pyrazol-4-ylsulfonyl]-4H,6H-pyrrolo[3,4-c]pyrazol-5-yl}-2-(2,3-difluorophenyl)-3-hydroxypropan-1-one | 488 |
| 55 | 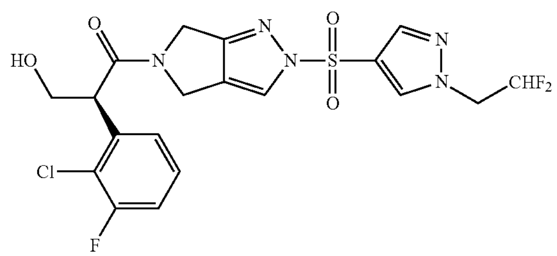 [SMILES: O=C([C@H](CO)c1cccc(F)c1Cl)N1Cc2cn(S(=O)(=O)c3cnn(CC(F)F)c3)nc2C1] | (2S)-2-(2-chloro-3-fluorophenyl)-1-{2-[1-(2,2-difluoroethyl)pyrazol-4-ylsulfonyl]-4H,6H-pyrrolo[3,4-c]pyrazol-5-yl}-3-hydroxypropan-1-one | 504 |
| 56 | 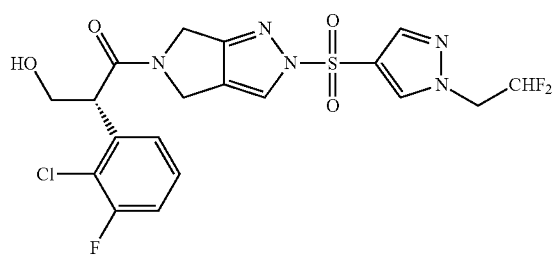 [SMILES: O=C([C@@H](CO)c1cccc(F)c1Cl)N1Cc2cn(S(=O)(=O)c3cnn(CC(F)F)c3)nc2C1] | (2R)-2-(2-chloro-3-fluorophenyl)-1-{2-[1-(2,2-difluoroethyl)pyrazol-4-ylsulfonyl]-4H,6H-pyrrolo[3,4-c]pyrazol-5-yl}-3-hydroxypropan-1-one | 504 |
| 57 | 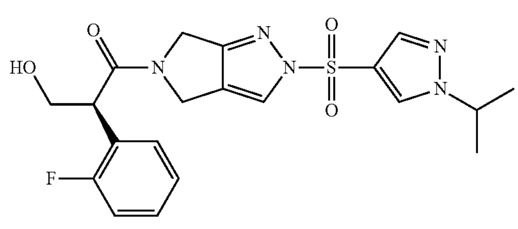 [SMILES: CC(C)n1cc(S(=O)(=O)n2cc3c(n2)CN(C(=O)[C@H](CO)c2ccccc2F)C3)cn1] | (2S)-2-(2-(fluorophenyl)-3-hydroxy-1-[2-(1-isopropylpyrazol-4-ylsulfonyl)-4H,6H-pyrrolo[3,4-c]pyrazol-5-yl]propan-1-one | 448 |
| 58 | 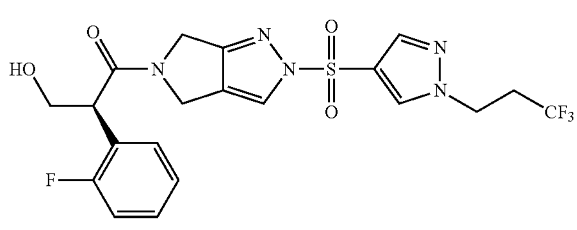 [SMILES: O=C([C@H](CO)c1ccccc1F)N1Cc2cn(S(=O)(=O)c3cnn(CCC(F)(F)F)c3)nc2C1] | (S)-2-(2-fluorophenyl)-3-hydroxy-1-(2-((1-(3,3,3-trifluoropropyl)-1H-pyrazol-4-yl)sulfonyl)-2,6-dihydropyrrolo[3,4-c]pyrazol-5(4H)-yl)propan-1-one | 502 |

TABLE 1-continued

| Compd No. | Structure | IUPAC Name | Mass Found (M + 1) |
|---|---|---|---|
| 59 | 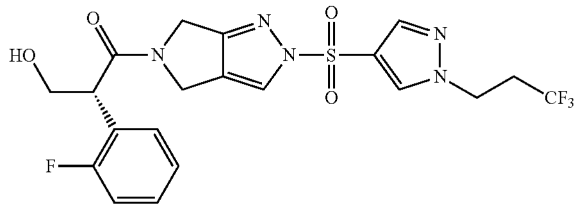 [SMILES: O=C([C@@H](CO)c1ccccc1F)N1Cc2cn(S(=O)(=O)c3cnn(CCC(F)(F)F)c3)nc2C1] | (R)-2-(2-fluorophenyl)-3-hydroxy-1-(2-((1-(3,3,3-trifluoropropyl)-1H-pyrazol-4-yl)sulfonyl)-2,6-dihydropyrrolo[3,4-c]pyrazol-5(4H)-yl)propan-1-one | 502 |
| 60 | 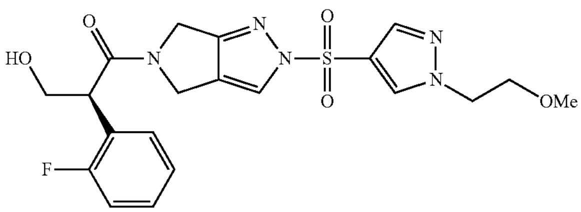 [SMILES: COCCn1cc(S(=O)(=O)n2cc3c(n2)CN(C(=O)[C@H](CO)c2ccccc2F)C3)cn1] | (2S)-2-(2-fluorophenyl)-3-hydroxy-1-{2-[1-(2-methoxyethyl)pyrazol-4-ylsulfonyl]-4H,6H-pyrrolo[3,4-c]pyrazol-5-yl}propan-1-one | 464 |
| 61 | 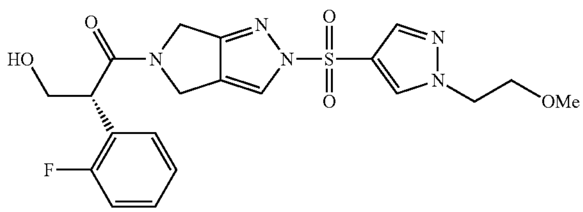 [SMILES: COCCn1cc(S(=O)(=O)n2cc3c(n2)CN(C(=O)[C@@H](CO)c2ccccc2F)C3)cn1] | (2R)-2-(2-fluorophenyl)-3-hydroxy-1-{2-[1-(2-methoxyethyl)pyrazol-4-ylsulfonyl]-4H,6H-pyrrolo[3,4-c]pyrazol-5-yl}propan-1-one | 464 |
| 62 | 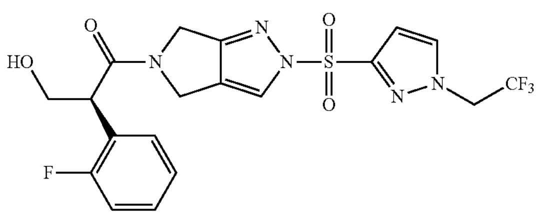 [SMILES: O=C([C@H](CO)c1ccccc1F)N1Cc2cn(S(=O)(=O)c3ccn(CC(F)(F)F)n3)nc2C1] | (2S)-2-(2-fluorophenyl)-3-hydroxy-1-{2-[1-(2,2,2-trifluoroethyl)pyrazol-3-ylsulfonyl]-4H,6H-pyrrolo[3,4-c]pyrazol-5-yl}propan-1-one | 488 |
| 63 | 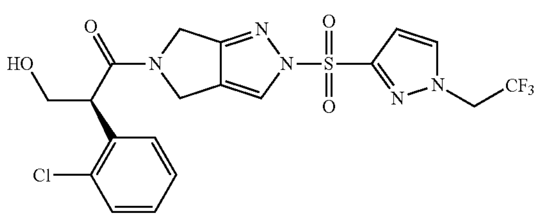 [SMILES: O=C([C@H](CO)c1ccccc1Cl)N1Cc2cn(S(=O)(=O)c3ccn(CC(F)(F)F)n3)nc2C1] | (2S)-2-(2-chlorophenyl)-3-hydroxy-1-[2-[1-(2,2,2-trifluoroethyl)pyrazol-3-ylsulfonyl]-4H,6H-pyrrolo[3,4-c]pyrazol-5-yl]propan-1-one | 504 |
| 64 | 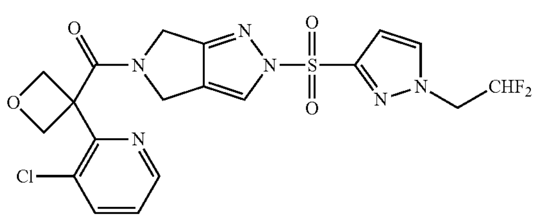 [SMILES: O=C(N1Cc2cn(S(=O)(=O)c3ccn(CC(F)F)n3)nc2C1)C1(c2ncccc2Cl)COC1] | 3-chloro-2-(3-{2-[1-(2,2-difluoroethyl)pyrazol-3-ylsulfonyl]-4H,6H-pyrrolo[3,4-c]pyrazole-5-carbonyl}oxetan-3-yl)pyridine | 499 |
| 65 | 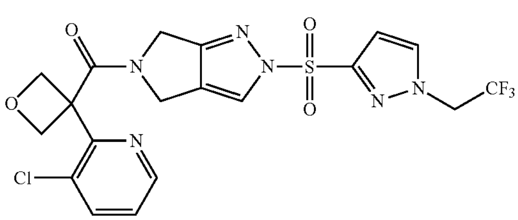 [SMILES: O=C(N1Cc2cn(S(=O)(=O)c3ccn(CC(F)(F)F)n3)nc2C1)C1(c2ncccc2Cl)COC1] | (3-(3-chloropyridin-2-yl)oxetan-3-yl)(2-((1-(2,2,2-trifluoroethyl)-1H-pyrazol-3-yl)sulfonyl)-2,6-dihydropyrrolo[3,4-c]pyrazol-5(4H)-yl)methanone | 517 |

TABLE 1-continued

| Compd No. | Structure | IUPAC Name | Mass Found (M + 1) |
|---|---|---|---|
| 66 | 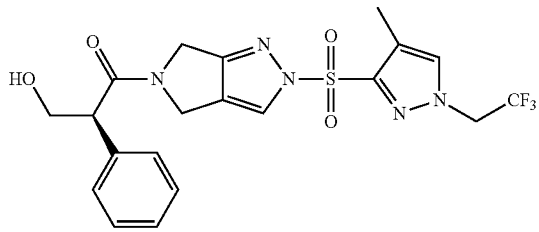 [SMILES: Cc1cn(CC(F)(F)F)nc1S(=O)(=O)n1cc2c(n1)CN(C(=O)[C@H](CO)c1ccccc1)C2] | (2S)-3-hydroxy-1-{2-[4-methyl-1-(2,2,2-trifluoroethyl)pyrazol-3-ylsulfonyl]-4H,6H-pyrrolo[3,4-c]pyrazol-5-yl}-2-phenylpropan-1-one | 483 |
| 67 | 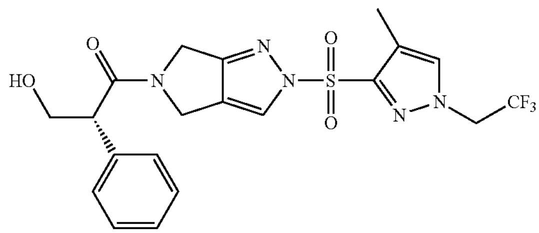 [SMILES: Cc1cn(CC(F)(F)F)nc1S(=O)(=O)n1cc2c(n1)CN(C(=O)[C@@H](CO)c1ccccc1)C2] | (2R)-3-hydroxy-1-{2-[4-methyl-1-(2,2,2-trifluoroethyl)pyrazol-3-ylsulfonyl]-4H,6H-pyrrolo[3,4-c]pyrazol-5-yl}-2-phenylpropan-1-one | 483 |
| 68 | 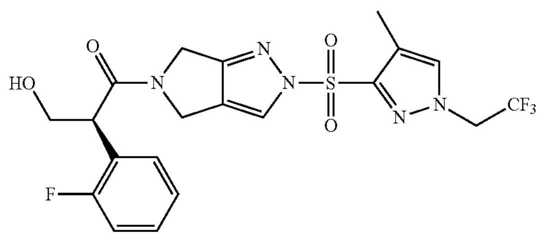 [SMILES: Cc1cn(CC(F)(F)F)nc1S(=O)(=O)n1cc2c(n1)CN(C(=O)[C@H](CO)c1ccccc1F)C2] | (2S)-2-(2-fluorophenyl)-3-hydroxy-1-{2-[4-methyl-1-(2,2,2-trifluoroethyl)pyrazol-3-ylsulfonyl]-4H,6H-pyrrolo[3,4-c]pyrazol-5-yl}propan-1-one | 502 |
| 69 | 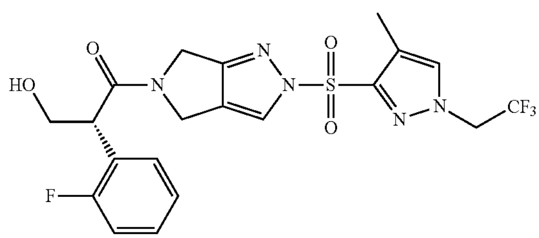 [SMILES: Cc1cn(CC(F)(F)F)nc1S(=O)(=O)n1cc2c(n1)CN(C(=O)[C@@H](CO)c1ccccc1F)C2] | (2R)-2-(2-fluorophenyl)-3-hydroxy-1-{2-[4-methyl-1-(2,2,2-trifluoroethyl)pyrazol-3-ylsulfonyl]-4H,6H-pyrrolo[3,4-c]pyrazol-5-yl}propan-1-one | 502 |
| 70 | 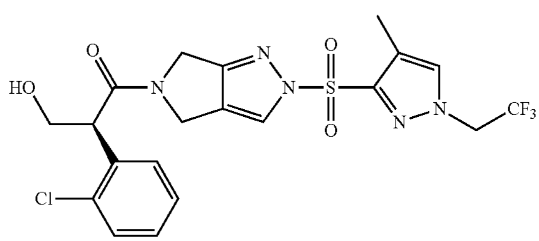 [SMILES: Cc1cn(CC(F)(F)F)nc1S(=O)(=O)n1cc2c(n1)CN(C(=O)[C@H](CO)c1ccccc1Cl)C2] | (2S)-2-(2-chlorophenyl)-3-hydroxy-1-{2-[4-methyl-1-(2,2,2-trifluoroethyl)pyrazol-3-ylsulfonyl]-4H,6H-pyrrolo[3,4-c]pyrazol-5-yl}propan-1-one | 518 |
| 71 | 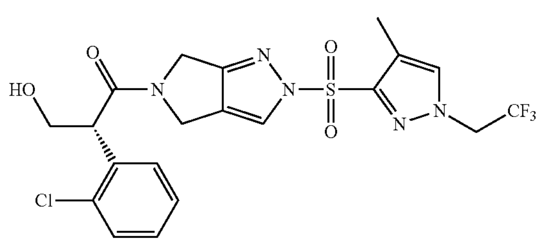 [SMILES: Cc1cn(CC(F)(F)F)nc1S(=O)(=O)n1cc2c(n1)CN(C(=O)[C@@H](CO)c1ccccc1Cl)C2] | (2R)-2-(2-chlorophenyl)-3-hydroxy-1-{2-[4-methyl-1-(2,2,2-trifluoroethyl)pyrazol-3-ylsulfonyl]-4H,6H-pyrrolo[3,4-c]pyrazol-5-yl}propan-1-one | 518 |

TABLE 1-continued

| Compd No. | Structure | IUPAC Name | Mass Found (M + 1) |
|---|---|---|---|
| 72 | 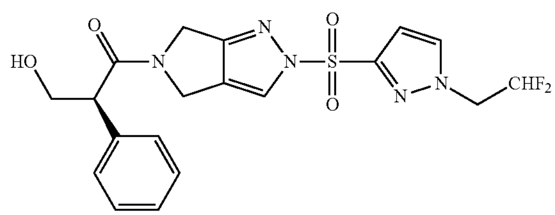 [SMILES: O=C([C@H](CO)c1ccccc1)N1Cc2cn(S(=O)(=O)c3ccn(CC(F)F)n3)nc2C1] | (2S)-1-{2-[1-(2,2-difluoroethyl)pyrazol-3-ylsulfonyl]-4H,6H-pyrrolo[3,4-c]pyrazol-5-yl}-3-hydroxy-2-phenylpropan-1-one | 452 |
| 73 | 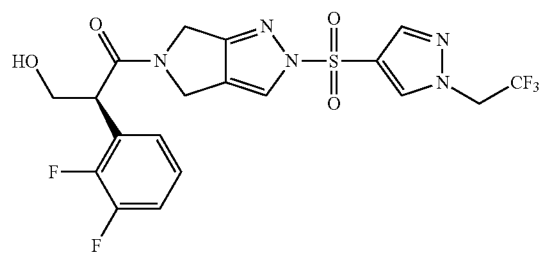 [SMILES: O=C([C@H](CO)c1cccc(F)c1F)N1Cc2cn(S(=O)(=O)c3cnn(CC(F)(F)F)c3)nc2C1] | (2S)-2-(2,3-difluorophenyl)-3-hydroxy-1-{2-[1-(2,2,2-trifluoroethyl)pyrazol-4-ylsulfonyl]-4H,6H-pyrrolo[3,4-c]pryazol-5-yl}propan-1-one | 506 |
| 74 | 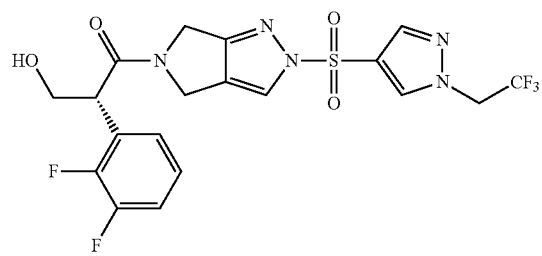 [SMILES: O=C([C@@H](CO)c1cccc(F)c1F)N1Cc2cn(S(=O)(=O)c3cnn(CC(F)(F)F)c3)nc2C1] | (2R)-2-(2,3-difluorophenyl)-3-hydroxy-1-{2-[1-(2,2,2-trifluoroethyl)pyrazol-4-ylsulfonyl]-4H,6H-pyrrolo[3,4-c]pryazol-5-yl}propan-1-one | 506 |
| 75 | 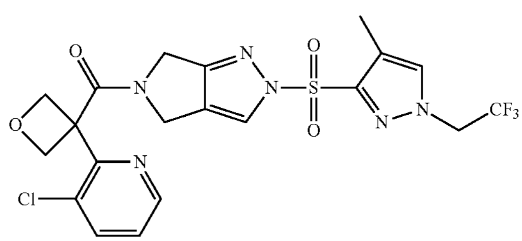 [SMILES: Cc1cn(CC(F)(F)F)nc1S(=O)(=O)n1cc2c(n1)CN(C(=O)C1(c3ncccc3Cl)COC1)C2] | (3-(3-chloropyridin-2-yl)oxetan-3-yl)(2-((4-methyl-1-(2,2,2-trifluoroethyl)-1H-pyrazol-3-yl)sulfonyl)-2,6-dihydropyrrolo[3,4-c]pyrazol-5(4H)-yl)methanone | 531 |
| 76 | 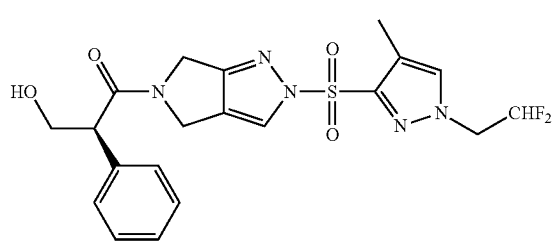 [SMILES: Cc1cn(CC(F)F)nc1S(=O)(=O)n1cc2c(n1)CN(C(=O)[C@H](CO)c1ccccc1)C2] | (2S)-1-{2-[1-(2,2-difluoroethyl)-4-methylpyrazol-3-ylsulfonyl]-4H,6H-pyrrolo[3,4-c]pyrazol-5-yl}-3-hydroxy-2-phenylpropan-1-one | 466 |
| 77 | 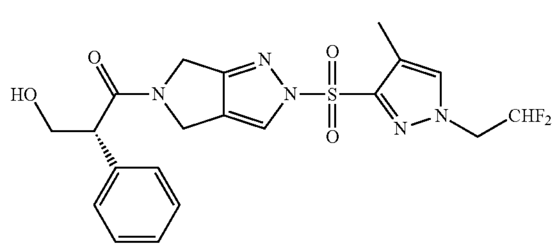 [SMILES: Cc1cn(CC(F)F)nc1S(=O)(=O)n1cc2c(n1)CN(C(=O)[C@@H](CO)c1ccccc1)C2] | (2R)-1-{2-[1-(2,2-difluoroethyl)-4-methylpyrazol-3-ylsulfonyl]-4H,6H-pyrrolo[3,4-c]pyrazol-5-yl}-3-hydroxy-2-phenylpropan-1-one | 466 |

TABLE 1-continued

| Compd No. | Structure | IUPAC Name | Mass Found (M + 1) |
|---|---|---|---|
| 78 | 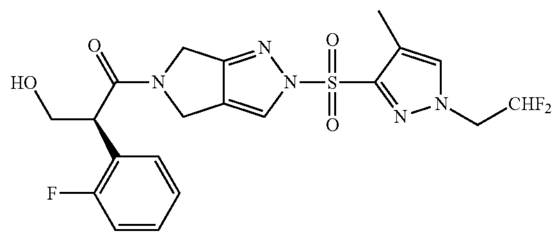 [SMILES: Cc1cn(CC(F)F)nc1S(=O)(=O)n1cc2c(n1)CN(C(=O)[C@H](CO)c1ccccc1F)C2] | (2S)-1-{2-[1-(2,2-difluoroethyl)-4-methylpyrazol-3-ylsulfonyl]-4H,6H-pyrrolo[3,4-c]pyrazol-5-yl}-2-(2-fluorophenyl)-3-hydroxypropan-1-one | 484 |
| 79 | 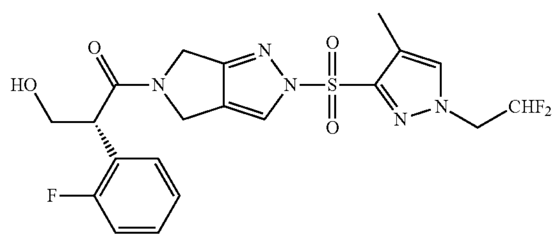 [SMILES: Cc1cn(CC(F)F)nc1S(=O)(=O)n1cc2c(n1)CN(C(=O)[C@@H](CO)c1ccccc1F)C2] | (2R)-1-{2-[1-(2,2-difluoroethyl)-4-methylpyrazol-3-ylsulfonyl]-4H,6H-pyrrolo[3,4-c]pyrazol-5-yl}-2-(2-fluorophenyl)-3-hydroxypropan-1-one | 484 |
| 80 | 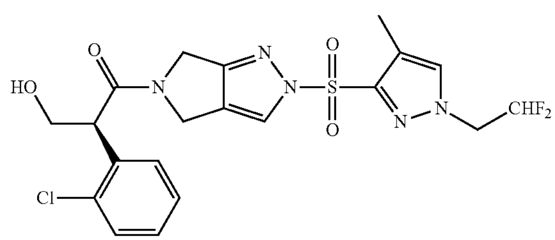 [SMILES: Cc1cn(CC(F)F)nc1S(=O)(=O)n1cc2c(n1)CN(C(=O)[C@H](CO)c1ccccc1Cl)C2] | (2S)-2-(2-chlorophenyl)-1-(2-{[1-(2,2-difluoroethyl)-4-methyl-1H-pyrazol-3-yl]sulfonyl}-2H,4H,5H,6H-pyrrolo[3,4-c]pyrazol-5-yl)-3-hydroxypropan-1-one | 500 |
| 81 | 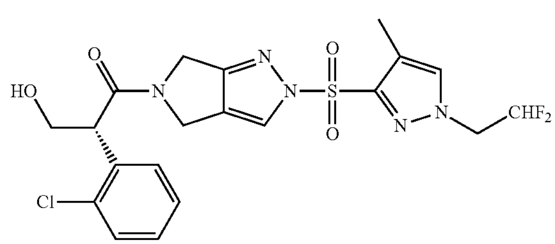 [SMILES: Cc1cn(CC(F)F)nc1S(=O)(=O)n1cc2c(n1)CN(C(=O)[C@@H](CO)c1ccccc1Cl)C2] | (2R)-2-(2-chlorophenyl)-1-{2-[1-(2,2-difluoroethyl)-4-methylpyrazol-3-ylsulfonyl]-4H,6H-pyrrolo[3,4-c]pyrazol-5-yl}-3-hydroxypropan-1-one | 500 |
| 82 | 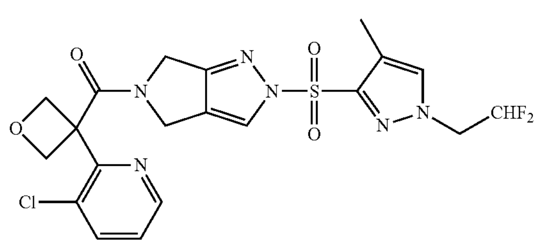 [SMILES: Cc1cn(CC(F)F)nc1S(=O)(=O)n1cc2c(n1)CN(C(=O)C1(c3ncccc3Cl)COC1)C2] | 3-chloro-2-(3-{2-[1-(2,2-difluoroethyl)-4-methylpyrazol-3-ylsulfonyl]-4H,6H-pyrrolo[3,4-c]pyrazole-5-carbonyl}oxetan-3-yl)pyridine | 513 |
| 83 | 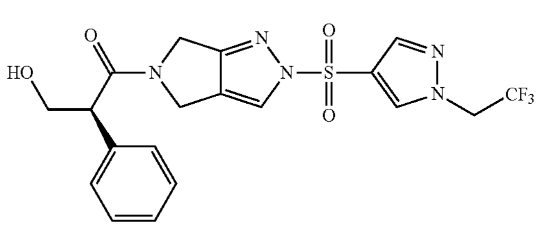 [SMILES: O=C([C@H](CO)c1ccccc1)N1Cc2cn(S(=O)(=O)c3cnn(CC(F)(F)F)c3)nc2C1] | (2S)-3-hydroxy-2-phenyl-1-{2-[1-(2,2,2-trifluoroethyl)pyrazol-4-ylsulfonyl]-4H,6H-pyrrolo[3,4-c]pyrazol-5-yl}propan-1-one | 470 |

TABLE 1-continued

| Compd No. | Structure | IUPAC Name | Mass Found (M + 1) |
|---|---|---|---|
| 84 | 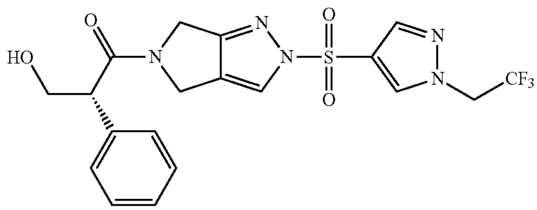 [SMILES: O=C([C@@H](CO)c1ccccc1)N1Cc2cn(S(=O)(=O)c3cnn(CC(F)(F)F)c3)nc2C1] | (2R)-3-hydroxy-2-phenyl-1-{2-[1-(2,2,2-trifluoroethyl)pyrazol-4-ylsulfonyl]-4H,6H-pyrrolo[3,4-c]pyrazol-5-yl}propan-1-one | 470 |
| 85* | 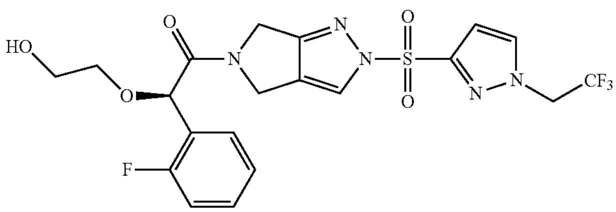 [SMILES: O=C([C@H](OCCO)c1ccccc1F)N1Cc2cn(S(=O)(=O)c3ccn(CC(F)(F)F)n3)nc2C1] | (2R)-2-(2-fluorophenyl)-2-(2-hydroxyethoxy)-1-[2-[1-(2,2,2-trifluoromethyl)pyrazol-3-ylsulfonyl]-4H,6H-pyrrolo[3,4-c]pyrazol-5-yl]ethanone  OR  (2S)-2-(2-fluorophenyl)-2-(2-hydroxyethoxy)-1-[2-[1-(2,2,2-trifluoroethyl)pyrazol-3-ylsulfonyl]-4H,6H-pyrrolo[3,4-c]pyrazol-5-yl]ethanone | 518 |
| 86* | 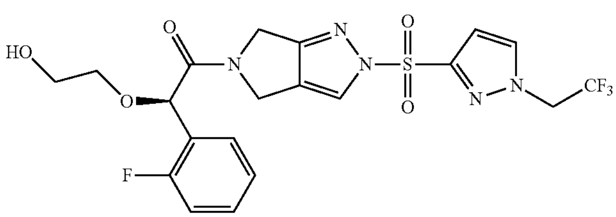 [SMILES: O=C([C@H](OCCO)c1ccccc1F)N1Cc2cn(S(=O)(=O)c3ccn(CC(F)(F)F)n3)nc2C1] | (2R)-2-(2-fluorophenyl)-2-(2-hydroxyethoxy-1-[2-[1-(2,2,2-trifluoroethyl)pyrazol-3-ylsulfonyl]-4H,6H-pyrrolo[3,4-c]pyrazol-5-yl]ethanone  OR  (2S)-2-(2-fluorophenyl)-2-(2-hydroxyethoxy)-1-[2-[1-(2,2,2-trifluoroethyl)pyrazol-3-ylsulfonyl]-4H,6H-pyrrolo[3,4-c]pyrazol-5-yl]ethanone | 518 |
| 87 | 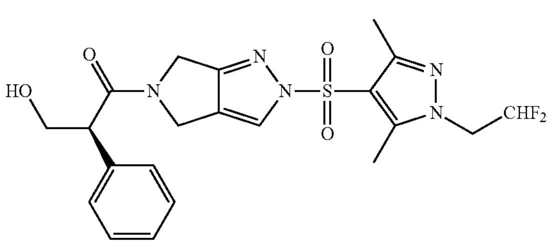 [SMILES: Cc1nn(CC(F)F)c(C)c1S(=O)(=O)n1cc2c(n1)CN(C(=O)[C@H](CO)c1ccccc1)C2] | (2S)-1-[2-[1-(2,2-difluoroethyl)-3,5-dimethylpyrazol-4-ylsulfonyl]-4H,6H-pyrrolo[3,4-c]pyrazol-5-yl]-3-hydroxy-2-phenylpropan-1-one | 480 |

TABLE 1-continued

| Compd No. | Structure | IUPAC Name | Mass Found (M + 1) |
|---|---|---|---|
| 88 | 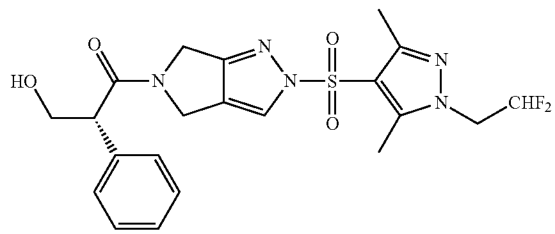 [SMILES: Cc1nn(CC(F)F)c(C)c1S(=O)(=O)n1cc2c(n1)CN(C(=O)[C@@H](CO)c1ccccc1)C2] | (2R)-1-[2-[1-(2,2-difluoroethyl)-3,5-dimethylpyrazol-4-ylsulfonyl]-4H,6H-pyrrolo[3,4-c]pyrazol-5-yl]-3-hydroxy-2-phenylpropan-1-one | 480 |
| 89 | 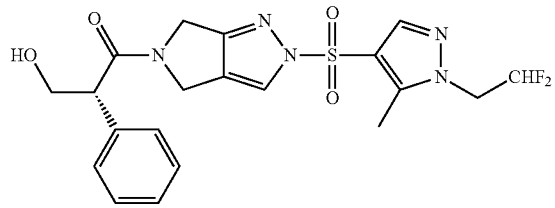 [SMILES: Cc1c(S(=O)(=O)n2cc3c(n2)CN(C(=O)[C@@H](CO)c2ccccc2)C3)cnn1CC(F)F] | (R)-1-(2-((1-(2,2-difluoroethyl)-5-methyl-1H-pyrazol-4-yl)sulfonyl)-2,6-dihydropyrrolo[3,4-c]pyrazol-5(4H)-yl)-3-hydroxy-2-phenylpropan-1-one | 466 |
| 90 | 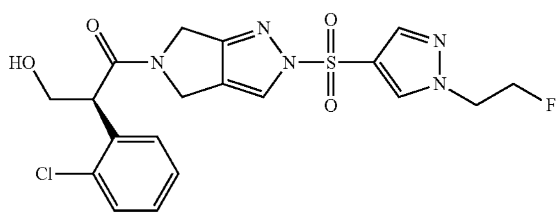 [SMILES: O=C([C@H](CO)c1ccccc1Cl)N1Cc2cn(S(=O)(=O)c3cnn(CCF)c3)nc2C1] | (2S)-2-(2-chlorophenyl)-1-{2-[1-(2-fluoroethyl)pyrazol-4-ylsulfonyl]-4H,6H-pyrrolo[3,4-c]pyrazol-5-yl}-3-hydroxypropan-1-one | 468 |
| 91 | 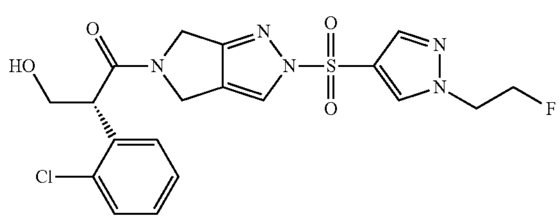 [SMILES: O=C([C@@H](CO)c1ccccc1Cl)N1Cc2cn(S(=O)(=O)c3cnn(CCF)c3)nc2C1] | (2R)-2-(2-chlorophenyl)-1-{2-[1-(2-fluoroethyl)pyrazol-4-ylsulfonyl]-4H,6H-pyrrolo[3,4-c]pyrazol-5-yl}-3-hydroxypropan-1-one | 468.1 |
| 92* | 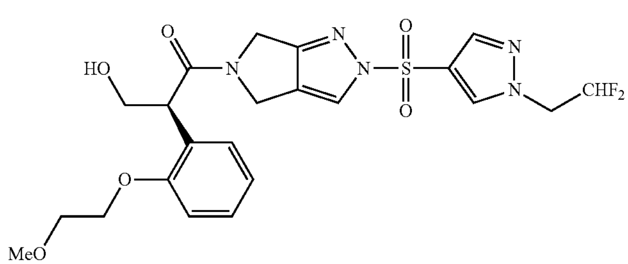 [SMILES: COCCOc1ccccc1[C@@H](CO)C(=O)N1Cc2cn(S(=O)(=O)c3cnn(CC(F)F)c3)nc2C1] | (S)-1-(2-((1-(2,2-difluoroethyl)-1H-pyrazol-4-yl)sulfonyl)-2,6-dihydropyrrolo[3,4-c]pyrazol-5(4H)-yl)-3-hydroxy-2-(2-(2-methoxyethoxy)phenyl)propan-1-one | 526 |
| | OR | OR | |
| | | (R)-1-(2-((1-(2,2-difluoroethyl)-1H-pyrazol-4-yl)sulfonyl)-2,6-dihydropyrrolo[3,4-c]pyrazol-5(4H)-yl)-3-hydroxy-2-(2-(2-methoxyethoxy)phenyl)propan-1-one | |

TABLE 1-continued

| Compd No. | Structure | IUPAC Name | Mass Found (M + 1) |
|---|---|---|---|
| 93* | 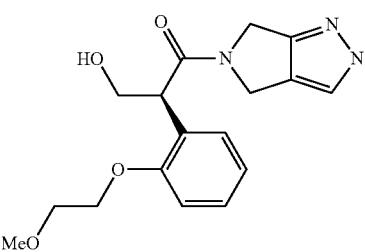 OR 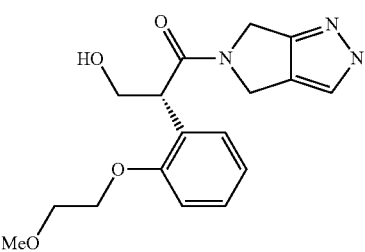 | (S)-1-(2-((1-(2,2-difluoroethyl)-1H-pyrazol-4-yl)sulfonyl)-2,6-dihydropyrrolo[3,4-c]pyrazol-5(4H)-yl)-3-hydroxy-2-(2-(2-methoxyethoxy)phenyl)propan-1-one OR (R)-1-(2-((1-(2,2-difluoroethyl)-1H-pyrazol-4-yl)sulfonyl)-2,6-dihydropyrrolo[3,4-c]pyrazol-5(4H)-yl)-3-hydroxy-2-(2-(2-methoxyethoxy)phenyl)propan-1-one | 526 |
| 94 | 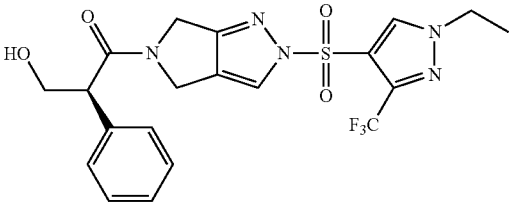 | (2S)-1-{2-[1-ethyl-3-(trifluoromethyl)pyrazol-4-ylsulfonyl]-4H,6H-pyrrolo[3,4-c]pyrazol-5-yl}-3-hydroxy-2-phenylpropan-1-one | 484 |
| 95 | 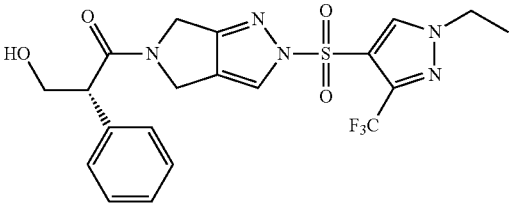 | (2R)-1-{2-{[1-ethyl-3-(trifluoromethyl)pyrazol-4-ylsulfonyl]-4H,6H-pyrrolo[3,4-c]pyrazol-5-yl}-3-hydroxy-2-phenylpropan-1-one | 484 |
| 96 | 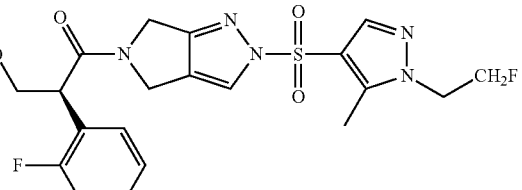 | (2S)-1-(2-{1-[2,2-difluoroethyl]-5-methyl-1H-pyrazol-4-yl]sulfonyl}-2H,4H,5H,6H-pyrrolo[3,4-c]pyrazol-5-yl)-3-hydroxy-2-phenylpropan-1-one | 466 |
| 97 | 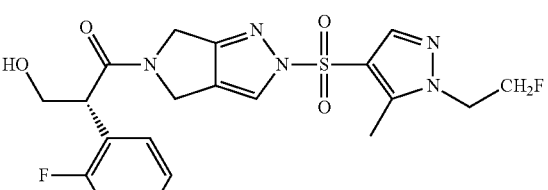 | (2R)-1-{2-[1-(2-fluoroethyl)-5-methylpyrazol-4-ylsulfonyl]-4H,6H-pyrrolo[3,4-c]pyrazol-5-yl}-2-(2-fluorophenyl)-3-hydroxypropan-1-one | 466 |

TABLE 1-continued

| Compd No. | Structure | IUPAC Name | Mass Found (M + 1) |
|---|---|---|---|
| 98 | 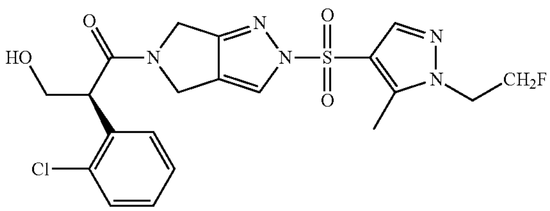 | (2S)-2-(2-chlorophenyl)-1-{2-[1-(2-fluoroethyl)-5-methylpyrazol-4-ylsulfonyl]-4H,6H-pyrrolo[3,4-c]pyrazol-5-yl}-3-hydroxypropan-1-one | 482 |
| 99 | 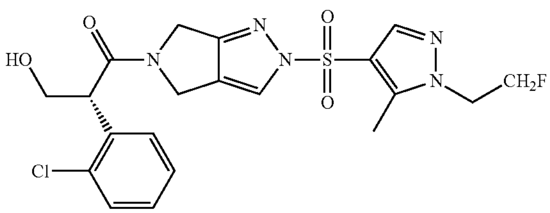 | (2R)-2-(2-chlorophenyl)-1-{2-[1-(2-fluoroethyl)-5-methylpyrazol-4-ylsulfonyl]-4H,6H-pyrrolo[3,4-c]pyrazol-5-yl}-3-hydroxypropan-1-one | 482 |
| 100 | 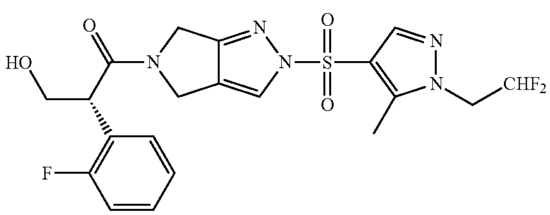 [SMILES: Cc1c(S(=O)(=O)n2cc3c(n2)CN(C(=O)[C@@H](CO)c2ccccc2F)C3)cnn1CC(F)F] | (R)-1-(2-((1-(2,2-difluoroethyl)-5-methyl-1H-pyrazol-4-yl)sulfonyl)-2,6 dihydropyrrolo[3,4-c]pyrazol-5(4H)-yl)-2-(2-fluorophenyl)-3-hydroxypropan-1-one | 484 |
| 101 | 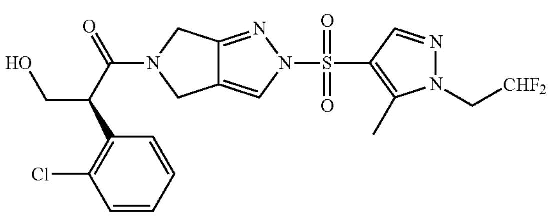 [SMILES: Cc1c(S(=O)(=O)n2cc3c(n2)CN(C(=O)[C@H](CO)c2ccccc2Cl)C3)cnn1CC(F)F] | (2S)-2-(2-chlorophenyl)-1-{2-[1-(2,2-difluoroethyl)-5-methylpyrazol-4-ylsulfonyl]-4H,6H-pyrrolo[3,4-c]pyrazol-5-yl}-3-hydroxypropan-1-one | 500 |
| 102 | 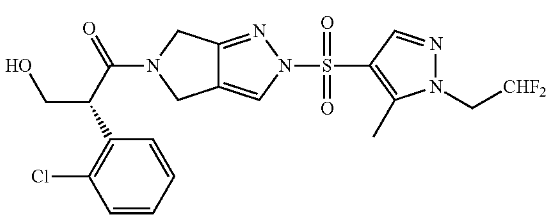 [SMILES: Cc1c(S(=O)(=O)n2cc3c(n2)CN(C(=O)[C@@H](CO)c2ccccc2Cl)C3)cnn1CC(F)F] | (2R)-2-(2-chlorophenyl)-1-{2-[1-(2,2-difluoroethyl)-5-methylpyrazol-4-ylsulfonyl]-4H,6H-pyrrolo[3,4-c]pyrazol-5-yl}-3-hydroxypropan-1-one | 500 |
| 103 | 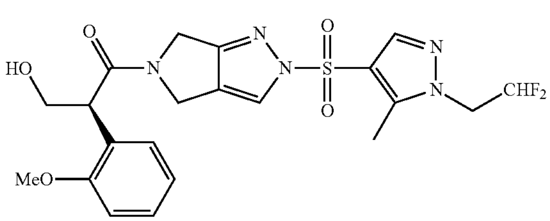 [SMILES: COc1ccccc1[C@@H](CO)C(=O)N1Cc2cn(S(=O)(=O)c3cnn(CC(F)F)c3C)nc2C1] | (2S)-1-{2-[1-(2,2-difluoroethyl)-5-methylpyrazol-4-ylsulfonyl]-4H,6H-pyrrolo[3,4-c]pyrazol-5-yl}-3-hydroxy-2-(2-methoxyphenyl)propan-1-one | 496 |
| 104 | 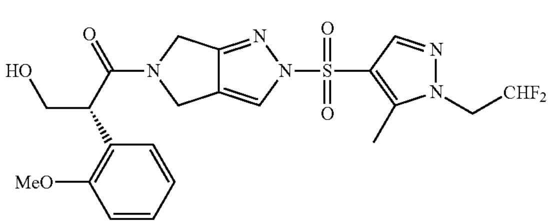 [SMILES: COc1ccccc1[C@H](CO)C(=O)N1Cc2cn(S(=O)(=O)c3cnn(CC(F)F)c3C)nc2C1] | (2R)-1-{2-[1-(2,2-difluoroethyl)-5-methylpyrazol-4-ylsulfonyl]-4H,6H-pyrrolo[3,4-c]pyrazol-5-yl}-3-hydroxy-2-(2-methoxyphenyl)propan-1-one | 496 |

TABLE 1-continued

| Compd No. | Structure | IUPAC Name | Mass Found (M + 1) |
|---|---|---|---|
| 105 | 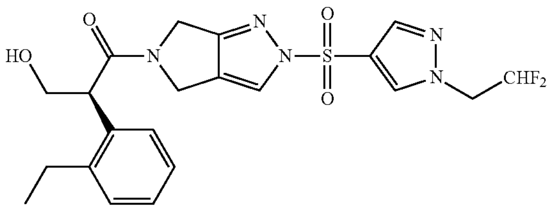 | (S)-1-(2-((1-(2,2-difluoroethyl)-1H-pyrazol-4-yl)sulfonyl)-2,6-dihydropyrrolo[3,4-c]pyrazol-5(4H)-yl)-2-(2-ethylphenyl)-3-hydroxypropan-1-one | 480 |
| 106 | 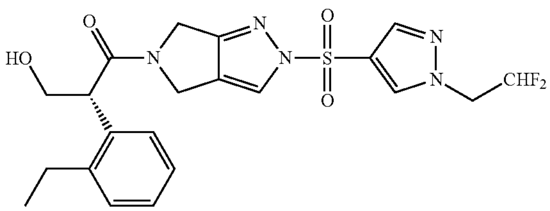 | (R)-1-(2-((1-(2,2-difluoroethyl)-1H-pyrazol-4-yl)sulfonyl)-2,6-dihydropyrrolo[3,4-c]pyrazol-5(4H)-yl)-2-(2-ethylphenyl)-3-hydroxypropan-1-one | 480 |
| 107 | 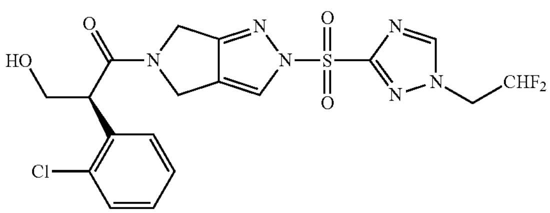 [SMILES: O=C([C@H](CO)c1ccccc1Cl)N1Cc2cn(S(=O)(=O)c3ncn(CC(F)F)n3)nc2C1] | (2S)-2-(2-chlorophenyl)-1-{2-[1-(2,2-difluoroethyl)-1,2,4-triazol-3-ylsulfonyl]-4H,6H-pyrrolo[3,4-c]pyrazol-5-yl}-3-hydroxypropan-1-one | 487 |
| 108 | 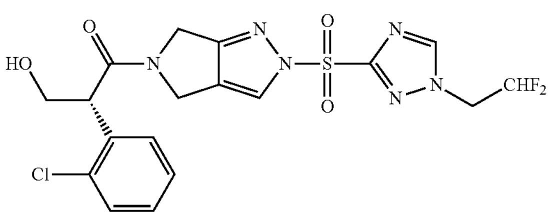 [SMILES: O=C([C@@H](CO)c1ccccc1Cl)N1Cc2cn(S(=O)(=O)c3ncn(CC(F)F)n3)nc2C1] | (2R)-2-(2-chlorophenyl)-1-{2-[1-(2,2-difluoroethyl)-1,2,4-triazol-3-ylsulfonyl]-4H,6H-pyrrolo[3,4-c]pyrazol-5-yl}-3-hydroxypropan-1-one | 487 |
| 109* | OR | (S)-1-(2-((1-(2,2-difluoroethyl)-1H-pyrazol-4-yl)sulfonyl)-2,6-dihydropyrrolo[3,4-c]pyrazol-5(4H)-yl)-3-hydroxy-2-(2-(2-hydroxyethoxy)phenyl)propan-1-one OR (R)-1-(2-((1-(2,2-difluoroethyl)-1H-pyrazol-4-yl)sulfonyl)-2,6-dihydropyrrolo[3,4-c]pyrazol-5(4H)-yl)-3-hydroxy-2-(2-(2-hydroxyethoxy)phenyl)propan-1-one | 512 |

TABLE 1-continued

| Compd No. | Structure | IUPAC Name | Mass Found (M + 1) |
|---|---|---|---|
| 110* | 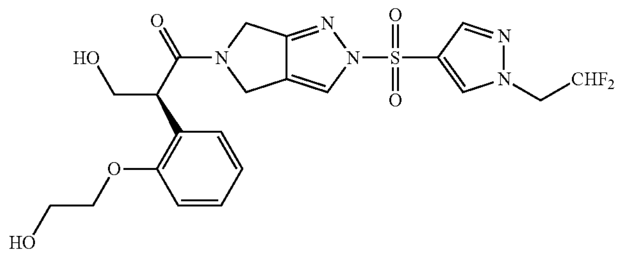 [SMILES: O=C([C@H](CO)c1ccccc1OCCO)N1Cc2cn(S(=O)(=O)c3cnn(CC(F)F)c3)nc2C1] | (S)-1-(2-((1-(2,2-difluoroethyl)-1H-pyrazol-4-yl)sulfonyl)-2,6-dihydropyrrolo[3,4-c]pyrazol-5(4H)-yl)-3-hydroxy-2-(2-(2-hydroxyethoxy)phenyl)propan-1-one | 512 |
| | OR | OR | |
| | | (R)-1-(2-((1-(2,2-difluoroethyl)-1H-pyrazol-4-yl)sulfonyl)-2,6-dihydropyrrolo[3,4-c]pyrazol-5(4H)-yl)-3-hydroxy-2-(2-(2-hydroxyethoxy)phenyl)propan-1-one | |
| 111 | 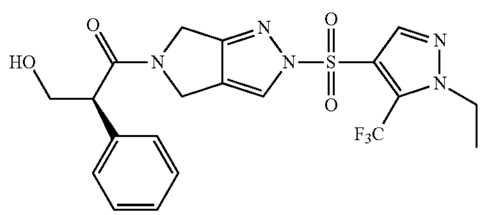 [SMILES: CCn1ncc(S(=O)(=O)n2cc3c(n2)CN(C(=O)[C@H](CO)c2ccccc2)C3)c1C(F)(F)F] | (2S)-1-{2-[1-ethyl-5-(trifluoromethyl)pyrazol-4-ylsulfonyl]-4H,6H-pyrrolo[3,4-c]pyrazol-5-yl}-3-hydroxy-2-phenylpropan-1-one | 484 |
| 112 | 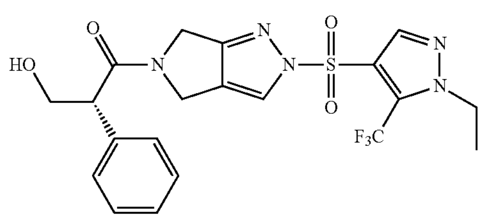 [SMILES: CCn1ncc(S(=O)(=O)n2cc3c(n2)CN(C(=O)[C@@H](CO)c2ccccc2)C3)c1C(F)(F)F] | (2R)-1-{2-[1-ethyl-5-(trifluoromethyl)pyrazol-4-ylsulfonyl]-4H,6H-pyrrolo[3,4-c]pyrazol-5-yl}-3-hydroxy-2-phenylpropan-1-one | 484 |
| 113 | 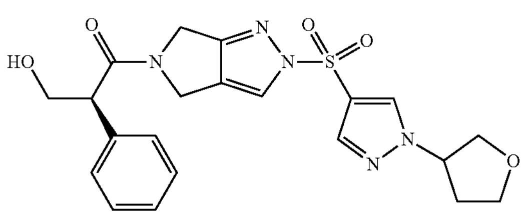 [SMILES: O=C([C@H](CO)c1ccccc1)N1Cc2cn(S(=O)(=O)c3cnn(C4CCOC4)c3)nc2C1] | (2S)-3-hydroxy-1-(2-{[1-(oxolan-3-yl)-1H-pyrazol-4-yl]sulfonyl}-2H,4H,5H,6H-pyrrolo[3,4-c]pyrazol-5-yl)-2-phenylpropan-1-one | 458.45 |
| 114 | 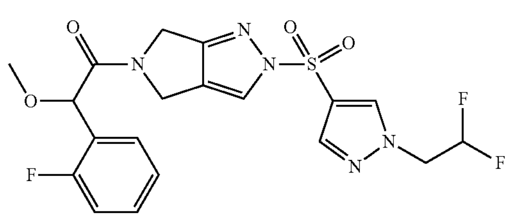 [SMILES: COC(C(=O)N1Cc2cn(S(=O)(=O)c3cnn(CC(F)F)c3)nc2C1)c1ccccc1F] | (2S)-1-{2-[1-(2,2-difluoroethyl)pyrazol-4-ylsulfonyl]-4H,6H-pyrrolo[3,4-c]pyrazol-5-yl}-2-(2,3-difluorophenyl)-3-hydroxypropan-1-one | 470.2 |

TABLE 1-continued

| Compd No. | Structure | IUPAC Name | Mass Found (M + 1) |
|---|---|---|---|
| 115 | 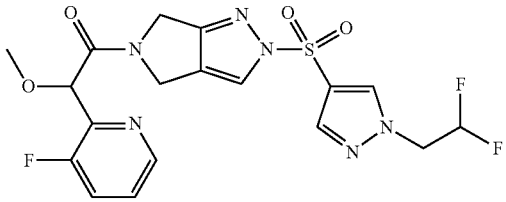 [SMILES: COC(C(=O)N1Cc2cn(S(=O)(=O)c3cnn(CC(F)F)c3)nc2C1)c1ncccc1F] | 1-(2-{[1-(2,2-difluoroethyl)-1H-pyrazol-4-yl]sulfonyl}-2H,4H,56H,6H-pyrrolo[3,4-c]pyrazol-5-yl)-2-(3-fluoropyridin-2-yl)-2-methoxyethan-1-one | 471 |
| 116 | 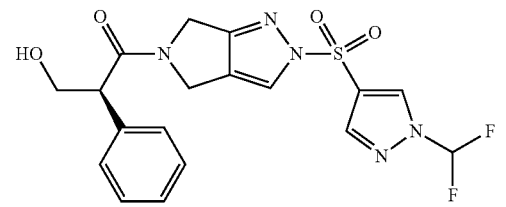 [SMILES: O=C([C@H](CO)c1ccccc1)N1Cc2cn(S(=O)(=O)c3cnn(C(F)F)c3)nc2C1] | (2S)-1-(2-{[1-(difluoromethyl)-1H-pyrazol-4-yl]sulfonyl}-2H,4H,5H,6H-pyrrolo[3,4-c]pyrazol-5-yl)-3-hydroxy-2-phenylpropan-1-one | 438.04 |
| 117 | 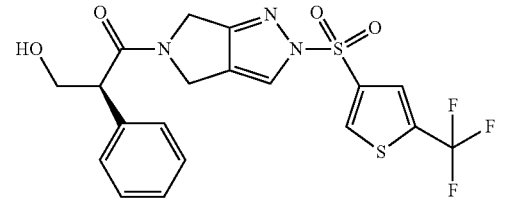 [SMILES: O=C([C@H](CO)c1ccccc1)N1Cc2cn(S(=O)(=O)c3csc(C(F)(F)F)c3)nc2C1] | (2S)-3-hydroxy-2-phenyl-1-(2-{[5-(trifluoromethyl)thiophen-3-yl]sulfonyl}-2H,4H,5H,6H-pyrrolo[3,4-c]pyrazol-5-yl)propan-1-one | 471.95 |
| 118 | 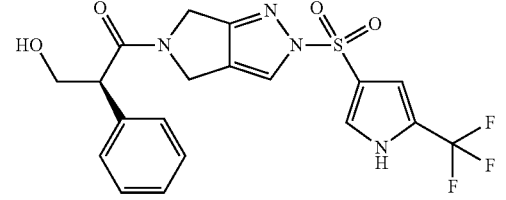 | (2S)-3-hydroxy-2-phenyl-1-(2-{[5-(trifluoromethyl)-1H-pyrrol-3-yl]sulfonyl}-2H,4H,5H,6H-pyrrolo[3,4-c]pyrazol-5-yl)propan-1-one | 455.12 |
| 119 | 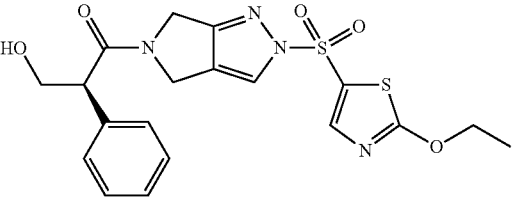 [SMILES: CCOc1ncc(S(=O)(=O)n2cc3c(n2)CN(C(=O)[C@H](CO)c2ccccc2)C3)s1] | (2S)-1-{2-[(2-ethoxy-1,3-thiazol-5-yl)sulfonyl]-2H,4H,5H,6H-pyrrolo[3,4-c]pyrazol-5-yl}-3-hydroxy-2-phenylpropan-1-one | 449.12 |
| 120 | 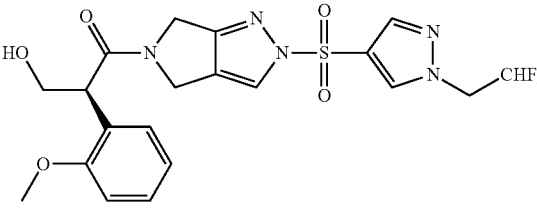 | (2S)-1-{2-[1-(2,2-difluoroethyl)pyrazol-4-ylsulfonyl]-4H,6H-pyrrolo[3,4-c]pyrazol-5-yl}-3-hydroxy-2-(2-methoxyphenyl)propan-1-one | 482 |
| 121 | 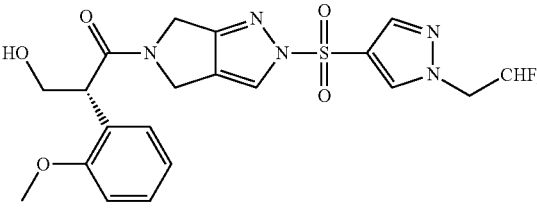 | (2R)-1-{2-[1-(2,2-difluoroethyl)pyrazol-4-ylsulfonyl]-4H,6H-pyrrolo[3,4-c]pyrazol-5-yl}-3-hydroxy-2-(2-methoxyphenyl)propan-1-one | 482 |

TABLE 1-continued

| Compd No. | Structure | IUPAC Name | Mass Found (M + 1) |
|---|---|---|---|
| 122 | 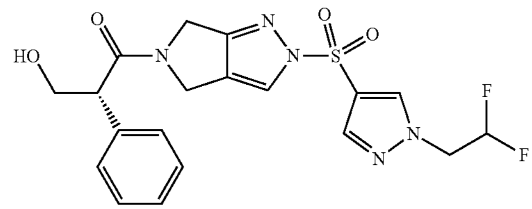 [SMILES: O=C([C@@H](CO)c1ccccc1)N1Cc2cn(S(=O)(=O)c3cnn(CC(F)F)c3)nc2C1] | (2R)-1-(2-{[1-(2,2-difluoroethyl)-1H-pyrazol-4-yl]sulfonyl}-2H,4H,5H,6H-pyrrolo[3,4-c]pyrazol-5-yl)-3-hydroxy-2-phenylpropan-1-one | 452.12 |
| 123* | 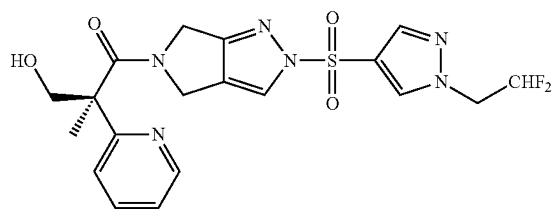 [SMILES: C[C@](CO)(C(=O)N1Cc2cn(S(=O)(=O)c3cnn(CC(F)F)c3)nc2C1)c1ccccn1] | (2S)-1-(2-{[1-(2,2-difluoroethyl)-1H-pyrazol-4-yl]sulfonyl}-2H,4H,5H,6H-pyrrolo[3,4-c]pyrazol-5-yl)-3-hydroxy-2-methyl-2-(pyridin-2-yl)propan-1-one | 467 |
| | OR | OR | |
| | | (2R)-1-(2-{[1-(2,2-difluoroethyl)-1H-pyrazol-4-yl]sulfonyl}-2H,4H,5H,6H-pyrrolo[3,4-c]pyrazol-5-yl)-3-hydroxy-2-methyl-2-(pyridin-2-yl)propan-1-one | |

*Absolute stereochemistry not determined

III. Pharmaceutical Compositions and Modes of Administration

Compounds provided herein are usually administered in the form of pharmaceutical compositions. Thus, provided herein are also pharmaceutical compositions that comprise one or more of the compounds described herein or a pharmaceutically acceptable salt, a stereoisomer, or a mixture of stereoisomers thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, a stereoisomer, or a mixture of stereoisomers thereof, the active ingredient is usually diluted by an excipient and/or enclosed within such a carrier that can be in the form of a capsule, sachet, paper or other container. When the excipient serves as a diluent, it can be in the form of a solid, semisolid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, a stereoisomer, or a mixture of stereoisomers thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, a stereoisomer, or a mixture of stereoisomers thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

IV. Methods of Treatment

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

In certain embodiments, the subject matter disclosed herein is directed to a method of activating PKR and/or PKRM2, including methods of treating a disease or disorder in a subject by administering a therapeutically effective amount of a compound of Formula I, a pharmaceutically acceptable salt thereof, or a pharmaceutical composition comprising a compound of Formula I. In certain embodiments, the disease or disorder is selected from the group consisting of PKD (pyruvate kinase deficiency), SCD (e.g., sickle cell anemia), and thalassemia (e.g., beta-thalassemia).

In certain embodiments, the subject matter disclosed herein is directed to a method of treating a subject afflicted with a disease associated with decreased activity of PKR and/or PKM2, comprising administering to the subject an effective amount of a compound of Formula I, a pharmaceutically acceptable salt thereof, or a pharmaceutical composition comprising a compound of Formula I. In certain embodiments, the disease associated with decreased activity of PKR is selected from the group consisting of hereditary non-spherocytic hemolytic anemia, hemolytic anemia (e.g., chronic hemolytic anemia caused by phosphoglycerate kinase deficiency), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), and anemia of chronic diseases.

In certain embodiments, the subject matter described herein is directed to a method of treating a disease or disorder associated with modulation of PKR and/or PKM2 in a subject, comprising administering to the subject an effective amount of a compound of Formula I, a pharmaceutically acceptable salt thereof, or a pharmaceutical composition comprising a compound of Formula I.

In certain embodiments, the subject matter described herein is directed to a method of treating cancer in a subject in need thereof, comprising administering an effective amount of a compound of Formula I, a pharmaceutically acceptable salt thereof, or a pharmaceutical composition comprising a compound of Formula I. In certain embodiments, the cancer is selected from the group consisting of bladder cancer, breast cancer (e.g., ductal carcinoma), cervical cancer (e.g., squamous cell carcinoma), colorectal cancer (e.g., adenocarcinoma), esophageal cancer (e.g., squamous cell carcinoma), gastric cancer (e.g., adenocarcinoma, medulloblastoma, colon cancer, choriocarcinoma, squamous cell carcinoma), head and neck cancer, hematologic cancer (e.g., acute lymphocytic anemia, acute myeloid leukemia, acute lymphoblastic B cell leukemia, anaplastic large cell lymphoma, B-cell lymphoma, Burkitt's lymphoma, chronic lymphocytic leukemia, chronic eosinophillic leukemia/hypereosinophillic syndrome, chronic myeloid leukemia, Hodgkin's lymphoma, mantle cell lymphoma, multiple myeloma, T-cell acute lymphoblastic leukemia), lung cancer (e.g., bronchioloalveolar adenocarcinoma, mesothelioma, mucoepidermoid carcinoma, small-cell lung cancer, non-small cell lung cancer, adenocarcinoma, squamous cell carcinoma), liver cancer (e.g., hepatocellular carcinoma), lymphoma, neurological cancer (e.g., glioblastoma, neuroblastoma, neuroglioma), ovarian (e.g., adenocarcinoma), pancreatic cancer (e.g., ductal carcinoma), prostate cancer (e.g., adenocarcinoma), renal cancer (e.g., renal cell carcinoma, clear cell renal carcinoma), sarcoma (e.g., chondrosarcoma, Ewings sarcoma, fibrosarcoma, multipotential sarcoma, osteosarcoma, rhabdomyosarcoma, synovial sarcoma), skin cancer (e.g., melanoma, epidermoid carcinoma, squamous cell carcinoma), thyroid cancer (e.g., medullary carcinoma), and uterine cancer. In a preferred embodiment, the cancer is lung cancer.

In certain embodiments, the methods of administering and treating described herein further comprise co-administration of one or more additional pharmaceutically active compounds.

In a combination therapy, the pharmaceutically active compounds can be administered at the same time, in the same formulation, or at different times. Such combination therapy comprises co-administration of a compound of Formula I or a pharmaceutically acceptable salt thereof with at least one additional pharmaceutically active compound. Combination therapy in a fixed dose combination therapy comprises co-administration of a compound of Formula I or a pharmaceutically acceptable salt thereof with at least one additional pharmaceutically active compound in a fixed-dose formulation. Combination therapy in a free dose combination therapy comprises co-administration of a compound of Formula I or a pharmaceutically acceptable salt thereof and at least one additional pharmaceutically active compound in free doses of the respective compounds, either by simultaneous administration of the individual compounds or by sequential use of the individual compounds over a period of time.

V. Methods of Preparing Compounds of Formula I and Pharmaceutically Acceptable Salts Thereof The starting materials and reagents used in preparing the compounds described herein are either available from commercial suppliers such as Sigma-Aldrich Chemical Co., (Milwaukee, Wis.), Bachem (Torrance, Calif.), or are prepared by methods known to those skilled in the art following procedures set forth in references such as Fieser and Fieser's *Reagents for Organic Synthesis*, Volumes 1-17 (John Wiley and Sons, 1991); *Rodd's Chemistry of Carbon Compounds*, Volumes 1-5 and Supplementals (Elsevier Science Publishers, 1989); *Organic Reactions*, Volumes 1-40 (John Wiley and Sons, 1991), *March's Advanced Organic Chemistry*, (John Wiley and Sons, 4th Edition) and *Larock's Comprehensive Organic Transformations* (VCH Publishers Inc., 1989). These schemes are merely illustrative of some methods by which the compounds of this disclosure can be synthesized, and various modifications to these schemes can be made and will be suggested to one skilled in the art reading this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Synthetic chemistry transformations and protecting group methodologies (protection and deprotection) useful in synthesizing compounds and necessary reagents and intermediates are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); and L. Paquette, ed., *Encyclopedia of Reagents for Organic Synthesis*, John Wiley and Sons (1995) and subsequent editions thereof.

Compounds may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus, according to a further aspect, there is provided a compound library comprising at least 2 compounds, or pharmaceutically acceptable salts thereof.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

The subject matter described herein includes but is not limited to the following embodiments:

1a. A compound of Formula I:

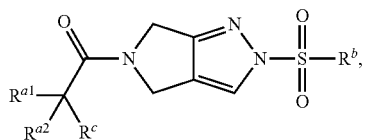

wherein, $R^{a1}$ is hydroxy, $C_1$-$C_3$ alkoxy, hydroxy-$C_1$-$C_3$ alkoxy, or hydroxy-$C_1$-$C_3$ alkyl;

$R^{a2}$ is hydrogen or $C_1$-$C_3$ alkyl;

or $R^{a1}$ and $R^{a2}$, together with the carbon atom to which they are each attached, form a 4- to 5-membered heterocyclyl;

$R^c$ is phenyl or pyridinyl, each optionally substituted with one or two substituents independently selected in each instance from the group consisting of halo, $C_1$-$C_3$ alkyl, $C_1$-$C_3$ alkoxy, hydroxy-$C_1$-$C_3$ alkoxy, ($C_1$-$C_3$ alkoxy)-$C_1$-$C_3$ alkoxy, hydroxy-$C_1$-$C_3$ alkyl, and ($C_1$-$C_3$ alkoxy)-$C_1$-$C_3$ alkyl; and $R^b$ is a thiazol-2(3H)-one or a 5-membered heteroaryl ring, each optionally substituted with one, two, or three substituents independently selected in each instance from the group consisting of $C_1$-$C_3$ alkyl, halo-$C_1$-$C_3$ alkyl, halo-$C_1$-$C_3$ alkoxy, halo, $C_1$-$C_3$ alkoxy, ($C_1$-$C_3$ alkoxy)-$C_1$-$C_3$ alkyl, ($C_1$-$C_3$-alkoxy)-$C_1$-$C_3$ alkoxy, 3- to 6-membered cycloalkyl, 4- to 6-membered heterocyclyl, phenyl, and 5- or 6-membered heteroaryl; or a pharmaceutically acceptable salt thereof.

1b. A compound of Formula I.

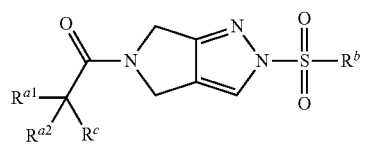

wherein, $R^{a1}$ is hydroxy or $C_1$-$C_3$ hydroxyalkyl;

$R^{a2}$ is hydrogen or $C_1$-$C_3$ alkyl;

or $R^{a1}$ and $R^{a2}$, together with the carbon atom to which they are each attached, form a 4- to 5-membered heterocyclyl;

$R^c$ is phenyl or pyridinyl, each optionally substituted with one or two substituents, each independently selected from the group consisting of halo; and $R^b$ is a 5-membered heteroaryl ring, optionally substituted with one or two substituents, each independently selected from the group consisting of $C_1$-$C_3$ alkyl and $C_1$-$C_3$ haloalkyl;

or a pharmaceutically acceptable salt thereof.

2b. The compound of embodiment 1b or 1a, or a pharmaceutically acceptable salt thereof, wherein $R^{a1}$ is $C_1$-$C_3$ hydroxyalkyl.

3a. The compound of embodiment 1a, or a pharmaceutically acceptable salt thereof, wherein $R^{a1}$ is —OH, —CH$_2$OH, —CH(OH)CH$_3$, —OCH$_3$, or —OCH$_2$CH$_2$OH.

3b. The compound of embodiment 1b or 3a, or a pharmaceutically acceptable salt thereof, wherein $R^{a1}$ is —OH, —CH$_2$OH, or —CH(OH)CH$_3$.

4b. The compound of any one of embodiments 1b-3b, 1a or 3a, or a pharmaceutically acceptable salt thereof, wherein $R^{a1}$ is —CH$_2$OH.

5b. The compound of any one of embodiments 1b-4b, 1a, or 3a, or a pharmaceutically acceptable salt thereof, wherein $R^{a2}$ is hydrogen or —CH$_3$.

6b. The compound of embodiment 5b, or a pharmaceutically acceptable salt thereof, wherein $R^{a2}$ is hydrogen.

7b. The compound of embodiment 1b or 1a, or a pharmaceutically acceptable salt thereof, wherein $R^{a1}$ and $R^{a2}$, together with the carbon atom to which they are each attached, form an oxetanyl ring.

8a. The compound of any one of embodiments 1b-7b, 1a, or 3a, or a pharmaceutically acceptable salt thereof, wherein $R^c$ is phenyl or pyridinyl, each optionally substituted with one or two halos.

8b. The compound of any one of embodiments 1b-7b, 1a, 3a, or 8a or a pharmaceutically acceptable salt thereof, wherein $R^c$ is phenyl or pyridinyl, each optionally substituted with one halo.

9b. The compound of embodiment 8b, or a pharmaceutically acceptable salt thereof, wherein $R^c$ is phenyl or pyridinyl, each optionally substituted with fluoro or chloro.

10b. The compound of embodiment 8b, 8a, or 9b, or a pharmaceutically acceptable salt thereof, wherein $R^c$ is phenyl or pyridinyl, each optionally substituted with fluoro.

11b. The compound of embodiment 8b, 8a, or 9b, or a pharmaceutically acceptable salt thereof, wherein $R^c$ is phenyl, 2-fluorophenyl, 2-chlorophenyl, or pyridin-2-yl.

12b. The compound of embodiment 11b, or a pharmaceutically acceptable salt thereof, wherein $R^c$ is phenyl, 2-fluorophenyl, or pyridin-2-yl.

13b. The compound of embodiment 12b, or a pharmaceutically acceptable salt thereof, wherein $R^c$ is 2-fluorophenyl.

12a. The compound of any one of embodiments 1b-13b, 1a, 3a, or 8a, or a pharmaceutically acceptable salt thereof, wherein $R^c$ is

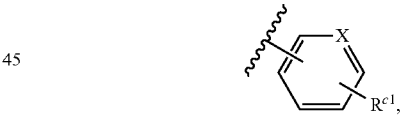

wherein, X is CH or N; and $R^{c1}$ is hydrogen, fluoro, or chloro.

14b. The compound of any one of embodiments 1b-9b, 1a, 3a, 8a, or 12a, or a pharmaceutically acceptable salt thereof, wherein $R^c$ is

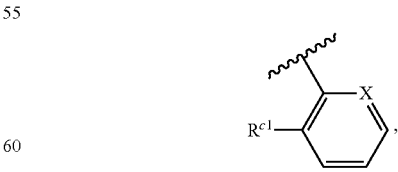

wherein X is CH or N; and $R^{c1}$ is hydrogen, fluoro, or chloro.

14a. The compound of any one of embodiments 1b-9b, 1a, 3a, 8a, or 12a, wherein $R^c$ is phenyl.

15a. The compound of any one of embodiments 1b-7b, 1a, 3a, 8a, or 12a, or a pharmaceutically acceptable salt thereof, wherein $R^c$ is phenyl substituted ortho with $C_1$-$C_3$ alkyl, ($C_1$-$C_3$-alkoxy)-$C_1$-$C_3$ alkoxy, $C_1$-$C_3$ alkoxy, or hydroxy-$C_1$-$C_3$ alkoxy.

16a. The compound of embodiment 15a, or a pharmaceutically acceptable salt thereof, wherein $R^c$ is phenyl substituted ortho with —$CH_3$, —$CH_2CH_3$, —$CH_2CH_2CH_3$, —$OCH_3$, —$OCH_2CH_3$, methoxy-$C_1$-$C_3$ alkoxy, —$OCH_2CH_2OH$, or —$OCH_2CH_2CH_2OH$.

17a. The compound of embodiment 16a, or a pharmaceutically acceptable salt thereof, wherein $R^c$ is phenyl substituted ortho with —$CH_2CH_3$, —$OCH_3$, —$OCH_2CH_2OH$, or —$OCH_2CH_2OCH_3$.

18a. The compound of any one of embodiments 2b-14b, 1a, 3a, 8a, 12a, 14a, 15a, 16a, or 17a, or a pharmaceutically acceptable salt thereof, wherein $R^b$ is a thiazol-2(3H)-one or a 5-membered heteroaryl ring substituted with one or two substituents, each independently selected from the group consisting of $C_1$-$C_3$ alkyl, halo-$C_1$-$C_3$ alkoxy, halo-$C_1$-$C_3$ alkyl, ($C_1$-$C_3$ alkoxy)-$C_1$-$C_3$ alkyl, $C_1$-$C_3$ alkoxy, phenyl, and 4- to 6-membered heterocyclyl.

19a. The compound of embodiment 18a, or a pharmaceutically acceptable salt thereof, wherein $R^b$ is a thiazol-2(3H)-one or a 5-membered heteroaryl ring substituted with one or two substituents, each independently selected from the group consisting of —$CH_3$, —$CH_2CH_3$, —$CH_2CH_2CH_3$, —$CH(CH_3)_2$, fluoro-$C_1$-$C_3$ alkyl, fluoro-$C_1$-$C_3$ alkoxy, phenyl, 5-membered heterocyclyl, methoxy-$C_1$-$C_3$ alkyl, —$OCH_2CH_3$, and —$OCH_3$.

20a. The compound of embodiment 19a, or a pharmaceutically acceptable salt thereof, wherein $R^b$ is a thiazol-2(3H)-one or a 5-membered heteroaryl ring substituted with one or two substituents, each independently selected from the group consisting of —$CH_3$, —$CH_2CH_3$, —$CF_3$, —$CH_2CHF_2$, —$CH_2CH_2CF_3$, —$CHF_2$, —$OCH_2CHF_2$, phenyl, —$OCH_2CF_3$, —$CH_2CF_3$, —$CH_2CH_2F$, —$CH_2CH_2OCH_3$, —$OCH_2CH_3$, —$OCH_3$, and tetrahydrofuranyl.

15b. The compound of any one of embodiments 1b-14b, 1a, 3a, 12a, or 18a, or a pharmaceutically acceptable salt thereof, wherein $R^b$ is a 5-membered heteroaryl ring substituted with one $C_1$-$C_3$ haloalkyl and optionally further substituted with one $C_1$-$C_3$ alkyl.

16b. The compound of any one of embodiments 1b-14b, 1a, 3a, 12a, or 18a, or a pharmaceutically acceptable salt thereof, wherein $R^b$ is a 5-membered heteroaryl ring substituted with one substituent selected from the group consisting of $C_1$-$C_3$ alkyl and $C_1$-$C_3$ haloalkyl.

17b. The compound of embodiment 16b, or a pharmaceutically acceptable salt thereof, wherein $R^b$ is a 5-membered heteroaryl ring substituted with one $C_1$-$C_3$ haloalkyl.

18b. The compound of any one of embodiments 1b-14b, 1a, 3a, 12a, or 18a, or a pharmaceutically acceptable salt thereof, wherein $R^b$ is a 5-membered heteroaryl ring substituted with two substituents, each independently selected from the group consisting of $C_1$-$C_3$ alkyl and $C_1$-$C_3$ haloalkyl.

19b. The compound of embodiment 18b, or a pharmaceutically acceptable salt thereof, wherein $R^b$ is a 5-membered heteroaryl ring substituted with one $C_1$-$C_3$ alkyl and one $C_1$-$C_3$ haloalkyl.

20b. The compound of any one of embodiments 1b-19b, 1a, 3a, 8a, 12a, 14a, 15a, 16a, 17a, 18a, 19a, or 20a, or a pharmaceutically acceptable salt thereof, wherein the 5-membered heteroaryl ring of $R^b$ contains one, two, or three nitrogen ring atoms.

27a. The compound of embodiment 20b, wherein the 5-membered heteroaryl ring of $R^b$ is pyrazolyl, imidazolyl, pyrrolyl, oxazolyl, triazolyl, or thiazolyl.

21b. The compound of any one of embodiments 1b-20b, 1a, 3a, 8a, 12a, 14a, 15a, 16a, 17a, 18a, 19a, 20a, or 27a, or a pharmaceutically acceptable salt thereof, wherein the 5-membered heteroaryl ring of $R^b$ is pyrazolyl.

29a. The compound of any one of embodiments 1b-21b, 1a, 3a, 8a, 12a, 14a, 15a, 16a, 17a, 18a, 19a, 20a, or 27a, or a pharmaceutically acceptable salt thereof, wherein $R^b$ is

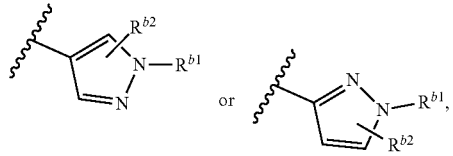

wherein, $R^{b1}$ is halo-$C_1$-$C_3$ alkyl, methoxy-$C_1$-$C_3$ alkyl, $C_1$-$C_3$ alkyl, hydrogen, or tetrahydrofuranyl; and $R^{b2}$ is hydrogen, halo-$C_1$-$C_3$ alkyl, or $C_1$-$C_3$ alkyl.

30a. The compound of any one of embodiments 1b-21b, 1a, 3a, 8a, 12a, 14a, 15a, 16a, 17a, 18a, 19a, 20a, 27a, or 29a, or a pharmaceutically acceptable salt thereof, wherein $R^b$ is

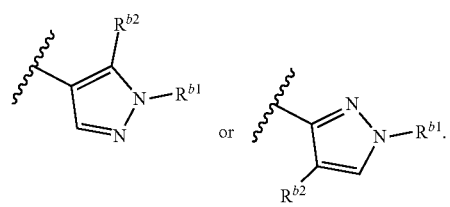

22b. The compound of any one of embodiments 1b-21b, 1a, 3a, 8a, 12a, 14a, 15a, 16a, 17a, 18a, 19a, 20a, 27a, 29a, or 30a, or a pharmaceutically acceptable salt thereof, wherein $R^b$ is

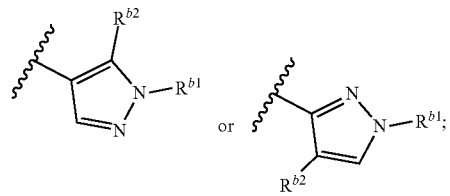

wherein $R^{b1}$ is $C_1$-$C_3$ haloalkyl; and $R^{b2}$ is hydrogen or $C_1$-$C_3$ alkyl.

23b. The compound of embodiment 22b, 29a, or 30a, or a pharmaceutically acceptable salt thereof, wherein $R^{b2}$ is hydrogen.

24b. The compound of embodiment 22b, 29a, or 30a, or a pharmaceutically acceptable salt thereof, wherein $R^{b2}$ is $C_1$-$C_3$ alkyl.

25b. The compound of embodiment 24b, or a pharmaceutically acceptable salt thereof, wherein $R^{b2}$ is —$CH_3$.

26b. The compound of any one of embodiments 22b-25b, 29a, or 30a, or a pharmaceutically acceptable salt thereof, wherein $R^{b1}$ is $C_1$-$C_3$ fluoroalkyl.

36a. The compound of embodiment 26b, or a pharmaceutically acceptable salt thereof, wherein $R^{b1}$ is —$CHF_2$, —$CH_2CH_2CF_3$, —$CH_2CH_2F$, —$CH_2CHF_2$, or —$CH_2CF_3$.

27b. The compound of embodiment 26b or 36a, or a pharmaceutically acceptable salt thereof, wherein $R^{b1}$ is —CH$_2$CH$_2$F, —CH$_2$CHF$_2$, or —CH$_2$CF$_3$.

28b. The compound of embodiment 26b, 36a, or 27b, or a pharmaceutically acceptable salt thereof, wherein $R^{b1}$ is —CH$_2$CH$_2$F.

29b. The compound of embodiment 26b, 36a, or 27b, or a pharmaceutically acceptable salt thereof, wherein $R^{b1}$ is —CH$_2$CHF$_2$.

30b. The compound of embodiment 26b, 36a, or 27b, or a pharmaceutically acceptable salt thereof, wherein $R^{b1}$ is —CH$_2$CF$_3$.

37a. The compound of embodiment 29a or 30a, or a pharmaceutically acceptable salt thereof, wherein $R^{b1}$ is $C_1$-$C_3$ alkyl; and $R^{b2}$ is fluoro-$C_1$-$C_3$ alkyl.

38a. The compound of embodiment 37a, or a pharmaceutically acceptable salt thereof, wherein $R^{b1}$ is —CH$_2$CH$_3$; and $R^{b2}$ is —CF$_3$.

39a. The compound of embodiment 29a or 30a, or a pharmaceutically acceptable salt thereof, wherein $R^{b1}$ is —CH$_2$CH$_2$OCH$_3$ or tetrahydrofuranyl; and $R^{b2}$ is hydrogen.

40a. The compound of embodiment 27a, or a pharmaceutically acceptable salt thereof, wherein the 5-membered heteroaryl ring of $R^b$ is thiazolyl.

41a. The compound of embodiment 40a, or a pharmaceutically acceptable salt thereof, wherein $R^b$ is

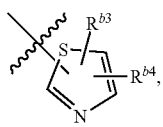

wherein, $R^{b3}$ is halo $C_1$-$C_3$ alkoxy, $C_1$-$C_3$ alkyl, halo $C_1$-$C_3$ alkyl, or $C_1$-$C_3$ alkoxy; and
$R^{b4}$ is hydrogen or $C_1$-$C_3$ alkyl.

42a. The compound of embodiment 41a, or a pharmaceutically acceptable salt thereof, wherein $R^b$ is

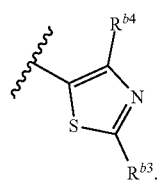

43a. The compound of embodiment 41a or 42a, or a pharmaceutically acceptable salt thereof, wherein $R^{b3}$ is —CH$_3$, —CH$_2$CH$_2$CF$_3$, —OCH$_2$CHF$_2$, —OCH$_2$CHF$_3$, —OCH$_3$, or —OCH$_2$CH$_3$; and $R^{b4}$ is —CH$_3$.

44a. The compound of any one of embodiments 1b-30b, 1a, 3a, 8a, 12a, 14a, 15a, 16a, 17a, 18a, 19a, or 20a, or a pharmaceutically acceptable salt thereof, wherein $R^b$ is a 5-membered heteroaryl ring, wherein the 5-membered heteroaryl ring of $R^b$ is thiophenyl.

45a. The compound of embodiment 44a, or a pharmaceutically acceptable salt thereof, wherein $R^b$ is

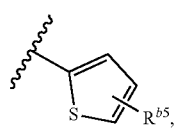

wherein, $R^{b5}$ is halo, $C_1$-$C_3$ alkyl, phenyl, or halo-$C_1$-$C_3$ alkyl.

46a. The compound of embodiment 45a, or a pharmaceutically acceptable salt thereof, wherein $R^b$ is

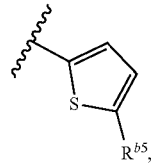

47a. The compound of embodiment 45a or 46a, or a pharmaceutically acceptable salt thereof, wherein $R^b$s is phenyl, —CH$_2$CH$_3$, —CF$_3$, bromo, or —CH$_2$CH$_2$CF$_3$.

48a. The compound of any one of embodiments 1a, 2b-14b, 14a-19a, or 20a, or a pharmaceutically acceptable salt thereof, wherein $R^b$ is a thiazol-2(3H)-one.

49a. The compound of embodiment 48a, or a pharmaceutically acceptable salt thereof, wherein $R^b$ is

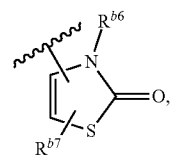

wherein $R^{b6}$ is selected from the group consisting of hydrogen, $C_1$-$C_3$ alkyl, and halo-$C_1$-$C_3$ alkyl; and $R^{b7}$ is selected from the group consisting of hydrogen and $C_1$-$C_3$ alkyl.

50a. The compound of embodiment 48a or 49a, or a pharmaceutically acceptable salt thereof, wherein $R^b$ is

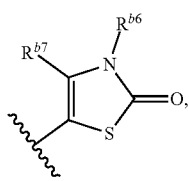

wherein $R^{b6}$ is selected from the group consisting of methyl, ethyl, and —CH$_2$CHF$_2$; and $R^{b7}$ is methyl.

51a. The compound of any one of embodiments 1a, 2b-14b, 14a-19a, 20a, or 27a, or a pharmaceutically acceptable salt thereof, wherein the 5-membered heteroaryl ring of $R^b$ is an imidazolyl.

52a. The compound of embodiment 51a, or a pharmaceutically acceptable salt thereof, wherein $R^b$ is

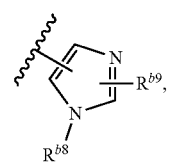

wherein $R^{b8}$ and $R^{b9}$ are each independently selected from the group consisting of hydrogen, $C_1$-$C_3$ alkyl, and halo-$C_1$-$C_3$ alkyl.

53a. The compound of embodiment 52a, or a pharmaceutically acceptable salt thereof, wherein $R^b$ is

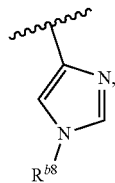

wherein $R^{b8}$ is halo-$C_1$-$C_3$ alkyl; and $R^{b9}$ is hydrogen.

54a. The compound of embodiment 52a or 53a, or a pharmaceutically acceptable salt thereof, wherein $R^{b8}$ is —$CH_2CF_2H$.

55a. The compound of any one of embodiments 1a, 2b-14b, 14a-19a, 20a, or 27a, or a pharmaceutically acceptable salt thereof, wherein the 5-membered heteroaryl ring of $R^b$ is a pyrrolyl.

56a. The compound of embodiment 55a, or a pharmaceutically acceptable salt thereof, where $R^b$ is

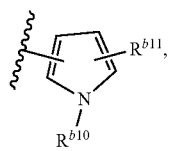

wherein $R^{b10}$ and $R^{b11}$ are each independently selected from the group consisting of hydrogen, $C_1$-$C_3$ alkyl, and halo-$C_1$-$C_3$ alkyl.

57a. The compound of embodiment 56a, or a pharmaceutically acceptable salt thereof, wherein $R^b$ is

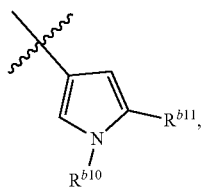

wherein $R^{b10}$ is hydrogen and $R^{b11}$ is halo-$C_1$-$C_3$ alkyl.

58a. The compound of embodiment 56a or 57a, or a pharmaceutically acceptable salt thereof, wherein $R^{b11}$ is —$CF_3$.

59a. The compound of any one of embodiments 1a, 2b-14b, 14a-19a, 20a, or 27a, or a pharmaceutically acceptable salt thereof, wherein the 5-membered heteroaryl ring of $R^b$ is a triazolyl.

60a. The compound of embodiment 59a, or a pharmaceutically acceptable salt thereof, wherein $R^b$ is

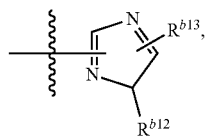

wherein $R^{b12}$ and $R^{13}$ are each independently selected from the group consisting of hydrogen, $C_1$-$C_3$ alkyl, and halo-$C_1$-$C_3$ alkyl.

61a. The compound of embodiment 60a, or a pharmaceutically acceptable salt thereof, wherein $R^b$ is

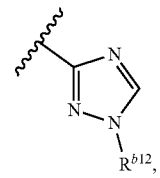

wherein $R^{b13}$ is hydrogen and $R^{b12}$ is halo-$C_1$-$C_3$ alkyl.

62a. The compound of embodiment 60a or 61a, or a pharmaceutically acceptable salt thereof, wherein $R^{b12}$ is —$CH_2CHF_2$.

63a. The compound of any one of embodiments 1a, 2b-14b, 14a-19a, 20a, or 27a, or a pharmaceutically acceptable salt thereof, wherein $R^b$ is an oxazolyl.

64a. The compound of embodiment 63a, or a pharmaceutically acceptable salt thereof, wherein $R^b$ is

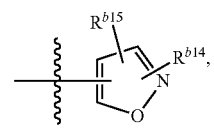

wherein $R^{b14}$ and $R^{b15}$ are each independently selected from the group consisting of hydrogen, $C_1$-$C_3$ alkyl, and halo-$C_1$-$C_3$ alkyl.

65a. The compound of embodiment 64a, or a pharmaceutically acceptable salt thereof, wherein $R^b$ is

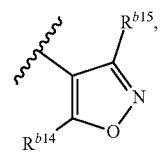

wherein $R^{b14}$ and $R^{b15}$ are each $C_1$-$C_3$ alkyl.

66a. The compound of embodiment 64a or 65a, or a pharmaceutically acceptable salt thereof, wherein $R^{b14}$ and $R^{b15}$ are each methyl.

67a. The compound of any one of embodiments 1b-30b, 1a, 3a, 8a, 12a, 14a, 15a, 16a, 17a, 18a, 19a, 20a, 27a, 29a, 30a, 36a, or 37a-66a, or a pharmaceutically acceptable salt thereof, wherein the compound is of Formula I-Ia

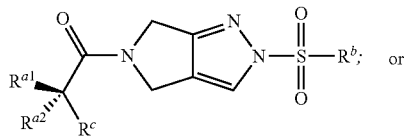

I-Ia or

Formula I-Ib

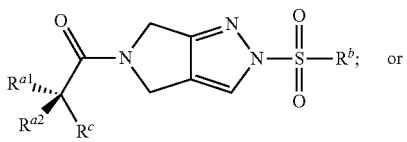

Formula II

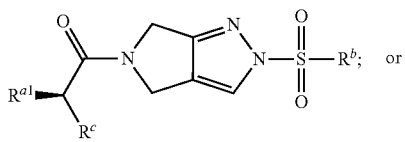

Formula III

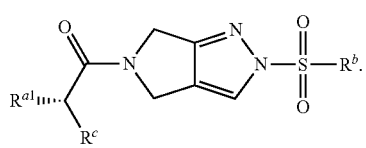

31b. The compound of any one of embodiments 1b-14b, 1a, 3a, 8a, 12a, 18a-20a, 15b-20b, 27a, 21b, 29a-30a, 22b-26b, 36a, 27b, 28b-30b, or 37a-67a or a pharmaceutically acceptable salt thereof, wherein the compound is of Formula IA

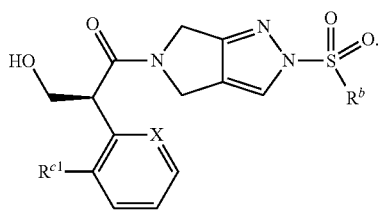

68a. The compound of any one of embodiments 1b-14b, 1a, 3a, 8a, 12a, 18a-20a, 15b-20b, 27a, 21b, 29a-30a, 22b-26b, 36a, 27b, 28b-30b, or 37a-67a, or a pharmaceutically acceptable salt thereof, wherein the compound is of Formula IB

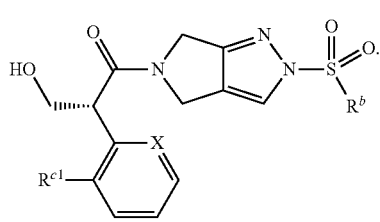

32b. The compound of embodiment 1a or 1b, selected from Table 1, or a pharmaceutically acceptable salt thereof.

33b. A pharmaceutical composition comprising a compound of any one of embodiments 1b-32b, 1a, 3a, 8a, 12a, 14a-20a, 27a, 29a-30a, 36a, or 37a-67a, or a pharmaceutically acceptable salt thereof, and a pharmaceutically acceptable excipient.

34b. A method of treating a disease or disorder associated with modulation of pyruvate kinase (PKR) and/or PKM2 in a subject, comprising administering to the subject an effective amount of a compound of any one of embodiments 1b-32b, 1a, 3a, 8a, 12a, 14a-20a, 27a, 29a-30a, 36a, or 37a-67a, or a pharmaceutically acceptable salt thereof, or the pharmaceutical composition of embodiment 33b.

35b. A method of activating PKR and/or PKM2 in a subject, comprising administering to the subject an effective amount of a compound of any one of embodiments 1b-32b, 1a, 3a, 8a, 12a, 14a-20a, 27a, 29a-30a, 36a, or 37a-67a, or a pharmaceutically acceptable salt thereof, or the pharmaceutical composition of embodiment 33b.

36b. A method of treating a subject afflicted with a disease associated with decreased activity of PKR and/or PKM2, comprising administering to the subject an effective amount of a compound of any one of embodiments 1b-32b, 1a, 3a, 8a, 12a, 14a-20a, 27a, 29a-30a, 36a, or 37a-67a, or a pharmaceutically acceptable salt thereof, or the pharmaceutical composition of embodiment 33b.

37b. The method of embodiment 34b or 36b, wherein the disease is selected from the group consisting of sickle cell disease, sickle cell anemia, thalassemia, hereditary non-spherocytic hemolytic anemia, hemolytic anemia, hereditary spherocytosis, hereditary elliptocytosis, abetalipoproteinemia, paroxysmal nocturnal hemoglobinuria, acquired hemolytic, and anemia of chronic diseases.

38c. The method of embodiment 34b, 36b, or 37b, wherein the disease is selected from the group consisting of sickle cell disease, sickle cell anemia, thalassemia, hereditary non-spherocytic hemolytic anemia, hemolytic anemia, hereditary spherocytosis, hereditary elliptocytosis, abetalipoproteinemia, paroxysmal nocturnal hemoglobinuria, acquired hemolytic, cancer, and anemia of chronic diseases.

39c. The method of embodiment 37b or 38c, wherein the disease is selected from the group consisting of sickle cell disease and thalassemia.

40c. The method of embodiment 39c, wherein the thalassemia is beta-thalassemia.

1. A compound of Formula I:

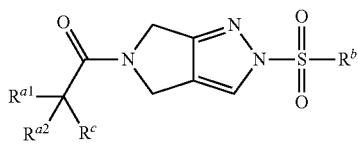

wherein, $R^{a1}$ is hydroxy, $C_1$-$C_3$ alkoxy, hydroxy-$C_1$-$C_3$ alkoxy, or hydroxy-$C_1$-$C_3$ alkyl;

$R^{a2}$ is hydrogen or $C_1$-$C_3$ alkyl;

or $R^{a1}$ and $R^{a2}$, together with the carbon atom to which they are each attached, form a 4- to 5-membered heterocyclyl;

$R^c$ is phenyl or pyridinyl, each optionally substituted with one or two substituents independently selected in each instance from the group consisting of halo, $C_1$-$C_3$ alkyl, $C_1$-$C_3$ alkoxy, hydroxy-$C_1$-$C_3$ alkoxy, ($C_1$-$C_3$ alkoxy)-$C_1$-$C_3$ alkoxy, hydroxy-$C_1$-$C_3$ alkyl, and ($C_1$-$C_3$ alkoxy)-$C_1$-$C_3$ alkyl; and $R^b$ is a thiazol-2(3H)-one or a 5-membered heteroaryl ring, each optionally substituted with one, two, or three substituents independently selected in each instance from the group consisting of $C_1$-$C_3$ alkyl, halo-$C_1$-$C_3$ alkyl, halo-$C_1$-$C_3$ alkoxy, halo, $C_1$-$C_3$ alkoxy, ($C_1$-$C_3$ alkoxy)-$C_1$-$C_3$ alkyl, ($C_1$-$C_3$-alkoxy)-$C_1$-$C_3$ alkoxy, 3- to 6-membered cycloalkyl, 4- to 6-membered heterocyclyl, phenyl, and 5- or 6-membered heteroaryl; or a pharmaceutically acceptable salt thereof.

2. The compound of embodiment 1, or a pharmaceutically acceptable salt thereof, wherein $R^{a1}$ is hydroxy-$C_1$-$C_3$ alkyl.

3. The compound of embodiment 1, or a pharmaceutically acceptable salt thereof, wherein $R^{a1}$ is —OH, —$CH_2OH$, —$CH(OH)CH_3$, —$OCH_3$, or —$OCH_2CH_2OH$.

4. The compound of embodiment 3, or a pharmaceutically acceptable salt thereof, wherein $R^{a1}$ is —$CH_2OH$.

5. The compound of any one of embodiments 1-4, or a pharmaceutically acceptable salt thereof, wherein $R^{a2}$ is hydrogen or —$CH_3$.

6. The compound of embodiment 5, or a pharmaceutically acceptable salt thereof, wherein $R^{a2}$ is hydrogen.

7. The compound of embodiment 1, or a pharmaceutically acceptable salt thereof, wherein $R^{a1}$ and $R^{a2}$, together with the carbon atom to which they are each attached, form an oxetanyl ring.

8. The compound of any one of embodiments 1-7, or a pharmaceutically acceptable salt thereof, wherein $R^c$ is phenyl or pyridinyl, each optionally substituted with one or two halos.

9. The compound of embodiment 8, or a pharmaceutically acceptable salt thereof, wherein $R^c$ is phenyl or pyridinyl, each optionally substituted with one halo.

10. The compound of embodiment 9, or a pharmaceutically acceptable salt thereof, wherein $R^c$ is phenyl or pyridinyl, each optionally substituted with fluoro or chloro.

11. The compound of any one of embodiments 8-10, or a pharmaceutically acceptable salt thereof, wherein $R^c$ is phenyl, 2-fluorophenyl, 2-chlorophenyl, or pyridin-2-yl.

12. The compound of any one of embodiments 1-11, or a pharmaceutically acceptable salt thereof, wherein $R^c$ is

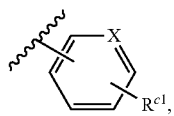

wherein, X is CH or N; and
$R^{c1}$ is hydrogen, fluoro, or chloro.

13. The compound of embodiment 12, or a pharmaceutically acceptable salt thereof, wherein $R^c$ is

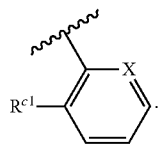

14. The compound of any one of embodiments 1-13, wherein $R^c$ is phenyl.

15. The compound of any one of embodiments 1-7, or a pharmaceutically acceptable salt thereof, wherein $R^c$ is phenyl substituted ortho with $C_1$-$C_3$ alkyl, ($C_1$-$C_3$-alkoxy)-$C_1$-$C_3$ alkoxy, $C_1$-$C_3$ alkoxy, or hydroxy-$C_1$-$C_3$ alkoxy.

16. The compound of embodiment 15, or a pharmaceutically acceptable salt thereof, wherein $R^c$ is phenyl substituted ortho with —$CH_3$, —$CH_2CH_3$, —$CH_2CH_2CH_3$, —$OCH_3$, —$OCH_2CH_3$, methoxy-$C_1$-$C_3$ alkoxy, —$OCH_2CH_2OH$, or —$OCH_2CH_2CH_2OH$.

17. The compound of embodiment 16, or a pharmaceutically acceptable salt thereof, wherein $R^c$ is phenyl substituted ortho with —$CH_2CH_3$, —$OCH_3$, —$OCH_2CH_2OH$, or —$OCH_2CH_2OCH_3$.

18. The compound of any one of embodiments 1-17, or a pharmaceutically acceptable salt thereof, wherein $R^b$ is a thiazol-2(3H)-one or a 5-membered heteroaryl ring substituted with one or two substituents, each independently selected from the group consisting of $C_1$-$C_3$ alkyl, halo-$C_1$-$C_3$ alkoxy, halo-$C_1$-$C_3$ alkyl, ($C_1$-$C_3$ alkoxy)-$C_1$-$C_3$ alkyl, $C_1$-$C_3$ alkoxy, phenyl, and 4- to 6-membered heterocyclyl.

19. The compound of embodiment 18, or a pharmaceutically acceptable salt thereof, wherein $R^b$ is a thiazol-2(3H)-one or a 5-membered heteroaryl ring substituted with one or two substituents, each independently selected from the group consisting of —$CH_3$, —$CH_2CH_3$, —$CH_2CH_2CH_3$, —$CH(CH_3)_2$, fluoro-$C_1$-$C_3$ alkyl, fluoro-$C_1$-$C_3$ alkoxy, phenyl, 5-membered heterocyclyl, methoxy-$C_1$-$C_3$ alkyl, —$OCH_2CH_3$, and —$OCH_3$.

20. The compound of embodiment 19, or a pharmaceutically acceptable salt thereof, wherein $R^b$ is a thiazol-2(3H)-one or a 5-membered heteroaryl ring substituted with one or two substituents, each independently selected from the group consisting of —$CH_3$, —$CH_2CH_3$, —$CF_3$, —$CH_2CHF_2$, —$CH_2CH_2CF_3$, —$CHF_2$, —$OCH_2CHF_2$, phenyl, —$OCH_2CF_3$, —$CH_2CF_3$, —$CH_2CH_2F$, —$CH_2CH_2OCH_3$, —$OCH_2CH_3$, —$OCH_3$, and tetrahydrofuranyl.

21. The compound of embodiment 18, or a pharmaceutically acceptable salt thereof, wherein $R^b$ is a 5-membered heteroaryl ring substituted with one halo-$C_1$-$C_3$ alkyl and optionally further substituted with one $C_1$-$C_3$ alkyl.

22. The compound of embodiment 18, or a pharmaceutically acceptable salt thereof, wherein $R^b$ is a 5-membered heteroaryl ring substituted with one substituent selected from the group consisting of $C_1$-$C_3$ alkyl and halo-$C_1$-$C_3$ alkyl.

23. The compound of embodiment 22, or a pharmaceutically acceptable salt thereof, wherein $R^b$ is a 5-membered heteroaryl ring substituted with one halo-$C_1$-$C_3$ alkyl.

24. The compound of embodiment 18, or a pharmaceutically acceptable salt thereof, wherein $R^b$ is a 5-membered heteroaryl ring substituted with two substituents, each independently selected from the group consisting of $C_1$-$C_3$ alkyl and halo-$C_1$-$C_3$ alkyl.

25. The compound of embodiment 24, or a pharmaceutically acceptable salt thereof, wherein $R^b$ is a 5-membered heteroaryl ring substituted with one $C_1$-$C_3$ alkyl and one halo-$C_1$-$C_3$ alkyl.

26. The compound of any one of embodiments 1-25, or a pharmaceutically acceptable salt thereof, wherein $R^b$ is a 5-membered heteroaryl ring comprising one, two, or three nitrogen ring atoms.

27. The compound of embodiment 26, wherein the 5-membered heteroaryl ring of $R^b$ is pyrazolyl, imidazolyl, pyrrolyl, oxazolyl, triazolyl, or thiazolyl.

28. The compound of embodiment 27, or a pharmaceutically acceptable salt thereof, wherein the 5-membered heteroaryl ring of $R^b$ is pyrazolyl.

29. The compound of any one of embodiments 1-28, or a pharmaceutically acceptable salt thereof, wherein $R^b$ is

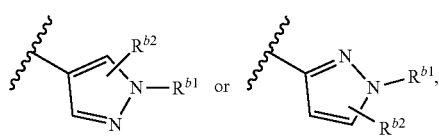

wherein, $R^{b1}$ is halo-$C_1$-$C_3$ alkyl, methoxy-$C_1$-$C_3$ alkyl, $C_1$-$C_3$ alkyl, hydrogen, or tetrahydrofuranyl; and
$R^{b2}$ is hydrogen, halo-$C_1$-$C_3$ alkyl, or $C_1$-$C_3$ alkyl.

30. The compound of any one of embodiments 1-29, or a pharmaceutically acceptable salt thereof, wherein $R^b$ is

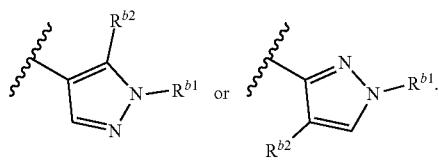

31. The compound of embodiment 29 or 30, or a pharmaceutically acceptable salt thereof, wherein $R^{b1}$ is halo-$C_1$-$C_3$ alkyl; and $R^{b2}$ is hydrogen or $C_1$-$C_3$ alkyl.
32. The compound of any one of embodiments 29-31, or a pharmaceutically acceptable salt thereof, wherein $R^{b2}$ is hydrogen.
33. The compound of any one of embodiments 29-31, or a pharmaceutically acceptable salt thereof, wherein $R^{b2}$ is $C_1$-$C_3$ alkyl.
34. The compound of embodiment 33, or a pharmaceutically acceptable salt thereof, wherein $R^{b2}$ is —$CH_3$.
35. The compound of any one of embodiments 29-34, or a pharmaceutically acceptable salt thereof, wherein $R^{b1}$ is fluoro-$C_1$-$C_3$ alkyl.
36. The compound of embodiment 35, or a pharmaceutically acceptable salt thereof, wherein $R^{b1}$ is —$CHF_2$, —$CH_2CH_2CF_3$, —$CH_2CH_2F$, —$CH_2CHF_2$, or —$CH_2CF_3$.
37. The compound of embodiment 29 or 30, or a pharmaceutically acceptable salt thereof, wherein $R^{b1}$ is $C_1$-$C_3$ alkyl; and $R^{b2}$ is fluoro-$C_1$-$C_3$ alkyl.
38. The compound of embodiment 37, or a pharmaceutically acceptable salt thereof, wherein $R^{b1}$ is —$CH_2CH_3$; and $R^{b2}$ is —$CF_3$.
39. The compound of embodiment 29 or 30, or a pharmaceutically acceptable salt thereof, wherein $R^{b1}$ is —$CH_2CH_2OCH_3$ or tetrahydrofuranyl; and $R^{b2}$ is hydrogen.
40. The compound of embodiment 27, or a pharmaceutically acceptable salt thereof, wherein the 5-membered heteroaryl ring of $R^b$ is thiazolyl.
41. The compound of embodiment 40, or a pharmaceutically acceptable salt thereof, wherein $R^b$ is

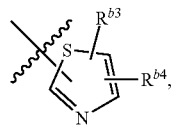

wherein, $R^{b3}$ is halo-$C_1$-$C_3$ alkoxy, $C_1$-$C_3$ alkyl, halo-$C_1$-$C_3$ alkyl, or $C_1$-$C_3$ alkoxy; and
$R^{b4}$ is hydrogen or $C_1$-$C_3$ alkyl.
42. The compound of embodiment 41, or a pharmaceutically acceptable salt thereof, wherein $R^b$ is

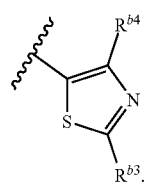

43. The compound of embodiment 41 or 42, or a pharmaceutically acceptable salt thereof, wherein $R^{b3}$ is —$CH_3$, —$CH_2CH_2CF_3$, —$OCH_2CHF_2$, —$OCH_2CHF_3$, —$OCH_3$, or —$OCH_2CH_3$; and $R^{b4}$ is —$CH_3$.
44. The compound of any one of embodiments 1-25, or a pharmaceutically acceptable salt thereof, wherein $R^b$ is a 5-membered heteroaryl ring, wherein the 5-membered heteroaryl ring of $R^b$ is thiophenyl.
45. The compound of embodiment 44, or a pharmaceutically acceptable salt thereof, wherein $R^b$ is

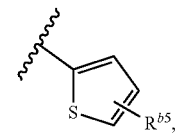

wherein, $R^{b5}$ is halo, $C_1$-$C_3$ alkyl, phenyl, or halo-$C_1$-$C_3$ alkyl.
46. The compound of embodiment 45, or a pharmaceutically acceptable salt thereof, wherein $R^b$ is

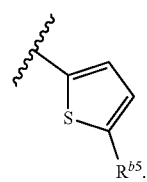

47. The compound of embodiment 45 or 46, or a pharmaceutically acceptable salt thereof, wherein $R^{b5}$ is phenyl, —$CH_2CH_3$, —$CF_3$, bromo, or —$CH_2CH_2CF_3$.
48. The compound of embodiment 1, selected from Table 1, or a pharmaceutically acceptable salt thereof.
49. A pharmaceutical composition comprising a compound of any one of embodiments 1-48, or a pharmaceutically acceptable salt thereof, and a pharmaceutically acceptable excipient.
50. A method of treating a disease or disorder associated with modulation of pyruvate kinase (PKR) and/or PKM2 in a subject, comprising administering to the subject an effective amount of a compound of any one of embodiments 1-48, or a pharmaceutically acceptable salt thereof, or the pharmaceutical composition of embodiment 49.
51. A method of activating PKR and/or PKM2 in a subject, comprising administering to the subject an effective amount of a compound of any one of embodiments 1-48, or a pharmaceutically acceptable salt thereof, or the pharmaceutical composition of embodiment 49.
52. A method of treating a subject afflicted with a disease associated with decreased activity of PKR and/or PKM2, comprising administering to the subject an effective amount of a compound of any one of embodiments 1-48, or a pharmaceutically acceptable salt thereof, or the pharmaceutical composition of embodiment 49.
53. The method of embodiment 52, wherein the disease is selected from the group consisting of sickle cell disease, sickle cell anemia, thalassemia, hereditary non-spherocytic hemolytic anemia, hemolytic anemia, hereditary spherocytosis, hereditary elliptocytosis, abetalipoproteinemia, paroxysmal nocturnal hemoglobinuria, acquired hemolytic, cancer, and anemia of chronic diseases.

54. The method of embodiment 53, wherein the disease is selected from the group consisting of sickle cell disease and thalassemia.
55. The method of embodiment 54, wherein the thalassemia is beta-thalassemia.

The following examples are offered by way of illustration and not by way of limitation.

EXAMPLES

I. Synthetic Examples

Example 1.1

Synthesis of 1-(2,2-difluoroethyl)-4-{2H,4H,5H,6H-pyrrolo[3,4-c]pyrazole-2-sulfonyl}-1H-pyrazole (Intermediate I-7)

Step 1

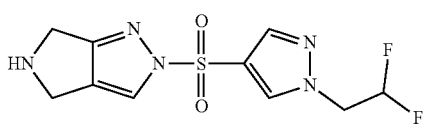 [SMILES: O=S(=O)(c1cnn(CC(F)F)c1)n1cc2c(n1)CNC2]

Into a 500-mL 3-necked round-bottom flask, was placed 4-iodopyrazole (20.00 g, 103.11 mmol, 1.00 eq.) in DMF (250.00 mL) followed by the addition of NaH (4.95 g, 206.21 mmol, 2.00 eq.), at 0° C. The resulting mixture was stirred for 0.5 h at room temperature, then 1,1-difluoro-2-iodoethane (29.69 g, 154.66 mmol, 1.50 eq.) was added dropwise with stirring at 0° C. The resulting solution was stirred overnight at room temperature, then it was quenched by the addition of water/ice. The resulting solution was extracted with 3×200 mL of ethyl acetate and the organic layers were combined and dried over anhydrous sodium sulfate and concentrated. The residue was applied onto a silica gel column and eluted with THF/PE (8%). This resulted in 21 g (78.94%) of 1-(2,2-difluoroethyl)-4-iodopyrazole as a colorless oil. LCMS (ES) [M+1]$^+$ m/z: 259.

Step 2

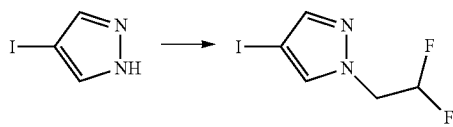 [SMILES: Ic1cn[nH]c1 ; FC(F)Cn1cc(I)cn1]

Into a 500-mL round-bottom flask purged and maintained at room temperature in an atmosphere of nitrogen, was placed 1-(2,2-difluoroethyl)-4-iodopyrazole (21.00 g, 81.39 mmol, 1.00 eq.), benzyl mercaptan (30.33 g, 244.17 mmol, 3.00 eq.), dioxane (250.00 mL), DIEA (31.56 g, 244.19 mmol, 3.00 eq.), XantPhos (9.42 g, 16.28 mmol, 0.20 eq.) and Pd$_2$(dba)$_3$ (7.45 g, 8.14 mmol, 0.10 eq.). The resulting mixture was stirred overnight at 100° C., then it was cooled to room temperature and concentrated. The residue was applied onto a silica gel column and eluted with THF/PE (5%). This resulted in 14.4 g (69.57%) of 4-(benzylsulfanyl)-1-(2,2-difluoroethyl)pyrazole as a yellow oil. LCMS (ES) [M−1]$^+$ m/z: 255.

Step 3

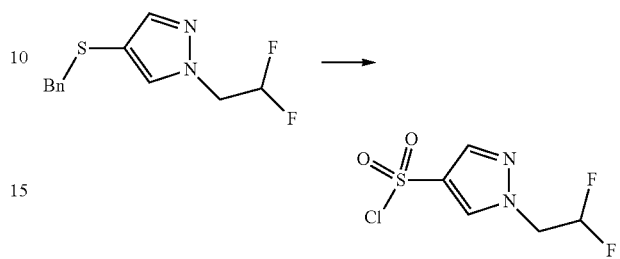

Into a 250-mL round-bottom flask was placed 4-(benzylsulfanyl)-1-(2,2-difluoroethyl)pyrazole (14.40 g, 56.63 mmol, 1.00 eq.), HOAc (180.00 mL), and H$_2$O (20.00 mL). This was followed by the addition of NCS (22.68 g, 169.85 mmol, 3.00 eq.), at 0° C. and the resulting solution was stirred for 1 h at room temperature, then it was concentrated. The residue was applied onto a silica gel column and eluted with THF/PE (10%). This resulted in 11 g (84.24%) of 1-(2,2-difluoroethyl)pyrazole-4-sulfonyl chloride as a yellow oil. LCMS (ES) [M−Cl+OH−1]$^−$ m/z: 211.

Step 4

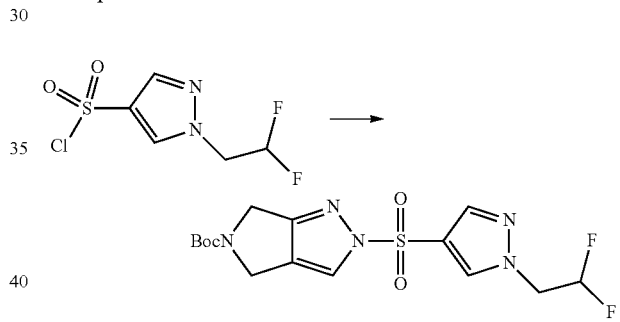

Into a 250-mL 3-necked round-bottom flask, was placed tert-butyl 2H,4H,6H-pyrrolo[3,4-c]pyrazole-5-carboxylate (11.00 g, 52.57 mmol, 1.00 eq.) in THF (180.00 mL) followed by the addition of NaH (1.64 g, 68.34 mmol, 1.30 eq.), at 0° C. To this was then added 1-(2,2-difluoroethyl)pyrazole-4-sulfonyl chloride (13.34 g, 57.85 mmol, 1.10 eq.) dropwise with stirring at 0° C. and the resulting solution was stirred for 1 h at 0° C. The reaction was then quenched by the addition of 5 mL of HOAc and extracted with 3×200 mL of dichloromethane. The organic layers were combined, dried over anhydrous sodium sulfate, and concentrated. The residue was diluted with 200 mL of MTBE and the solids were collected by filtration. This resulted in 15.3 g (72.15%) of tert-butyl 2-[1-(2,2-difluoroethyl)pyrazol-4-ylsulfonyl]-4H,6H-pyrrolo[3,4-c]pyrazole-5-carboxylate as a white solid. LCMS (ES) [M+1]$^+$ m/z: 404.

Step 5

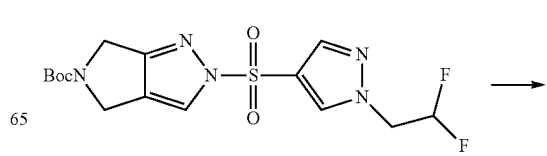

-continued

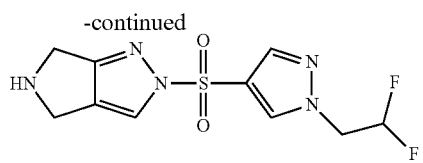

Into a 250-mL round-bottom flask, was placed tert-butyl 2-[1-(2,2-difluoroethyl)pyrazol-4-ylsulfonyl]-4H,6H-pyrrolo[3,4-c]pyrazole-5-carboxylate (15.30 g, 37.93 mmol, 1.00 eq.), DCM (200.00 mL), and lutidine (16.26 g, 151.71 mmol, 4.00 eq.) followed by the addition of TMSOTf (25.29 g, 113.78 mmol, 3.00 eq.) dropwise with stirring at 0° C. The resulting solution was stirred for 1 h at 0° C., then it was quenched by the addition of water/ice. The resulting mixture was concentrated and the crude product (30 g) was purified by Prep-HPLC with the following conditions: Column, XBridge Prep C18 OBD Column, 19 cm, 150 mm, 5 um; mobile phase, Water (0.1% FA) and CAN (5% Phase B up to 20% in 11 min); Detector, 254. This resulted in the title compound (Intermediate-7) (10 g, 86.9%) as a white solid. LCMS (ES) [M+1]$^+$ m/z: 304.

Example 1.2

Synthesis of (2R,3S)-2-(2-chlorophenyl)-3-hydroxybutanoic acid, (2S,3R)-2-(2-chlorophenyl)-3-hydroxybutanoic acid, (2R,3R)-2-(2-chlorophenyl)-3-hydroxybutanoic acid, and (2S,3S)-2-(2-chlorophenyl)-3-hydroxybutanoic acid (Intermediate II-9)

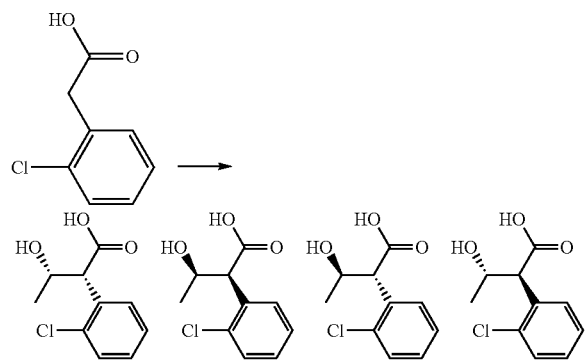

Into a 250-mL 3-necked round-bottom flask purged and maintained in a nitrogen atmosphere at room temperature, was placed (2-chlorophenyl)acetic acid (5.00 g, 29.31 mmol, 1.0 eq.) in THF (50 mL). The reaction was cooled to −78° C., and a solution of LDA (4.3 mL, 32.24 mmol, 1.1 eq.) was added dropwise and the reaction was stirred for 2 h at −78° C. A solution of acetaldehyde (2.58 g, 58.62 mmol, 2.0 eq.) was then added dropwise and the resulting solution was stirred for 2 h allowing it to warm from −78° C. to 0° C. The reaction mixture was then quenched with saturated NH$_4$Cl (20 mL), extracted with EtOAc (50 mL×3), dried, and concentrated. The residue was pre-purified by silica gel column chromatography, followed by separation by Pre CHIRAL_HPLC with the following conditions: Column: Lux Amylose-1, 50*250 mm, 10 um; Mobile phase: A=n-Hexanes, B=Ethanol; Flow rate: 90 mL/min; Gradient: 50% B in 50 min; 220 nm. This resulted in the following four products:

The 1$^{st}$ fraction with Retention time=1.894 min in ANAL_SFC: (500 mg, 7.95%); LCMS (ES) [M−1]$^-$ m/z: 213. This material was assigned as Intermediate II-9a The 2$^{nd}$ fraction with Retention time=1.944 min in ANAL_SFC: (500 mg, 7.95%); LCMS (ES) [M−1]$^-$ m/z: 213. This material was assigned as Intermediate II-9c The 3$^{rd}$ fraction with Retention time=2.082 min in ANAL_SFC: (500 mg, 7.95%); LCMS (ES) [M−1]$^-$ m/z: 213. This material was assigned as Intermediate II-9b The 4$^{th}$ fraction with Retention time=2.440 min in ANAL_SFC: (500 mg, 7.95%); LCMS (ES) [M−1]$^-$ m/z: 213. This material was assigned as Intermediate II-9d Example 1.3

Synthesis of (S)-2-(2-fluorophenyl)-3-hydroxypropanoic acid (Intermediate II-10)

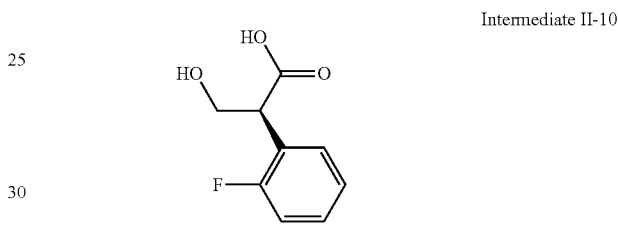

Step 1

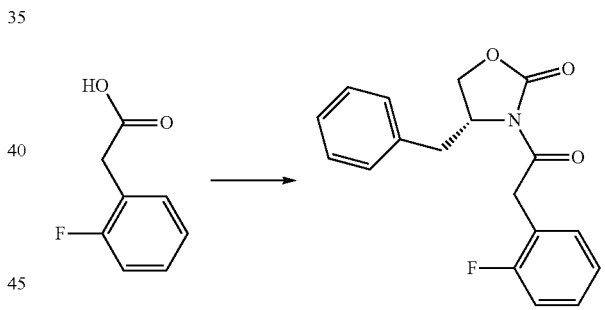

Into a 250-mL 3-necked round-bottom flask purged and maintained in an atmosphere of nitrogen at room temperature, was placed (4R)-4-benzyl-1,3-oxazolidin-2-one (10.00 g, 56.43 mmol, 1.0 eq.) in THF (100 mL). The mixture was cooled to −78° C., and a solution of n-BuLi in hexanes (25.0 mL, 263.27 mmol, 4.6 eq.) was added drop wise. After the reaction was stirred at −78° C. for 1 h, another solution of (2-fluorophenyl)acetyl chloride (10.71 g, 62.07 mmol, 1.1 eq.) in THF (20 mL) was added. The resulting solution was stirred for 2 h and allowed to warm from −78° C. to 0° C. The reaction was then quenched by the addition of 50 mL of saturated NH$_4$Cl. The resulting solution was extracted with 3×80 mL of ethyl acetate, dried over anhydrous sodium sulfate, and concentrated. The residue was applied onto a silica gel column and eluted with ethyl acetate/petroleum ether (1:50 to 1:5). This resulted in 12.5 g (70.69%) of (4R)-4-benzyl-3-[2-(2-fluorophenyl)acetyl]-1,3-oxazolidin-2-one as an off-white solid. LCMS (ES) [M+1]$^+$ m/z: 314.

Step 2

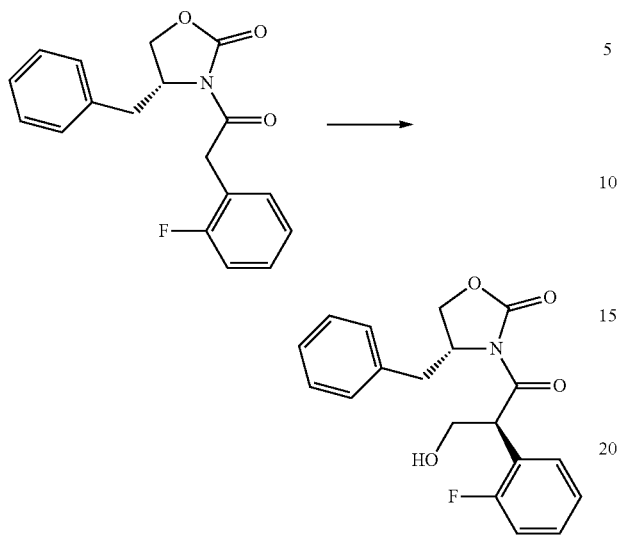

Into a 100 mL 3-necked round-bottom flask purged and maintained in an atmosphere of nitrogen at room temperature, was placed (4R)-4-benzyl-3-[2-(2-fluorophenyl)acetyl]-1,3-oxazolidin-2 one (2.50 g, 7.98 mmol, 1.0 eq.) and DCM (30 mL). After the reaction was cooled to 0° C., a solution of TiCl$_4$ (1.66 g, 8.78 mmol, 1.1 eq.) in DCM (5 mL) was added dropwise. The reaction was stirred for 5 min, DIEA (1.13 g, 8.78 mmol, 1.1 eq.) was added, and the mixture was stirred at 0° C. for 1 h. Then 1,3,5-trioxane (0.86 g, 9.57 mmol, 1.2 eq.) and TiCl$_4$ (1.66 g, 8.78 mmol, 1.1 eq.) were added. The resulting solution was stirred for another 2 h at 0° C. then it was quenched with saturated NH$_4$Cl (10 mL). The mixture was extracted with DCM (50 mL×3) and the combined organic layers were dried and concentrated. The residue was purified by silica gel column chromatography (PE/EA=100:1 to 1:1) to give (4R)-4-benzyl-3-[(2S)-2-(2-fluorophenyl)-3-hydroxypropanoyl]-1,3-oxazolidin-2-one (2 g, 73.00%) as a yellow gum. LCMS (ES) [M+1]$^+$ m/z: 344.

Step 3

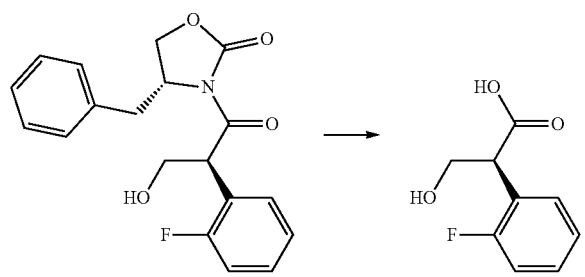 [SMILES: O=C1OC[C@@H](Cc2ccccc2)N1C(=O)[C@H](CO)c1ccccc1F ; O=C(O)[C@H](CO)c1ccccc1F]

Into a 100 mL round-bottom flask, was placed (4R)-4-benzyl-3-[(2S)-2-(2-fluorophenyl)-3-hydroxypropanoyl]-1,3-oxazolidin-2-one (2.00 g, 5.83 mmol, 1.0 eq.) and THF (8 mL) After the reaction was cooled to 0° C., a solution of LiOH.H$_2$O (0.49 g, 11.65 mmol, 2.0 eq.) in H$_2$O (2 mL) and H$_2$O$_2$ (30%) (0.99 g, 29.12 mmol, 5.0 eq.) was added dropwise. The reaction was stirred at 0° C. for 2 h then it was quenched with saturated Na$_2$SO$_3$ (10 mL) and extracted with DCM (50 mL×5). The aqueous mixture was adjusted with HCl (5 N) to pH=3, extracted with 5×30 mL of DCM, dried over anhydrous sodium sulfate, and concentrated. The residue was purified by prep. HPLC (C18 silica gel column with Phase A: Water/0.05% TFA, Mobile Phase B: ACN; Flow rate: 1.5 mL/min; Gradient: 5% B to 100% B in 1.2 min, hold 0.6 min). This resulted in (2S)-2-(2-fluorophenyl)-3-hydroxypropanoic acid (0.4 g, 37.29%) as a yellow solid.

CHIRAL_HPLC: Retention time 0.716 min. $^1$H-NMR: (300 MHz, DMSO-d$_6$, ppm): δ 12.5 (br, 1H), 7.42-7.28 (m, 2H), 7.21-7.15 (m, 2H), 4.95 (br, 1H), 3.98-3.90 (m, 2H), 3.69-3.61 (m, 1H); LCMS (ES) [M−1]$^-$ m/z: 183.0; Retention time 0.716 min.

Example 1.4

Synthesis of (S)-2-(2-fluorophenyl)-3-hydroxypropanoic acid (Intermediate II-11)

Intermediate II-11

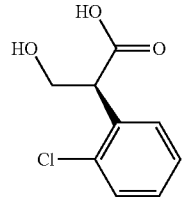

Step 1

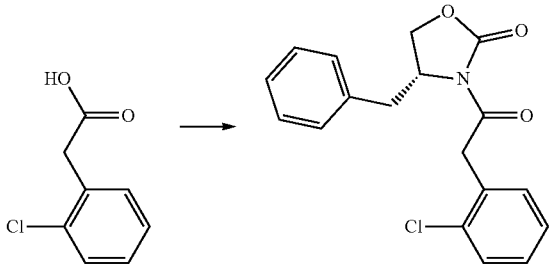 [SMILES: O=C(O)Cc1ccccc1Cl ; O=C(Cc1ccccc1Cl)N1C(=O)OC[C@H]1Cc1ccccc1]

Into a 100-mL 3-necked round-bottom flask purged and maintained in an atmosphere of nitrogen at room temperature, was placed (4R)-4-benzyl-1,3-oxazolidin-2-one (1.00 g, 5.64 mmol, 1.00 eq.) in THF (15.00 mL) and the mixture was cooled to −78° C. This was followed by the addition of n-butyllithium in hexanes (2.48 mL, 6.20 mmol, 1.10 eq.) dropwise with stirring at −78° C. After 1 h, (2-chlorophenyl)acetyl chloride (1.60 g, 8.46 mmol, 1.50 eq.) was added dropwise with stirring at −78° C. After 1 h the reaction was quenched by the addition of 3 mL of Sat. NH$_4$Cl cooled to room temperature, extracted with 3×20 mL of ethyl acetate and the organic layers were combined, dried over anhydrous sodium sulfate, and concentrated. The residue was applied onto a silica gel column and eluted with THF/PE (10.6%). This resulted in 1 g (53.73%) of (4R)-4-benzyl-3-[2-(2-chlorophenyl)acetyl]-1,3-oxazolidin-2-one as a yellow oil. LCMS (ES) [M+1]$^+$ m/z: 330.

Step 2

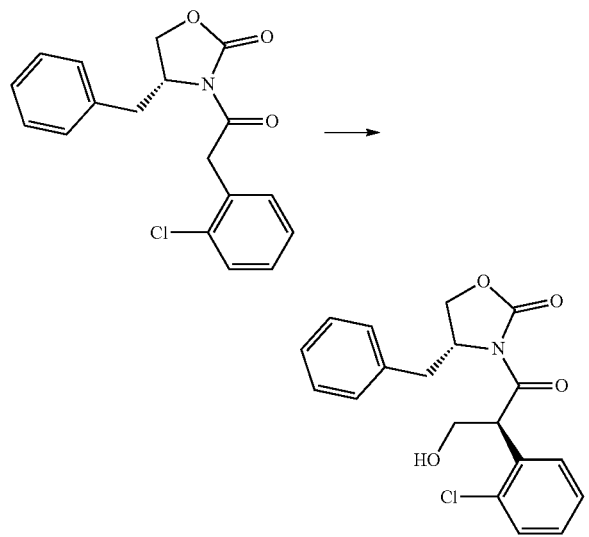

Into a 100-mL 3-necked round-bottom flask, was placed (4R)-4-benzyl-3-[2-(2-chlorophenyl)acetyl]-1,3-oxazolidin-2-one (1.00 g, 3.03 mmol, 1.00 eq.) and DCM (20.00 mL). This was followed by the addition of a solution of TiCl$_4$ (0.63 g, 3.34 mmol, 1.10 eq.) in DCM (2.00 mL) dropwise with stirring at 0° C. After 5 min, DIEA (0.45 g, 3.48 mmol, 1.15 eq.) was added dropwise with stirring at 0° C. and the resulting solution was stirred for 30 min at 0° C. A solution of trioxane (0.30 g, 3.34 mmol, 1.10 eq.) in DCM (2.00 mL) was then added dropwise with stirring at 0° C. After 5 min, a solution of TiCl$_4$ (0.63 g, 3.34 mmol, 1.10 eq.) in DCM (2.00 mL) was added dropwise with stirring at 0° C. and the resulting solution was stirred for 1 h at 0° C. The reaction was then quenched by the addition of 5 mL of Sat. NH$_4$Cl, extracted with 3×20 mL of dichloromethane. The combined organic layers were combined, washed with 20 ml of Sat. NaHCO$_3$, dried over anhydrous sodium sulfate, and concentrated. This resulted in 0.8 g (73.32%) of (4R)-4-benzyl-3-[(2S)-2-(2-chlorophenyl)-3-hydroxypropanoyl]-1,3-oxazolidin-2-one as a yellow oil. LCMS (ES) [M+1]$^+$ m/z: 360.

Step 3

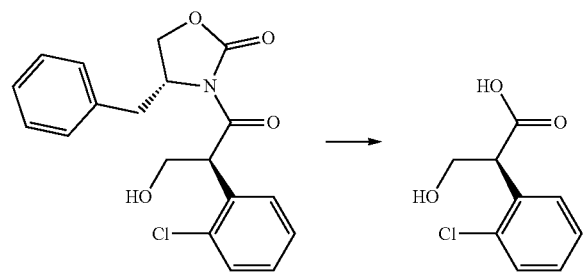 [SMILES: O=C1OC[C@@H](Cc2ccccc2)N1C(=O)[C@H](CO)c1ccccc1Cl ; O=C(O)[C@H](CO)c1ccccc1Cl]

Into a 100-mL 3-necked round-bottom flask, was placed (4R)-4-benzyl-3-[(2S)-2-(2-chlorophenyl)-3-hydroxypropanoyl]-1,3-oxazolidin-2-one (0.80 g, 2.22 mmol, 1.00 eq.) in THF (9.00 mL) and H$_2$O (2.00 mL). This was followed by the addition of a solution of H$_2$O$_2$ (0.38 g, 11.12 mmol, 5.00 eq.) in water (1 mL) dropwise with stirring at 0° C., followed by the addition of a solution of LiOH H$_2$O (0.19 g, 4.45 mmol, 2.00 eq.) in water (1 mL) dropwise with stirring at 0° C. The resulting solution was stirred for 2 h at 0° C. then it was quenched by the addition of 3 mL of Sat. NaSO$_3$. The resulting solution was extracted with 2×10 mL of dichloromethane and the aqueous layers were combined. The pH value of the solution was adjusted to 3 with HCl (1 mol/L) and extracted with 3×20 mL of DCM/MeOH=10/1. The organic layers were combined, dried over anhydrous sodium sulfate, and concentrated. The crude product (0.5 g) was purified by Prep-HPLC with the following conditions: Column, XBridge Prep C18 OBD Column, 19 cm, 150 mm, 5 um; mobile phase, Water (FA) and CAN (5% Phase B up to 30% in 11 min); Detector, 254. This resulted in 170 mg (38.11%) of (2S)-2-(2-chlorophenyl)-3-hydroxypropanoic acid as an off-white solid. LCMS (ES) [M−1]$^+$ m/z: 199.

Example 1.5

Synthesis of (2S)-1-(2-{[1-(2,2-difluoroethyl)-1H-pyrazol-4-yl]sulfonyl}-2H,4H,5H,6H-pyrrolo[3,4-c]pyrazol-5-yl)-3-hydroxy-2-phenylpropan-1-one (Compound 1)

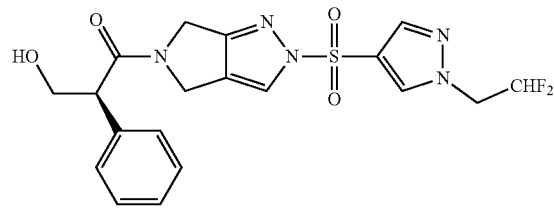

Into a 250-mL 3-necked round-bottom flask, was placed (S)-tropic acid (3.50 g, 21.06 mmol, 1.00 eq.), 1-(2,2-difluoroethyl)-4-{2H,4H,5H,6H-pyrrolo[3,4-c]pyrazole-2-sulfonyl}-1H-pyrazole (Intermediate I-7, 6.39 g, 21.06 mmol, 1.00 eq.), DMF (50.00 mL), and NMM (4.26 g, 42.12 mmol, 2.00 eq.). This was followed by the addition of HATU (9.61 g, 25.27 mmol, 1.20 eq.), in portions at 0° C. The resulting solution was stirred for 2 h at room temperature. The crude product (10 g) was purified by Prep-HPLC with the following conditions: Column, Sunfire Prep C18 OBD Column, 50*250 mm 5 um 10 nm; mobile phase, Water (0.1% FA), and ACN (15% PhaseB up to 50% in 15 min); Detector, 254. This resulted in 5.7 g (59.95%) of (2S)-1-[2-[1-(2,2-difluoroethyl)pyrazol-4-ylsulfonyl]-4H,6H-pyrrolo[3,4-c]pyrazol-5-yl]-3-hydroxy-2-phenylpropan-1-one as a white solid. $^1$H-NMR: (300 MHz, DMSO-d$_6$, ppm): δ 8.70 (d, J=1.9 Hz, 1H), 8.17 (s, 1H), 8.11 (s, 1H), 7.41-7.18 (m, 5H), 6.41 (tt, J=54.5, 3.6 Hz, 1H), 4.96-4.65 (m, 4H), 4.56-4.26 (m, 3H), 4.07-3.93 (m, 2H), 3.59-3.47 (m, 1H). LCMS13-PH-MY-PK-440-0: (ES, m/z): [M+H]$^+$: 452.

Example 1.6

Synthesis of (2S)-1-(2-{[1-(2,2-difluoroethyl)-1H-pyrazol-4-yl]sulfonyl}-2H,4H,5H,6H-pyrrolo[3,4-c]pyrazol-5-yl)-2-(2-fluorophenyl)-3-hydroxypropan-1-one (Compound 2)

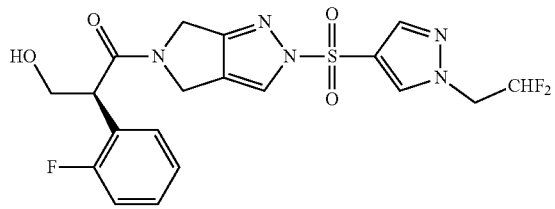 [SMILES: O=C([C@H](CO)c1ccccc1F)N1Cc2cn(S(=O)(=O)c3cnn(CC(F)F)c3)nc2C1]

Into a 20-mL vail, was placed (S)-2-(2-fluorophenyl)-3-hydroxypropanoic acid (Intermediate II-10; 100 mg, 0.54 mmol, 1.00 eq.), DMF (5.00 mL), 1-(2,2-difluoroethyl)-4-{2H,4H,5H,6H-pyrrolo[3,4-c]pyrazole-2-sulfonyl}-1H-pyrazole (Intermediate I-7, 182 mg, 0.65 mmol, 1.20 eq.), and NMM (0.18 mL, 0.65 mmol, 3.00 eq.) followed by the addition of HATU (251 mg, 0.65 mmol, 1.20 eq.) at 0° C. The resulting solution was stirred for 1 h at the same temperature. The reaction solution was then directly purified by Prep-HPLC (Sunfire Prep C18 OBD Column, 50*250 mm, 5 um 10 nm, Mobile Phase A: Water (0.1% FA), Mobile Phase B: CH$_3$CN, Flow rate: 90 mL/min, Gradient: 5% B to 35% B in 15 min, Detector, 220 nm) to provide the title compound as a white solid (137.0 mg, 54%). $^1$H-NMR: (300 MHz, DMSO-d6, ppm): δ 8.71 (s, 1H), 8.19 (d, J=2.4 Hz, 1H), 8.12 (s, 1H), 7.43-7.28 (m, 2H), 7.24-7.14 (m, 2H), 6.61 (tt, J=54.3 Hz, 3.6 Hz, 1H), 4.96 (dd, J=22.5, 14.4 Hz, 1H), 4.77 (td, J=15.0, 3.6 Hz, 2H), 4.54-4.24 (m, 4H), 4.02 (t, J=9.0 Hz, 1H), 3.64-3.57 (m, 1H); LCMS: (ES, m/z): [M+H]$^+$: 470.

Example 1.7

Synthesis of (2S)-2-(2-fluorophenyl)-3-hydroxy-1-(2-{[1-(2,2,2-trifluoroethyl)-1H-pyrazol-4-yl]sulfonyl}-2H,4H,5H,6H-pyrrolo[3,4-c]pyrazol-5-yl)propan-1-one (Compound 3)

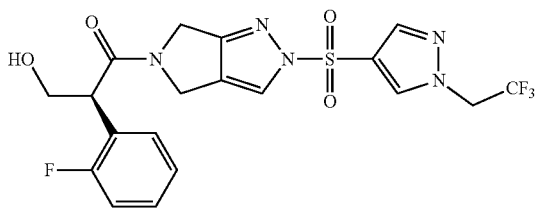 [SMILES: O=C([C@H](CO)c1ccccc1F)N1Cc2cn(S(=O)(=O)c3cnn(CC(F)(F)F)c3)nc2C1]

Step 1

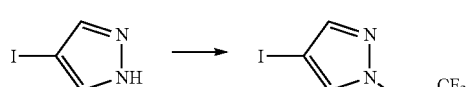

Into a 500-mL round-bottom flask, was placed 4-iodopyrazole (5.00 g, 25.78 mmol, 1.00 eq.), DMF (100 mL), 2,2,2-trifluoroethyl trifluoromethanesulfonate (7.48 g, 32.23 mmol, 1.25 eq.), and Cs$_2$CO$_3$ (16.80 g, 51.55 mmol, 2 eq.). The resulting solution was stirred for 2 h at 25° C. The reaction was then quenched by the addition of 100 mL of water, extracted with 3×200 mL of ethyl acetate, and the organic layers were combined, washed with 3×200 mL of brine, dried over anhydrous sodium sulfate, filtered and concentrated. The residue was applied onto a silica gel column and eluted with THF/petroleum ether (1:20). This resulted in 6.50 g (91.36%) of 4-iodo-1-(2,2,2-trifluoroethyl)pyrazole as light yellow oil. LCMS (ES) [M+1]$^+$ m/z 277.

Step 2

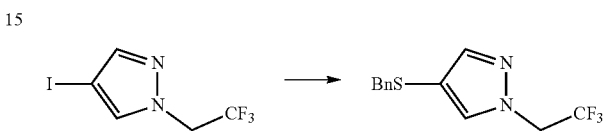

Into a 250-mL 3-necked round-bottom flask purged and maintained with an inert atmosphere of nitrogen, was placed 4-iodo-1-(2,2,2-trifluoroethyl)pyrazole (6.50 g, 23.55 mmol, 1.00 eq.), toluene (100 mL), DIEA (6.09 g, 47.10 mmol, 2.00 eq.), Pd$_2$(dba)$_3$ (2.16 g, 2.35 mmol, 0.10 eq.), XantPhos (2.73 g, 4.72 mmol, 0.20 eq.), and benzyl mercaptan (8.77 g, 70.65 mmol, 3.00 eq.), and the resulting solution was stirred overnight at 100° C. The resulting mixture was then concentrated under vacuum and the residue was applied onto a silica gel column and eluted with ethyl acetate/petroleum ether (1:10). This resulted in 5.00 g (77.97%) of 4-(benzylsulfanyl)-1-(2,2,2-trifluoroethyl)pyrazole as a yellow oil. LCMS (ES) [M+1]$^+$ m/z 273.

Step 3

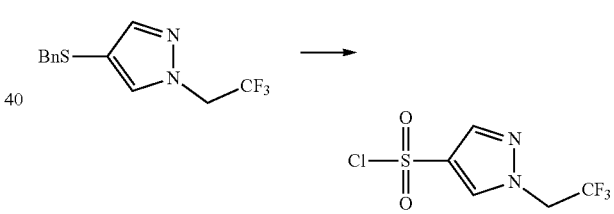

Into a 250-mL round-bottom flask, was placed 4-(benzylsulfanyl)-1-(2,2,2-trifluoroethyl)pyrazole (5.00 g, 18.36 mmol, 1.00 eq.), HOAc (45 mL), H$_2$O (5 mL), and NCS (9.81 g, 73.46 mmol, 4.00 eq.) and the resulting solution was stirred for 4 h at 25° C. The resulting mixture was then concentrated under vacuum and the residue was applied onto a silica gel column and eluted with ethyl acetate/petroleum ether (1:5). This resulted in 4.00 g (87.62%) of 1-(2,2,2-trifluoroethyl)pyrazole-4-sulfonyl chloride as a yellow oil.

Step 4

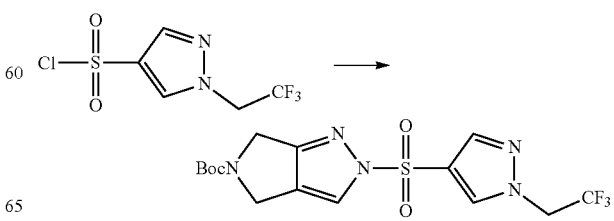

Into a 100-mL 3-necked round-bottom flask was placed t-butyl 2H,4H,6H-pyrrolo[3,4-c]pyrazole-5-carboxylate (3.37 g, 16.09 mmol, 1.00 eq.), and THF (50 mL), followed by the addition of NaH (0.77 g, 19.31 mmol, 1.20 eq., 60%) at 0° C. The resulting solution was stirred for 30 min at 0° C., then 1-(2,2,2-trifluoroethyl)pyrazole-4-sulfonyl chloride (4 g, 16.09 mmol, 1.00 eq.) was added at 0° C. and the resulting solution was stirred for 1 h at 0° C. The reaction was then quenched by the addition of 50 mL of water, extracted with 3×100 mL of ethyl acetate, and the organic layers were combined, washed with 3×100 mL of brine, dried over anhydrous sodium sulfate, and concentrated under vacuum. The residue was applied onto a silica gel column and eluted with ethyl acetate/petroleum ether (1:3). The product was purified by Prep-SFC with the following conditions: Column: CHIRAL RT Cellulose-SC, 3*25 cm; Mobile Phase A: $CO_2$, Mobile Phase B: MeOH—Preparative; Flow rate: 75 mL/min; Gradient: isocratic 15% B; Column Temperature: 35; Back Pressure (bar): 100; Wave Length: 220 nm; RT1 (min): 3.6; RT2 (min): 4.4; Sample Solvent: MeOH:DCM=1:1; Injection Volume: 1 mL; This resulted in 2.20 g (32.45%) of t-butyl 2-[1-(2,2,2-trifluoroethyl)pyrazol-4-ylsulfonyl]-4H,6H-pyrrolo[3,4-c]pyrazole-5-carboxylate as a white solid. LCMS (ES) [M+1]$^+$ m/z 422.

Step 5

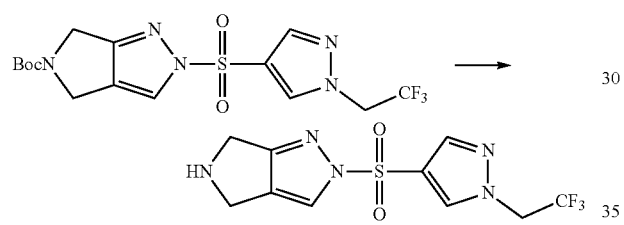

Into a 100-mL round-bottom flask, was placed t-butyl 2-[1-(2,2,2-trifluoroethyl)pyrazol-4-ylsulfonyl]-4H,6H-pyrrolo[3,4-c]pyrazole-5-carboxylate (2.20 g, 5.22 mmol, 1.00 eq.), DCM (10 mL), and lutidine (2.24 g, 20.90 mmol, 4.00 eq.) followed by the addition of trimethylsilyl triflate (3.48 g, 15.66 mmol, 3.00 eq.) at 0° C. and the resulting solution was stirred for 2 h at 0° C. The reaction was then quenched by the addition of 1 mL of MeOH and concentrated under vacuum. The residue was applied onto a silica gel column and eluted with ethyl acetate/petroleum ether (20:1). This resulted in the title compound (Intermediate I-10, 1.65 g, 98.4%) as an off-white solid. LCMS (ES) [M+1]$^+$ m/z 322.

Step 6

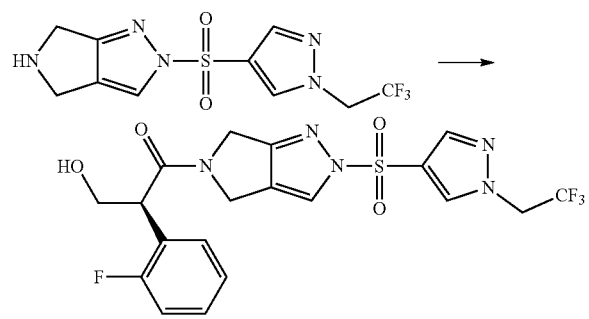

Into a 50-mL round-bottom flask, was placed (2S)-2-(2-fluorophenyl)-3-hydroxypropanoic acid (Intermediate II-10; 75 mg, 0.41 mmol, 1.00 eq.), DMF (5 mL), 4-{2H,4H,5H,6H-pyrrolo[3,4-c]pyrazole-2-sulfonyl}-1-(2,2,2-trifluoroethyl)-1H-pyrazole (144 mg, 0.45 mmol, 1.10 eq.), and NMM (82 mg, 0.81 mmol, 2.00 eq.) followed by the addition of HATU (186 mg, 0.49 mmol, 1.20 eq.) at 0° C. The resulting solution was stirred for 1 h at 25° C. The crude product was purified by Prep-HPLC with the following conditions (Prep-HPLC-001): Column, Sunfire Prep C18 OBD Column, 50*250 mm, 5 m 10 nm; mobile phase, Water and ACN (15% Phase B up to 50% in 15 min); Detector, uv. 254 nm. This resulted in the title compounds as a white solid (135.1 mg, 68.1%). $^1$H NMR (400 MHz, DMSO-d$_6$) δ 8.79 (s, 1H), 8.21-8.14 (m, 2H), 7.39 (t, J=7.7 Hz, 1H), 7.35-7.27 (m, 1H), 7.23-7.13 (m, 2H), 5.22 (q, J=8.9 Hz, 2H), 4.96-4.82 (m, 2H), 4.56-4.35 (m, 2H), 4.35-4.22 (m, 2H), 3.99 (t, J=9.2 Hz, 1H), 3.67-3.57 (m, 1H); LCMS (ES) [M+1]$^+$ m/z 488. CHIRAL HPLC: Retention time 5.566 min.

Example 1.8

Synthesis of (2R)-1-(2-{[1-(2,2-difluoroethyl)-1H-pyrazol-4-yl]sulfonyl}-2H,4H,5H,6H-pyrrolo[3,4-c]pyrazol-5-yl)-2-hydroxy-2-phenylethan-1-one (Compound 4)

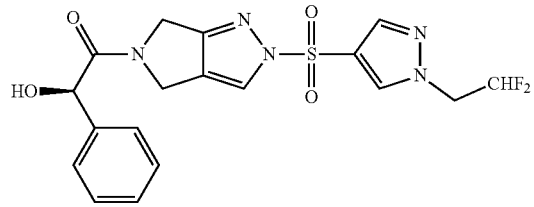 [SMILES: O=C([C@H](O)c1ccccc1)N1Cc2cn(S(=O)(=O)c3cnn(CC(F)F)c3)nc2C1]

Into a 20-mL vial, was placed (R)-mandelic acid (70.00 mg, 0.46 mmol, 1.00 eq.), 1-(2,2-difluoroethyl)-4-{2H,4H,5H,6H-pyrrolo[3,4-c]pyrazole-2-sulfonyl}-1H-pyrazole (Intermediate I-7, 139.54 mg, 0.46 mmol, 1.00 eq.), DMF (5.00 mL), and NMM (93.07 mg, 0.92 mmol, 2.00 eq.), followed by the addition of HATU (209.92 mg, 0.55 mmol, 1.20 eq.), in portions at 0° C. The resulting solution was stirred for 1 h at room temperature. The crude product (300 mg) was purified by Prep-HPLC (Column, Sunfire Prep C18 OBD Column, 50*250 mm 5 um 10 nm; mobile phase, Water (0.1% FA) and ACN (15% Phase B up to 50% in 15 min)) to provide the title compound as white solid (106.5 mg, 52.9%). $^1$H-NMR: (300 MHz, DMSO-d$_6$, ppm): δ 8.71 (d, J=2.2 Hz, 1H), 8.20-8.14 (m, 1H), 8.11 (s, 1H), 7.47-7.23 (m, 5H), 6.42 (tt, J=54.5, 3.6 Hz, 1H), 5.32 (d, J=4.9 Hz, 1H), 4.83-4.72 (m, 1H), 4.69 (ddd, J=15.4, 3.6, 1.6 Hz, 2H), 4.60-4.24 (m, 3H); LCMS (ES, m/z): [M+H]$^+$: 438.

Example 1.9

Synthesis of (2S)-1-(2-{[1-(2-fluoroethyl)-1H-pyrazol-4-yl]sulfonyl}-2H,4H,5H,6H-pyrrolo[3,4-c]pyrazol-5-yl)-2-(2-fluorophenyl)-3-hydroxypropan-1-one (Compound 5)

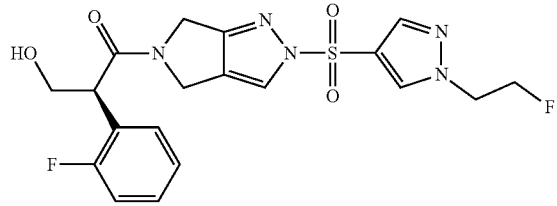

Step 1

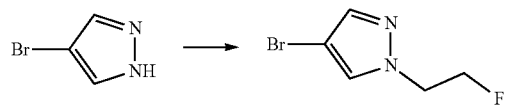

Into a 100-mL round-bottom flask, was placed 4-bromopyrazole (1.50 g, 10.206 mmol, 1.00 eq.), ethane, 1-fluoro-2-iodo- (2.66 g, 15.291 mmol, 1.50 eq.), $Cs_2CO_3$ (6.65 g, 20.412 mmol, 2 eq.), and DMF (30.00 mL) and the resulting solution was stirred for 8 h at room temperature. The reaction mixture was then extracted with 3×50 mL of dichloromethane and the organic layers were combined, dried over anhydrous sodium sulfate and concentrated under vacuum. The residue was applied onto a silica gel column and eluted with THF/PE (1:4). This resulted in 1.5 g (76.15%) of 4-bromo-1-(2-fluoroethyl)pyrazole as an off-white solid. LCMS (ES) [M+1]+ m/z: 193.

Step 2

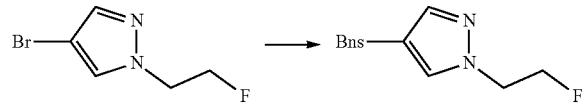

Into a 100-mL round-bottom flask, was placed 4-bromo-1-(2-fluoroethyl)pyrazole (1.50 g, 7.771 mmol, 1.00 eq.), benzyl mercaptan (1.93 g, 15.539 mmol, 2.00 eq.), XantPhos (0.45 g, 0.777 mmol, 0.1 eq.), $Pd_2(dba)_3$ (1.42 g, 1.554 mmol, 0.2 eq.), DIEA (2.01 g, 15.543 mmol, 2 eq.), and dioxane (30.00 mL), and the resulting solution was stirred for 24 h at 100° C. The reaction mixture was then cooled to room temperature. The residue was applied onto a silica gel column and eluted with THF:PE (1:3). This resulted in 1.3 g (70.79%) of 4-(benzylsulfanyl)-1-(2-fluoroethyl)pyrazole as a light yellow oil. LCMS (ES) [M+1]+ m/z: 237.

Step 3

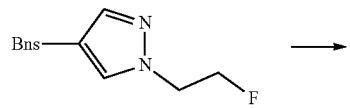

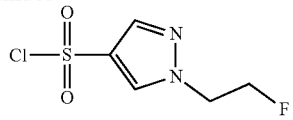

Into a 100-mL round-bottom flask, was placed 4-(benzylsulfanyl)-1-(2-fluoroethyl)pyrazole (1.30 g, 5.501 mmol, 1.00 eq.), NCS (2.20 g, 16.503 mmol, 3.00 eq.), HOAc (27.00 mL), and $H_2O$ (3.00 mL) and the resulting solution was stirred for 6 h at room temperature. The mixture was then extracted with 3×30 mL of dichloromethane and the organic layers were combined, dried over anhydrous sodium sulfate, and concentrated under vacuum. The residue was applied onto a silica gel column and eluted with ethyl acetate/petroleum ether (1:3). This resulted in 630 mg (53.86%) of 1-(2-fluoroethyl)pyrazole-4-sulfonyl chloride as a light yellow oil.

Step 4

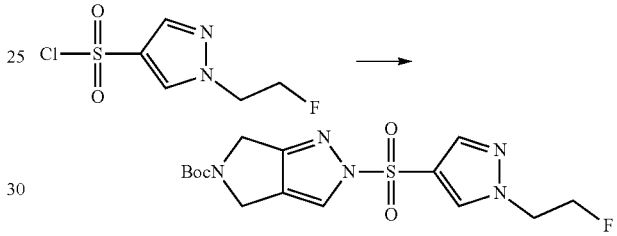

Into a 100-mL round-bottom flask, was placed 1-(2-fluoroethyl)pyrazole-4-sulfonyl chloride (630.00 mg, 2.963 mmol, 1.00 eq.), t-butyl 2H,4H,6H-pyrrolo[3,4-c]pyrazole-5-carboxylate (682.01 mg, 3.259 mmol, 1.1 eq.), NaH (106.66 mg, 4.445 mmol, 1.50 eq.), and THF (20.00 mL) and the resulting mixture was stirred for 4 h at room temperature. The reaction was then quenched by the addition of water, extracted with 3×30 mL of dichloromethane and the organic layers were combined, dried over anhydrous sodium sulfate, and concentrated under vacuum. The residue was applied onto a silica gel column and eluted with ethyl acetate/petroleum ether (1:3). This resulted in 750 mg (65.68%) of t-butyl 2-[1-(2-fluoroethyl)pyrazol-4-ylsulfonyl]-4H,6H-pyrrolo[3,4-c]pyrazole-5-carboxylate as an off-white solid. LCMS (ES) [M+1]+ m/z: 386.

Step 5

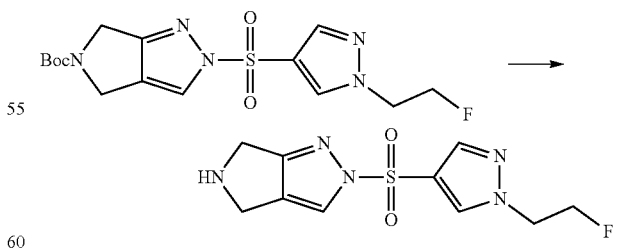

Into a 100-mL round-bottom flask, was placed t-butyl 2-[1-(2-fluoroethyl)pyrazol-4-ylsulfonyl]-4H,6H-pyrrolo[3,4-c]pyrazole-5-carboxylate (750.00 mg, 1.946 mmol, 1.00 eq.), TMSOTf (1.30 g, 5.849 mmol, 3.01 eq.), and 2,6-dimethylpyridine (834.07 mg, 7.784 mmol, 4.00 eq.) and the resulting mixture was stirred for 4 h at room temperature.

The reaction was then quenched by the addition of 30 mL of water and concentrated under vacuum. The resulting mixture was washed with 5×30 mL of H₂O and the solids were collected by filtration. This resulted in 1-(2-fluoroethyl)-4-{2H,4H,5H,6H-pyrrolo[3,4-c]pyrazole-2-sulfonyl}-1H-pyrazole as a white solid (290 mg, 52.23). LCMS (ES) [M+1]⁺ m/z: 286.

Step 6

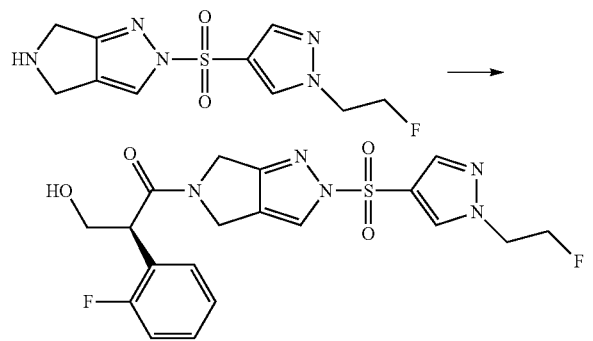

Into a 50-mL round-bottom flask, was placed 1-(2-fluoroethyl)-4-{2H,4H,5H,6H-pyrrolo[3,4-c]pyrazole-2-sulfonyl}-1H-pyrazole (130.00 mg, 0.456 mmol, 1.00 eq.), (2S)-2-(2-fluorophenyl)-3-hydroxypropanoic acid (Intermediate II-10; 100.70 mg, 0.547 mmol, 1.20 eq.), HATU (259.88 mg, 0.683 mmol, 1.5 eq.), DIEA (117.78 mg, 0.911 mmol, 2 eq.), and DMF (20.00 mL) and the resulting solution was stirred for 4 h at room temperature. The mixture was then extracted with 3×30 mL of dichloromethane and the organic layers were combined, dried over anhydrous sodium sulfate, and concentrated under vacuum. The crude product was purified by Prep-HPLC (Column: Sunfire Prep C18 OBD Column, 50*250 mm, 5 m 10 nm; Mobile Phase A: Water (0.1% FA), Mobile Phase B: ACN; Flow rate: 90 mL/min; Gradient: 15% B to 50% B in 12 min, 50% B; Wave Length: 220 nm to provide the title compound as a white solid (130.9 mg, 63.63%). ¹H NMR (300 MHz, DMSO-d₆) δ 8.71 (s, 1H), 8.17 (d, J=2.3 Hz, 1H), 8.07 (s, 1H), 7.45-7.35 (m, 1H), 7.30 (dd, J=7.9, 6.1 Hz, 1H), 7.25-7.11 (m, 2H), 4.99-4.81 (m, 2H), 4.70 (t, J=4.7 Hz, 1H), 4.55 (t, J=4.8 Hz, 1H), 4.51-4.41 (m, 2H), 4.37 (d, J=16.6 Hz, 1H), 4.33-4.21 (m, 2H), 4.02-3.96 (m, 1H), 3.60 (dt, J=11.0, 5.8 Hz, 1H). LCMS (ES) [M+1]⁺ m/z: 452.

Example 1.10

Synthesis of (2S,3S)-1-(2-{[1-(2,2-difluoroethyl)-1H-pyrazol-4-yl]sulfonyl}-2H,4H,5H,6H-pyrrolo[3,4-c]pyrazol-5-yl)-3-hydroxy-2-phenylbutan-1-one (Compound 6)

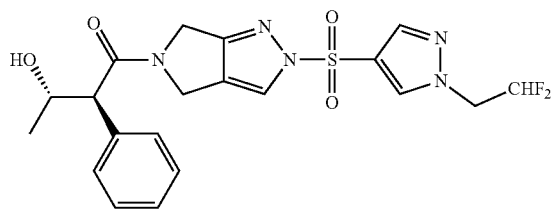

To a solution of (2S,3S)-3-hydroxy-2-phenylbutanoic acid (synthesized as described for Intermediate II-10 using acetaldehyde instead of 1,3,5-trioxane in step 2; 60.00 mg, 0.333 mmol, 1.00 eq.), NMM (67.36 mg, 0.666 mmol, 2.00 eq.), and 1-(2,2-difluoroethyl)-4-[4H,5H,6H-pyrrolo[3,4-c]pyrazole-2-sulfonyl]pyrazole (Intermediate I-7; 100.98 mg, 0.333 mmol, 1.00 eq.) in DMF (2.00 mL, 12.922 mmol, 38.81 eq.) was added HATU (139.26 mg, 0.366 mmol, 1.10 eq.) in portions at 0° C. under a nitrogen atmosphere. The resulting mixture was stirred for 1 h at room temperature under a nitrogen atmosphere. The crude product was purified by Prep-HPLC with the following conditions (Prep-HPLC-001): Column, Sunfire Prep C18 OBD Column, 50*250 mm, 5 μm 10 nm; mobile phase, Water (0.1% FA), and ACN (18% Phase B up to 60% in 20 min); Detector, uv. 254 nm. to afford (2S,3S)-1-[2-[1-(2,2-difluoroethyl)pyrazol-4-ylsulfonyl]-4H,6H-pyrrolo[3,4-c]pyrazol-5-yl]-3-hydroxy-2-phenylbutan-1-one (103 mg, 66.46%) as a white solid. 1H NMR (300 MHz, DMSO-d6) δ 8.70 (s, 1H), 8.18 (d, J=8.5 Hz, 1H), 8.11 (s, 1H), 7.46-7.36 (m, 2H), 7.35-7.19 (m, 3H), 6.41 (tt, J=54.4, 3.6 Hz, 1H), 4.91 (t, J=13.5 Hz, 1H), 4.72 (td, J=15.1, 3.6 Hz, 2H), 4.57-4.17 (m, 4H), 3.70 (dd, J=9.1, 1.9 Hz, 1H), 0.86 (d, J=6.2 Hz, 3H); LCMS (ES) [M+1]+ m/z: 466.

Example 1.11

Synthesis of (2S,3R)-1-(2-{[1-(2,2-difluoroethyl)-1H-pyrazol-4-yl]sulfonyl}-2H,4H,5H,6H-pyrrolo[3,4-c]pyrazol-5-yl)-3-hydroxy-2-phenylbutan-1-one (Compound 7)

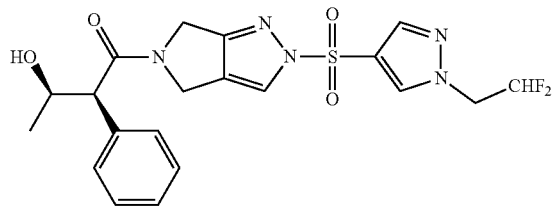

To a solution of (2S,3R)-3-hydroxy-2-phenylbutanoic acid (synthesized as described for Intermediate II-10 using acetaldehyde instead of 1,3,5-trioxane in step 2; 60.00 mg, 0.333 mmol, 1.00 eq.), NMM (67.36 mg, 0.666 mmol, 2.00 eq.) and 1-(2,2-difluoroethyl)-4-[4H,5H,6H-pyrrolo[3,4-c]pyrazole-2-sulfonyl]pyrazole (Intermediate I-7; 100.98 mg, 0.333 mmol, 1.00 eq.) in DMF (1.00 mL, 12.922 mmol, 38.81 eq.) was added HATU (139.26 mg, 0.366 mmol, 1.10 eq.) in portions at 0° C. under a nitrogen atmosphere. The resulting mixture was stirred for 1 h at room temperature under a nitrogen atmosphere. The crude product was purified by Prep-HPLC with the following conditions (Prep-HPLC-001): Column, Sunfire Prep C18 OBD Column, 50*250 mm, 5 m 10 nm; mobile phase, Water (0.1% FA) and ACN (15% PhaseB up to 60% in 20 min); Detector, uv. 254 nm. to afford (2S,3R)-1-[2-[1-(2,2-difluoroethyl)pyrazol-4-ylsulfonyl]-4H,6H-pyrrolo[3,4-c]pyrazol-5-yl]-3-hydroxy-2-phenylbutan-1-one (91 mg, 58.72%) as a white solid. ¹H NMR (300 MHz, DMSO-d₆) δ8.70 (s, 1H), 8.17 (s, 1H), 8.11 (s, 1H), 7.46-7.35 (m, 2H), 7.34-0.18 (m, 3H), 6.41 (tt, J=54.5, 3.5 Hz, 1H), 4.91 (dd, J=24.0, 14.3 Hz, 1H), 4.71 (td, J=15.1, 3.6 Hz, 2H), 4.54-4.24 (m, 3H), 4.22-4.06 (m, 1H), 3.69 (d, J=8.0 Hz, 1H), 1.15 (d, J=6.0 Hz, 3H); LCMS (ES) [M+1]⁺ m/z: 466.

Example 1.12

Synthesis of 3-chloro-2-(3-[2-[1-(2,2-difluoroethyl)pyrazol-4-ylsulfonyl]-4H,6H-pyrrolo[3,4-c]pyrazole-5-carbonyl]oxetan-3-yl)pyridine (Compound 8)

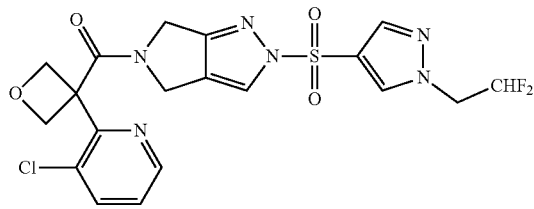

Step 1

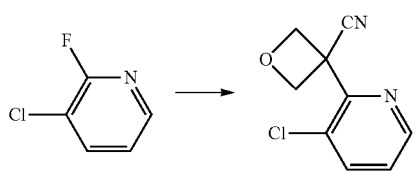 [SMILES: Fc1ncccc1Cl ; N#CC1(c2ncccc2Cl)COC1]

Into a 50-mL 3-necked round-bottom flask, was placed 3-chloro-2-fluoropyridine (1.20 g, 9.12 mmol, 1.00 eq.), oxetane-3-carbonitrile (839 mg, 10.10 mmol, 1.10 eq.) in toluene (20.00 mL), followed by the addition of KHMDS (1M in THF) (11.00 mL, 10.94 mmol, 1.2 eq.) at 0° C. After addition, the resulting solution was stirred for 30 min at room temperature. The reaction was then quenched by the addition of NH$_4$Cl (aq) (30.00 mL), and extracted with ethyl acetate (50.00 mL×2). The combined organic phase was dried over anhydrous sodium sulfate, filtered, and concentrated under reduced pressure. The residue was purified by silica gel column eluting with ethyl acetate/petroleum ether (1/3) to afford 3-(3-chloropyridin-2-yl)oxetane-3-carbonitrile as a yellow solid (1.38 g, 78%). LCMS (ES) [M+1]$^+$ m/z: 195.

Step 2

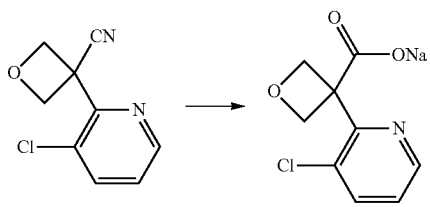

Into a 100-mL round-bottom flask, was placed 3-(3-chloropyridin-2-yl)oxetane-3-carbonitrile (1.38 g, 7.09 mmol, 1.00 eq.), H$_2$O (10.00 mL), EtOH (20.00 mL), and NaOH (1.14 g, 28.50 mmol, 4.00 eq.) and the mixture was stirred for 12 h at 80° C. The reaction was then cooled to room temperature and directly purified by Flash-Prep-HPLC with the following conditions: C18-120 g column, CH$_3$CN/H$_2$O, from 5% to 40% within 12 min, Flowrate: 70 mL/min, Detector, 254 nm. The fraction of target was freezing dried, this resulted in 1.0 g (60%) of sodium 3-(3-chloropyridin-2-yl)oxetane-3-carboxylate as a white solid. LCMS (ES) [M−Na+H+1]$^+$ m/z: 214.

Step 3

Into a 20-mL vial, was placed sodium 3-(3-chloropyridin-2-yl)oxetane-3-carboxylate (110 mg, 0.46 mmol, 1.00 eq.), DMF (3.0 mL), 1-(2,2-difluoroethyl)-4-{2H,4H,5H,6H-pyrrolo[3,4-c]pyrazole-2-sulfonyl}-1H-pyrazole (Intermediate I-7, 142 mg, 0.46 mmol, 1.00 eq.), and NMM (94.45 mg, 0.93 mmol, 2.00 eq.) followed by the addition of HATU (213 mg, 0.56 mmol, 1.20 eq.) in three batches at 0° C. The resulting solution was stirred for 1 h at room temperature. The reaction solution was purified by Flash-Prep-HPLC with the following conditions: Sunfire Prep C18 OBD Column, 50*250 mm, 5 m 10 nm, Mobile Phase A: Water (0.1% FA), Mobile Phase B: CH$_3$CN, Flow rate: 90 mL/min, Gradient: 15% B to 50% B in 15 min, Wavelength: 220 nm. The fraction of the target was freeze dried, this resulted in 3-chloro-2-(3-[2-[1-(2,2-difluoroethyl)pyrazol-4-ylsulfonyl]-4H,6H-pyrrolo[3,4-c]pyrazole-5-carbonyl]oxetan-3-yl)pyridine as a white solid (109.3 mg, 47%). 1H-NMR: (300 MHz, DMSO-d$_6$, ppm): δ 8.71-8.69 (m, 2H), 8.15 (d, J=18.0 Hz, 1H), 8.08 (s, 1H), 8.01-7.96 (m, 1H), 7.62-7.46 (m, 1H), 6.41 (t, J=54.3 Hz, 1H), 5.23 (dd, J=6.0, 3.3 Hz, 2H), 5.13 (d, J=6.0 Hz, 2H), 4.77-4.65 (m, 2H), 4.51 (d, J=9.3 Hz, 2H), 3.70 (d, J=7.8 Hz, 2H). LCMS: (ES, m/z): [M+H]$^+$: 499.

Example 1.13

Synthesis of (2S)-2-(2-chlorophenyl)-1-[2-[1-(2,2-difluoroethyl)pyrazol-4-ylsulfonyl]-4H,6H-pyrrolo[3,4-c]pyrazol-5-yl]-3-hydroxypropan-1-one (Compound 9)

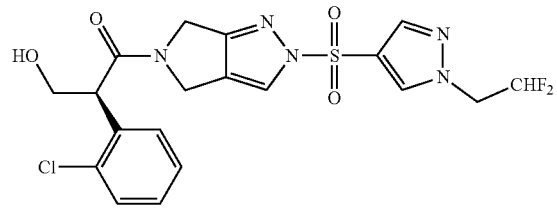

Into a 20-mL vial, was placed 1-(2,2-difluoroethyl)-4-{2H,4H,5H,6H-pyrrolo[3,4-c]pyrazole-2-sulfonyl}-1H-pyrazole (Intermediate I-7, 150.00 mg, 0.49 mmol, 1.00 eq.), (2S)-2-(2-chlorophenyl)-3-hydroxypropanoic acid (Intermediate II-11; 99.22 mg, 0.49 mmol, 1.00 eq.), DMF (5.00 mL), and NMM (100.05 mg, 0.99 mmol, 2.00 eq.), followed by the addition of HATU (225.66 mg, 0.59 mmol, 1.20 eq.), in portions at 0° C. and the resulting solution was stirred for 2 h at room temperature. The crude product (300 mg) was purified by Prep-HPLC with the following conditions: Column, Sunfire Prep C18 OBD Column, 50*250 mm Sum 10 nm; mobile phase, Water (0.1% NH$_3$.H$_2$O) and ACN (15% Phase B up to 70% in 15 min); Detector, 254. This resulted in the title compound as a white solid (136.3 mg, 56.72%). $^1$H-NMR: (300 MHz, DMSO-d$_6$, ppm): δ 8.72 (s, 1H), 8.19 (s, 1H), 8.12 (d, J=1.9 Hz, 1H), 7.53-7.39 (m, 2H), 7.34-7.29 (m, 2H), 6.42 (t, J=3.6 Hz, 1H), 5.02-4.93 (m, 1H), 4.98-4.82 (m, 1H), 4.72 (td, J=15.1, 3.6 Hz, 2H), 4.58-4.33 (m, 3H), 4.31 (dd, J=13.8, 10.1 Hz, 1H), 4.04-3.89 (m, 1H), 3.57 (dq, J=10.1, 5.0 Hz, 1H). LCMS13-PH-MY-PK-448-0: (ES, m/z): [M+H]$^+$: 486.

Example 1.14

Synthesis of (2S)-1-(2-{[1-(2,2-difluoroethyl)-1H-pyrazol-4-yl]sulfonyl}-2H,4H,5H,6H-pyrrolo[3,4-c]pyrazol-5-yl)-3-hydroxy-2-methyl-2-(pyridin-2-yl)propan-1-one and (2R)-1-(2-{[1-(2,2-difluoroethyl)-1H-pyrazol-4-yl]sulfonyl}-2H,4H,5H,6H-pyrrolo[3,4-c]pyrazol-5-yl)-3-hydroxy-2-methyl-2-(pyridin-2-yl)propan-1-one (Compounds 10 and 123)

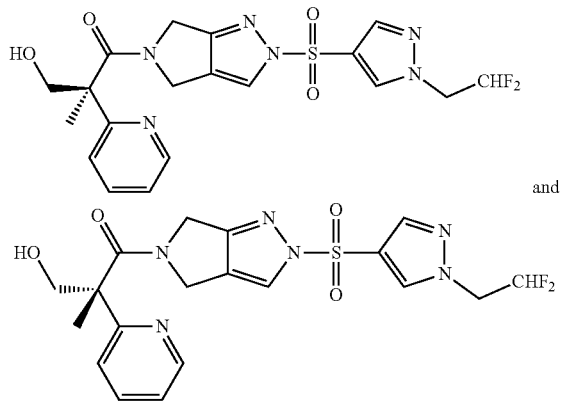

Procedure 1
Step 1

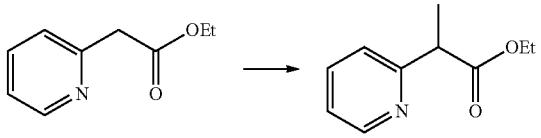

Into a 250-mL 3 neck round-bottom flask, was placed ethyl 2-(pyridin-2-yl)acetate (10.00 g, 60.536 mmol, 1.00 eq.), tetrahydrofuran (30 mL), HMPA (10.85 g, 60.536 mmol, 1.00 eq.), followed by the dropwise addition of LDA (30.00 mL, 60.500 mmol, 1.00 eq., 2M) at −78° C. The resulting solution was stirred for 0.5 h at −78° C., then dimethyl sulfate (7.64 g, 60.536 mmol, 1.00 eq.) was added dropwise at −78° C. and the resulting solution was stirred for 1 h at −78° C. The reaction was then quenched by the addition of 100 mL of water and extracted with 2×200 mL of ethyl acetate. The organic layer was dried over anhydrous sodium sulfate and concentrated under vacuum. The residue was applied onto a silica gel column and eluted with ethyl acetate/petroleum ether (1:10). This resulted in 9.5 g (87.56%) of ethyl 2-(pyridin-2-yl)propanoate as a light yellow oil. LCMS (ES) [M+1]$^+$ m/z: 180.

Step 2

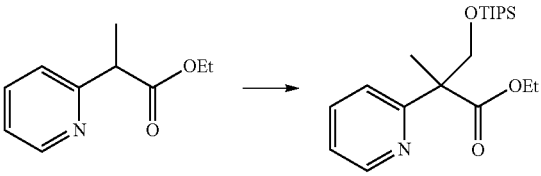

Into a 250-mL round-bottom flask, was placed ethyl 2-(pyridin-2-yl)propanoate (6.00 g, 33.479 mmol, 1.00 eq.) and tetrahydrofuran (60 mL). Then LDA (33.50 mL, 66.9 mmol, 1.00 eq., 2M) was added dropwise at −78° C. and the resulting solution was stirred for 1 h at −78° C. (chloromethoxy)triisopropylsilane (14.92 g, 66.957 mmol, 2.00 eq.) was then added and the resulting solution was stirred for 16 h at 25° C. The reaction was then quenched by the addition of 100 mL of water and extracted with 2×200 mL of ethyl acetate. The organic layer was dried over anhydrous sodium sulfate and concentrated under vacuum. The residue was applied onto a silica gel column and eluted with ethyl acetate/petroleum ether (1:10). This resulted in 9.8 g (80.07%) of ethyl 2-methyl-2-(pyridin-2-yl)-3-[(triisopropylsilyl)oxy]propanoate as a light yellow solid. LCMS (ES) [M+1]$^+$ m/z: 366.

Step 3

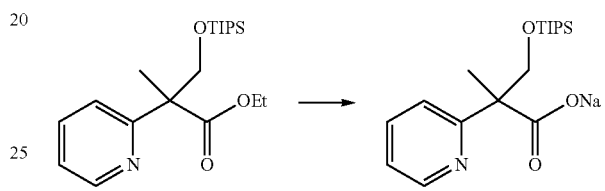

Into a 250-mL round-bottom flask, was placed ethyl 2-methyl-2-(pyridin-2-yl)-3-[(triisopropylsilyl)oxy]propanoate (8.90 g, 24.344 mmol, 1.00 eq.), tetrahydrofuran (20 mL), methanol (20 mL), water (20 mL), and NaOH (3.89 g, 97.377 mmol, 4.00 eq.) and the resulting solution was stirred for 16 h at 80° C. The crude reaction mixture was filtered and subjected to reverse phase preparative HPLC (Prep-C18, 20-45M, 120 g, Tianjin Bonna-Agela Technologies; gradient elution of 50% MeCN in water to 60% MeCN in water over a 10 min period to provide sodium 2-methyl-2-(pyridin-2-yl)-3-((triisopropylsilyl)oxy)propanoate as a yellow solid (5.4 g, 61.70%). LCMS (ES) [M-Na+H+1]$^+$ m/z: 338.

Step 4

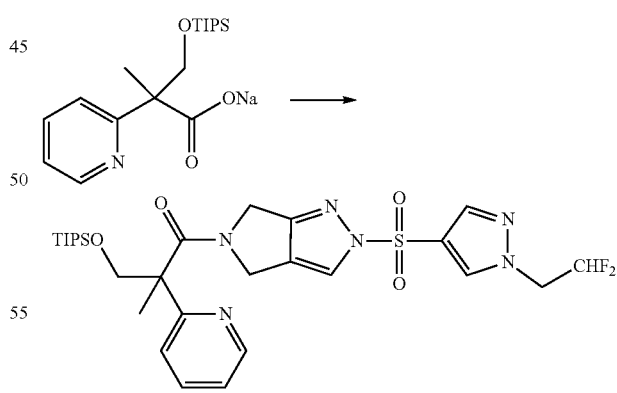

Into a 40-mL vial, was placed 1-(2,2-difluoroethyl)-4-{2H,4H,5H,6H-pyrrolo[3,4-c]pyrazole-2-sulfonyl}-1H-pyrazole (Intermediate I-7, 350.00 mg, 1.15 mmol, 1.00 eq.), racemic sodium 2-methyl-2-(pyridin-2-yl)-3-[(triisopropylsilyl)oxy]propanoate (414.89 mg, 1.15 mmol, 1.00 eq.), DMF (10.00 mL), and NMM (233.45 mg, 2.31 mmol, 2.00 eq.), followed by the addition of HATU (526.55 mg, 1.38 mmol, 1.20 eq.) drop-wise with stirring at 0° C. The resulting solution was stirred for 2 h at room temperature. The crude product (1 g) was purified by Prep-HPLC (Column, Sunfire Prep C18 OBD Column, 50*250 mm Sum 10 nm; mobile phase, Water (0.1% NH$_3$.H$_2$O) and ACN (25% PhaseB up to 80% in 15 min); Detector, 254), to provide 1-[2-[1-(2,2-difluoroethyl)pyrazol-4-ylsulfonyl]-4H,6H-pyrrolo[3,4-c]pyrazol-5-yl]-2-methyl-2-(pyridin-2-yl)-3-[(triisopropylsilyl)oxy]propan-1-one as an off-white solid (450 mg, 62.61%), LCMS (ES) [M+1]$^+$ m/z: 623.

Step 5

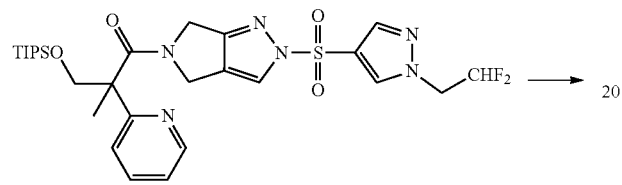

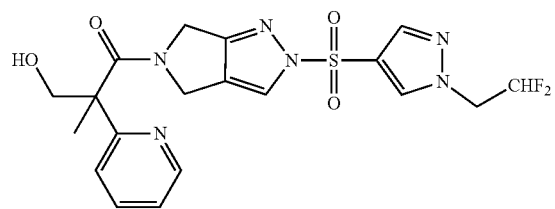

Into a 40-mL vial, was placed 1-[2-[1-(2,2-difluoroethyl)pyrazol-4-ylsulfonyl]-4H,6H-pyrrolo[3,4-c]pyrazol-5-yl]-2-methyl-2-(pyridin-2-yl)-3-[(triisopropylsilyl)oxy]propan-1-one (450.00 mg, 0.72 mmol, 1.00 eq.), THF (20.00 mL), H$_2$O (2.00 mL), and TFA (2.00 mL) and the resulting solution was stirred overnight at 40° C. The crude product (500 mg) was purified by Prep-HPLC (Column, Sunfire Prep C18 OBD Column, 50*250 mm Sum 10 nm; mobile phase, Water (0.1% FA) and ACN (15% PhaseB up to 40% in 15 min); Detector, 254) to provide racemic 1-(2-{[1-(2,2-difluoroethyl)-1H-pyrazol-4-yl]sulfonyl}-2H,4H,5H,6H-pyrrolo[3,4-c]pyrazol-5-yl)-3-hydroxy-2-methyl-2-(pyridin-2-yl)propan-1-one as a white solid (240 mg, 71.21%).

Step 6

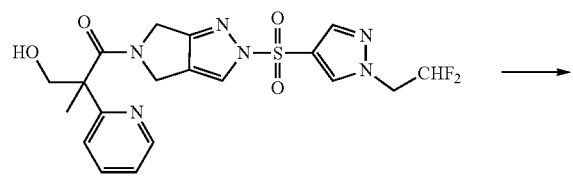

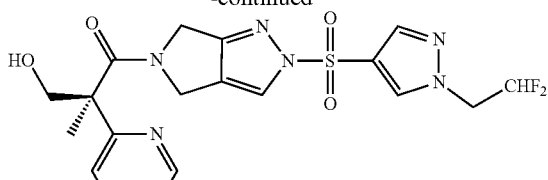

and

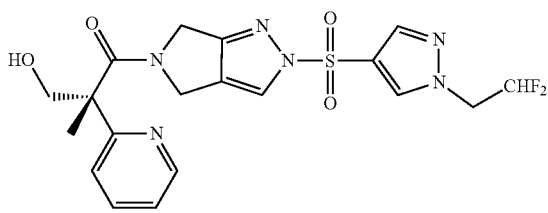

Racemic 1-(2-{[1-(2,2-difluoroethyl)-1H-pyrazol-4-yl]sulfonyl}-2H,4H,5H,6H-pyrrolo[3,4-c]pyrazol-5-yl)-3-hydroxy-2-methyl-2-(pyridin-2-yl)propan-1-one was subjected to separation by Prep-SFC (XA-Prep SFC150-1: Column, CHIRALPAK IE, 3*25 cm, 5 um; mobile phase, CO$_2$ (60%) and MEOH (0.1% 2M NH$_3$-MEOH)(40%); Detector, 254).

The fraction at RT=2.33 min was collected for Stereoisomer 1 (101.2 mg, 46.00%). $^1$H-NMR: (300 MHz, DMSO-d$_6$, ppm): δ 8.71-8.65 (m, 1H), 8.53 (d, J=4.7 Hz, 1H), 8.13-7.99 (m, 2H), 7.79 (t, J=7.8 Hz, 1H), 7.37 (d, J=7.9 Hz, 1H), 7.28 (dd, J=7.5, 4.9 Hz, 1H), 6.41 (t, J=54.4 Hz, 1H), 4.82-4.63 (m, 3H), 4.46 (d, J=14.2 Hz, 2H), 3.97 (d, J=10.9 Hz, 1H), 3.88 (d, J=14.1 Hz, 1H), 3.80 (d, J=10.9 Hz, 1H), 3.48 (dd, J=30.1, 14.1 Hz, 1H), 1.56 (s, 3H); LCMS13-PH-MY-PK-451-0A: (ES, m/z): [M+H]$^+$: 467.

Procedure 2

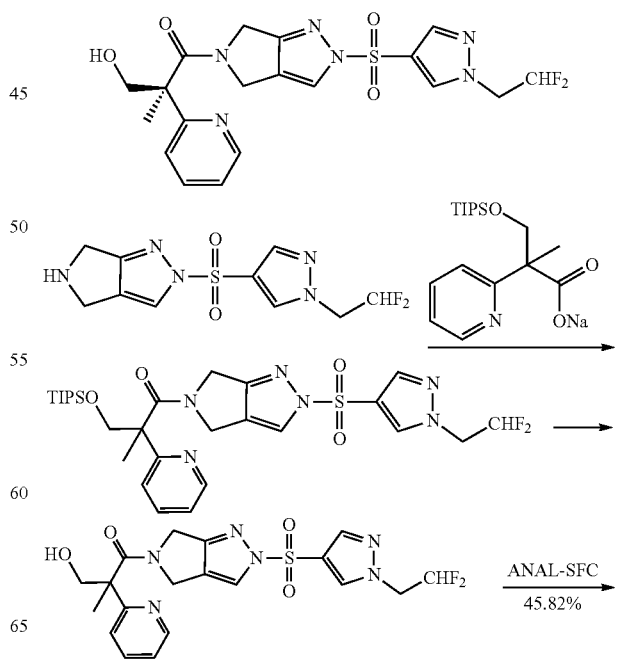

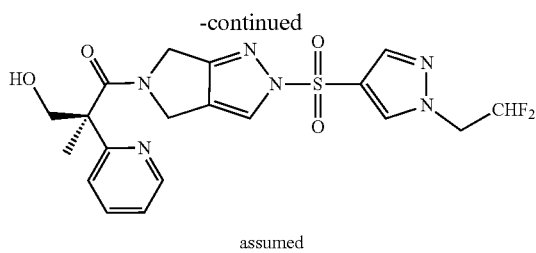

assumed

The 1-[2-[1-(2,2-difluoroethyl)pyrazol-4-ylsulfonyl]-4H,6H-pyrrolo[3,4-c]pyrazol-5-yl]-3-hydroxy-2-methyl-2-(pyridin-2-yl)propan-1-one (220 mg) was purified by Prep-SFC using the following conditions (XA-Prep SFC150-1): Column, CHIRALPAK IE, 3*25 cm, 5 um; mobile phase, $CO_2$ (60%) and MEOH (0.1% 2M $NH_3$-MEOH)(40%); Detector, 254.

The fraction at RT=2.094 min was collected as a white solid (100.8 mg, 45.82%) for Stereoisomer 2. ¹HNMR (300 MHz, DMSO-$d_6$) δ 8.68 (d, J=6.0 Hz, 1H), 8.53 (d, J=4.8 Hz, 1H), 8.13-7.99 (m, 2H), 7.79 (t, J=7.8 Hz, 1H), 7.37 (d, J=7.9 Hz, 1H), 7.28 (dd, J=7.5, 5.0 Hz, 1H), 6.41 (t, J=54.5 Hz, 1H), 4.77-4.63 (m, 3H), 4.46 (d, J=14.5 Hz, 2H), 3.97 (dd, J=11.0, 4.6 Hz, 1H), 3.88 (d, J=14.2 Hz, 1H), 3.80 (dd, J=10.9, 5.5 Hz, 1H), 3.48 (dd, J=30.0, 14.0 Hz, 1H), 1.56 (s, 3H). LCMS (ES) [M+1]⁺ m/z: 467.

Example 1.15

Synthesis of (2S)-1-(2-{[1-(2,2-difluoroethyl)-5-methyl-1H-pyrazol-4-yl]sulfonyl}-2H,4H,5H,6H-pyrrolo[3,4-c]pyrazol-5-yl)-3-hydroxy-2-phenylpropan-1-one (Compound 11)

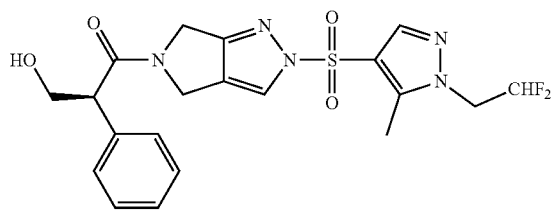 [SMILES: Cc1c(S(=O)(=O)n2cc3c(n2)CN(C(=O)[C@H](CO)c2ccccc2)C3)cnn1CC(F)F]

Step 1

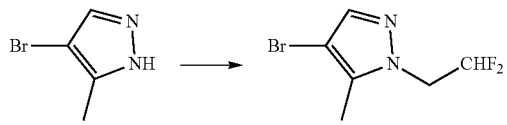

Into a 250-mL 3-necked round-bottom flask, was placed 3-bromo-1H-pyrazole (10.0 g, 62.50 mmol, 1.00 eq.) and DMF (100.00 mL) followed by the addition of NaH (60% in mineral oil) (3.0 g, 75.00 mmol, 1.20 equiv) in portions at 0° C. The resulting solution was stirred for 0.5 h at the same temperature, then 1,1-difluoro-2-iodoethane (17.91 g, 93.75 mmol, 1.50 eq.) was added drop wise with stirring at 0° C. The resulting solution was stirred for 12 h at room temperature then it was quenched by the addition of water/ice (100 mL) and extracted with 3×200 mL of ethyl acetate. The organic layers were combined, washed with brine (3×100 mL), dried over anhydrous sodium sulfate, filtered and concentrated. The residue was purified by silica gel column eluting with THF/PE (5%) to afford 7.9 g of the target as mixture of regioisomer. The mixture was further purified by SFC with conditions: CHIRALPAK IG, 3*25 cm, 5 μm, Mobile Phase A: $CO_2$ (1), Mobile Phase B: MeOH, Flow rate: 70 mL/min, Gradient: isocratic 25% B; Wavelength: 220 nm. RT1 (min): 2.17, RT2 (min): 2.75. The fraction of the target at RT=2.75 min was concentrated in vacuum resulting in 2.3 g (16%) of 4-bromo-1-(2,2-difluoroethyl)-5-methyl-1H-pyrazole as colorless oil. LCMS (ES) [M+1]⁺ m/z: 225. H-NMR-PH-GBT-ZL-PK-91-1: (300 MHz, $CDCl_3$, ppm): δ 7.46 (s, 1H), 6.25 (t, 1H), 4.40 (td, J=13.2, 4.5 Hz, 2H).

Step 2

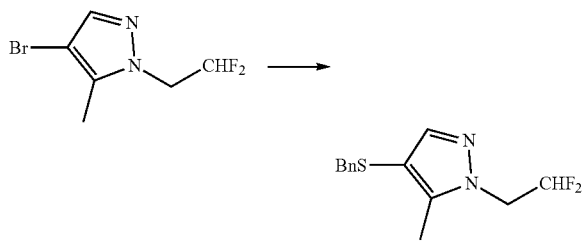

Into a 100-mL round-bottom flask purged and maintained in an inert atmosphere of nitrogen, was placed 4-bromo-1-(2,2-difluoroethyl)-5-methyl-1H-pyrazole (2.30 g, 10.27 mmol, 1.00 eq.), benzyl mercaptan (3.82 g, 30.81 mmol, 3.00 eq.), toluene (30.00 mL), DIEA (3.97 g, 30.81 mmol, 3.00 eq.), XantPhos (1.19 g, 2.05 mmol, 0.20 eq.), and $Pd_2(dba)_3$ (0.94 g, 1.02 mmol, 0.10 eq.), and the mixture was stirred for 48 h at 100° C. The reaction mixture was then cooled to room temperature and concentrated. The residue was purified by silica gel column eluting with HF/PE (5%). This resulted in 1.00 g (36%) of 4-(benzylthio)-1-(2,2-difluoroethyl)-5-methyl-1H-pyrazole as a yellow oil. LCMS (ES) [M+1]⁺ m/z: 269.

Step 3

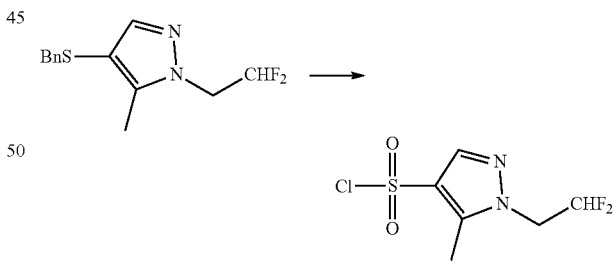

Into a 50-mL round-bottom flask, was placed 4-(benzylthio)-1-(2,2-difluoroethyl)-5-methyl-1H-pyrazole (1.00 g, 3.73 mmol, 1.00 eq.), HOAc (9.00 mL), and $H_2O$ (1.00 mL), followed by the addition of NCS (1.50 g, 11.19 mmol, 3.00 eq.) in one portion at a temperature below 20° C. The resulting solution was stirred for 1 h at room temperature then it was concentrated. The residue was purified by silica gel column eluting with THF/PE (20%) resulting in 800 mg (88%) of 1-(2,2-difluoroethyl)-5-methyl-1H-pyrazole-4-sulfonyl chloride as a white solid. LCMS (ES) [M–Cl+OH–1]⁻ m/z: 225.

Step 4

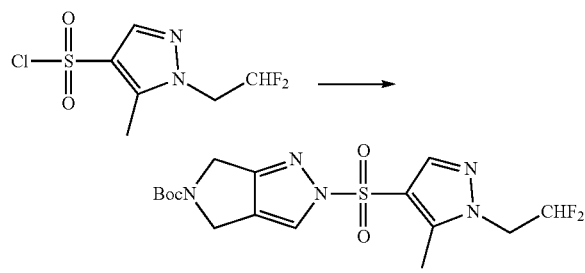

Into a 50-mL 3-necked round-bottom flask, was placed tert-butyl 2H,4H,6H-pyrrolo[3,4-c]pyrazole-5-carboxylate (685 mg, 3.28 mmol, 1.00 eq.) and THF (15.00 mL) followed by the addition of NaH (60% in mineral oil; 170 mg, 4.26 mmol, 1.30 eq.), in portions at 0° C. To this, 1-(2,2-difluoroethyl)-5-methyl-1H-pyrazole-4-sulfonyl chloride (800 mg, 3.28 mmol, 1.00 eq.) was added drop wise with stirring at the same temperature and the resulting solution was stirred for 1 h at 0° C. The reaction was then quenched by the addition of 0.5 mL of HOAc and extracted with 3×200 mL of dichloromethane. The organic layers were combined, dried over anhydrous sodium sulfate, filtered, and concentrated. The residue was diluted with 5 mL of MTBE and the solid thus formed was collected by filtration. This resulted in 600 mg (45%) of tert-butyl 2-((1-(2,2-difluoroethyl)-5-methyl-1H-pyrazol-4-yl)sulfonyl)-2,6-dihydropyrrolo[3,4-c]pyrazole-5(4H)-carboxylate as white solid. LCMS (ES) [M+1]$^+$ m/z: 418. The use of DMF as solvent instead of THF produced less than 1% regioisomer in LCMS.

Step 5

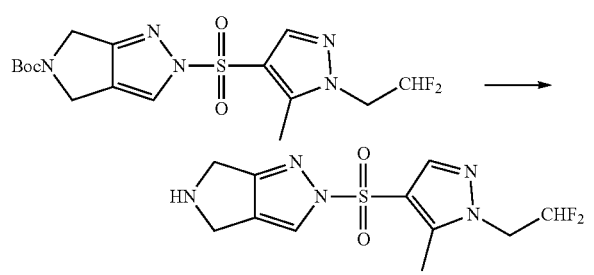

Into a 50-mL three necked round-bottom flask, was placed tert-butyl 2-((1-(2,2-difluoroethyl)-5-methyl-1H-pyrazol-4-yl)sulfonyl)-2,6-dihydropyrrolo[3,4-c]pyrazole-5(4H)-carboxylate (600 mg, 1.44 mmol, 1.00 eq.), DCM (10.00 mL), and lutidine (616 mg, 5.76 mmol, 4.00 eq.) followed by the addition of TMSOTf (959 mg, 4.32 mmol, 3.00 eq.) drop wise with stirring at 0° C. The resulting solution was stirred for 1 h at the same temperature, then it was quenched by the addition of water/ice (10 mL), and the crude product in the water phase was purified by Prep-HPLC with the following conditions: XBridge Prep C18 OBD Column, 19 cm, 150 mm, 5 um, mobile phase, Water (0.1% FA) and CH$_3$CN (5% Phase B up to 20% in 11 min), Detector, UV 254 nm. This resulted in 240 mg (53%) of 2-((1-(2,2-difluoroethyl)-5-methyl-1H-pyrazol-4-yl)sulfonyl)-2,4,5,6-tetrahydropyrrolo[3,4-c]pyrazole as a white solid. LCMS (ES) [M+1]$^+$ m/z: 318.

Step 6

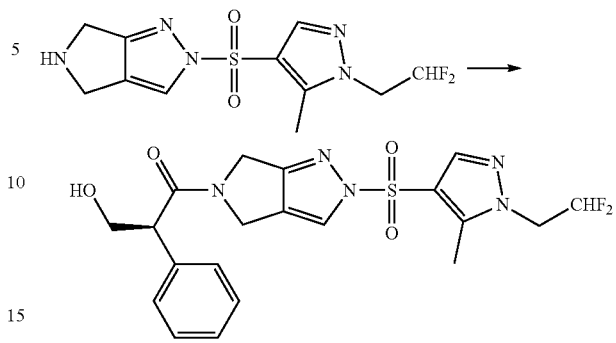

Into a 20-mL vial, was placed (S)-3-hydroxy-2-phenylpropanoic acid (43 mg, 0.26 mmol, 1.00 eq.), 2-((1-(2,2-difluoroethyl)-5-methyl-1H-pyrazol-4-yl)sulfonyl)-2,4,5,6-tetrahydropyrrolo[3,4-c]pyrazole (120 mg, 0.26 mmol, 1.00 eq.), DMF (3.00 mL), and NMM (53 mg, 0.52 mmol, 2.00 eq.) followed by the addition of HATU (198 mg, 0.52 mmol, 1.20 eq.), in portions at 0° C. The resulting solution was stirred for 1 h at the same temperature. The reaction solution was purified by Prep-HPLC with the following conditions: Sunfire Prep C18 OBD Column, 50*250 mm, 5 μm 10 nm, mobile phase, Water (0.1% FA) and CH$_3$CN (15% up to 50% in 12 min), Detector, UV 254 nm. The fraction of the target was freeze dried. This resulted in 85.3 mg (48%) of (S)-1-(2-((1-(2,2-difluoroethyl)-5-methyl-1H-pyrazol-4-yl)sulfonyl)-2,6-dihydropyrrolo[3,4-c]pyrazol-5(4H)-yl)-3-hydroxy-2-phenylpropan-1-one as white solid. $^1$H-NMR: (300 MHz, DMSO-d6, ppm): δ 8.20 (s, 1H), 8.04 (s, 1H), 7.40-7.25 (m, 5H), 6.37 (tt, J=54.3, 3.4 Hz, 1H), 4.96-4.76 (m, 2H), 4.65 (td, J=15.3, 3.3 Hz, 2H), 4.54-4.26 (m, 3H), 4.06-3.92 (m, 2H), 3.59-3.46 (m, 1H). LCMS: (ES, m/z): [M+H]$^+$: 466.

Example 1.16

Synthesis of (2S)-2-(2-chlorophenyl)-1-(2-{[1-(2,2-difluoroethyl)-1H-pyrazol-3-yl]sulfonyl}-2H,4H,5H,6H-pyrrolo[3,4-c]pyrazol-5-yl)-3-hydroxypropan-1-one Example 13

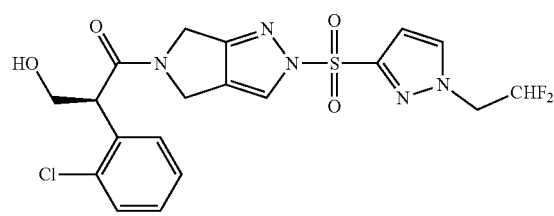 [SMILES: O=C([C@H](CO)c1ccccc1Cl)N1Cc2cn(S(=O)(=O)c3ccn(CC(F)F)n3)nc2C1]

Step 1

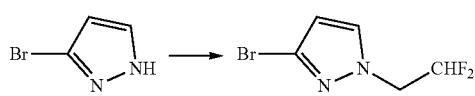 [SMILES: Brc1cc[nH]n1 ; FC(F)Cn1ccc(Br)n1]

Into a 500-mL 3-necked round-bottom flask, was placed 3-bromo-1H-pyrazole (15.0 g, 102.04 mmol, 1.00 eq.) and DMF (150.00 mL), followed by the addition of NaH (60% in mineral oil) (4.9 g, 122.45 mmol, 1.20 eq.), in portions at 0° C. The resulting solution was stirred for 0.5 h at the same temperature, then 1,1-difluoro-2-iodoethane (29.4 g, 153.06 mmol, 1.50 eq.) was added drop wise with stirring at 0° C. After addition, the resulting solution was stirred for 12 h at room temperature. The reaction was then quenched by the addition of water/ice (150 mL) and extracted with 3×200 mL of ethyl acetate. The organic layers were combined, washed with brine (3×150 mL), dried over anhydrous sodium sulfate, filtered, and concentrated under reduced pressure. The residue was purified by silica gel column eluting with THF/PE (8%). This resulted in 8.5 g (40%) of 3-bromo-1-(2,2-difluoroethyl)-1H-pyrazole as a colorless oil. LCMS (ES) [M+1]$^+$ m/z: 211. $^1$H-NMR: (300 MHz, CDCl$_3$) δ 7.36 (d, J=2.4 Hz, 1H), 6.33 (d, J=2.4 Hz, 1H), 6.07 (t, J=55.2 Hz, 1H), 4.42 (td, J=13.5, 4.5 Hz, 2H).

Step 2

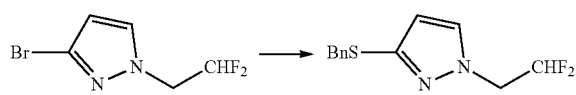

Into a 500-mL round-bottom flask purged and maintained in an inert atmosphere of nitrogen, was placed 3-bromo-1-(2,2-difluoroethyl)-1H-pyrazole (8.00 g, 37.9 mmol, 1.00 eq.), benzyl mercaptan (14.12 g, 113.7 mmol, 3.00 eq.), dioxane (100.00 mL), DIEA (14.67 g, 113.7 mmol, 3.00 eq.), XantPhos (4.39 g, 7.58 mmol, 0.20 eq.) and Pd$_2$(dba)$_3$ (4.38 g, 3.79 mmol, 0.10 eq.). The mixture was stirred for 24 h at 100° C. The reaction mixture was then cooled to room temperature and concentrated. The residue was purified by silica gel column eluting with THF/PE (5%). This resulted in 5 g (52%) of 3-(benzylthio)-1-(2,2-difluoroethyl)-1H-pyrazole as a yellow oil. LCMS (ES) [M+1]$^+$ m/z: 255.

Step 3

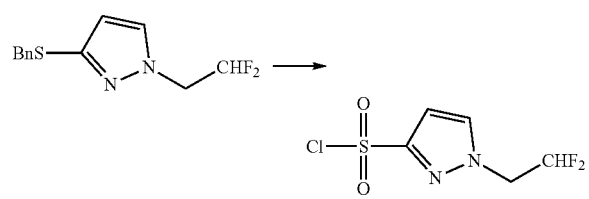

Into a 250-mL round-bottom flask, was placed 3-(benzylthio)-1-(2,2-difluoroethyl)-1H-pyrazole (5.00 g, 19.69 mmol, 1.00 eq.), HOAc (54.00 mL), and H$_2$O (6.00 mL) followed by the addition of NCS (7.91 g, 50.07 mmol, 3.00 eq.), in portions below 20° C. The resulting solution was stirred for 1 h at room temperature, and then concentrated. The residue was applied onto a silica gel column and eluted with THF/PE (10%). This resulted in 3.8 g (69%) of 1-(2,2-difluoroethyl)-1H-pyrazole-3-sulfonyl chloride as a yellow oil. LCMS (ES) [M−Cl+OH−1]$^−$ m/z: 211.

Step 4

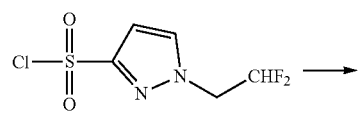

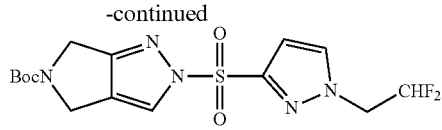

Into a 250-mL 3-necked round-bottom flask, was placed tert-butyl 2H,4H,6H-pyrrolo[3,4-c]pyrazole-5-carboxylate (2.9 g, 13.88 mmol, 1.00 eq.) and THF (50.00 mL) followed by the addition of NaH (60% in mineral oil; 0.83 g, 20.82 mmol, 1.50 eq.), in portions at 0° C. To this 1-(2,2-difluoroethyl)-1H-pyrazole-3-sulfonyl chloride (3.8 g, 16.52 mmol, 1.20 eq.) was added drop wise with stirring at 0° C. The resulting solution was stirred for 1 h at 0° C., then it was quenched by the addition of 5 mL of H$_2$O and extracted with 3×100 mL of ethyl acetate. The organic layers were combined, dried over anhydrous sodium sulfate, filtered, and concentrated under reduced pressure. The residue was diluted with 30 mL of MTBE, and the solid was collected by filtration. This resulted in 3.5 g (62%) of tert-butyl 2-((1-(2,2-difluoroethyl)-1H-pyrazol-3-yl)sulfonyl)-2,6-dihydropyrrolo[3,4-c]pyrazole-5(4H)-carboxylate as a light yellow solid. LCMS (ES) [M+1]$^+$ m/z: 404.

Step 5

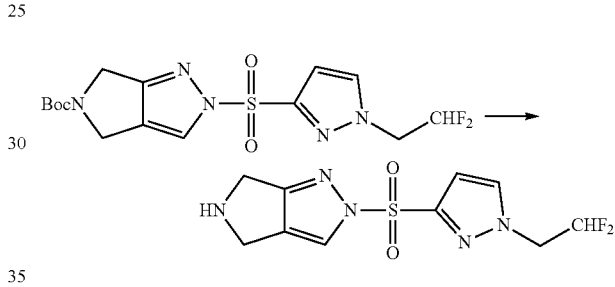

Into a 250-mL round-bottom flask, was placed tert-butyl 2-((1-(2,2-difluoroethyl)-1H-pyrazol-3-yl)sulfonyl)-2,6-dihydropyrrolo[3,4-c]pyrazole-5(4H)-carboxylate (2.5 g, 6.20 mmol, 1.00 eq.), DCM (50.00 mL), and lutidine (2.66 g, 24.80 mmol, 4.00 eq.), followed by the addition of TMSOTf (4.13 g, 18.60 mmol, 3.00 eq.) drop wise with stirring at 0° C. The resulting solution was stirred for 1 h at 0° C., then it was quenched by the addition of water/ice 20 mL. The crude product in H$_2$O was purified by Prep-HPLC with the following conditions: XBridge Prep C18 OBD Column, 19 cm, 150 mm, 5 um, mobile phase, Water (0.1% FA) and CH$_3$CN (5% Phase B up to 20% in 11 min), Detector, UV 254 nm. This resulted in 1.6 (85%) of 2-((1-(2,2-difluoroethyl)-1H-pyrazol-3-yl)sulfonyl)-2,4,5,6-tetrahydropyrrolo[3,4-c]pyrazole as a white solid. LCMS (ES) [M+1]$^+$ m/z: 304.

Step 6

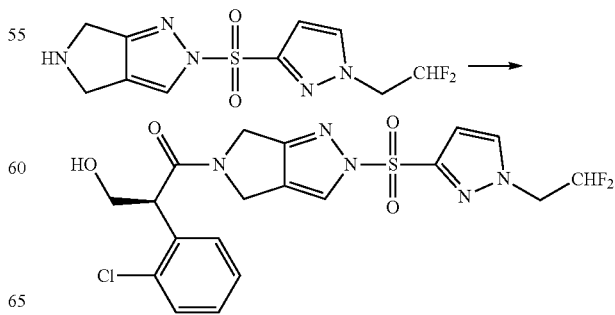

Into a 20-mL vial, was placed (2S)-2-(2-chlorophenyl)-3-hydroxypropanoic acid (80.00 mg, 0.39 mmol, 1.00 eq.), 1-(2,2-difluoroethyl)-3-[4H,5H,6H-pyrrolo[3,4-c]pyrazole-2-sulfonyl]pyrazole (120.94 mg, 0.39 mmol, 1.00 eq.), DMF (5.00 mL), and NMM (80.67 mg, 0.79 mmol, 2.00 eq.), followed by the addition of HATU (181.95 mg, 0.49 mmol, 1.20 eq.), in portions at 0° C. The resulting solution was stirred for 1 h at room temperature. The crude product (300 mg) was purified by Prep-HPLC with the following conditions: Column, Sunfire Prep C18 OBD Column, 50*250 mm Sum 10 nm; mobile phase, Water (0.1% $NH_3$—$H_2O$), and ACN (15% PhaseB up to 70% in 15 min); Detector, 254. This resulted in 104.4 mg (53.88%) of (2S)-2-(2-chlorophenyl)-1-[2-[1-(2,2-difluoroethyl)pyrazol-3-ylsulfonyl]-4H,6H-pyrrolo[3,4-c]pyrazol-5-yl]-3-hydroxypropan-1-one as a white solid. $^1$H-NMR: (300 MHz, DMSO-$d_6$, ppm): δ 8.23 (s, 1H), 8.07 (d, J=2.5 Hz, 1H), 7.50-7.42 (m, 2H), 7.37-7.23 (m, 2H), 6.99 (d, J=2.4 Hz, 1H), 6.40 (tt, J=54.3, 3.5 Hz, 1H), 4.99 (dd, J=5.5, 3.3 Hz, 1H), 4.99-4.83 (m, 1H), 4.78 (td, J=15.3, 3.5 Hz, 2H), 4.58-4.25 (m, 4H), 3.97 (tdd, J=8.7, 5.9, 2.9 Hz, 1H), 3.58 (dq, J=10.1, 5.0 Hz, 1H). LCMS: (ES, m/z): [M+H]$^+$: 486.

Example 1.17

Synthesis of (2S)-1-(2-{[1-(2,2-difluoroethyl)-1H-pyrazol-3-yl]sulfonyl}-2H,4H,5H,6H-pyrrolo[3,4-c]pyrazol-5-yl)-2-(2-fluorophenyl)-3-hydroxypropan-1-one (Compound 12)

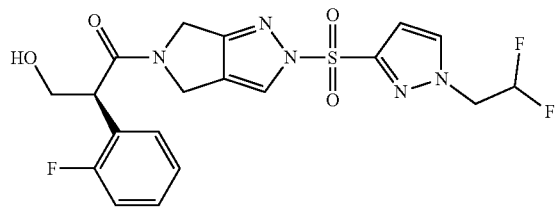 [SMILES: O=C([C@H](CO)c1ccccc1F)N1Cc2cn(S(=O)(=O)c3ccn(CC(F)F)n3)nc2C1]

Step 1

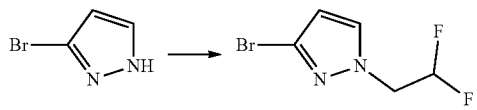 [SMILES: Brc1cc[nH]n1 ; FC(F)Cn1ccc(Br)n1]

Into a 500-mL 3-necked round-bottom flask, was placed 3-bromo-1H-pyrazole (15.0 g, 102.04 mmol, 1.00 eq.), DMF (150.00 mL), followed by the addition of NaH (60% in mineral oil; 4.9 g, 122.45 mmol, 1.20 eq.), in portions at 0° C. and the resulting solution was stirred for 0.5 h at the same temperature. 1,1-difluoro-2-iodoethane (29.4 g, 153.06 mmol, 1.50 eq.) was then added dropwise and the resulting solution was stirred for 12 h at room temperature. The reaction was then quenched by the addition of water/ice (150 mL), and extracted with 3×200 mL of ethyl acetate. The organic layer was combined and washed with brine (150 mL×3), dried over anhydrous sodium sulfate, filtered, and concentrated under reduced pressure; the residue was purified by silica gel column with THF/PE (8%) to provide 8.5 g (40%) of 3-bromo-1-(2,2-difluoroethyl)-1H-pyrazole as a colorless oil. $^1$H-NMR (300 MHz, CDCl$_3$) δ 7.36 (d, J=2.4 Hz, 1H), 6.33 (d, J=2.4 Hz, 1H), 6.07 (t, J=55.2 Hz, 1H), 4.42 (td, J=13.5, 4.5 Hz, 2H); LCMS (ES) [M+1]$^+$ m/z: 211.

Step 2

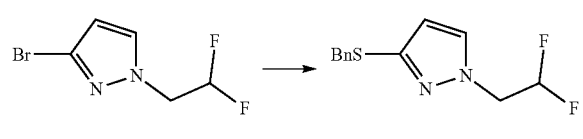

Into a 500-mL round-bottom flask purged and maintained in an inert atmosphere of nitrogen, was placed 3-bromo-1-(2,2-difluoroethyl)-1H-pyrazole (8.00 g, 37.9 mmol, 1.00 eq.), benzyl mercaptan (14.12 g, 113.7 mmol, 3.00 eq.), dioxane (100.00 mL), DIEA (14.67 g, 113.7 mmol, 3.00 eq.), XantPhos (4.39 g, 7.58 mmol, 0.20 eq.), and Pd$_2$(dba)$_3$ (4.38 g, 3.79 mmol, 0.10 eq.). The mixture was stirred for 24 h at 100° C. The reaction mixture was then cooled to room temperature and concentrated. The residue was purified by silica gel column with THF/PE (5%) to provide 5 g (52%) of 3-(benzylthio)-1-(2,2-difluoroethyl)-1H-pyrazole as a yellow oil. LCMS (ES) [M+1]$^+$ m/z: 255.

Step 3

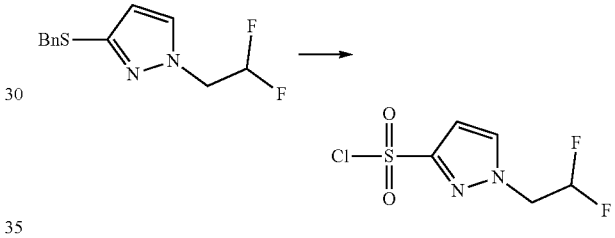

Into a 250-mL round-bottom flask, was placed 3-(benzylthio)-1-(2,2-difluoroethyl)-1H-pyrazole (5.00 g, 19.69 mmol, 1.00 eq.), HOAc (54.00 mL), and H$_2$O 6.00 mL), followed by the addition of NCS (7.91 g, 50.07 mmol, 3.00 eq.), in portions below 20° C. The resulting solution was stirred for 1 h at room temperature, and then concentrated. The residue was applied onto a silica gel column with THF/PE (10%). This resulted in 3.8 g (69%) of 1-(2,2-difluoroethyl)-1H-pyrazole-3-sulfonyl chloride as a yellow oil. LCMS (ES) [M−Cl+OH−1]$^-$ m/z: 211.

Step 4

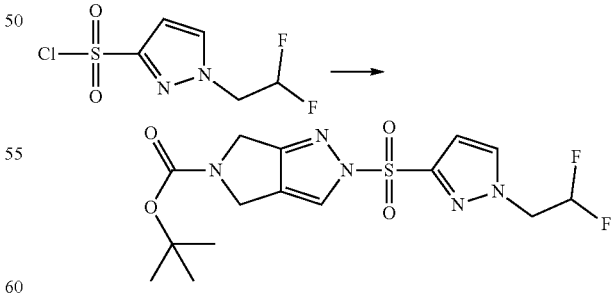

Into a 250-mL 3-necked round-bottom flask, was placed tert-butyl 2H,4H,6H-pyrrolo[3,4-c]pyrazole-5-carboxylate (2.9 g, 13.88 mmol, 1.00 eq.) in THF (50.00 mL) followed by the addition of NaH (60% in mineral oil; 0.83 g, 20.82 mmol, 1.50 eq.), in portions at 0° C. 1-(2,2-difluoroethyl)-1H-pyrazole-3-sulfonyl chloride (3.8 g, 16.52 mmol, 1.20 eq.) was then added dropwise and the resulting solution was stirred for 1 h at 0° C. The reaction was then quenched by the addition of 5 mL of H₂O and extracted with 3×100 mL of EA. The organic layers were combined and dried over anhydrous sodium sulfate, filtered, and concentrated under reduced pressure. The residue was diluted with 30 mL of MTBE and the solid was collected by filtration. This resulted in 3.5 g (62%) of tert-butyl 2-((1-(2,2-difluoroethyl)-1H-pyrazol-3-yl)sulfonyl)-2,6-dihydropyrrolo[3,4-c]pyrazole-5(4H)-carboxylate as a light yellow solid. LCMS (ES) [M+1]⁺ m/z: 404.

Step 5

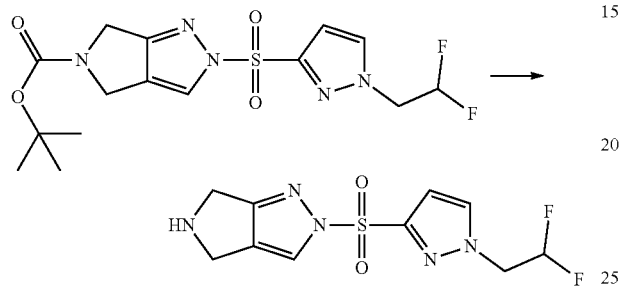

Into a 250-mL round-bottom flask, was placed tert-butyl 2-((1-(2,2-difluoroethyl)-1H-pyrazol-3-yl)sulfonyl)-2,6-dihydropyrrolo[3,4-c]pyrazole-5(4H)-carboxylate (2.5 g, 6.20 mmol, 1.00 eq.), DCM (50.00 mL), and lutidine (2.66 g, 24.80 mmol, 4.00 eq.), followed by the addition of TMSOTf (4.13 g, 18.60 mmol, 3.00 eq.) dropwise. The resulting solution was stirred for 1 h at 0° C., and then quenched by the addition of water/ice 20 mL. The crude product in H₂O was purified by Prep-HPLC with the following conditions: XBridge Prep C18 OBD Column, 19 cm, 150 mm, 5 um, mobile phase, Water (0.1% FA) and CH₃CN (5% Phase B up to 20% in 11 min), Detector, UV 254 nm. This resulted in 1.6 g (85%) of 2-((1-(2,2-difluoroethyl)-1H-pyrazol-3-yl)sulfonyl)-2,4,5,6-tetrahydropyrrolo[3,4-c]pyrazole as a white solid. LCMS (ES) [M+1]⁺ m/z: 304.

Step 6

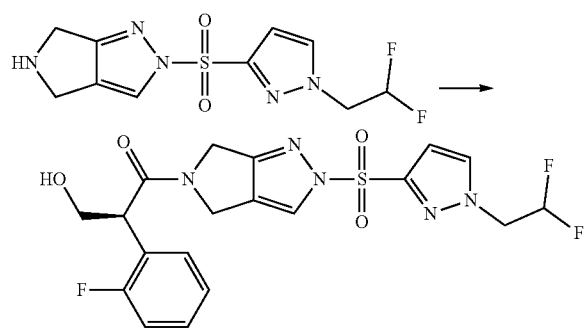

Into a 8-mL vial, was placed 2-((1-(2,2-difluoroethyl)-1H-pyrazol-3-yl)sulfonyl)-2,4,5,6-tetrahydropyrrolo[3,4-c]pyrazole (197 mg, 0.65 mmol, 1.20 eq.), DMF (4.0 mL), (S)-2-(2-fluorophenyl)-3-hydroxypropanoic acid (Intermediate II-10; 100 mg, 0.54 mmol, 1.00 eq.), and NMM (165 mg, 1.63 mmol, 3.00 eq.), followed by the addition of HATU (247 mg, 0.65 mmol, 1.20 eq.) with stirring at 0° C. After addition, the resulting solution was stirred for 1 h at the same temperature. The reaction mixture was then directly purified by Prep-HPLC with the following conditions: Sunfire Prep C18 OBD Column, 50*250 mm, 5 µm, 10 nm, Mobile Phase A: water (0.1% FA), Mobile Phase B: CH₃CN, Flow rate: 90 mL/min, Gradient: from 15% B to 50% B in 12 min, Detector, 220 nm. This resulted in 97 mg of (S)-1-(2-((1-(2,2-difluoroethyl)-1H-pyrazol-3-yl)sulfonyl)-2,6-dihydropyrrolo[3,4-c]pyrazol-5(4H)-yl)-2-(2-fluorophenyl)-3-hydroxypropan-1-one as a white solid. ¹H-NMR-PH-GBT-MY-PK-464-0: (400 MHz, DMSO-d₆, ppm): δ 8.22 (dd, J=2.8, 1.2 Hz, 1H), 8.07 (d, J=2.4 Hz, 1H), 7.43-7.38 (m, 1H), 7.35-7.29 (m, 1H), 7.23-7.15 (m, 2H), 6.99 (d, J=2.4 Hz, 1H), 6.54 (tt, J=54.0, 3.6 Hz, 1H), 4.95-4.86 (m, 2H), 4.82 (td, J=10.8, 3.6 Hz, 2H), 4.52-4.25 (m, 4H), 4.02 (t, J=9.6 Hz, 1H), 3.64-3.58 (m, 1H). LCMS: (ES, m/z): [M+H]⁺: 470.

Example 1.18

Synthesis of (2S)-1-(2-{[1-(2,2-difluoroethyl)-5-methyl-1H-pyrazol-4-yl]sulfonyl}-2H,4H,5H,6H-pyrrolo[3,4-c]pyrazol-5-yl)-2-(2-fluorophenyl)-3-hydroxypropan-1-one (Compound 14)

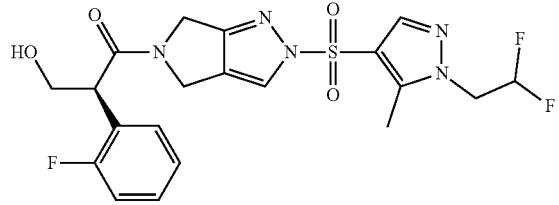 [SMILES: Cc1c(S(=O)(=O)n2cc3c(n2)CN(C(=O)[C@H](CO)c2ccccc2F)C3)cnn1CC(F)F]

Step 1

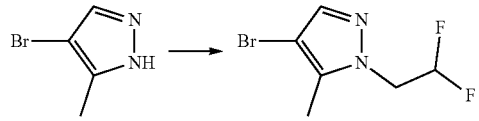

Into a 250-mL 3-necked round-bottom flask, was placed 3-bromo-1H-pyrazole (10.0 g, 62.50 mmol, 1.00 eq.) in DMF (100.00 mL) followed by the addition of NaH (60% in mineral oil) (3.0 g, 75.00 mmol, 1.20 eq.), in portions at 0° C. The resulting solution was stirred for 0.5 h at the same temperature. 1,1-difluoro-2-iodoethane (17.91 g, 93.75 mmol, 1.50 eq.) was then added dropwise with stirring at 0° C. The resulting solution was stirred for 12 h at room temperature, then the reaction was quenched by the addition of water/ice (100 mL) and extracted with 3×200 mL of ethyl acetate. The organic layers were combined, washed with brine (100 mL×3), dried over anhydrous sodium sulfate, filtered, and concentrated. The residue was purified by silica gel column with THF/PE (5%), generating a 7.9 g mixture of the target and the regio-isomer. The mixture was further purified by SFC with the following conditions: CHIRAL-PAK IG, 3*25 cm, 5 µm, Mobile Phase A: CO₂ (1), Mobile Phase B: MeOH, Flow rate: 70 mL/min, Gradient: isocratic 25% B; Wave Length: 220 nm. RT1 (min): 2.17, RT2 (min): 2.75. The fraction of the target at 2.75 min was concentrated in vacuum, resulting in 2.3 g (16%) of 4-bromo-1-(2,2-difluoroethyl)-5-methyl-1H-pyrazole as a colorless oil.

¹H-NMR: (300 MHz, CDCl₃, ppm): δ 7.46 (s, 1H), 6.25 (t, 1H), 4.40 (td, J=13.2, 4.5 Hz, 2H). LCMS (ES) [M+1]⁺ m/z: 225.

Step 2

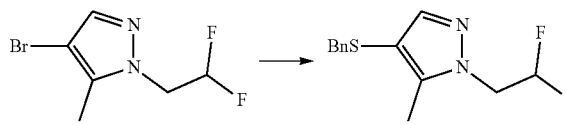

Into a 100-mL round-bottom flask purged and maintained in an inert atmosphere of nitrogen, was placed 4-bromo-1-(2,2-difluoroethyl)-5-methyl-1H-pyrazole (2.30 g, 10.27 mmol, 1.00 eq.), benzyl mercaptan (3.82 g, 30.81 mmol, 3.00 eq.), toluene (30.00 mL), DIEA (3.97 g, 30.81 mmol, 3.00 eq.), XantPhos (1.19 g, 2.05 mmol, 0.20 eq.), and Pd₂(dba)₃ (0.94 g, 1.02 mmol, 0.10 eq.), and the mixture was stirred for 48 h at 100° C. The reaction mixture was then cooled to room temperature and concentrated. The residue was purified by silica gel column with THF/PE (5%) to provide 1.00 g (36%) of 4-(benzylthio)-1-(2,2-difluoroethyl)-5-methyl-1H-pyrazole as a yellow oil. LCMS (ES) [M+1]⁺ m/z: 269.

Step 3

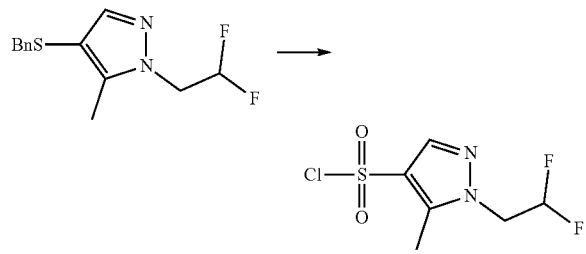

Into a 50-mL round-bottom flask, was placed 4-(benzylthio)-1-(2,2-difluoroethyl)-5-methyl-1H-pyrazole (1.00 g, 3.73 mmol, 1.00 eq.), HOAc (9.00 mL), and H₂O (1.00 mL) followed by the addition of NCS (1.50 g, 11.19 mmol, 3.00 eq.) in one portion at a temperature below 20° C. The resulting solution was stirred for 1 h at room temperature, then it was concentrated. The residue was purified by silica gel column with THF/PE (20%) to provide 800 mg (88%) of 1-(2,2-difluoroethyl)-5-methyl-1H-pyrazole-4-sulfonyl chloride as a white solid. LCMS (ES) [M−Cl+OH−1]⁻ m/z: 225.

Step 4

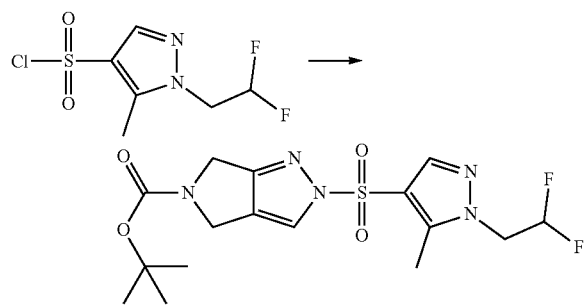

Into a 50-mL 3-necked round-bottom flask, was placed tert-butyl 2H,4H,6H-pyrrolo[3,4-c]pyrazole-5-carboxylate (685 mg, 3.28 mmol, 1.00 eq.) in THF (15.00 mL) followed by the addition of NaH (60% in mineral oil; 170 mg, 4.26 mmol, 1.30 eq.), in portions at 0° C. 1-(2,2-difluoroethyl)-5-methyl-1H-pyrazole-4-sulfonyl chloride (800 mg, 3.28 mmol, 1.00 eq.) was then added dropwise and the resulting solution was stirred for 1 h at 0° C. The reaction was then quenched by the addition of 0.5 mL of HOAc and extracted with 3×200 mL of dichloromethane. The organic layers were combined, dried over anhydrous sodium sulfate, filtered, and concentrated. The residue was diluted with 5 mL of MTBE and the solid was collected by filtration. This resulted in 600 mg (45%) of tert-butyl 2-((1-(2,2-difluoroethyl)-5-methyl-1H-pyrazol-4-yl)sulfonyl)-2,6-dihydropyrrolo[3,4-c]pyrazole-5(4H)-carboxylate as a white solid. LCMS (ES) [M+1]⁺ m/z: 418.

Step 5

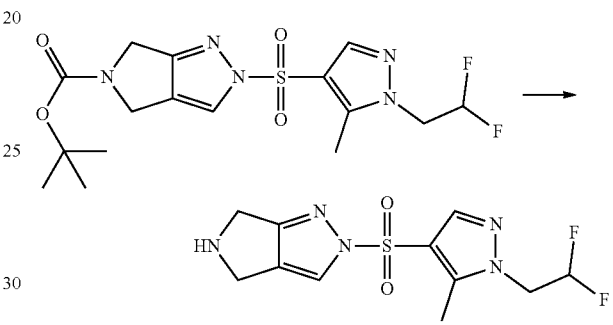

Into a 50-mL three necked round-bottom flask, was placed tert-butyl 2-((1-(2,2-difluoroethyl)-5-methyl-1H-pyrazol-4-yl)sulfonyl)-2,6-dihydropyrrolo[3,4-c]pyrazole-5(4H)-carboxylate (600 mg, 1.44 mmol, 1.00 eq.), DCM (10.00 mL), and lutidine (616 mg, 5.76 mmol, 4.00 eq.), followed by the addition of TMSOTf (959 mg, 4.32 mmol, 3.00 eq.) dropwise. The resulting solution was stirred for 1 h at the same temperature. The reaction was then quenched by the addition of water/ice (10 mL) and the crude product in the water phase was directly purified by Prep-HPLC with the following conditions: XBridge Prep C18 OBD Column, 19 cm, 150 mm, 5 um, mobile phase, Water (0.1% FA) and CH₃CN (5% Phase B up to 20% in 11 min), Detector, UV 254 nm. This resulted in 240 mg (53%) of 2-((1-(2,2-difluoroethyl)-5-methyl-1H-pyrazol-4-yl)sulfonyl)-2,4,5,6-tetrahydropyrrolo[3,4-c]pyrazole as a white solid. LCMS (ES) [M+1]⁺ m/z: 318.

Step 6

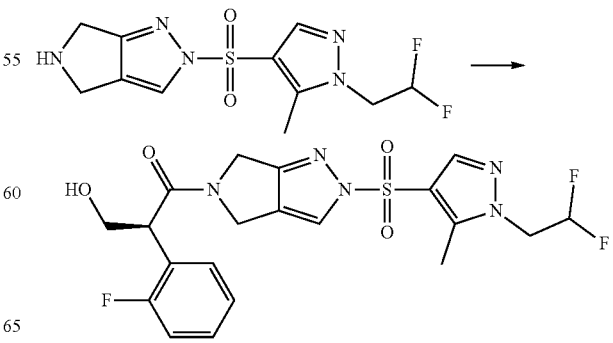

Into a 8-mL vial, was placed (S)-2-(2-fluorophenyl)-3-hydroxypropanoic acid (Intermediate II-10; 100 mg, 0.54 mmol, 1.00 eq.), DMF (4.00 mL), 2-((1-(2,2-difluoroethyl)-5-methyl-1H-pyrazol-4-yl)sulfonyl)-2,4,5,6-tetrahydropyrrolo[3,4-c]pyrazole (225 mg, 0.71 mmol, 1.30 eq.), and NMM (0.18 mL, 1.63 mmol, 3.00 eq.), followed by the addition of HATU (247 mg, 0.65 mmol, 1.20 eq.). The resulting solution was stirred for 1 h at the same temperature. The reaction solution was purified by Prep-HPLC with the following conditions: XSelect CSH Prep C18 OBD Column, 19*150 mm, m, Mobile Phase A: water (0.1% FA), Mobile Phase B: CH$_3$CN, Flow rate: 20 mL/min, Gradient: from 29% B to 45% B in 8 min, Detector, 220 nm. This resulted in 96 mg of (S)-1-(2-((1-(2,2-difluoroethyl)-5-methyl-1H-pyrazol-4-yl)sulfonyl)-2,6-dihydropyrrolo[3,4-c]pyrazol-5(4H)-yl)-2-(2-fluorophenyl)-3-hydroxypropan-1-one as a white solid. $^1$H-NMR-PH-GBT-ZL-PK-97-0: (300 MHz, DMSO-d$_6$, ppm): δ 8.21 (d, J=2.4 Hz, 1H), 8.04 (s, 1H), 7.42-7.28 (m, 2H), 7.24-7.14 (m, 2H), 6.60 (tt, J=54.3, 3.3 Hz, 1H), 4.96-4.84 (m, 2H), 4.74 (td, J=15.3, 3.6 Hz, 2H), 4.53-4.40 (m, 2H), 4.35-4.24 (m 2H), 4.03-3.95 (m, 1H), 3.65-3.56 (m, 1H), 2.52 (s, 3H). LCMS-PH-GBT-ZL-PK-97-0: (ES, m/z): [M+H]$^+$: 484.

Example 1.19

Synthesis of (2S)-1-{2-[(2,4-dimethyl-1,3-thiazol-5-yl)sulfonyl]-2H,4H,5H,6H-pyrrolo[3,4-c]pyrazol-5-yl}-3-hydroxy-2-phenylpropan-1-one (Compound 15)

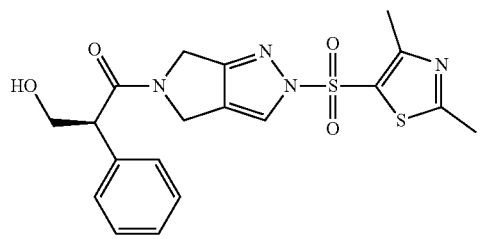 [SMILES: Cc1nc(C)c(S(=O)(=O)n2cc3c(n2)CN(C(=O)[C@H](CO)c2ccccc2)C3)s1]

Step 1

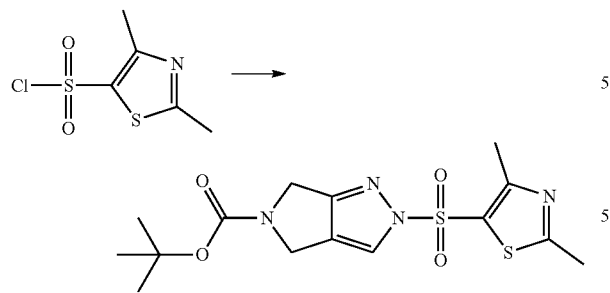

To a suspension of sodium hydride (124.24 mg; 3.11 mmol; 1.30 eq.) in THF (15 mL) under N$_2$ in an ice bath was added a solution of tert-butyl 2H,4H,5H,6H-pyrrolo[3,4-c]pyrazole-5-carboxylate (500.00 mg; 2.39 mmol; 1.00 eq.) in THF (3 mL) over 5 min. The mixture was allowed to stir in ice bath for 30 min. A solution of 2,4-dimethyl-1,3-thiazole-5-sulfonyl chloride (505.84 mg; 2.39 mmol; 1.00 eq.) in THF (2 mL) was then added slowly. The mixture was allowed to stir in the ice bath for 45 min while warming up to ambient temperature. The reaction mixture was then quenched and diluted with NH$_4$Cl (0.5 mL of AcOH was also added) and was extracted twice with a 1:3 mixture of IPA:CHCl$_3$. The combined organics were washed with water and brine, dried over Na$_2$SO$_4$, filtered and concentrated to provide a dark oil. The crude material was purified on a silica gel column eluting with 0-40% EtOAc in heptane to provide the desired product as a light-yellow solid (638 mg; 74%).

Step 2

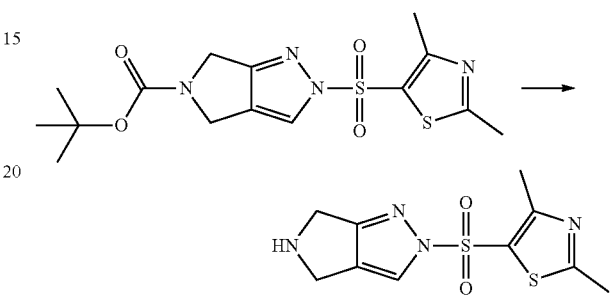

To a mixture of tert-butyl 2-[(dimethyl-1,3-thiazol-5-yl)sulfonyl]-2H,4H,5H,6H-pyrrolo[3,4-c]pyrazole-5-carboxylate (295.00 mg; 0.77 mmol; 1.00 eq.) in 1,2-dichloroethane (5.90 mL) was added ZnBr$_2$ (518.35 mg; 2.30 mmol; 3.00 eq.). This mixture was allowed to stir at 55° C. Several extra portions of ZnBr$_2$ were added to drive the reaction to completion.

After 60 h the mixture was cooled to ambient temperature, diluted with water, quenched with 2.5 mL of aqueous ammonium hydroxide, and extracted with a 3:1 mix of CHCl$_3$:IPA. The combined organics were washed with brine, dried over MgSO$_4$, filtered, and concentrated to provide a tan wax. $^1$H NMR showed partial conversion to the desired product with still ~25% SM present. This material was taken on to the next step without further purification.

Step 3

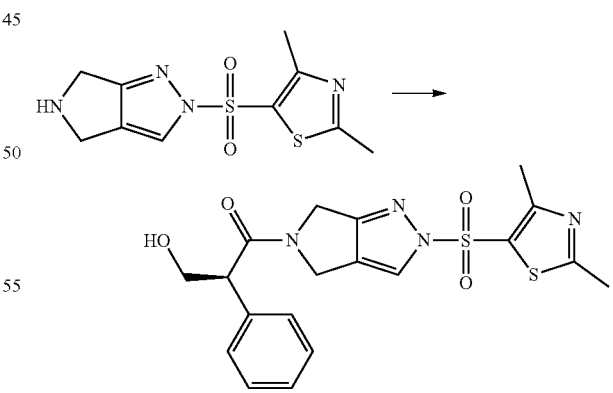

To a mixture of (2S)-3-hydroxy-2-phenylpropanoic acid (113.95 mg; 0.69 mmol; 1.30 eq.), 2,4-dimethyl-5-{2H,4H,5H,6H-pyrrolo[3,4-c]pyrazole-2-sulfonyl}-1,3-thiazole (150.00 mg; 0.53 mmol; 1.00 eq.) and Hunig's base (0.18 mL; 1.06 mmol; 2.00 eq.) in DMF (5.28 mL) was added HATU (260.74 mg; 0.69 mmol; 1.30 eq.) and the resulting mixture was stirred at ambient temperature. After 2.5 h the mixture was diluted with 1:1 PhMe/EtOAc and washed with an equal amount of water. The organic phase was dried over MgSO₄, filtered and concentrated. The crude material was purified on a silica gel column eluting with 0-30% EtOAc in heptane to separate the unreacted SM, and then at 80% EtOAc in heptane to isolate the desired product as a colorless solid consistent with the desired product (51.8 mg, 23%). ¹HNMR (400 MHz, DMSO-d₆) δ 8.23 (d, J=1.4 Hz, 1H), 7.35-7.17 (m, 5H), 4.92-4.80 (m, 1H), 4.78 (dd, J=5.1, 2.1 Hz, 1H, OH), 4.50-4.24 (m, 3H), 4.01-3.90 (m, 2H), 3.54-3.44 (m, 1H), 2.62 (s, 3H), 2.52 (d, J=2.6 Hz, 3H). LCMS (ES) [M+1]₊ m/z: 433.04.

Example 1.20

Synthesis of (2S)-1-{2-[(3,5-dimethyl-1,2-oxazol-4-yl)sulfonyl]-2H,4H,5H,6H-pyrrolo[3,4-c]pyrazol-5-yl}-3-hydroxy-2-phenylpropan-1-one (Compound 16)

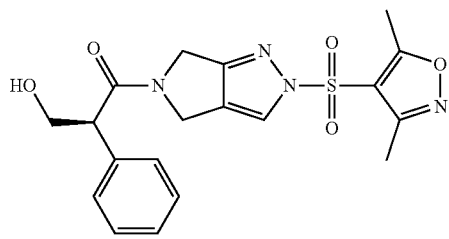 [SMILES: Cc1noc(C)c1S(=O)(=O)n1cc2c(n1)CN(C(=O)[C@H](CO)c1ccccc1)C2]

The title compound was synthesized according the 3-step procedure described for Compound 15 using 3,5-dimethyl-4-isoxazolesulfonyl chloride instead of 2,4-dimethyl-1,3-thiazole-5-sulfonyl chloride in step 1. (2S)-1-{2-[(3,5-dimethyl-1,2-oxazol-4-yl)sulfonyl]-2H,4H,5H,6H-pyrrolo[3,4-c]pyrazol-5-yl}-3-hydroxy-2-phenylpropan-1-one was isolated as a colorless solid (85 mg, 54%). ¹HNMR (400 MHz, DMSO-d₆) δ 8.26 (dd, J=2.7, 1.3 Hz, 1H), 7.35-7.24 (m, 4H), 7.21 (ddq, J=7.0, 4.5, 2.3 Hz, 1H), 4.93-4.80 (m, 1H), 4.80-4.75 (m, 1H, OH), 4.51-4.24 (m, 3H), 4.01 3.91 (m, 2H), 3.49 (td, J=4.4, 1.9 Hz, 1H), 2.65 (s, 3H), 2.29 (d, J=3.0 Hz, 3H). LCMS (ES) [M+1]⁺ m/z: 417.03.

Example 1.21

Synthesis of (2S)-3-hydroxy-2-phenyl-1-(2-{[5-(3,3,3-trifluoropropyl)thiophen-2-yl]sulfonyl}-2H,4H,5H,6H-pyrrolo[3,4-c]pyrazol-5-yl)propan-1-one (Compound 17)

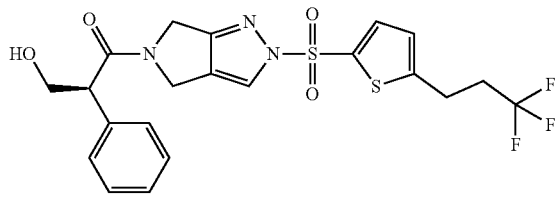 [SMILES: O=C([C@H](CO)c1ccccc1)N1Cc2cn(S(=O)(=O)c3ccc(CCC(F)(F)F)s3)nc2C1]

Step 1

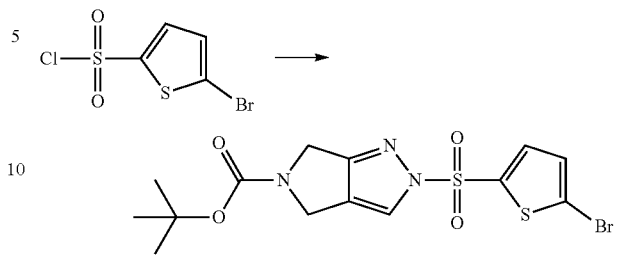

To a suspension of sodium hydride (124.24 mg; 3.11 mmol; 1.30 eq.) in THF (15 mL) under N₂ in an ice bath was added a solution of tert-butyl 2H,4H,5H,6H-pyrrolo[3,4-c]pyrazole-5-carboxylate (500.00 mg; 2.39 mmol; 1.00 eq.) in THF (3 mL) over 5 min. The mixture was allowed to stir in the ice bath for 30 min. A solution of 5-bromo-2-thiophenesulfonyl chloride (624.97 mg; 2.39 mmol; 1.00 eq.) in THF (2 mL) was then added slowly and the resulting mixture was allowed to stir while warming up to ambient temperature. After 90 min the reaction mixture was quenched and diluted with NH₄Cl (0.5 mL of AcOH was also added), and was extracted twice with a 1:3 mixture of IPA:CHCl₃. The combined organics were washed with brine, dried over Na₂SO₄, filtered, and concentrated to provide a tan solid. A portion was collected as is (850 mg). The rest of the crude material was absorbed onto a silica gel plug and purified on a silica gel column eluting with 0-40% EtOAc in heptane to provide an off-white solid consistent with the desired product (135 mg; 94%).

Step 2

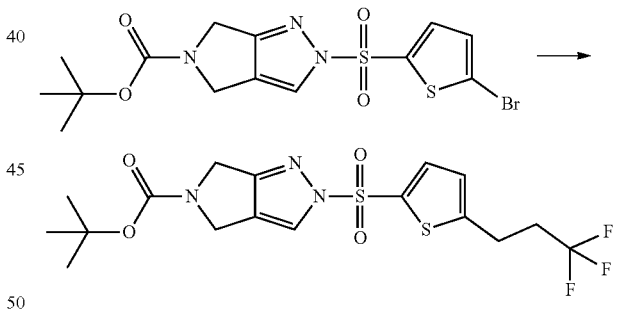

A mixture of potassium trifluoro(3,3,3-trifluoropropyl)boranuide (46.96 mg; 0.23 mmol; 1.00 eq.), tert-butyl 2-[(5-bromothiophen-2-yl)sulfonyl]-2H,4H,5H,6H-pyrrolo[3,4-c]pyrazole-5-carboxylate (100.00 mg; 0.23 mmol; 1.00 eq.), cesium carbonate (225.05 mg; 0.69 mmol; 3.00 eq.), palladium acetate (2.58 mg; 0.01 mmol; 0.05 eq.) and RuPhos (10.74 mg; 0.02 mmol; 0.10 eq.) in toluene (1.15 mL) and water (0.38 mL) in a sealed vial was heated to 95° C. After 4 h the mixture was cooled to ambient temperature, quenched, and diluted with sat. NH₄Cl and extracted with DCM. The organic phase was dried over MgSO₄, filtered, and concentrated to provide a dark yellow oil. The residue was purified on a silica gel column eluting with 0-30% EtOAc in heptane to provide the desired product as a colorless solid (63 mg; 60%).

Step 3

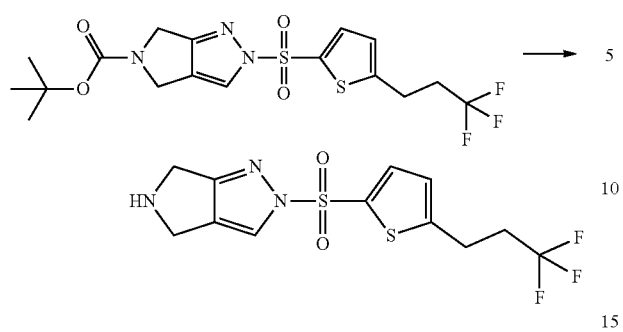

To a mixture of tert-butyl 2-{[5-(3,3,3-trifluoropropyl)thiophen-2-yl]sulfonyl}-2H,4H,5H,6H-pyrrolo[3,4-c]pyrazole-5-carboxylate (63.00 mg; 0.14 mmol; 1.00 eq.) in 1,2-dichloroethane (1.26 mL) was added ZnBr$_2$ (94.27 mg; 0.42 mmol; 3.00 eq.). This mixture was allowed to stir at 55° C. After overnight the mixture was cooled to ambient temperature, diluted with water, quenched with 0.5 mL of aqueous ammonium hydroxide, and extracted with a 3:1 mixture of CHCl$_3$:IPA. The combined organics were washed with brine, dried over MgSO$_4$, filtered, and concentrated to provide a light-yellow semisolid. This material was taken on to the next step without further purification assuming 100% yield (49 mg).

Step 4

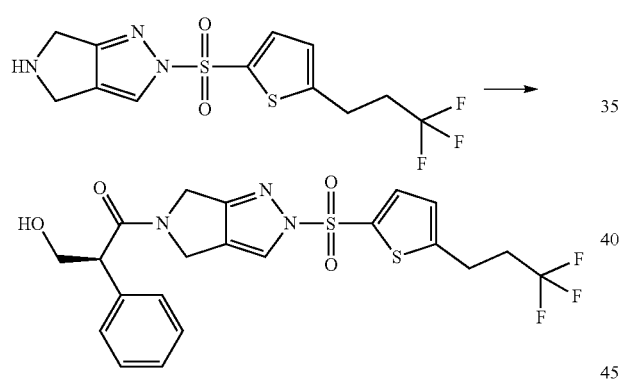

To a mixture of (2S)-3-hydroxy-2-phenylpropanoic acid (30.13 mg; 0.18 mmol; 1.30 eq.), 2-{[5-(3,3,3-trifluoropropyl)thiophen-2-yl]sulfonyl}-2H,4H,5H,6H-pyrrolo[3,4-c]pyrazole (49.00 mg; 0.14 mmol; 1.00 eq.) and Hunig's base (0.05 mL; 0.28 mmol; 2.00 eq.) in DMF (1.39 mL) was added HATU (68.93 mg; 0.18 mmol; 1.30 eq.) and the resulting mixture was stirred at ambient temperature. After 2 h the mixture was diluted with 1:1 PhMe/EtOAc and washed with an equal amount of water. The organic phase was dried over MgSO$_4$, filtered and concentrated. The crude material was purified on a silica gel column eluting with 0-100% EtOAc in heptane, to provide (2S)-3-hydroxy-2-phenyl-1-(2-{[5-(3,3,3-trifluoropropyl)thiophen-2-yl]sulfonyl}-2H,4H,5H,6H-pyrrolo[3,4-c]pyrazol-5-yl)propan-1-one as a colorless solid (20.4 mg; 29%). $^1$HNMR (400 MHz, DMSO-d$_6$) δ 8.18-8.15 (m, 1H), 7.77 (dd, J=3.9, 0.7 Hz, 1H), 7.37-7.17 (m, 5H), 7.11 (ddq, J=4.0, 1.8, 0.9 Hz, 1H), 4.90-4.78 (m, 1H), 4.77 (dd, J=5.2, 3.2 Hz, 1H), 4.48-4.35 (m, 2H), 4.33-4.23 (m, 1H), 3.99-3.91 (m, 2H), 3.53-3.45 (m, 1H), 3.08 (dd, J=9.6, 6.5 Hz, 2H), 2.72-2.60 (m, 2H). LCMS (ES) [M+1]$^+$ m/z: 499.89.

Example 1.22

Synthesis of (2S)-3-hydroxy-2-phenyl-1-{2-[(5-phenylthiophen-2-yl)sulfonyl]-2H,4H,5H,6H-pyrrolo[3,4-c]pyrazol-5-yl}propan-1-one (Compound 18)

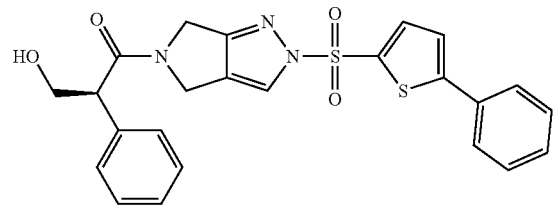 [SMILES: O=C([C@H](CO)c1ccccc1)N1Cc2cn(S(=O)(=O)c3ccc(-c4ccccc4)s3)nc2C1]

The title compound was synthesized according the 4-step procedure described for Compound 17 using phenyl boronic acid instead of potassium trifluoro(3,3,3-trifluoropropyl)boranuide in step 2. (2S)-3-Hydroxy-2-phenyl-1-{2-[(5-phenylthiophen-2-yl)sulfonyl]-2H,4H,5H,6H-pyrrolo[3,4-c]pyrazol-5-yl}propan-1-one was isolated as a colorless solid (4.2 mg; 32%). $^1$HNMR (400 MHz, DMSO-d$_6$) δ8.21 (d, J=1.4 Hz, 1H), 7.91 (dd, J=4.1, 1.1 Hz, 1H), 7.73-7.68 (m, 2H), 7.61 (dd, J=4.1, 1.5 Hz, 1H), 7.47-7.39 (m, 3H), 7.34-7.23 (m, 4H), 7.23-7.16 (m, 1H), 4.85 (dd, J=30.2, 14.4 Hz, 1H), 4.78-4.72 (m, 1H), 4.50-4.36 (m, 2H), 4.30 (dd, J=19.4, 12.6 Hz, 1H), 3.99-3.89 (m, 2H), 3.49 (dd, J=8.7, 4.0 Hz, 1H). LCMS (ES) [M+1]$^+$ m/z: 479.92.

Example 1.23

Synthesis of (2S)-1-{2-[(5-bromothiophen-2-yl)sulfonyl]-2H,4H,5H,6H-pyrrolo[3,4-c]pyrazol-5-yl}-3-hydroxy-2-phenylpropan-1-one (Compound 19)

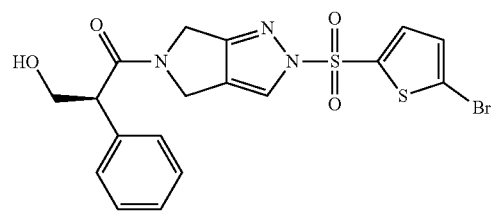

Step 1

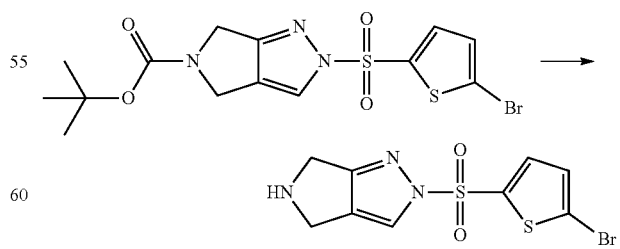

To a mixture of tert-butyl 2-[(5-bromothiophen-2-yl)sulfonyl]-2H,4H,5H,6H-pyrrolo[3,4-c]pyrazole-5-carboxylate (step 1, synthesis of Compound 17), 135.00 mg; 0.31 mmol; 1.00 eq.) in 1,2-dichloroethane (2.70 mL) was added zincbromide (209.98 mg; 0.93 mmol; 3.00 eq.). This mixture was allowed to stir at 55° C. overnight. The reaction mixture was cooled to ambient temperature, diluted with water, quenched with 1.5 mL of aqueous ammonium hydroxide, and extracted with a 3:1 mix of CHCl₃:IPA. The combined organics were washed with brine, dried over MgSO₄, filtered, and concentrated to provide a tan solid. This material was taken on to the next step without further purification assuming 100% yield (100 mg).

Step 2

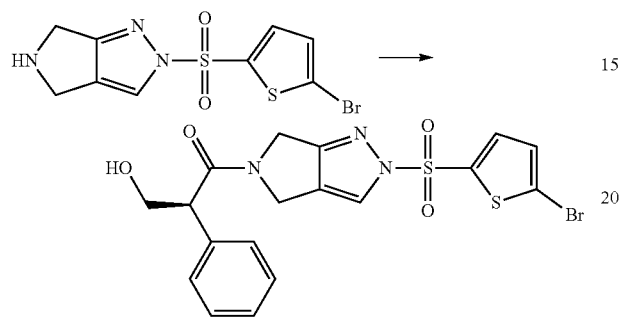

To a mixture of (2S)-3-hydroxy-2-phenylpropanoic acid (64.64 mg; 0.39 mmol; 1.30 eq.), 2-[(5-bromothiophen-2-yl)sulfonyl]-2H,4H,5H,6H-pyrrolo[3,4-c]pyrazole (100.00 mg; 0.30 mmol; 1.00 eq.) and Hunig's base (0.10 mL; 0.60 mmol; 2.00 eq.) in DMF (2.99 mL) was added HATU (147.90 mg; 0.39 mmol; 1.30 eq.) and the resulting mixture was stirred at ambient temperature. After 2.5 h the mixture was diluted with 1:1 PhMe/EtOAc and washed with an equal amount of water. The organic phase was dried over MgSO₄, filtered and concentrated. The crude material was purified on a silica gel column eluting with 0-80% EtOAc in heptane to provide (2S)-1-{2-[(5-bromothiophen-2-yl)sulfonyl]-2H,4H,5H,6H-pyrrolo[3,4-c]pyrazol-5-yl}-3-hydroxy-2-phenylpropan-1-one as a colorless solid (44.2 mg, 31%). ¹HNMR (400 MHz, DMSO-d₆) δ 8.18 (d, J=1.3 Hz, 1H), 7.75 (dt, J=4.2, 1.1 Hz, 1H), 7.40 (dt, J=4.1, 1.4 Hz, 1H), 7.34-7.18 (m, 5H), 4.93-4.80 (m, 1H), 4.79-4.76 (m, 1H), 4.49-4.25 (m, 3H), 4.00-3.90 (m, 2H), 3.53-3.45 (m, 1H). LCMS (ES) [M+1]⁺ m/z: 481.83/483.74.

Example 1.24

Synthesis of (2S)-3-hydroxy-1-(2-{[4-methyl-2-(3,3,3-trifluoropropyl)-1,3-thiazol-5-yl]sulfonyl}-2H,4H,5H,6H-pyrrolo[3,4-c]pyrazol-5-yl)-2-phenylpropan-1-one (Compound 20)

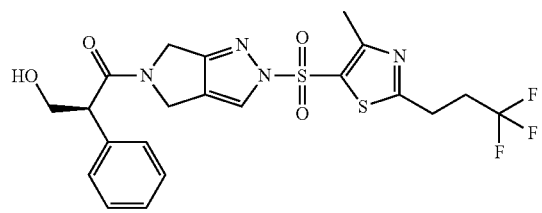

The title compound was synthesized according the 4-step procedure described for Compound 17 using 2-chloro-4-methyl-1,3-thiazole-5-sulfonyl chloride instead of 5-bromo-2-thiophenesulfonyl chloride in step 1. (2S)-3-hydroxy-1-(2-{[4-methyl-2-(3,3,3-trifluoropropyl)-1,3-thiazol-5-yl]sulfonyl}-2H,4H,5H,6H-pyrrolo[3,4-c]pyrazol-5-yl)-2-phenylpropan-1-one was isolated as a colorless solid (6.3 mg; 28%). ¹HNMR (400 MHz, DMSO-d6) δ 8.26 (d, J=1.3 Hz, 1H), 7.35-7.25 (m, 4H), 7.24-7.17 (m, 1H), 4.85 (dd, J=28.9, 14.4 Hz, 1H), 4.77 (dq, J=5.0, 2.9 Hz, 1H), 4.50-4.34 (m, 2H), 4.34-4.25 (m, 1H), 3.96 (dd, J=8.4, 2.5 Hz, 2H), 3.49 (td, J=5.4, 4.7, 3.0 Hz, 1H), 3.27-3.20 (m, 2H), 2.79-2.66 (m, 2H), 2.54 (d, J=2.5 Hz, 3H). LCMS (ES) [M+1]⁺ m/z: 515.04.

Example 1.25

Synthesis of (2S)-1-{2-[(5-ethylthiophen-2-yl)sulfonyl]-2H,4H,5H,6H-pyrrolo[3,4-c]pyrazol-5-yl}-3-hydroxy-2-phenylpropan-1-one (Compound 21)

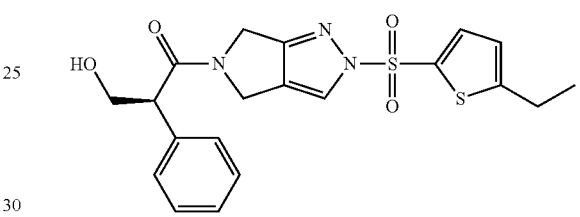

The title compound was synthesized according the 4-step procedure described for Compound 17 using potassium ethyltrifluoroboronate instead of potassium trifluoro(3,3,3-trifluoropropyl)boranuide in step 2. (2S)-1-{2-[(5-ethylthiophen-2-yl)sulfonyl]-2H,4H,5H,6H-pyrrolo[3,4-c]pyrazol-5-yl}-3-hydroxy-2-phenylpropan-1-one was isolated as a colorless solid (10.0 mg; 36%). ¹HNMR (400 MHz, DMSO-d₆) δ8.16 (d, J=1.1 Hz, 1H), 7.74 (dt, J=4.0, 1.2 Hz, 1H), 7.30 (dtdd, J=9.4, 7.8, 6.1, 1.5 Hz, 4H), 7.23-7.17 (m, 1H), 6.99 (dp, J=3.8, 1.1 Hz, 1H), 4.90-4.78 (m, 1H), 4.48-4.36 (m, 2H), 4.33-4.23 (m, 1H), 4.00-3.90 (m, 2H), 3.53-3.45 (m, 1H), 2.87-2.79 (m, 2H), 1.18 (td, J=7.5, 1.1 Hz, 3H). LCMS (ES) [M+1]⁻ m/z: 432.04.

Example 1.26

Synthesis of (2S)-3-hydroxy-1-(2-{[4-methyl-2-(2,2,2-trifluoroethoxy)-1,3-thiazol-5-yl]sulfonyl}-2H,4H,5H,6H-pyrrolo[3,4-c]pyrazol-5-yl)-2-phenylpropan-1-one (Compound 22)

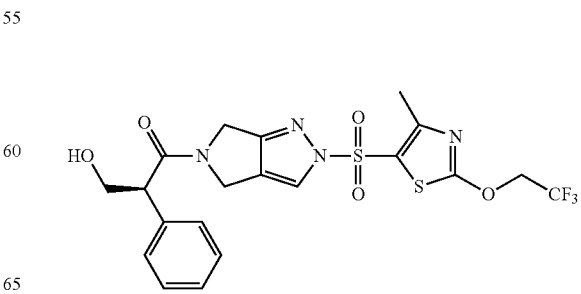

Step 1

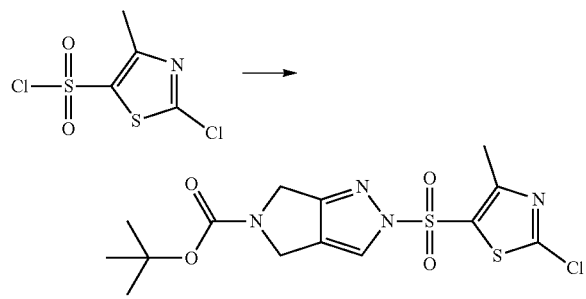

To a suspension of sodium hydride (141.64 mg; 3.54 mmol; 1.30 eq.) in THF (15 mL) under $N_2$ in ice bath was added a solution of tert-butyl 2H,4H,5H,6H-pyrrolo[3,4-c]pyrazole-5-carboxylate (570.00 mg; 2.72 mmol; 1.00 eq.) in THF (3 mL) over 5 min. The mixture was allowed to stir in ice bath for 30 min. A solution of 2-chloro-4-methyl-1,3-thiazole-5-sulfonyl chloride (632.28 mg; 2.72 mmol; 1.00 eq.) in THF (2 mL) was then added slowly. The mixture was allowed to stir in the ice bath for 45 min while warming up to ambient temperature. After 2 h the reaction mixture was quenched and diluted with saturated solution of $NH_4Cl$ (2 mL of AcOH were also added) and was extracted twice with a 1:3 mixture of IPA:$CHCl_3$. The combined organics were washed with water and brine, dried over $MgSO_4$, filtered, and concentrated to provide a red oil. The crude material was purified on a silica gel column eluting with 0-50% EtOAc in heptane, to provide tert-butyl 2-[(2-chloro-4-methyl-1,3-thiazol-5-yl)sulfonyl]-2H,4H,5H,6H-pyrrolo[3,4-c]pyrazole-5-carboxylate as a colorless solid (542 mg; 49%).

Step 2

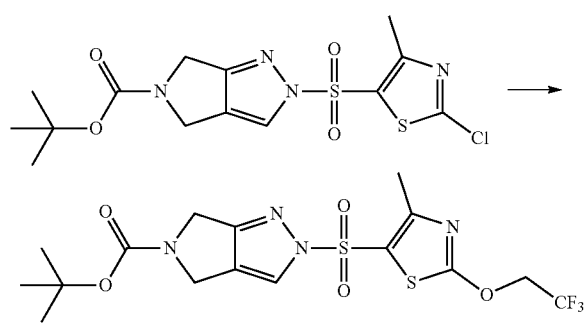

A mixture of tert-butyl 2-[(2-chloro-4-methyl-1,3-thiazol-5-yl)sulfonyl]-2H,4H,5H,6H-pyrrolo[3,4-c]pyrazole-5-carboxylate (40.00 mg; 0.10 mmol; 1.00 eq.), 2,2,2-trifluoroethanol (0.01 mL; 0.20 mmol; 2.00 eq.) and cesium carbonate (96.56 mg; 0.30 mmol; 3.00 eq.) in acetonitrile (2.00 mL) was stirred at ambient temperature overnight. The mixture was then diluted with EtOAc and washed with water. The organic phase was dried over $MgSO_4$, filtered, and concentrated to provide a colorless oil. The crude was purified on a silica gel column eluting with 0-20% EtOAc in heptane, to provide tert-butyl 2-{[4-methyl-2-(2,2,2-trifluoroethoxy)-1,3-thiazol-5-yl]sulfonyl}-2H,4H,5H,6H-pyrrolo[3,4-c]pyrazole-5-carboxylate as a colorless solid (30 mg; 65%).

Step 3

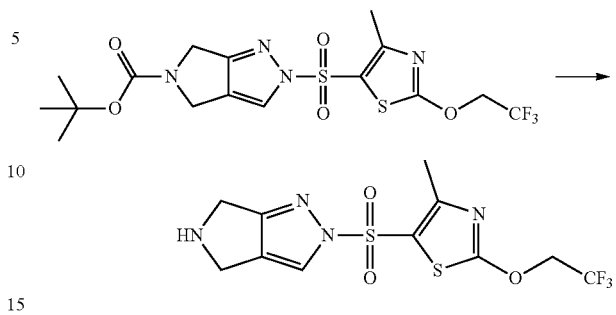

To a solution of tert-butyl 2-{[4-methyl-2-(2,2,2-trifluoroethoxy)-1,3-thiazol-5-yl]sulfonyl}-2H,4H,5H,6H-pyrrolo[3,4-c]pyrazole-5-carboxylate (30.00 mg; 0.06 mmol; 1.00 eq.) in dichloromethane (0.18 mL) cooled to 0° C. was added trifluoroacetic acid (0.36 mL; 12.00 V) and the mixture was stirred at 0° C. After 1 h the mixture was concentrated in vacuo and dried under high vacuum for 1 h. The crude material was taken on to the next step without further purification assuming 100% yield (23 mg free base; 31 mg TFA salt).

Step 4

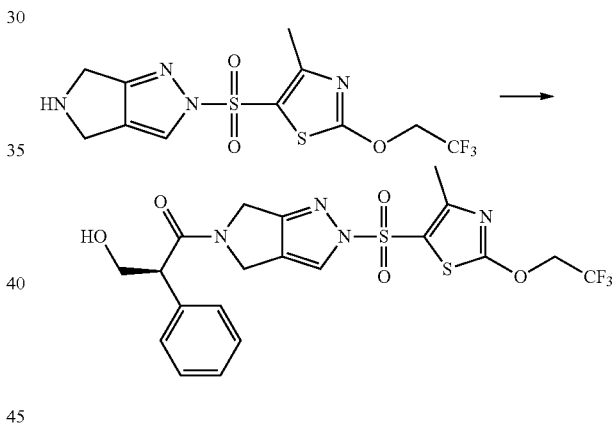

To a mixture of (2S)-3-hydroxy-2-phenylpropanoic acid (13.88 mg; 0.08 mmol; 1.30 eq.), 4-methyl-5-{2H,4H,5H,6H-pyrrolo[3,4-c]pyrazole-2-sulfonyl}-2-(2,2,2-trifluoroethoxy)-1,3-thiazole; trifluoroacetic acid (31.00 mg; 0.06 mmol; 1.00 eq.) and Hunig's base (0.02 mL; 0.13 mmol; 2.00 eq.) in DMF (0.64 mL) was added HATU (31.77 mg; 0.08 mmol; 1.30 eq.) and the resulting mixture was stirred at ambient temperature. After 1 h the mixture was diluted with 1:1 PhMe/EtOAc and washed with an equal amount of water. The organic phase was then concentrated. The crude was purified on a silica gel column eluting with 0-80% EtOAc in heptane, to provide (2S)-3-hydroxy-1-(2-{[4-methyl-2-(2,2,2-trifluoroethoxy)-1,3-thiazol-5-yl]sulfonyl}-2H,4H,5H,6H-pyrrolo[3,4-c]pyrazol-5-yl)-2-phenylpropan-1-one as a colorless solid (17.8 mg, 53%). $^1$HNMR (400 MHz, DMSO-$d_6$) δ 8.35 (dd, J=2.6, 1.3 Hz, 1H), 7.39-7.26 (m, 4H), 7.22 (td, J=7.2, 1.4 Hz, 1H), 5.00 (qd, J=8.4, 1.3 Hz, 2H), 4.97-4.85 (m, 1H), 4.80 (t, J=5.4 Hz, 1H), 4.59-4.42 (m, 2H), 4.42-4.31 (m, 1H), 4.03-3.93 (m, 2H), 3.56-3.45 (m, 1H), 2.54 (d, J=1.4 Hz, 3H). LCMS (ES) [M+1]$^+$ m/z: 516.95.

Example 1.27

Synthesis of (2S)-2-(2-fluorophenyl)-3-hydroxy-1-{2-[(2-methoxy-4-methyl-1,3-thiazol-5-yl)sulfonyl]-2H,4H,5H,6H-pyrrolo[3,4-c]pyrazol-5-yl}propan-1-one (Compound 23)

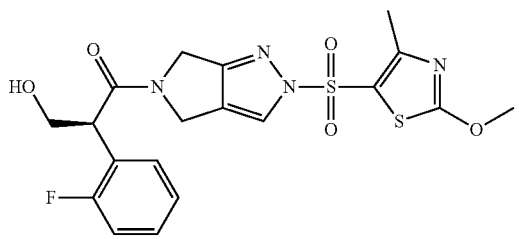 [SMILES: COc1nc(C)c(S(=O)(=O)n2cc3c(n2)CN(C(=O)[C@H](CO)c2ccccc2F)C3)s1]

The title compound was synthesized according the 4-step procedure described for Compound 22 using methanol instead of 2,2,2-trifluoroethanol in step 2 and using (S)-2-(2-fluorophenyl)-3-hydroxypropanoic acid (Intermediate II-10) instead of (2S)-3-hydroxy-2-phenylpropanoic acid in step 4. (2S)-2-(2-fluorophenyl)-3-hydroxy-1-{2-[(2-methoxy-4-methyl-1,3-thiazol-5-yl)sulfonyl]-2H,4H,5H,6H-pyrrolo[3,4-c]pyrazol-5-yl}propan-1-one was isolated as a colorless solid (6.0 mg; 32%). $^1$HNMR (400 MHz, DMSO-d$_6$) δ8.25-8.17 (m, 1H), 7.36 (td, J=7.6, 2.0 Hz, 1H), 7.31-7.23 (m, 1H), 7.20-7.09 (m, 2H), 4.96-4.79 (m, 2H), 4.52-4.34 (m, 2H), 4.33-4.18 (m, 2H), 4.04 (d, J=1.0 Hz, 3H), 4.00-3.91 (m, 1H), 3.56 (dq, J=10.9, 5.8 Hz, 1H), 2.45 (dd, J=2.2, 1.0 Hz, 3H). LCMS (ES) [M+1]$^+$ m/z: 466.96.

Example 1.28

Synthesis of (2S)-1-(2-{[1-(2,2-difluoroethyl)-1H-imidazol-4-yl]sulfonyl}-2H,4H,5H,6H-pyrrolo[3,4-c]pyrazol-5-yl)-3-hydroxy-2-phenylpropan-1-one (Compound 24)

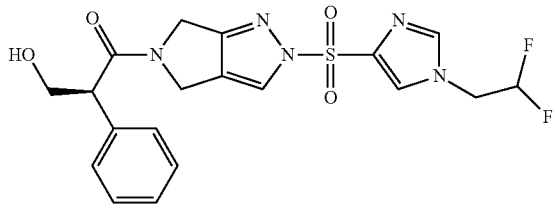 [SMILES: O=C([C@H](CO)c1ccccc1)N1Cc2cn(S(=O)(=O)c3cn(CC(F)F)cn3)nc2C1]

Step 1

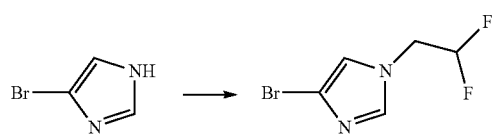 [SMILES: Brc1c[nH]cn1 ; FC(F)Cn1cnc(Br)c1]

To a mixture of 4-bromo-1H-imidazole (500.00 mg; 3.40 mmol; 1.00 eq.) and cesium carbonate (1163.85 mg; 3.57 mmol; 1.05 eq.) in dimethyl sulfoxide (6.80 mL) at ambient temperature was added 2,2-difluoroethyl trifluoromethanesulfonate (1092.60 mg; 5.10 mmol; 1.50 eq.) and the mixture was stirred at ambient temperature After 3.5 h the mixture was diluted with water, extracted with EtOAc, dried over MgSO$_4$, filtered, and concentrated to provide a yellow oil. The crude material was purified on a silica gel eluting with 0-50% EtOAc in heptane to provide the desired product as a colorless oil (292 mg; 40%).

Step 2

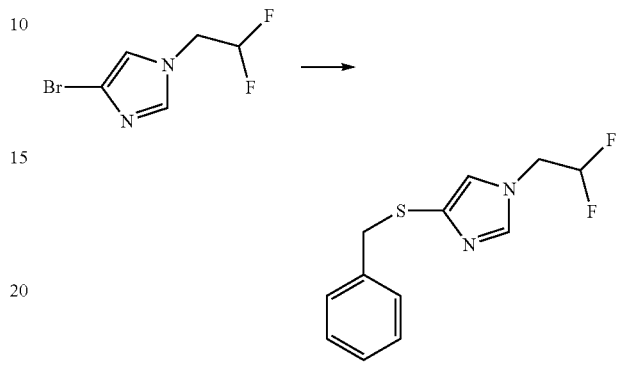

A mixture of 4-bromo-1-(2,2-difluoroethyl)-1H-imidazole (100.00 mg; 0.47 mmol; 1.00 eq.), Xantphos (27.42 mg; 0.05 mmol; 0.10 eq.), Pd$_2$(dba)$_3$ (86.79 mg; 0.09 mmol; 0.20 eq.), Hunig's base (0.17 mL; 0.95 mmol; 2.00 eq.) and benzyl hydrosulfide (0.11 mL; 0.95 mmol; 2.00 eq.) in 1,4-dioxane (2.37 mL) was subjected to 3 cycles of evacuation/back-filling with Ar and then it was stirred at 100° C. under Ar. After 22 h the mixture was cooled to ambient temperature and concentrated. The residue was purified on a silica gel column eluting with 0-40% EtOAc in heptane to provide a yellow oil consistent with the desired product, albeit contaminated by a small amount of unreacted SM. The product (70 mg) was taken on to the next step without further purification.

Step 3

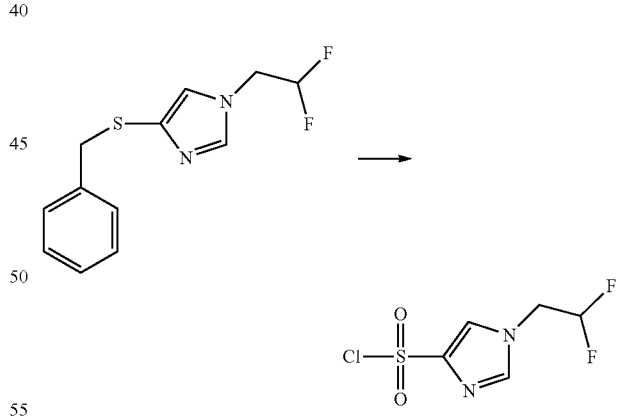

A mixture of 4-(benzylsulfanyl)-1-(2,2-difluoroethyl)-1H-imidazole (20.00 mg; 0.08 mmol; 1.00 eq.) and 1-chloro-2,5-pyrrolidinedione (31.51 mg; 0.24 mmol; 3.00 eq.) in acetic acid (0.39 mL) and water (0.04 mL) was stirred at ambient temperature; After 3 h (no reaction observed) dichloro-dimethyl-hydantoin (3 eq). After 1 h the mixture was diluted with EtOAc and washed with water, dried over MgSO$_4$, filtered and concentrated. The residue was purified on a silica gel column eluting with 0-80% EtOAc in heptane, to provide the desired product as a colorless solid (16.5 mg; 93%).

Step 4

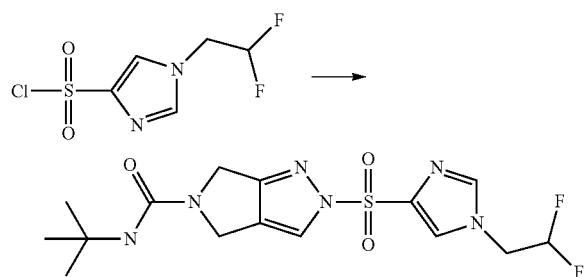

To a suspension of sodium hydride (3.73 mg; 0.09 mmol; 1.30 eq.) in THF (1 mL) under N₂ in an ice bath was added a solution of tert-butyl 2H,4H,5H,6H-pyrrolo[3,4-c]pyrazole-5-carboxylate (15.00 mg; 0.07 mmol; 1.00 eq.) in THF (0.5 mL) drop-wise. The mixture was allowed to stir in the ice bath for 20 min. A solution of 1-(2,2-difluoroethyl)-1H-imidazole-4-sulfonyl chloride (16.53 mg; 0.07 mmol; 1.00 eq.) in THF (0.5 mL) was then added slowly. The mixture was allowed to stir while warming up to ambient temperature. After 1 h the reaction mixture was quenched and diluted with NH₄Cl (few drops of AcOH was also added). This mixture was extracted twice with a 1:3 mixture of IPA:CHCl₃. The combined organics were washed with water, dried over MgSO₄, filtered, and concentrated to provide a colorless oil. The crude material was purified on a silica gel column eluting with 0-40% EtOAc in heptane to provide the desired product as a colorless solid (20 mg; 72%).

Step 5

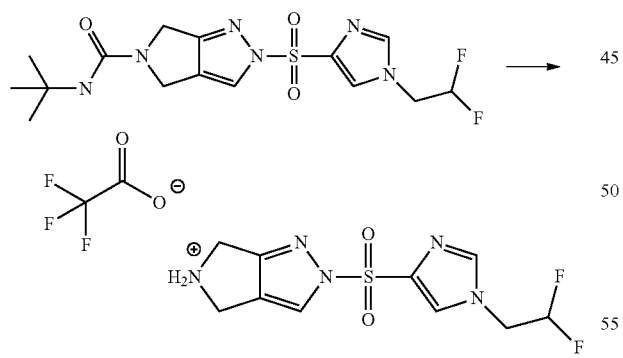

To a solution of tert-butyl 2-{[1-(2,2-difluoroethyl)-1H-imidazol-4-yl]sulfonyl}-2H,4H,5H,6H-pyrrolo[3,4-c]pyrazole-5-carboxylate (20.00 mg; 0.05 mmol; 1.00 eq.) in dichloromethane (0.12 mL) cooled to 0° C. was added TFA (0.24 mL; 12.00 V) and the mixture was stirred at 0° C. After 1 h the mixture was concentrated in vacuo and dried under high vacuum for 1 h. The crude material was taken on to the next step without further purification assuming 100% yield (15 mg free base; 20 mg TFA salt).

Step 6

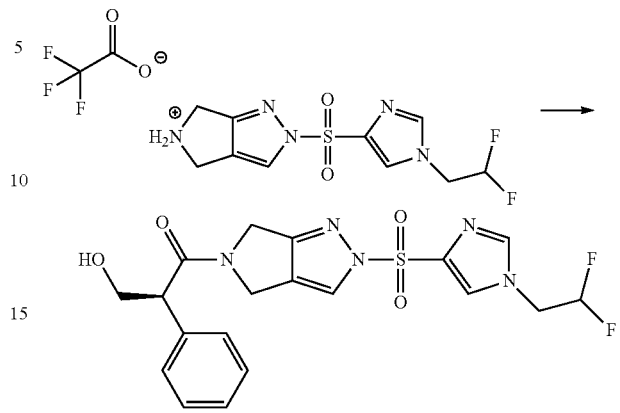

To a mixture of (2S)-3-hydroxy-2-phenylpropanoic acid (10.35 mg; 0.06 mmol; 1.30 eq.), 1-(2,2-difluoroethyl)-4-{2H,4H,5H,6H-pyrrolo[3,4-c]pyrazole-2-sulfonyl}-1H-imidazole; TFA (20.00 mg; 0.05 mmol; 1.00 eq.) and Hunig's base (0.02 mL; 0.10 mmol; 2.00 eq.) in DMF (0.48 mL) was added HATU (23.69 mg; 0.06 mmol; 1.30 eq.) and the resulting mixture was stirred at ambient temperature. After 1 h the mixture was diluted with 1:1 PhMe/EtOAc and washed with an equal amount of water. The organic phase was then concentrated. The crude material was purified on a silica gel column eluting with 0-100% EtOAc in heptane to provide (2S)-1-(2-{[1-(2,2-difluoroethyl)-1H-imidazol-4-yl]sulfonyl}-2H,4H,5H,6H-pyrrolo[3,4-c]pyrazol-5-yl)-3-hydroxy-2-phenylpropan-1-one as a colorless solid (6.4 mg; 29%). ¹HNMR (400 MHz, DMSO-d₆) δ 8.24-8.18 (m, 1H), 8.13 (d, J=2.7 Hz, 1H), 7.90 (dd, J=2.0, 1.0 Hz, 1H), 7.35-7.24 (m, 4H), 7.24-7.17 (m, 1H), 6.50-6.17 (m, 1H), 4.93-4.79 (m, 1H), 4.80-4.70 (m, 3H), 4.50-4.33 (m, 2H), 4.29 (dd, J=17.9, 13.2 Hz, 1H), 3.96 (dd, J=8.1, 2.2 Hz, 2H), 3.49 (dd, J=5.9, 3.5 Hz, 1H). LCMS (ES) [M+1]⁺ m/z: 452.05.

Example 1.29

Synthesis of (2S)-3-hydroxy-1-{2-[(2-methoxy-4-methyl-1,3-thiazol-5-yl)sulfonyl]-2H,4H,5H,6H-pyrrolo[3,4-c]pyrazol-5-yl}-2-phenylpropan-1-one OR 5-({5-[(2S)-3-hydroxy-2-phenylpropanoyl]-2H,4H,5H,6H-pyrrolo[3,4-c]pyrazol-2-yl}sulfonyl)-3,4-dimethyl-2,3-dihydro-1,3-thiazol-2-one (Compound 25)

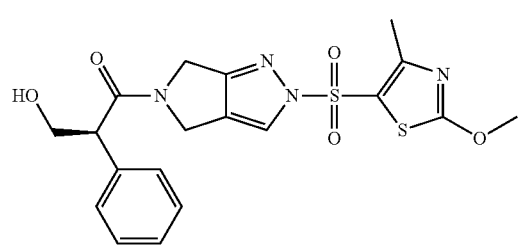

OR

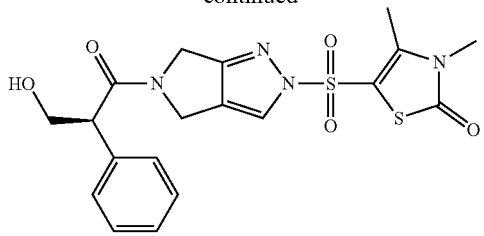

Step 1

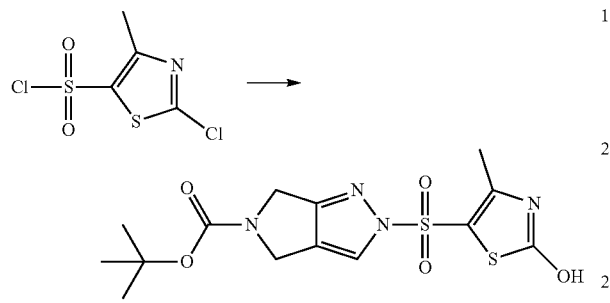

To a suspension of sodium hydride (124.24 mg; 3.11 mmol; 1.30 eq.) in THF (15 mL) under nitrogen in an ice bath was added a solution of tert-butyl 2H,4H,5H,6H-pyrrolo[3,4-c]pyrazole-5-carboxylate (500.00 mg; 2.39 mmol; 1.00 eq.) in THF (3 mL) over 5 min. The mixture was allowed to stir in the ice bath for 30 min. A suspension of 2-chloro-4-methyl-1,3-thiazole-5-sulfonyl chloride (554.63 mg; 2.39 mmol; 1.00 eq.) in THF (2 mL) was then added slowly. The mixture was allowed to stir in the ice bath for 45 min while warming up to ambient temperature. After 2 h the reaction mixture was quenched and diluted with NH$_4$Cl (2 mL of AcOH was also added) and extracted twice with a 1:3 mixture of IPA:CHCl$_3$. The combined organics were washed with water and brine, dried over MgSO$_4$, filtered, and concentrated to provide a yellow oil. The crude material was purified on a silica gel column, eluting with 0-50% EtOAc in heptane to provide tert-butyl 2-[(2-hydroxy-4-methyl-1,3-thiazol-5-yl)sulfonyl]-2H,4H,5H,6H-pyrrolo[3,4-c]pyrazole-5-carboxylate as a colorless solid (234 mg; 25%). $^1$HNMR was not conclusive but LCMS was consistent with the hydroxy byproduct. This material was carried on without further purification.

Step 2

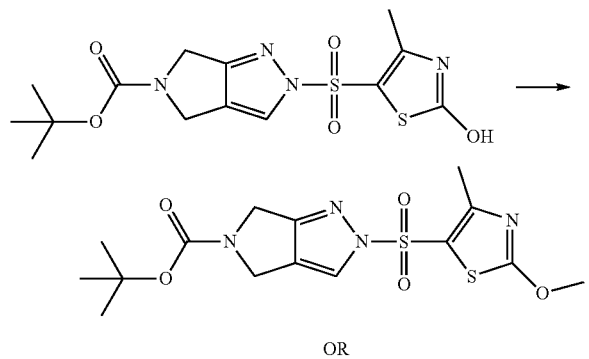

To a mixture of tert-butyl 2-[(2-hydroxy-4-methyl-1,3-thiazol-5-yl)sulfonyl]-2H,4H,5H,6H-pyrrolo[3,4-c]pyrazole-5-carboxylate (60.00 mg; 0.16 mmol; 1.00 eq.) and potassium carbonate (64.28 mg; 0.47 mmol; 3.00 eq.) in acetone (1.55 mL) at ambient temperature was added iodomethane (0.02 mL; 0.31 mmol; 2.00 eq.), and the mixture was stirred at ambient temperature overnight. The mixture was diluted with EtOAc, washed with water and brine and dried over MgSO$_4$. To give after concentration a yellow oil. The crude material was purified by on a silica gel column, eluting with 0-40% EtOAc in heptane to provide tert-butyl 2-[(2-methoxy-4-methyl-1,3-thiazol-5-yl)sulfonyl]-2H,4H,5H,6H-pyrrolo[3,4-c]pyrazole-5-carboxylate OR tert-butyl 2-[(3,4-dimethyl-2-oxo-2,3-dihydro-1,3-thiazol-5-yl)sulfonyl]-2H,4H,5H,6H-pyrrolo[3,4-c]pyrazole-5-carboxylate as a colorless oil (13 mg; 21%).

Step 3

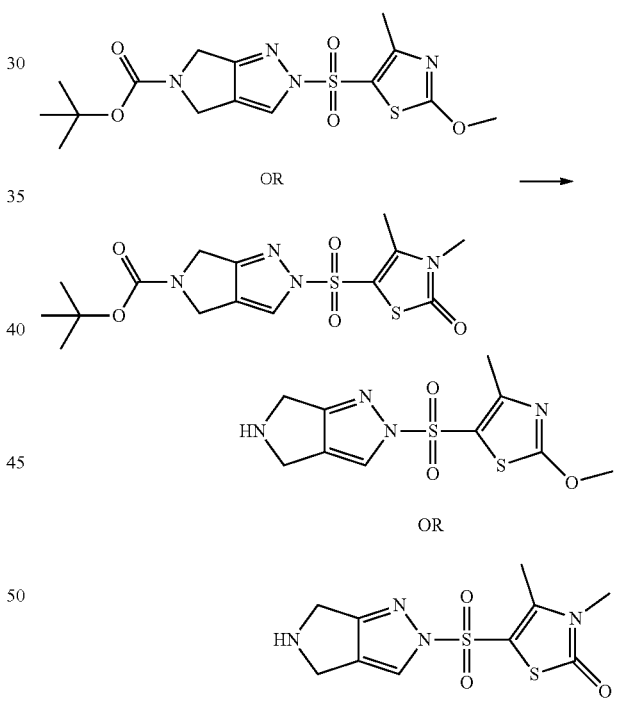

To a mixture of tert-butyl 2-[(2-methoxy-4-methyl-1,3-thiazol-5-yl)sulfonyl]-2H,4H,5H,6H-pyrrolo[3,4-c]pyrazole-5-carboxylate OR tert-butyl 2-[(3,4-dimethyl-2-oxo-2,3-dihydro-1,3-thiazol-5-yl)sulfonyl]-2H,4H,5H,6H-pyrrolo[3,4-c]pyrazole-5-carboxylate (13.00 mg; 0.03 mmol; 1.00 eq.) in 1,2-dichloroethane (0.26 mL) was added zincbromide (21.93 mg; 0.10 mmol; 3.00 eq.) and the resulting mixture was allowed to stir at 55° C. overnight. The mixture was then cooled to ambient temperature, diluted with water, quenched with 0.5 mL of aqueous ammonium hydroxide, and extracted with a 3:1 mix of CHCl$_3$:IPA. The combined organics were washed with brine, dried over MgSO$_4$, filtered and concentrated to provide 2-methoxy-4-methyl-5-{2H, 4H,5H,6H-pyrrolo[3,4-c]pyrazole-2-sulfonyl}-1,3-thiazole OR 3,4-dimethyl-5-{2H,4H,5H,6H-pyrrolo[3,4-c]pyrazole-2-sulfonyl}-2,3-dihydro-1,3-thiazol-2-one as a gray solid. This material was taken on to the next step without further purification assuming 100% yield (~9.5 mg).

Step 4

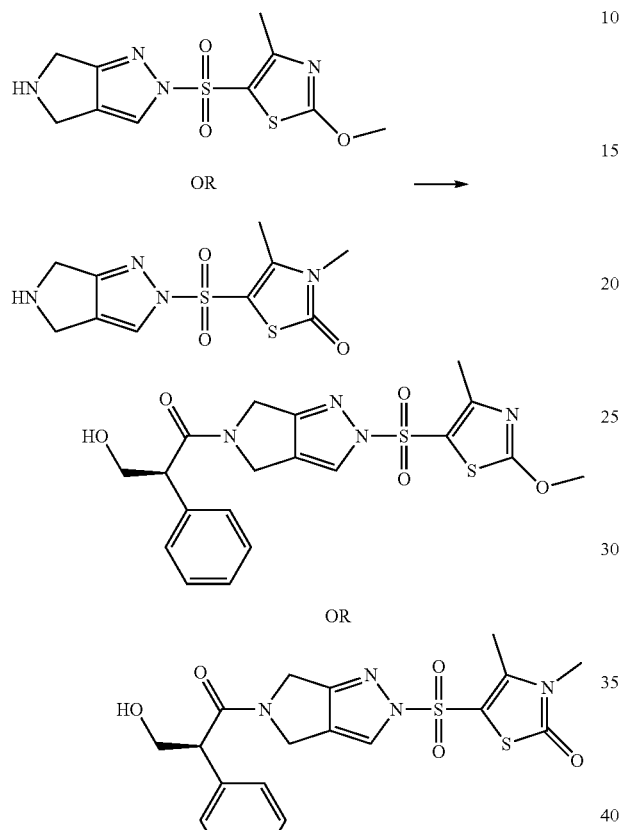

To a mixture of (2S)-3-hydroxy-2-phenylpropanoic acid (6.83 mg; 0.04 mmol; 1.30 eq.), 2-methoxy-4-methyl-5-{2H,4H,5H,6H-pyrrolo[3,4-c]pyrazole-2-sulfonyl}-1,3-thiazole OR 3,4-dimethyl-5-{2H,4H,5H,6H-pyrrolo[3,4-c]pyrazole-2-sulfonyl}-2,3-dihydro-1,3-thiazol-2-one (9.50 mg; 0.03 mmol; 1.00 eq.) and Hunig's base (0.01 mL; 0.06 mmol; 2.00 eq.) in DMF (0.32 mL) was added HATU (15.63 mg; 0.04 mmol; 1.30 eq.) and the resulting mixture was stirred at ambient temperature. After 2.5 h the mixture was diluted with 1:1 PhMe/EtOAc and washed with an equal amount of water. The organic phase was dried over MgSO$_4$, filtered and concentrated. The crude material was purified on a silica gel column eluting with 0-100% EtOAc in heptane to provide (2S)-3-hydroxy-1-{2-[(2-methoxy-4-methyl-1,3-thiazol-5-yl)sulfonyl]-2H,4H,5H,6H-pyrrolo[3,4-c]pyrazol-5-yl}-2-phenylpropan-1-one OR 5-({5-[(2S)-3-hydroxy-2-phenylpropanoyl]-2H,4H,5H,6H-pyrrolo[3,4-c]pyrazol-2-yl}sulfonyl)-3,4-dimethyl-2,3-dihydro-1,3-thiazol-2-one as a colorless, very fluffy solid consistent with the desired product (3.0 mg, 21%). $^1$HNMR (400 MHz, DMSO-d$_6$) δ8.17 (dq, J=2.0, 1.0 Hz, 1H), 7.35-7.20 (m, 5H), 4.86 (dd, J=31.8, 14.4 Hz, 1H), 4.78 (q, J=5.2 Hz, 1H), 4.52-4.26 (m, 3H), 4.01-3.91 (m, 2H), 3.50 (q, J=3.6 Hz, 1H), 3.18 (dd, J=1.8, 0.9 Hz, 3H), 2.46 (d, J=0.9 Hz, 3H). LCMS (ES) [M+1]$^+$ m/z: 449.11.

Example 1.30

Synthesis of (2S)-3-hydroxy-1-{2-[(2-ethoxy-4-methyl-1,3-thiazol-5-yl)sulfonyl]-2H,4H,5H,6H-pyrrolo[3,4-c]pyrazol-5-yl}-2-phenylpropan-1-one OR 3-ethyl-5-({5-[(2S)-3-hydroxy-2-phenylpropanoyl]-2H,4H,5H,6H-pyrrolo[3,4-c]pyrazol-2-yl}sulfonyl)-4-methyl-2,3-dihydro-1,3-thiazol-2-one (Compound 26)

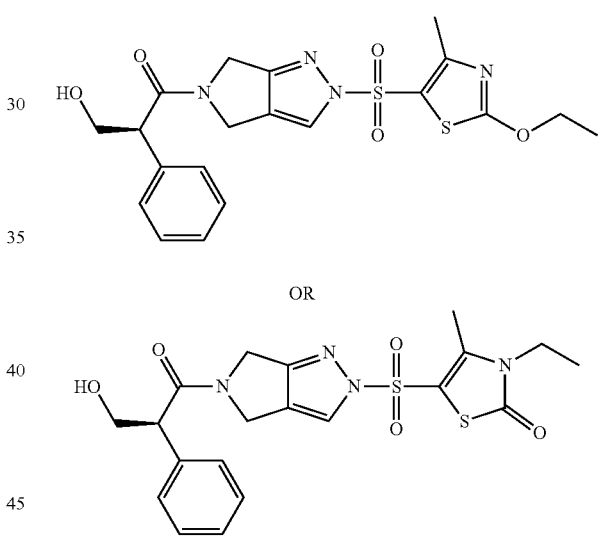

The title compound was synthesized according the 4-step procedure described for Compound 25 using ethyl iodide instead of iodomethane in step 2. (2S)-3-hydroxy-1-{2-[(2-ethoxy-4-methyl-1,3-thiazol-5-yl)sulfonyl]-2H,4H,5H,6H-pyrrolo[3,4-c]pyrazol-5-yl}-2-phenylpropan-1-one OR 3-ethyl-5-({5-[(2S)-3-hydroxy-2-phenylpropanoyl]-2H,4H,5H,6H-pyrrolo[3,4-c]pyrazol-2-yl}sulfonyl)-4-methyl-2,3-dihydro-1,3-thiazol-2-one was isolated as a colorless solid (2.0 mg; 22%). $^1$HNMR (400 MHz, DMSO-d$_6$) δ8.21-8.12 (m, 1H), 7.36-7.18 (m, 5H), 4.87 (dd, J=33.2, 14.3 Hz, 1H), 4.78 (t, J=4.8 Hz, 1H; OH), 4.39 (ddt, J=45.1, 20.1, 15.1 Hz, 3H), 4.01-3.92 (m, 2H), 3.75-3.65 (m, 2H), 3.50 (dt, J=7.8, 2.6 Hz, 1H), 2.50 (t, J=0.6 Hz, 3H), 1.13-1.07 (m, 3H). LCMS (ES) [M+1]$_+$ m/z: 462.92.

Example 1.31

Synthesis of (2S)-1-(2-{[2-(2,2-difluoroethoxy)-4-methyl-1,3-thiazol-5-yl]sulfonyl}-2H,4H,5H,6H-pyrrolo[3,4-c]pyrazol-5-yl)-3-hydroxy-2-phenylpropan-1-one or 3-(2,2-difluoroethyl)-5-({5-[(2S)-3-hydroxy-2-phenylpropanoyl]-2H,4H,5H,6H-pyrrolo[3,4-c]pyrazol-2-yl}sulfonyl)-4-methyl-2,3-dihydro-1,3-thiazol-2-one (Compound 27)

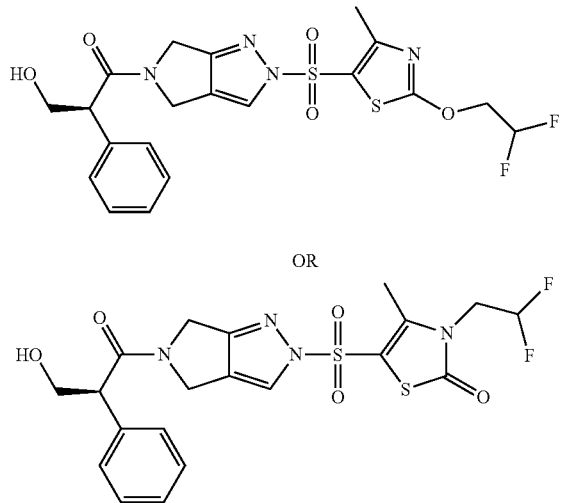

OR

The title compound was synthesized according the 4-step procedure described for Compound 25 using 2,2-difluoroethyl trifluoromethanesulfonate instead of iodomethane in step 2. (2S)-1-(2-{[2-(2,2-difluoroethoxy)-4-methyl-1,3-thiazol-5-yl]sulfonyl}-2H,4H,5H,6H-pyrrolo[3,4-c]pyrazol-5-yl)-3-hydroxy-2-phenylpropan-1-one OR 3-(2,2-difluoroethyl)-5-({5-[(2S)-3-hydroxy-2-phenylpropanoyl]-2H,4H,5H,6H-pyrrolo[3,4-c]pyrazol-2-yl}sulfonyl)-4-methyl-2,3-dihydro-1,3-thiazol-2-one was isolated as a colorless solid (5.4 mg; 45%). $^1$HNMR (400 MHz, DMSO-$d_6$) δ7.81 (dd, J=8.7, 1.3 Hz, 1H), 7.38-7.16 (m, 5H), 6.43-6.10 (m, 1H), 5.13-4.75 (m, 2H; contains OH signal), 4.64 (dd, J=17.5, 14.2 Hz, 1H), 4.58-4.30 (m, 2H), 4.28-4.16 (m, 2H), 4.03-3.88 (m, 2H), 3.51 (tdd, J=8.7, 6.2, 2.5 Hz, 1H), 2.52 (d, J=1.3 Hz, 3H). LCMS (ES) [M+1]$^+$ m/z: 498.96.

Example 1.32

Synthesis of (R)-1-(2-((1-(2,2-difluoroethyl)-1H-pyrazol-3-yl)sulfonyl)-2,6-dihydropyrrolo[3,4-c]pyrazol-5(4H)-yl)-2-(3-fluoropyridin-2-yl)-2-hydroxyethan-1-one and (S)-1-(2-((1-(2,2-difluoroethyl)-1H-pyrazol-3-yl)sulfonyl)-2,6-dihydropyrrolo[3,4-c]pyrazol-5(4H)-yl)-2-(3-fluoropyridin-2-yl)-2-hydroxyethan-1-one (Compounds 28 and 29)

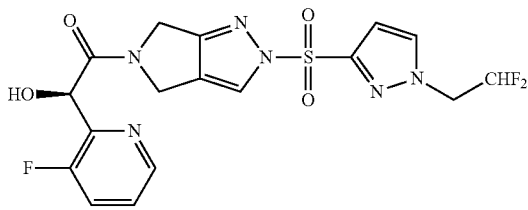

and

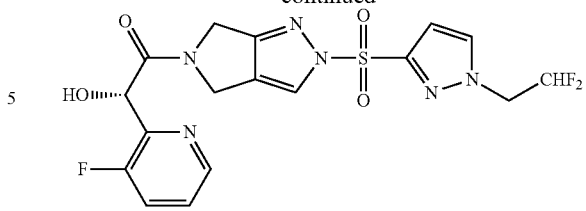

Into a 20 mL vial were added 1-(2,2-difluoroethyl)-3-[4H,5H,6H-pyrrolo[3,4-c]pyrazole-2-sulfonyl]pyrazol (Step 5, Example 1.16, 300 mg, 1.00 mmol, 1.00 eq.), (3-fluoropyridin-2-yl)(hydroxy)acetic acid hydrochloride (249 mg, 1.20 mmol, 1.20 eq.), DMF (5.00 mL), DIEA (387 mg, 3.00 mmol, 3.0 eq.). This was followed by the addition of HATU (456 mg, 1.20 mmol, 1.20 eq.) at 0° C. The resulting mixture was stirred for 2 h at room temperature. The reaction solution was purified by Prep-HPLC using these conditions: C18-120 g column, CH$_3$CN/H$_2$O (0.05% FA), from 10% to 80% in 12 min, Flow rate, 70 mL/min, Detector, 254 nm. The fraction of the target was freezing dried, giving 230 mg of 1-(2-((1-(2,2-difluoroethyl)-1H-pyrazol-3-yl)sulfonyl)-2,6-dihydropyrrolo[3,4-c]pyrazol-5(4H)-yl)-2-(3-fluoropyridin-2-yl)-2-hydroxyethan-1-one as white solid.

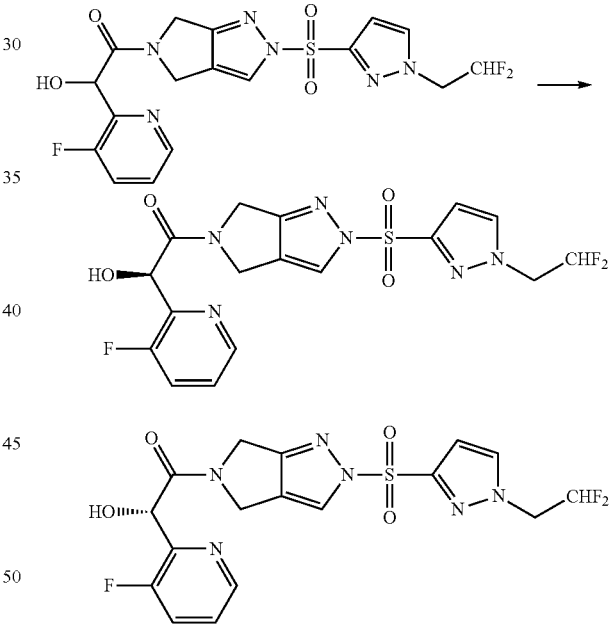

1-(2-((1-(2,2-difluoroethyl)-1H-pyrazol-3-yl)sulfonyl)-2,6-dihydropyrrolo[3,4-c]pyrazol-5(4H)-yl)-2-(3-fluoropyridin-2-yl)-2-hydroxyethan-1-one (230 mg) was separated by Chiral-Prep-HPLC using these conditions: CHIRAL ART Cellulose-SJ column, 3*25 cm, 5 μm, Mobile Phase A: CO$_2$ (1), Mobile Phase B: MeOH (0.1% 2 M NH$_3$-MeOH), Flow rate: 85 mL/min, Gradient: isocratic 35% B, hold 10 min, Wave Length: 220 nm. Two compounds were isolated. The fraction at 4.4 min was concentrated in vacuum, resulting in Stereoisomer 3 (83 mg, 21%) as a white solid. $^1$HNMR (300 MHz, DMSO-$d_6$) δ 8.40-8.36 (m, 1H), 8.21 (d, J=15.0 Hz, 1H), 8.08-8.06 (m, 1H), 7.80-7.71 (m, 1H), 7.52-7.44 (m, 1H), 7.00 (dd, J=2.4, 1.2 Hz, 1H), 6.41 (t, J=54.3 Hz, 1H), 5.81 (dd, J=6.9, 9.0 Hz, 1H), 5.64-5.59 (m, 1H), 4.91-4.73

(m, 3H), 4.61-4.29 (m, 2H), 4.16 (dd, J=9.0, 6.9 Hz, 1H). LCMS (ES) [M+1]⁺ m/z: 457. The fraction at 5.5 min was concentrated in vacuum, resulting in Stereoisomer 4. ¹H NMR (300 MHz, DMSO-d₆) δ 8.40-8.36 (m, 1H), 8.21 (d, J=15.0 Hz, 1H), 8.08-8.06 (m, 1H), 7.80-7.71 (m, 1H), 7.52-7.44 (m, 1H), 7.00 (dd, J=2.4, 1.2 Hz, 1H), 6.41 (t, J=54.3 Hz, 1H), 5.81 (dd, J=6.9, 9.0 Hz, 1H), 5.64-5.59 (m, 1H), 4.91-4.73 (m, 3H), 4.61-4.29 (m, 2H), 4.16 (dd, J=9.0, 6.9 Hz, 1H). LCMS (ES) [M+1]⁺ m/z: 457.

Example 1.33

Synthesis of (R)-1-(2-((1-(2,2-difluoroethyl)-1H-pyrazol-3-yl)sulfonyl)-2,6-dihydropyrrolo[3,4-c]pyrazol-5(4H)-yl)-2-(2-fluorophenyl)-3-hydroxypropan-1-one (Compound 30)

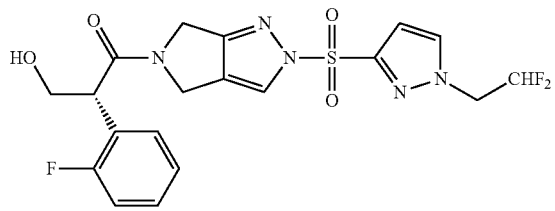

The title compound was synthesized from (R)-2-(2-fluorophenyl)-3-hydroxypropanoic acid (100.00 mg, 0.54 mmol, 1.00 eq.) and 1-(2,2-difluoroethyl)-4-{2H,4H,5H,6H-pyrrolo[3,4-c]pyrazole-2-sulfonyl}-1H-pyrazole (Intermediate I-7, 181.80 mg, 0.65 mmol, 1.20 eq.) according to the procedures described in Example 1.6. (R)-1-(2-((1-(2,2-difluoroethyl)-1H-pyrazol-3-yl)sulfonyl)-2,6-dihydropyrrolo[3,4-c]pyrazol-5(4H)-yl)-2-(2-fluorophenyl)-3-hydroxypropan-1-one was obtained as a white solid. ¹H NMR (300 MHz, DMSO-d₆) δ 8.71 (s, 1H), 8.18 (d, J=2.6 Hz, 1H), 8.11 (s, 1H), 7.59-6.98 (m, 4H), 6.42 (tt, J=54.4, 3.6 Hz, 1H), 5.12-4.50 (m, 3H), 4.70-4.13 (m, 4H), 3.99 (t, J=9.2 Hz, 1H), 3.60 (dt, J=10.6, 5.7 Hz, 1H). LCMS (ES) [M+1]⁺ m/z: 470.

Example 1.34

Synthesis of (S)-1-(2-((1-(2,2-difluoroethyl)-1H-pyrazol-3-yl)sulfonyl)-2,6-dihydropyrrolo[3,4-c]pyrazol-5(4H)-yl)-2-(3-fluoropyridin-2-yl)-3-hydroxypropan-1-one and (R)-1-(2-((1-(2,2-difluoroethyl)-1H-pyrazol-3-yl)sulfonyl)-2,6-dihydropyrrolo[3,4-c]pyrazol-5(4H)-yl)-2-(3-fluoropyridin-2-yl)-3-hydroxypropan-1-one (Compounds 31 and 32)

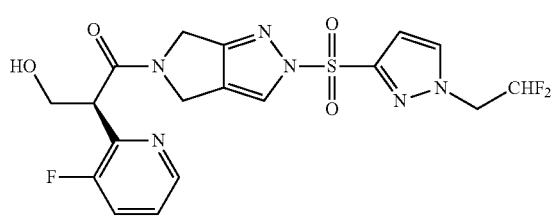

and

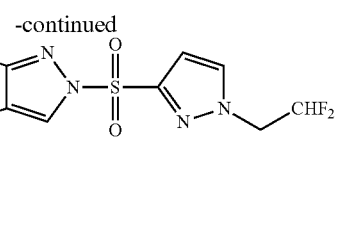

The title compounds were synthesized according to the procedures described for Compounds 28 and 29. The crude product was purified by Prep-HPLC using these conditions, SunFire Prep C18 OBD Column, 19×150 mm, 5um, mobile phase A, H₂O (0.1% FA); phase B, CH₃CN/MeOH (1/1) (5% up to 40% CH₃CN/MeOH in 15 min) followed by Prep-SFC using the following conditions: Column, CHIRAL ART Cellulose-SJ, 3*25 cm, 5 μm, Mobile Phase A, CO₂, Mobile Phase B, MeOH (0.1% 2M NH₃-MeOH), Gradient, isocratic 25% B, detector, 220 nm. This resulted in two stereoisomers: Stereoisomer 5, RT1: 5.58 min, (106.4 mg, 6.98%) as a white solid. ¹H NMR (300 MHz, DMSO-d₆) δ 8.39-8.36 (m, 1H), 8.22 (d, J=2.0 Hz, 1H), 8.07 (d, J=2.5 Hz, 1H), 7.73-765 (m, 1H), 7.42-7.36 (m, 1H), 7.00 (d, J=3.0 Hz, 1H), 6.40 (tt, J=57.0 Hz, 3.0 Hz, 1H), 4.93-4.73 (m, 4H), 4.53-4.34 (m, 3H), 4.26 (t, J=15.0 Hz, 1H), 4.10 (t, J=9.0 Hz, 1H), 3.97-3.90 (m, 1H). LCMS (ES) [M+1]⁺ m/z: 471. Stereoisomer 6, RT2: 6.68 min (101.4 mg, 6.65%) as a white solid. ¹H NMR (300 MHz, DMSO-d₆) δ 8.39-8.36 (m, 1H), 8.22 (d, J=2.2 Hz, 1H), 8.07 (d, J=2.5 Hz, 1H), 7.73-7.65 (m, 1H), 7.42-7.35 (m, 1H), 6.99 (d, J=2.4 Hz, 1H), 6.40 (tt, J=54.3 Hz, 3.6 Hz, 1H), 4.93-4.73 (m, 4H), 4.53-4.34 (m, 3H), 4.26 (t, J=15.3 Hz, 1H), 4.14-4.06 (m, 1H), 3.98-3.89 (m, 1H). LCMS (ES) [M+1]⁺ m/z: 471.

Example 1.35

Synthesis of (2R)-2-(2-fluorophenyl)-3-hydroxy-1-[2-[1-(2,2,2-trifluoroethyl)pyrazol-4-ylsulfonyl]-4H,6H-pyrrolo[3,4-c]pyrazol-5-yl]propan-1-one (Compound 33)

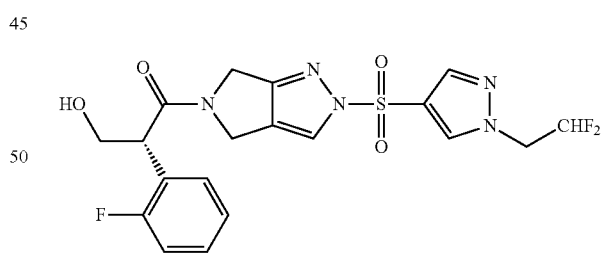

The title compound was synthesized from (2R)-2-(2-fluorophenyl)-3-hydroxypropanoic acid (75 mg, 0.41 mmol, 1.00 eq.) and 1-(2,2,2-trifluoroethyl)-4-{2H,4H,5H,6H-pyrrolo[3,4-c]pyrazole-2-sulfonyl}-1H-pyrazole (Intermediate I-10, 144 mg, 0.45 mmol, 1.10 eq.), following the procedure described on Step 6, Example 1.7. (2R)-2-(2-Fluorophenyl)-3-hydroxy-1-[2-[1-(2,2,2-trifluoroethyl)pyrazol-4-ylsulfonyl]-4H,6H-pyrrolo[3,4-c]pyrazol-5-yl]propan-1-one was isolated as a white powder (114.2 mg, 57.53%). ¹HNMR (300 MHz, DMSO-d₆) δ 8.78 (d, J=1.8 Hz, 1H), 8.21-8.15 (m, 2H), 7.39 (td, J=7.6, 3.8 Hz, 1H), 7.35-7.26 (m, 1H), 7.24-7.12 (m, 2H), 5.24 (q, J=8.9 Hz, 2H), 4.97-4.82 (m, 2H), 4.52-4.24 (m, 4H), 4.04-3.94 (m, 1H), 3.64-3.54 (m, 1H). LCMS (ES) [M+1]⁺ m/z: 488.

Example 1.36

Synthesis of (2S)-1-[2-[1-(2,2-difluoroethyl)pyrazol-4-ylsulfonyl]-4H,6H-pyrrolo[3,4-c]pyrazol-5-yl]-2-hydroxy-2-phenylethanone (Compound 34)

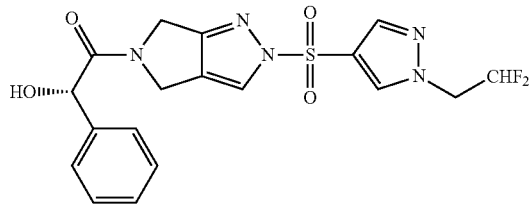 [SMILES: O=C([C@@H](O)c1ccccc1)N1Cc2cn(S(=O)(=O)c3cnn(CC(F)F)c3)nc2C1]

The title compound was synthesized from (S)-mandelic acid (70.00 mg, 0.46 mmol, 1.00 eq.) and Intermediate I-7 (139.54 mg, 0.46 mmol, 1.00 eq.) as described in Example 1.8. (2S)-1-[2-[1-(2,2-difluoroethyl)pyrazol-4-ylsulfonyl]-4H,6H-pyrrolo[3,4-c]pyrazol-5-yl]-2-hydroxy-2-phenylethanone was obtained as white solid (108 mg, 53.67%). ¹HNMR (300 MHz, DMSO-d₆) δ 8.71 (d, J=2.2 Hz, 1H), 8.17 (d, J=8.2 Hz, 1H), 8.11 (d, J=0.7 Hz, 1H), 7.47-7.24 (m, 5H), 6.42 (tt, J=54.5, 3.6 Hz, 1H), 5.32 (d, J=4.9 Hz, 1H), 4.83-4.72 (m, 1H), 4.69 (dq, J=15.2, 1.5 Hz, 2H), 4.60-4.24 (m, 3H). LCMS (ES) [M+1]⁺ m/z: 438.

Example 1.37

Synthesis of (2R)-1-[2-[1-(2-fluoroethyl)pyrazol-4-ylsulfonyl]-4H,6H-pyrrolo[3,4c]pyrazol-5-yl]-2-(2-fluorophenyl)-3-hydroxypropan-1-one (Compound 35)

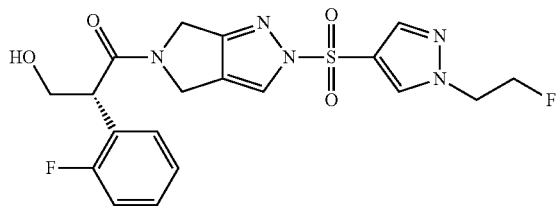 [SMILES: O=C([C@@H](CO)c1ccccc1F)N1Cc2cn(S(=O)(=O)c3cnn(CCF)c3)nc2C1]

The title compound was synthesized from (2R)-2-(2-fluorophenyl)-3-hydroxypropanoic acid (61.97 mg, 0.336 mmol, 1.20 eq.) and 1-(2-fluoroethyl)-4-[4H,5H,6H-pyrrolo[3,4-c]pyrazole-2-sulfonyl]pyrazole (80.00 mg, 0.280 mmol, 1.00 eq.) (Step 5, example 1.9) following the procedure described on Step 6, Example 1.9. (2R)-1-[2-[1-(2-fluoroethyl)pyrazol-4-ylsulfonyl]-4H,6H-pyrrolo[3,4c]pyrazol-5-yl]-2-(2-fluorophenyl)-3-hydroxypropan-1-one was obtained as a white solid 57.8 mg (45.66%). ¹H NMR (300 MHz, DMSO-d₆) δ 8.71 (d, J=3.3 Hz, 1H), 8.16 (d, J=3.1 Hz, 1H), 8.07 (d, J=3.3 Hz, 1H), 7.45-7.35 (m, 1H), 7.30 (dd, J=7.9, 6.1 Hz, 1H), 7.25-7.11 (m, 2H), 4.99-4.81 (m, 2H), 4.70 (t, J=4.7 Hz, 1H), 4.55 (t, J=4.8 Hz, 1H), 4.51-4.41 (m, 2H), 4.37 (d, J=16.6 Hz, 1H), 4.33-4.21 (m, 2H), 3.99 (td, J=9.4, 7.9, 3.3 Hz, 1H), 3.60 (dt, J=11.0, 5.8 Hz, 1H). LCMS (ES) [M+1]⁺ m/z: 452.

Example 1.38

Synthesis of (2R)-1-[2-[1-(2,2-difluoroethyl)pyrazol-4-ylsulfonyl]-4H,6H-pyrrolo[3,4-c]pyrazol-5-yl]-2-(2-fluorophenyl)-2-hydroxyethanone (Compound 36) and (2S)-1-[2-[1-(2,2-difluoroethyl)pyrazol-4-ylsulfonyl]-4H,6H-pyrrolo[3,4-c]pyrazol-5-yl]-2-(2-fluorophenyl)-2-hydroxyethanone (Compound 37)

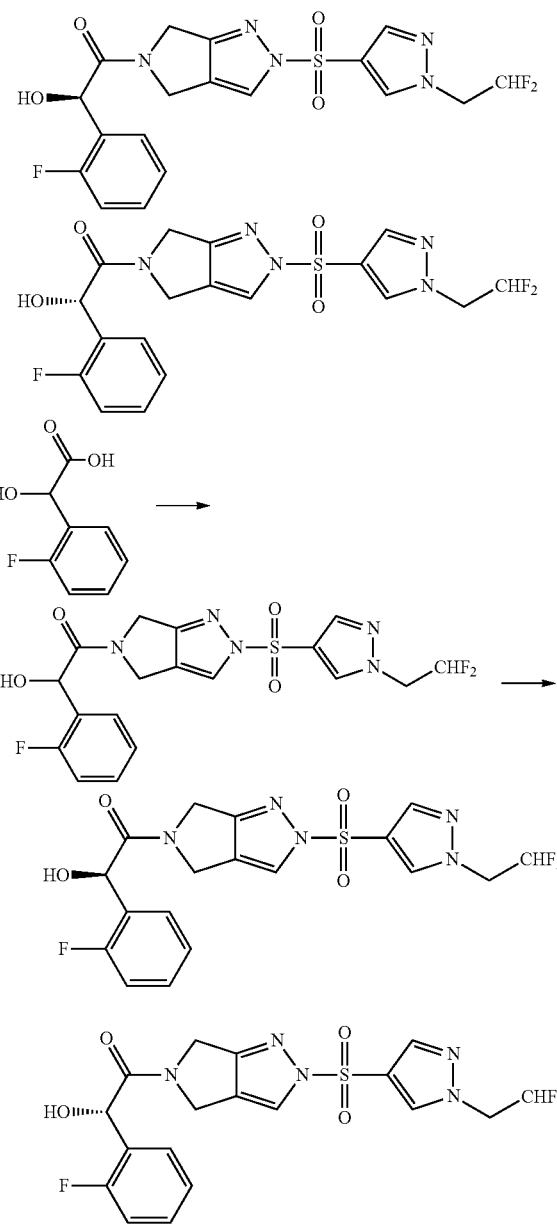

Into a 20-mL vial, were placed 1-(2,2-difluoroethyl)-4-[4H,5H,6H-pyrrolo[3,4-c]pyrazole-2-sulfonyl]pyrazole (Intermediate I-7, 300.00 mg, 0.99 mmol, 1.00 eq.), (2-fluorophenyl)(hydroxy)acetic acid (168.29 mg, 0.99 mmol, 1.00 eq.), DMF (10.00 mL) and NMM (200.10 mg, 1.98 mmol, 2.00 eq.). This was followed by the addition of HATU (451.33 mg, 1.187 mmol, 1.20 eq.), in portions at 0° C. The resulting solution was stirred for 2 h at room temperature. The crude product was purified by Prep-HPLC using the following conditions: column, Sunfire Prep C18 OBD Column, 50*250 mm, 5 μm, 10 nm; mobile phase, Water (0.5% NH₃.H₂O) and ACN (15% Phase B up to 60% in 15 min); Detector, 254. This resulted in 250 mg (55.50%) of 1-[2-[1-(2,2-difluoroethyl)pyrazol-4-ylsulfonyl]-4H,6H-pyrrolo[3,4-c]pyrazol-5-yl]-2-(2-fluorophenyl)-2-hydroxyethanone as white solid. LCMS (ES) [M+1]⁺ m/z: 456.

1-[2-[1-(2,2-Difluoroethyl)pyrazol-4-ylsulfonyl]-4H,6H-pyrrolo[3,4-c]pyrazol-5-yl]-2-(2-fluorophenyl)-2-hydroxyethanone was purified by Prep-SFC using the following conditions: column, (R,R)-WHELK-01-Kromasil, 2.11*25 cm, 5 μm; mobile phase, CO₂ (70%) and MeOH (30%); Detector, 254. (2R)-1-[2-[1-(2,2-Difluoroethyl)pyrazol-4-ylsulfonyl]-4H,6H-pyrrolo[3,4-c]pyrazol-5-yl]-2-(2-fluorophenyl)-2-hydroxyethanone was isolated as white solid (116 mg, 46.400%). Analytical SFC: 2.395 min. ¹HNMR (300 MHz, DMSO-d₆) δ 8.73 (d, J=1.8 Hz, 1H), 8.38 (dq, J=3.7, 1.7 Hz, 1H), 8.17 (d, J=15.7 Hz, 1H), 8.12 (s, 1H), 7.76 (dddd, J=10.0, 8.3, 3.7, 1.3 Hz, 1H), 7.48 (dtd, J=8.6, 4.4, 2.6 Hz, 1H), 6.42 (tt, J=54.4, 3.5 Hz, 1H), 5.61 (d, J=4.4 Hz, 1H), 4.85 (dd, J=19.6, 14.3 Hz, 1H), 4.73 (tdd, J=15.1, 3.7, 1.4 Hz, 2H), 4.63-4.39 (m, 2H), 4.13 (dd, J=25.1, 14.2 Hz, 1H). LCMS (ES) [M+1]⁺ m/z: 456.

(2S)-1-[2-[1-(2,2-Difluoroethyl)pyrazol-4-ylsulfonyl]-4H,6H-pyrrolo[3,4-c]pyrazol-5-yl]-2-(2-fluorophenyl)-2-hydroxyethanone was isolated as a white solid (115 mg, 46.00%). Analytical SFC: 1.708 min. ¹HNMR (300 MHz, DMSO-d₆) δ 8.72 (s, 1H), 8.19 (d, J=5.9 Hz, 1H), 8.12 (s, 1H), 7.47 (tdd, J=7.5, 5.4, 1.9 Hz, 1H), 7.37 (dtt, J=7.8, 4.6, 2.5 Hz, 1H), 7.27-7.12 (m, 2H), 6.42 (tt, J=54.4, 3.5 Hz, 1H), 5.91 (dd, J=15.0, 6.8 Hz, 1H), 5.55 (dd, J=6.8, 2.9 Hz, 1H), 4.85 (dd, J=20.7, 14.2 Hz, 1H), 4.72 (td, J=15.1, 3.6 Hz, 2H), 4.60-4.38 (m, 2H), 4.29 (dd, J=25.9, 14.2 Hz, 1H). LCMS (ES) [M+1]⁺ m/z: 456.

Example 1.39

Synthesis of (2R)-1-[2-[1-(2,2-difluoroethyl)pyrazol-4-ylsulfonyl]-4H,6H-pyrrolo[3,4-c]pyrazol-5-yl]-2-(3-fluoropyridin-2-yl)-2-hydroxyethanone and (2S)-1-[2-[1-(2,2-difluoroethyl)pyrazol-4-ylsulfonyl]-4H,6H-pyrrolo[3,4-c]pyrazol-5-yl]-2-(3-fluoropyridin-2-yl)-2-hydroxyethanone (Compounds 38 and 39)

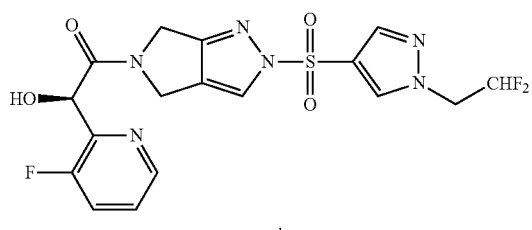

and

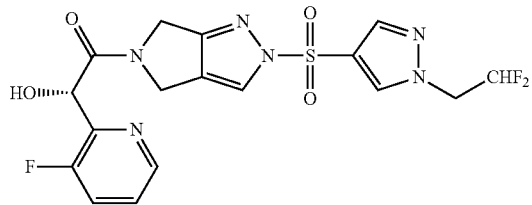

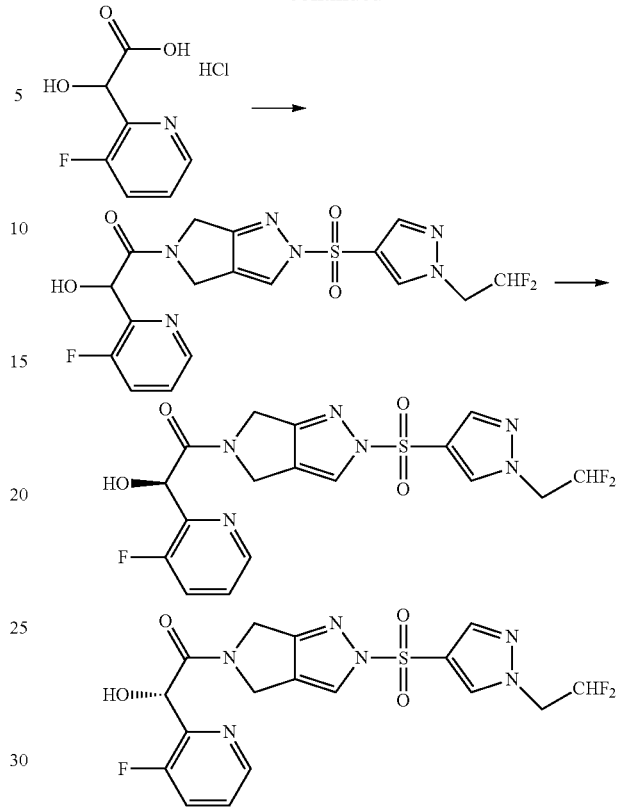

The title compound was synthesized from (3-fluoropyridin-2-yl)(hydroxy)acetic acid hydrochloride (328.54 mg, 1.58 mmol, 1.20 eq.) and Intermediate-7 (400.00 mg, 1.32 mmol, 1.00 eq.), following the procedure described for the synthesis of Compounds 36 and 37. 1-[2-[1-(2,2-difluoroethyl)pyrazol-4-ylsulfonyl]-4H,6H-pyrrolo[3,4-c]pyrazol-5-yl]-2-(3-fluoropyridin-2-yl)-2-hydroxyethanone was obtained as white solid (260 mg, 43.19%). LCMS (ES) [M+1]⁺ m/z: 457.

The 1-[2-[1-(2,2-difluoroethyl)pyrazol-4-ylsulfonyl]-4H,6H-pyrrolo[3,4-c]pyrazol-5-yl]-2-(3-fluoropyridin-2-yl)-2-hydroxyethanone (250.00 mg, 0.55 mmol, 1.00 eq.) was purified by Prep-SFC using the following conditions: Column, CHIRAL ART Cellulose-SJ, 3*25 cm, 5 μm; mobile phase, CO₂ (65%) and EtOH (0.1% 2M NH₃-MEOH) (35%); Detector, 254. Two stereoisomers were isolated; Stereoisomer 7: as a white solid (93.6 mg, 37.44%). Analytical SFC: 2.395 min. ¹HNMR (300 MHz, DMSO-d₆) δ 8.72 (d, J=1.8 Hz, 1H), 8.38 (dd, J=4.8, 2.1 Hz, 1H), 8.17 (d, J=15.8 Hz, 1H), 8.12 (s, 1H), 7.82-7.69 (m, 1H), 7.54-7.41 (m, 1H), 6.42 (t, J=54.3 Hz, 1H), 5.80 (s, 1H), 5.61 (s, 1H), 4.92-4.81 (m, 1H), 4.81-4.65 (m, 2H), 4.63-4.39 (m, 2H), 4.13 (dd, J=25.1, 14.2 Hz, 1H). LCMS (ES) [M+1]⁺ m/z: 457.

Stereoisomer 8 was also isolated as white solid (105.9 mg, 42.36%). Analytical SFC: 2.395 min. 1.708 min. ¹HNMR (300 MHz, DMSO-d₆) δ 8.73 (d, J=1.8 Hz, 1H), 8.38 (dq, J=3.7, 1.7 Hz, 1H), 8.17 (d, J=15.7 Hz, 1H), 8.12 (s, 1H), 7.76 (dddd, J=10.0, 8.3, 3.7, 1.3 Hz, 1H), 7.48 (dtd, J=8.6, 4.4, 2.6 Hz, 1H), 6.42 (tt, J=54.4, 3.5 Hz, 1H), 5.61 (d, J=4.4 Hz, 1H), 4.85 (dd, J=19.6, 14.3 Hz, 1H), 4.73 (tdd, J=15.1, 3.7, 1.4 Hz, 2H), 4.63-4.39 (m, 2H), 4.13 (dd, J=25.1, 14.2 Hz, 1H). LCMS (ES) [M+1]⁺ m/z: 457.

Example 1.40

Synthesis of (2R)-2-(2-fluorophenyl)-2-hydroxy-1-{2-[1-(2,2,2-trifluoroethyl)pyrazol-4-ylsulfonyl]-4H,6H-pyrrolo[3,4-c]pyrazol-5-yl}ethanone and (2S)-2-(2-fluorophenyl)-2-hydroxy-1-{2-[1-(2,2,2-trifluoroethyl)pyrazol-4-ylsulfonyl]-4H,6H-pyrrolo[3,4-c]pyrazol-5-yl}ethenone (Compounds 40 and 41)

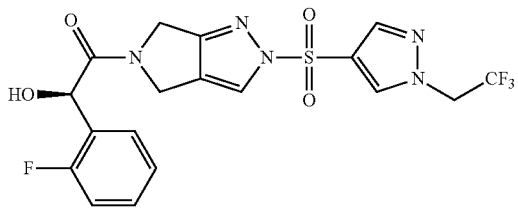

and

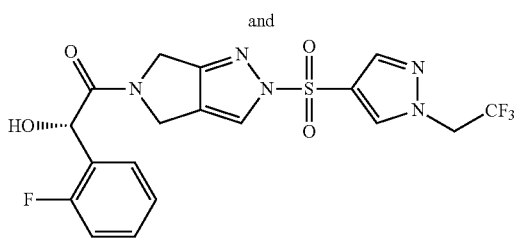

The title compound was synthesized from (2-fluorophenyl)(hydroxy)acetic acid (150 mg, 0.88 mmol, 1.00 eq.) and 1-(2,2,2-trifluoroethyl)-4-{2H,4H,5H,6H-pyrrolo[3,4-c]pyrazole-2-sulfonyl}-1H-pyrazole (Intermediate I-10, 283 mg, 0.88 mmol, 1.00 eq.) following the procedure described on Step 6, Example 1.7. The crude product was purified by Prep-HPLC using the following conditions (Prep-HPLC-001): Column, Sunfire Prep C18 OBD Column, 50*250 mm, 5 m; mobile phase, Water and ACN (23% ACN up to 60% in 15 min). The resulting mixture was concentrated under vacuum. The crude product was purified by Chiral-Prep-HPLC using the following conditions (XA-Prep SFC150-1): Column: CHIRAL ART Amylose-C NEO, 3*25 cm, 5 m; Mobile Phase A: $CO_2$, Mobile Phase B: MeOH (0.1% 2M $NH_3$-MeOH); Flow rate: 90 mL/min; Gradient: isocratic 20% B; Column Temperature (° C.): 35; Back Pressure (bar): 100; Wave Length: 220 nm. Two stereoisomers were isolated. CHIRAL_HPLC: Retention time: 1.195 min. For the other isomer, CHIRAL_HPLC: Retention time: 1.617 min.

Stereoisomer 9: RT1: 9.13 min, as a white solid (113 mg, 54.15%). $^1$H NMR (400 MHz, DMSO-$d_6$) δ 8.81 (s, 1H), 8.21-8.18 (m, 2H), 7.46 (q, J=7.5 Hz, 1H), 7.36 (s, 1H), 7.19 (dt, J=15.3, 7.3 Hz, 2H), 5.89 (dd, J=19.6, 6.8 Hz, 1H), 5.55 (dd, J=6.7, 4.0 Hz, 1H), 5.25 (q, J=8.9 Hz, 2H), 4.85 (dd, J=27.2, 14.2 Hz, 1H), 4.58-4.38 (m, 2H), 4.29 (dd, J=33.8, 14.2 Hz, 1H). LCMS (ES) [M+1]$^+$ m/z: 474.

Stereoisomer 10, RT2: 10.47 min, as a white solid (104.9 mg, 50.27%). $^1$H NMR (400 MHz, DMSO-d4) δ8.81 (s, 1H), 8.21-8.18 (m, 2H), 7.46 (q, J=7.5 Hz, 1H), 7.36 (s, 1H), 7.19 (dt, J=15.3, 7.3 Hz, 2H), 5.89 (dd, J=19.6, 6.8 Hz, 1H), 5.55 (dd, J=6.7, 4.0 Hz, 1H), 5.25 (q, J=8.9 Hz, 2H), 4.85 (dd, J=27.2, 14.2 Hz, 1H), 4.58-4.38 (m, 2H), 4.29 (dd, J=33.8, 14.2 Hz, 1H). LCMS (ES) [M+1]$^+$ m/z: 474.

Example 1.41

Synthesis of (S)-1-(2-((1-(2,2-difluoroethyl)-1H-pyrazol-4-yl)sulfonyl)-2,6-dihydropyrrolo[3,4-c]pyrazol-5(4H)-yl)-2-(3-fluoropyridin-2-yl)-3-hydroxypropan-1-one and (R)-1-(2-((1-(2,2-difluoroethyl)-1H-pyrazol-4-yl)sulfonyl)-2,6-dihydropyrrolo[3,4-c]pyrazol-5(4H)-yl)-2-(3-fluoropyridin-2-yl)-3-hydroxypropan-1-one (Compounds 42 and 43)

and

Step 1

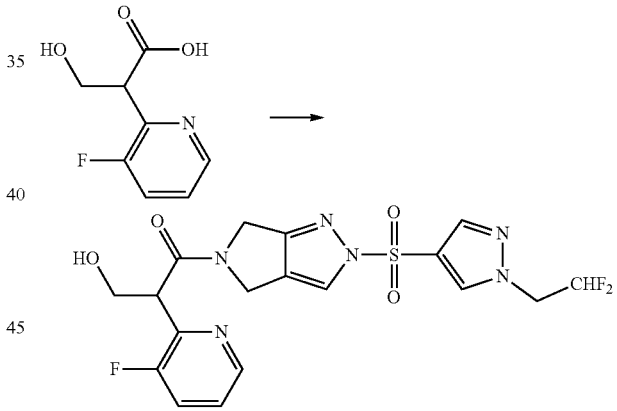

Into a 20 mL vial were added 2-(3-fluoropyridin-2-yl)-3-hydroxypropanoic acid (400 mg, 2.160 mmol, 1 eq.), 1-(2,2-difluoroethyl)-4-{4H,5H,6H-pyrrolo[3,4-c]pyrazole-2-sulfonyl}pyrazole (Intermediate I-7, 589.70 mg, 1.944 mmol, 0.9 eq.), DMF (8 mL), DIEA (335.05 mg, 2.592 mmol, 1.2 eq.), $T_3P$ (618.65 mg, 1.944 mmol, 0.9 eq.). The resulting mixture was stirred for 2 h at room temperature. The reaction solution was purified by Prep-HPLC using the following conditions: Sunfire Prep C18 OBD Column, 50*250 mm, 5 μm, 10 nm, mobile phase, water (0.1% FA) and $CH_3CN$ (10% up to 45% in 15 min), Detector, UV 254 nm. This resulted in 1-{2-[1-(2,2-difluoroethyl)pyrazol-4-ylsulfonyl]-4H,6H-pyrrolo[3,4-c]pyrazol-5-yl}-2-(3-fluoropyridin-2-yl)-3-hydroxypropan-1-one (250 mg, 24.60%) as a white solid. LCMS (ES) [M+1]$^+$ m/z: 471.

Step 2

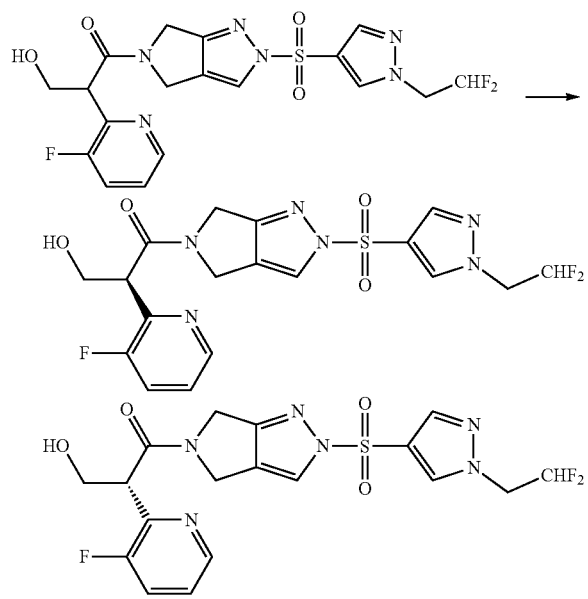

1-(2-((1-(2,2-difluoroethyl)-1H-pyrazol-4-yl)sulfonyl)-2,6-dihydropyrrolo[3,4-c]pyrazol-5(4H)-yl)-2-(3-fluoropyridin-2-yl)-3-hydroxypropan-1-one (250 mg) was separated by Chiral-Prep-SFC using the following conditions: Column: CHIRAL ART Cellulose-SJ, 3*25 cm, 5 m; Mobile Phase A: $CO_2$, Mobile Phase B: MeOH (0.1% 2M $NH_3$-MEOH); Flow rate: 80 mL/min; Gradient: isocratic 20% B; Column Temperature (° C.): 35; Back Pressure (bar): 100; Wave Length: 220 nm; RT1 (8.58 min): RT2 (9.63 min); Sample Solvent: MeOH. Two compounds were isolated. The fraction at 8.58 min was concentrated in vacuum to give Stereoisomer 11, 110 mg as a whitesolid. $^1$H NMR (400 MHz, DMSO-$d_6$) δ 8.72 (s, 1H), 8.38 (dq, J=3.6, 1.7 Hz, 1H), 8.18 (d, J=3.5 Hz, 1H), 8.12 (d, J=1.9 Hz, 1H), 7.69 (dddd, J=10.0, 8.4, 3.5, 1.3 Hz, 1H), 7.39 (dtd, J=8.5, 4.4, 2.2 Hz, 1H), 6.42 (tt, J=54.4, 3.6 Hz, 1H), 4.88 (dd, J=25.3, 13.9 Hz, 1H), 4.72 (td, J=15.1, 3.6 Hz, 2H), 4.49 (dd, J=16.0, 11.6 Hz, 1H), 4.46-4.32 (m, 2H), 4.25 (dd, J=21.2, 13.9 Hz, 1H), 4.10 (t, J=9.1 Hz, 1H), 3.94 (q, J=8.4 Hz, 1H). LCMS (ES) $[M+1]^+$ m/z: 471.

The fraction at 9.63 min was concentrated in vacuum to give Stereoisomer 12, 110 mg as a white solid. $^1$H NMR (400 MHz, DMSO-$d_6$) δ 8.72 (s, 1H), 8.38 (dq, J=3.5, 1.6 Hz, 1H), 8.18 (d, J=3.5 Hz, 1H), 8.12 (d, J=1.9 Hz, 1H), 7.69 (dddd, J=9.9, 8.3, 3.4, 1.4 Hz, 1H), 7.39 (dtd, J=8.6, 4.4, 2.2 Hz, 1H), 6.42 (tt, J=54.4, 3.6 Hz, 1H), 4.88 (dd, J=25.2, 13.9 Hz, 1H), 4.72 (td, J=15.1, 3.6 Hz, 2H), 4.49 (dd, J=15.9, 11.6 Hz, 1H), 4.46-4.32 (m, 2H), 4.25 (dd, J=21.2, 13.9 Hz, 1H), 4.10 (dd, J=10.5, 7.4 Hz, 1H), 3.94 (dt, J=10.0, 7.3 Hz, 1H). LCMS (ES) $[M+1]^+$ m/z: 471.

Example 1.42

Synthesis of (2S)-2-(2-fluorophenyl)-3-hydroxy-1-[2-[1-(2-methoxyethyl)pyrazol-3-ylsulfonyl]-4H,6H-pyrrolo[3,4-c]pyrazol-5-yl]propan-1-one (Compound 44)

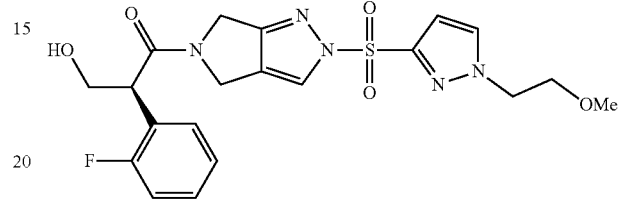

Step 1

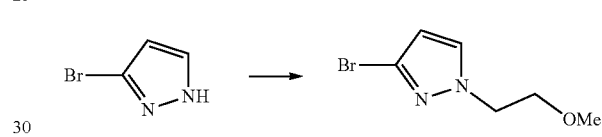

Into a 250-mL 3-necked round-bottom flask, was placed 3-bromo-1H-pyrazole (5.00 g, 34.01 mmol, 1.0 eq.), MeCN (75 mL), 2-bromoethyl methyl ether (7.09 g, 51.02 mmol, 1.5 eq.), KI (1.13 g, 6.80 mmol, 0.2 eq.), $Cs_2CO_3$ (22.17 g, 68.039 mmol, 2.0 eq.). The resulting solution was stirred for 5 hr at 25° C. The solids were filtered out. The resulting mixture was concentrated under vacuum. The residue was purified on a silica gel column with PE:THF (100:1 to 10:1). This resulted in 5.0 g (71.68%) of 3-bromo-1-(2-methoxyethyl)pyrazole as light yellow oil. LCMS (ES) $[M+1]^+$ m/z: 205/207.

Step 2

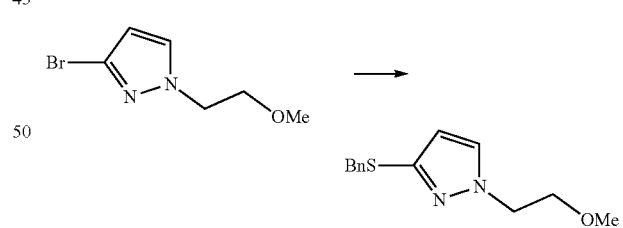

Into a 250-mL 3-necked round-bottom flask purged and maintained with an inert atmosphere of nitrogen, was placed 3-bromo-1-(2-methoxyethyl)pyrazole (5.00 g, 24.38 mmol, 1.0 eq.), toluene (75 mL), DIEA (0.63 g, 4.87 mmol, 0.2 eq.), $Pd_2(dba)_3 \cdot CHCl_3$ (2.52 g, 2.43 mmol, 0.1 eq.), XantPhos (35.27 g, 60.96 mmol, 2.5 eq.), benzyl mercaptan (6.06 g, 48.76 mmol, 2.0 eq.). The resulting solution was stirred for 48 hr at 110° C. The resulting mixture was concentrated. The residue was applied onto a silica gel column with EtOAc/PE (1:100 to 1:10). This resulted in 4.5 g (74.31%) of 3-(benzylsulfanyl)-1-(2-methoxyethyl)pyrazole as light yellow oil. LCMS (ES) $[M+1]^+$ m/z: 249.

Step 3

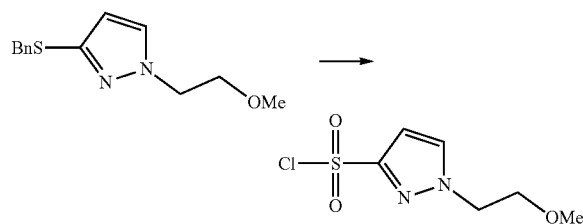

Into a 100-mL 3-necked round-bottom flask, was placed 3-(benzylsulfanyl)-1-(2-methoxyethyl)pyrazole (3.00 g, 12.08 mmol, 1.0 eq.), AcOH (24 mL), H$_2$O (8 mL). After the reaction was cooled to 0° C., NCS (6.45 g, 48.32 mmol, 4.0 eq.) was added in portions. The resulting solution was stirred for 5 hr at 0-25° C. The reaction was then quenched by the addition of 20 mL of water. The resulting solution was extracted with EtOAc (3×50 mL), dried in an oven under reduced pressure and concentrated. The residue was purified on a silica gel column with PE/THF (100:1 to 5:1) resulting in 1.6 g (58.95%) of 1-(2-methoxyethyl)pyrazole-3-sulfonyl chloride as light yellow oil. LCMS (ES) [M+1]$^+$ m/z: 225.

Step 4

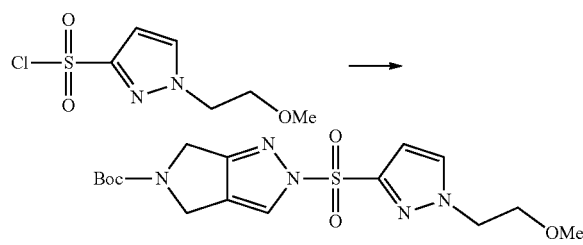

Into a 100 mL 3-necked round-bottom flask purged and maintained with an inert atmosphere of nitrogen, was placed tert-butyl 2H,4H,6H-pyrrolo[3,4-c]pyrazole-5-carboxylate (1.00 g, 4.77 mmol, 1.0 eq.) and THF (15 mL). After the reaction was cooled to 0° C., NaH (0.13 g, 5.25 mmol, 1.1 eq.) was added in portions. After the reaction stirred at 0° C. for 30 min, 1-(2-methoxyethyl)pyrazole-3-sulfonyl chloride (1.07 g, 4.779 mmol, 1.0 eq.) was added in portions. Then the resulting mixture was stirred for another 2 hr at 0° C. to room temperature. The resulting mixture was quenched with AcOH (2 mL) in 20 mL water, extracted with DCM (4×50 mL), dried over Na$_2$SO$_4$ and concentrated. The residue was triturated with EtOAc/PE=1:1 (10 mL) for 30 min. The product was collected by filtrate, the filter cake dried to give tert-butyl 2-[1-(2-methoxyethyl)pyrazol-3-ylsulfonyl]-4H,6H-pyrrolo[3,4-c]pyrazole-5-carboxylate (1.2 g, 63.18%) as an off white solid. LCMS (ES) [M+1]$^+$ m/z: 398.1.

Step 5

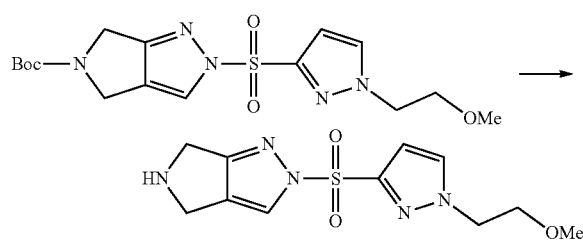

Into a 100 mL 3-necked round-bottom flask purged and maintained with an inert atmosphere of nitrogen, was placed tert-butyl 2-[1-(2-methoxyethyl)pyrazol-3-ylsulfonyl]-4H,6H-pyrrolo[3,4-c]pyrazole-5-carboxylate (500 mg, 1.25 mmol, 1.0 eq.), DCM (10 mL) and 2,6-dimethylpyridine (539 mg, 5.03 mmol, 4.0 eq.). After the reaction was cooled to 0° C., TMSOTf (838 mg, 3.77 mmol, 3.0 eq.) was added drop wise. After the reaction stirred at 0° C. for 3 h, the resulting mixture was quenched with 5 mL of water and concentrated. The precipitated solid was collected by filtrate, the filter cake dried to give 1-(2-methoxyethyl)-3-[4H,5H,6H-pyrrolo[3,4-c]pyrazole-2-sulfonyl]pyrazole (300 mg, 80.20%) as an off white solid. LCMS (ES) [M+1]$^+$ m/z: 298.1.

Step 6

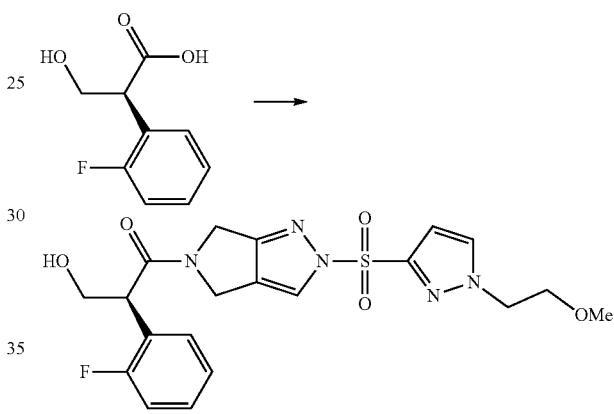

To a stirred solution of 1-(2-methoxyethyl)-3-[4H,5H,6H-pyrrolo[3,4-c]pyrazole-2-sulfonyl]pyrazole (120 mg, 0.40 mmol, 1.0 eq.) and (2S)-2-(2-fluorophenyl)-3-hydroxypropanoic acid (81 mg, 0.44 mmol, 1.1 eq.) in DMF (5 mL) NMM (102 mg, 1.01 mmol, 2.5 eq.) was added, after then, HATU (184 mg, 0.48 mmol, 1.2 eq.) was added in portions at 0° C. The resulting mixture was stirred for 1 h at 0° C. The resulting mixture was concentrated and purified by prep HPLC (Column, C18; mobile phase, Mobile phase: MeCN=5/1B: Water Flow rate: 20 mL/min Column: DAICEL CHIRALPAK IC, 250*20 mm, 220 nm Gradient: 50% B in 20 min; 220 nm) to give (2S)-2-(2-fluorophenyl)-3-hydroxy-1-[2-[1-(2-methoxyethyl)pyrazol-3-ylsulfonyl]-4H,6H-pyrrolo[3,4-c]pyrazol-5-yl]propan-1-one (140 mg, 74.84%) as an off white solid. CHIRAL_HPLC: Retention time 9.904 min. $^1$H NMR (400 MHz, DMSO-d$_6$) δ 8.20 (d, J=2.3 Hz, 1H), 7.98 (d, J=2.5 Hz, 1H), 7.40 (dd, J=8.7, 6.4 Hz, 1H), 7.36-7.26 (m, 1H), 7.19 (dq, J=15.0, 7.4, 6.6 Hz, 2H), 6.90 (d, J=2.4 Hz, 1H), 4.94-4.85 (m, 2H), 4.57-4.37 (m, 2H), 4.37-4.10 (m, 4H), 4.00 (t, J=9.2 Hz, 1H), 3.77-3.51 (m, 3H), 3.16 (d, J=3.9 Hz, 3H). LCMS (ES) [M+1]$^+$ m/z: 464.2.

Example 1.43

Synthesis of (2R)-2-(2-fluorophenyl)-3-hydroxy-1-[2-[1-(2-methoxyethyl)pyrazol-3-ylsulfonyl]-4H,6H-pyrrolo[3,4-c]pyrazol-5-yl]propan-1-one (Compound 45)

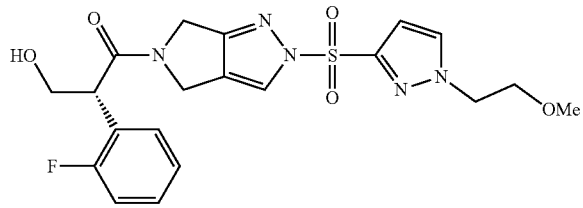 [SMILES: COCCn1ccc(S(=O)(=O)n2cc3c(n2)CN(C(=O)[C@@H](CO)c2ccccc2F)C3)n1]

The title compound was synthesized and purified according to the procedures described for Compound 44 using (2R)-2-(2-fluorophenyl)-3-hydroxypropanoic acid. (2R)-2-(2-fluorophenyl)-3-hydroxy-1-[2-[1-(2-methoxyethyl)pyrazol-3-ylsulfonyl]-4H,6H-pyrrolo[3,4-c]pyrazol-5-yl]propan-1-one was isolated as an off white solid. CHIRAL_HPLC: Retention time 8.588 min. $^1$H NMR (400 MHz, DMSO-$d_6$) δ 8.19 (d, J=3.2 Hz, 1H), 8.03-7.93 (m, 1H), 7.40 (tt, J=6.3, 3.1 Hz, 1H), 7.33-7.26 (m, 1H), 7.19 (dd, J=12.1, 6.4 Hz, 2H), 6.95-6.85 (m, 1H), 4.94-4.85 (m, 2H), 4.58-4.37 (m, 2H), 4.36-4.15 (m, 4H), 3.98 (d, J=9.8 Hz, 1H), 3.73-3.52 (m, 3H), 3.17 (d, J=3.9 Hz, 3H). LCMS (ES) [M+1]$^+$ m/z: 464.2.

Example 1.44

Synthesis of (R)-2-(2-chlorophenyl)-1-(2-((1-(2,2-difluoroethyl)-1H-pyrazol-4-yl)sulfonyl)-2,6-dihydropyrrolo[3,4-c]pyrazol-5(4H)-yl)-3-hydroxypropan-1-one (Compound 46)

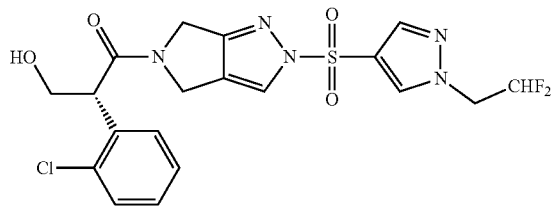 [SMILES: O=C([C@@H](CO)c1ccccc1Cl)N1Cc2cn(S(=O)(=O)c3cnn(CC(F)F)c3)nc2C1]

The title compound was synthesized from (R)-2-(2-chlorophenyl)-3-hydroxypropanoic acid (100 mg, 0.50 mmol, 1.00 eq.) and 1-(2,2-difluoroethyl)-4-{4H,5H,6H-pyrrolo[3,4-c]pyrazole-2-sulfonyl}pyrazole (Intermediate I-7, 167 mg, 0.55 mmol, 1.10 eq.), following the procedure described in Example 1.13. (R)-2-(2-Chlorophenyl)-1-(2-((1-(2,2-difluoroethyl)-1H-pyrazol-4-yl)sulfonyl)-2,6-dihydropyrrolo[3,4-c]pyrazol-5(4H)-yl)-3-hydroxypropan-1-one was isolated as a white solid (113 mg). $^1$HNMR (300 MHz, DMSO-$d_6$) δ 8.72 (s, 1H), 8.19 (s, 1H), 8.12 (d, J=1.8 Hz, 1H), 7.50-7.41 (m, 2H), 7.35-7.26 (m, 2H), 6.60 (tt, J=54.6, 3.6 Hz, 1H), 4.99-4.85 (m, 2H), 4.78 (td, J=15.0, 3.6 Hz, 2H), 4.55-4.27 (m, 4H), 4.02-3.93 (m, 1H), 3.62-3.54 (m, 1H). LCMS (ES) [M+1]$^+$ m/z: 486.

Example 1.46

Synthesis of (2S)-2-(2-chlorophenyl)-3-hydroxy-1-[2-[1-(2,2,2-trifluoroethyl)pyrazol-4-ylsulfonyl]-4H,6H-pyrrolo[3,4-c]pyrazol-5-yl]propan-1-one (Compound 47)

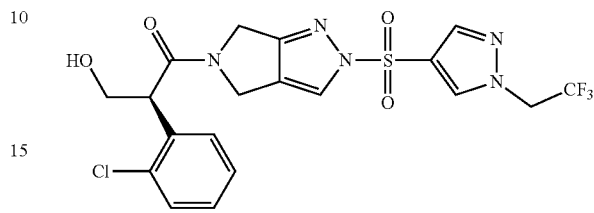

The title compound was synthesized from (2S)-2-(2-chlorophenyl)-3-hydroxypropanoic acid (90.00 mg, 0.45 mmol, 1.00 eq.) and 1-(2,2,2-trifluoroethyl)-4-{2H,4H,5H,6H-pyrrolo[3,4-c]pyrazole-2-sulfonyl}-1H-pyrazole (Intermediate I-10, 211.45 mg, 0.45 mmol, 1.00 eq.), following the procedure described on Step 6, Example 1.7. (2S)-2-(2-chlorophenyl)-3-hydroxy-1-[2-[1-(2,2,2-trifluoroethyl)pyrazol-4-ylsulfonyl]-4H,6H-pyrrolo[3,4-c]pyrazol-5-yl]propan-1-one was isolated as a white powder (120.1 mg, 53.13%). $^1$HNMR (300 MHz, DMSO-$d_6$) δ 8.81 (s, 1H), 8.20 (s, 1H), 8.18 (d, J=1.8 Hz, 1H), 7.53-7.39 (m, 2H), 7.38-7.23 (m, 2H), 5.32-5.17 (m, 2H), 4.97 (s, 1H), 4.95-4.82 (m, 1H), 4.56-4.45 (m, 1H), 4.44-4.34 (m, 2H), 4.33-4.26 (m, 1H), 3.97 (s, 1H), 3.57 (dd, J=10.1, 5.0 Hz, 1H). LCMS (ES) [M+1]$^+$ m/z: 504.

Example 1.47

Synthesis of (2R)-2-(2-chlorophenyl)-3-hydroxy-1-[2-[1-(2,2,2-trifluoroethyl)pyrazol-4-ylsulfonyl]-4H,6H-pyrrolo[3,4-c]pyrazol-5-yl]propan-1-one (Compound 48)

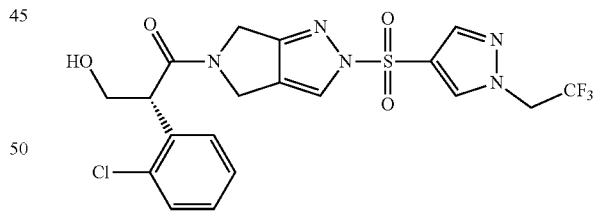

The title compound was synthesized from (2R)-2-(2-chlorophenyl)-3-hydroxypropanoic acid (90.00 mg, 0.45 mmol, 1.00 eq.) and Intermediate I-10 (211.45 mg, 0.45 mmol, 1.00 eq.), following the procedure described on Step 6, Example 1.7. (2R)-2-(2-Chlorophenyl)-3-hydroxy-1-[2-[1-(2,2,2-trifluoroethyl)pyrazol-4-ylsulfonyl]-4H,6H-pyrrolo[3,4-c]pyrazol-5-yl]propan-1-one was isolated as a white powder (121.3 mg, 53.66%). $^1$HNMR (300 MHz, DMSO-$d_6$) δ 8.81 (s, 1H), 8.20 (s, 1H), 8.18 (d, J=1.8 Hz, 1H), 7.53-7.38 (m, 2H), 7.38-7.23 (m, 2H), 5.32-5.17 (m, 2H), 5.02-4.82 (m, 2H), 4.56-4.45 (m, 1H), 4.43-4.33 (m, 2H), 4.34-4.26 (m, 1H), 3.97 (d, J=7.4 Hz, 1H), 3.57 (dq, J=10.0, 4.9 Hz, 1H). LCMS (ES) [M+1]$^+$ m/z: 504.

Example 1.48

Synthesis of (2S,3R)-3-hydroxy-2-phenyl-1-{2-[1-(2,2,2-trifluoroethyl)pyrazol-4-ylsulfonyl]-4H,6H-pyrrolo[3,4-c]pyrazol-5-yl}butan-1-one (Compound 49)

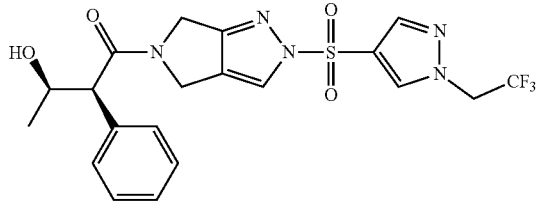 [SMILES: C[C@@H](O)[C@@H](C(=O)N1Cc2cn(S(=O)(=O)c3cnn(CC(F)(F)F)c3)nc2C1)c1ccccc1]

The title compound was synthesized from (2S,3R)-3-hydroxy-2-phenylbutanoic acid (50 mg, 0.28 mmol, 1.00 eq.), and 1-(2,2,2-trifluoroethyl)-4-{2H,4H,5H,6H-pyrrolo[3,4-c]pyrazole-2-sulfonyl}-1H-pyrazole (Intermediate I-10, 89 mg, 0.28 mmol, 1.00 eq.), following the procedure described on Step 6, Example 1.7. (2S,3R)-3-hydroxy-2-phenyl-1-{2-[1-(2,2,2-trifluoroethyl)pyrazol-4-ylsulfonyl]-4H,6H-pyrrolo[3,4-c]pyrazol-5-yl}butan-1-one was isolated as a white powder (76.7 mg, 57%). $^1$HNMR (300 MHz, DMSO-$d_6$) δ 8.79 (s, 1H), 8.18 (d, J=3.8 Hz, 2H), 7.43-7.35 (m, 2H), 7.34-7.22 (m, 3H), 5.24 (q, J=8.9 Hz, 2H), 4.91 (dd, J=24.0, 14.3 Hz, 1H), 4.55 (d, J=5.2 Hz, 1H), 4.48-4.24 (m, 3H), 4.18-4.12 (m, 1H), 3.69 (d, J=8.0 Hz, 1H), 1.15 (d, J=6.0 Hz, 3H). LCMS (ES) [M+1]$^+$ m/z: 484.

Example 1.49

Synthesis of (2S,3S)-3-hydroxy-2-phenyl-1-{2-[1-(2,2,2-trifluoroethyl)pyrazol-4-ylsulfonyl]-4H,6H-pyrrolo[3,4-c]pyrazol-5-yl}butan-1-one (Compound 50)

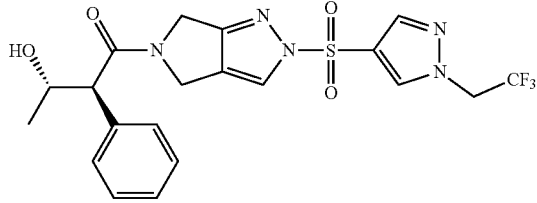 [SMILES: C[C@H](O)[C@@H](C(=O)N1Cc2cn(S(=O)(=O)c3cnn(CC(F)(F)F)c3)nc2C1)c1ccccc1]

The title compound was synthesized from (2S,3S)-3-hydroxy-2-phenylbutanoic acid (50 mg, 0.28 mmol, 1.00 eq.) and 1-(2,2,2-trifluoroethyl)-4-{2H,4H,5H,6H-pyrrolo[3,4-c]pyrazole-2-sulfonyl}-1H-pyrazole (Intermediate I-10, 89 mg, 0.28 mmol, 1.00 eq.), following the procedure described on Step 6, Example 1.7. (2S,3R)-3-hydroxy-2-phenyl-1-{2-[1-(2,2,2-trifluoroethyl)pyrazol-4-ylsulfonyl]-4H,6H-pyrrolo[3,4-c]pyrazol-5-yl}butan-1-one was isolated as a white powder (75.8 mg, 56%). $^1$HNMR (300 MHz, DMSO-$d_6$) δ 8.79 (t, J=1.0 Hz, 1H), 8.24-8.14 (m, 2H), 7.45-7.36 (m, 2H), 7.34-7.21 (m, 3H), 5.24 (q, J=9.0 Hz, 2H), 4.91 (t, J=13.5 Hz, 1H), 4.82 (dd, J=5.4, 3.8 Hz, 1H), 4.58-4.33 (m, 3H), 4.32-4.19 (m, 1H), 3.70 (dd, J=9.1, 2.2 Hz, 1H), 0.86 (d, J=6.2 Hz, 3H). LCMS (ES) [M+1]$^+$ m/z: 484.

Example 1.50

Synthesis of (2R)-1-{2-[1-(2,2-difluoroethyl)pyrazol-3-ylsulfonyl]-4H,6H-pyrrolo[3,4-c]pyrazol-5-yl}-2-(2-fluorophenyl)-2-hydroxyethanone (Compound 51)

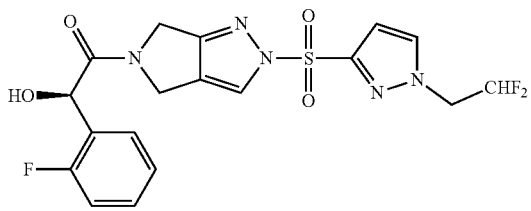 [SMILES: O=C([C@H](O)c1ccccc1F)N1Cc2cn(S(=O)(=O)c3ccn(CC(F)F)n3)nc2C1]

The title compound was synthesized from (R)-(2-fluorophenyl)(hydroxy)acetic acid (50 mg, 0.29 mmol, 1.00 eq.) and 1-(2,2-difluoroethyl)-3-{4H,5H,6H-pyrrolo[3,4-c]pyrazole-2-sulfonyl}pyrazole (89 mg, 0.29 mmol, 1.00 eq.) following the procedure described on Step 6, Example 1.16. (2R)-1-{2-[1-(2,2-difluoroethyl)pyrazol-3-ylsulfonyl]-4H,6H-pyrrolo[3,4-c]pyrazol-5-yl}-2-(2-fluorophenyl)-2-hydroxyethanone was isolated as a white solid (86.8 mg, 65%). $^1$HNMR (300 MHz, DMSO-$d_6$) δ 8.22 (d, J=4.0 Hz, 1H), 8.07 (d, J=2.5 Hz, 1H), 7.47 (q, J=7.2 Hz, 1H), 7.37 (s, 1H), 7.26-7.13 (m, 2H), 7.01-6.96 (m, 1H), 6.40 (tt, J=54.4, 3.9 Hz, 1H), 5.90 (dd, J=20.8, 6.6 Hz, 1H), 5.56 (t, J=6.2 Hz, 1H), 4.99-4.66 (m, 3H), 4.57-4.40 (m, 2H), 4.36-4.20 (m, 1H). LCMS (ES) [M+1]$^+$ m/z: 456.

Example 1.51

Synthesis of (3-(3-chloropyridin-2-yl)oxetan-3-yl)(2-((1-(2,2,2-trifluoroethyl)-1H-pyrazol-4-yl)sulfonyl)-2,6-dihydropyrrolo[3,4-c]pyrazol-5(4H)-yl)methanone (Compound 52)

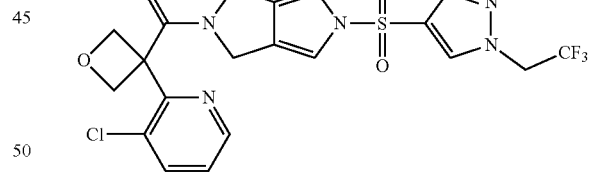

The title compound was synthesized from sodium 3-(3-chloropyridin-2-yl)oxetane-3-carboxylate (compound 8, example 1.12, 126 mg, 0.54 mmol, 1.00 eq.) and 1-(2,2,2-trifluoroethyl)-4-{2H,4H,5H,6H-pyrrolo[3,4-c]pyrazole-2-sulfonyl}-1H-pyrazole (Intermediate I-10, 172 mg, 0.54 mmol, 1.00 eq.) following the procedure described on Step 3, Example 1.7. (3-(3-Chloropyridin-2-yl)oxetan-3-yl)(2-((1-(2,2,2-trifluoroethyl)-1H-pyrazol-4-yl)sulfonyl)-2,6-dihydropyrrolo[3,4-c]pyrazol-5(4H)-yl)methanone was isolated as a white solid (102.1 mg, 37%). $^1$HNMR (300 MHz, DMSO-$d_6$) δ 8.78 (d, J=1.8 Hz, 1H), 8.70 (dd, J=4.7, 1.5 Hz, 1H), 8.19-8.06 (m, 2H), 7.99 (ddd, J=8.0, 3.9, 1.5 Hz, 1H), 7.49 (ddd, J=7.8, 4.7, 2.6 Hz, 1H), 5.24 (dt, J=9.3, 2.6 Hz, 4H), 5.13 (d, J=6.0 Hz, 2H), 4.51 (d, J=9.7 Hz, 2H), 3.70 (d, J=8.4 Hz, 2H). LCMS (ES) [M+1]$^+$ m/z: 517.

Example 1.52

Synthesis of (2S)-1-{2-[1-(2,2-difluoroethyl)pyrazol-4-ylsulfonyl]-4H,6H-pyrrolo[3,4-c]pyrazol-5-yl}-2-(2,3-difluorophenyl)-3-hydroxypropan-1-one (Compound 53)

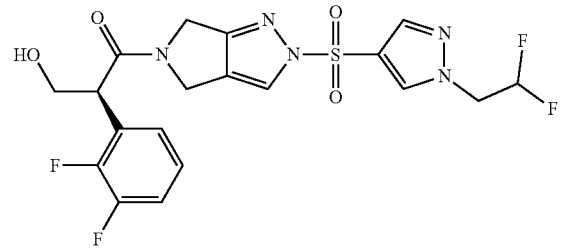 [SMILES: O=C([C@H](CO)c1cccc(F)c1F)N1Cc2cn(S(=O)(=O)c3cnn(CC(F)F)c3)nc2C1]

Step 1

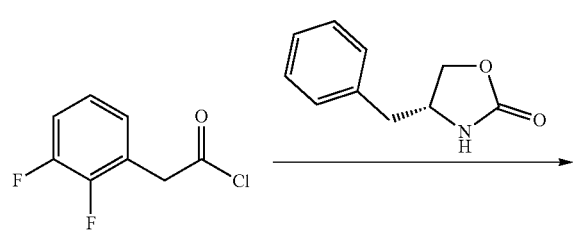

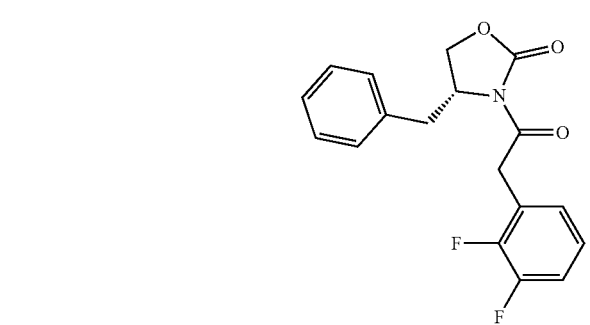

Into a 250-mL 3-necked round-bottom flask purged and maintained with an inert atmosphere of nitrogen, was placed a mixture of (2,3-difluorophenyl)acetyl chloride (10.0 g, 52.474 mmol, 1 eq.), THF (250 mL). n-BuLi (4.37 g, 68.216 mmol, 1.3 eq.) was added drop wise for 1 hour at –78° C., (4R)-4-benzyl-1,3-oxazolidin-2-one (7.44 g, 41.979 mmol, 0.8 eq.) was drop wised at –78° C. and the resulting solution was stirred for 2 hours at –78° C. to rt. The reaction was then quenched by the addition of 200 mL of water. The resulting solution was extracted with 3×150 mL of EtOAc and the resulting mixture was washed with 1×200 ml of brine. The mixture was dried over anhydrous sodium sulfate and concentrated. The residue was applied onto a silica gel column with EtOAc/PE (13/87). This resulted in 6.4 g (36.81%) of (4R)-4-benzyl-3-[2-(2,3-difluorophenyl)acetyl]-1,3-oxazolidin-2-one as yellow oil. LCMS (ES) [M+1]+ m/z: 332.

Step 2

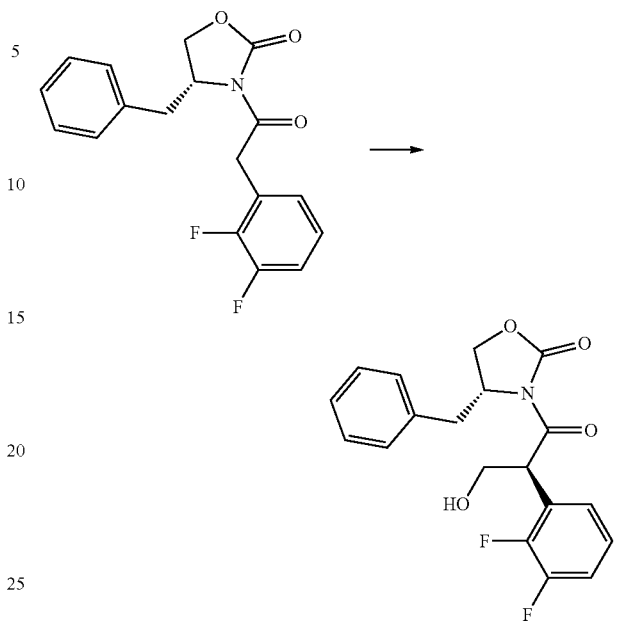

Into a 250-mL 3-necked round-bottom flask, to a stirred, cooled (0° C.) solution of (4R)-4-benzyl-3-[2-(2,3-difluorophenyl)acetyl]-1,3-oxazolidin-2-one (6.4 g, 19.317 mmol, 1 eq.) in DCM was added TiCl₄ (4.03 g, 21.249 mmol, 1.1 eq.) drop wise. The resulting yellow solution was stirred for ca. 5 min (0° C.) after which DIEA (2.87 g, 22.215 mmol, 1.15 eq.) was added drop wise. The resulting dark red-to-purple mixture was stirred for 1 h at 0° C., then (HCHO)₃ (1.91 g, 21.249 mmol, 1.1 eq.), and additional TiCl₄ (4.03 g, 21.249 mmol, 1.1 eq.) were added. The resulting mixture was stirred for an additional 2 hours at 0° C. and then quenched by the addition of saturated aqueous NH₄Cl (100 ml) (approximately an equal volume) and extracted with additional DCM (3×100 ml). The organic layer was washed with Sat. NaHCO₃ (200 ml), dried over anhydrous Na₂SO₄, and concentrated. This resulted is 7.3 g (crude) of (4R)-4-benzyl-3-[(2S)-2-(2,3-difluorophenyl)-3-hydroxypropanoyl]-1,3-oxazolidin-2-one) as yellow oil. LCMS (ES) [M+1]+ m/z: 362.

Step 3

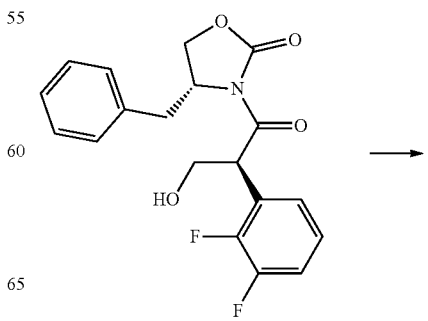

-continued

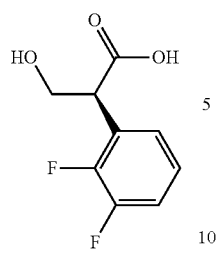

Into a 250-mL 3-necked round-bottom flask, was placed a mixture of (4R)-4-benzyl-3-[(2S)-2-(2,3-difluorophenyl)-3-hydroxypropanoyl]-1,3-oxazolidin-2-one (7.3 g, 20.202 mmol, 1 eq.), THF (64 mL), H$_2$O (16 mL), H$_2$O$_2$ (30%) (3.44 g, 101.010 mmol, 5.0 eq.) and LiOH.H$_2$O (1.70 g, 40.40 mmol, 2.0 eq.) at 0° C. The resulting solution was stirred for 2 hours at 0° C. The reaction was then quenched by the addition of sat. Na$_2$SO$_3$ (15 ml) and water (35 ml). The pH of the solution was adjusted to 1 with 2M HCl. The resulting solution was extracted with 3×100 mL of DCM/MeOH (10/1) dried over anhydrous Na$_2$SO$_3$ and concentrated. The residue was purified by silica gel column chromatography, eluted with PE/THF (1:4) to afford (2S)-2-(2,3-difluorophenyl)-3-hydroxypropanoic acid (2.6 g, 63.66%) as an off-white solid. LCMS (ES) [M+1]$^+$ m/z: 201.

Step 4

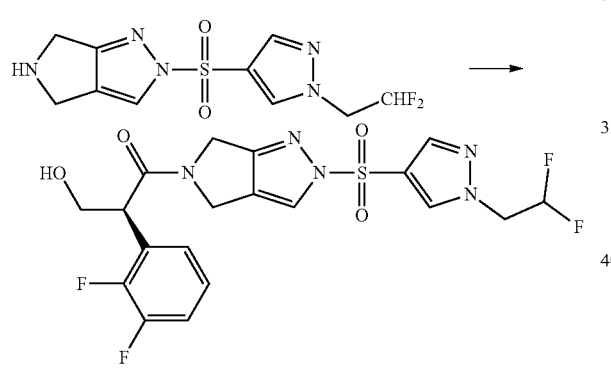

Into a 8-mL vial, was placed a mixture of (2S)-2-(2,3-difluorophenyl)-3-hydroxypropanoic acid (100 mg, 0.495 mmol, 1 eq.), DMF (2.00 mL), 1-(2,2-difluoroethyl)-4-{4H,5H,6H-pyrrolo[3,4-c]pyrazole-2-sulfonyl}pyrazole (Intermediate I-7, 225.04 mg, 0.742 mmol, 1.5 eq.), DIEA (191.80 mg, 1.485 mmol, 3.0 eq.), HATU (244.51 mg, 0.643 mmol, 1.3 eq.). The resulting solution was stirred for 2 hours at room temperature. The crude product was purified by Prep-HPLC using the following conditions (Prep-HPLC-001): Column: Sunfire Prep C18 OBD Column, 50*250 mm, 5 m; Mobile Phase A: Water (0.1% FA), Mobile Phase B: ACN; Flow rate: 90 mL/min; Gradient: 20% B to 55% B in 12 min, 55% B; Wave Length: 220 nm; RT1 (min): 12. This resulted in 99.4 mg (41.23%) of (2S)-1-{2-[1-(2,2-difluoroethyl) pyrazol-4-ylsulfonyl]-4H,6H-pyrrolo[3,4-c]pyrazol-5-yl}-2-(2,3-difluorophenyl)-3-hydroxypropan-1-one as a white solid. $^1$H NMR (300 MHz, DMSO-d$_6$): δ 8.71 (s, 1H), 8.18 (s, 1H), 8.11 (s, 1H), 7.35-7.31 (m, 1H), 7.21-7.16 (m, 2H), 6.37 (tt, J=54.3, 3.5 Hz, 1H), 4.95-4.85 (m, 2H), 4.75-4.67 (m, 2H), 4.49-4.27 (m, 4H), 3.98 (m, 1H), 3.64-3.63 (m, 1H). LCMS (ES) [M+1]$^+$ m/z: 488.

Example 1.53

Synthesis of (2R)-1-{2-[1-(2,2-difluoroethyl)pyrazol-4-ylsulfonyl]-4H,6H-pyrrolo[3,4-c]pyrazol-5-yl}-2-(2,3-difluorophenyl)-3-hydroxypropan-1-one (Compound 54)

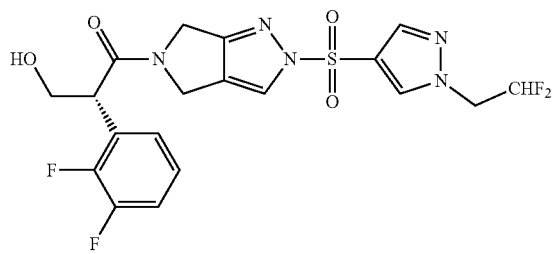 [SMILES: O=C([C@@H](CO)c1cccc(F)c1F)N1Cc2cn(S(=O)(=O)c3cnn(CC(F)F)c3)nc2C1]

Step 1

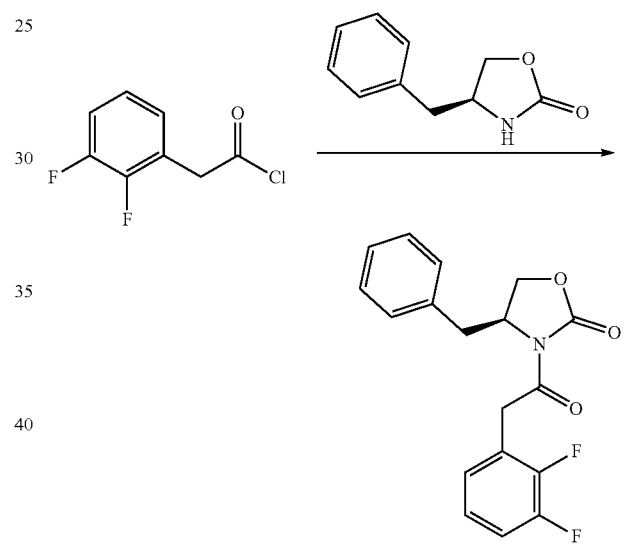

Into a 250-mL 3-necked round-bottom flask purged and maintained with an inert atmosphere of nitrogen, was placed a mixture of (2,3-difluorophenyl) acetyl chloride (10.0 g, 52.474 mmol, 1 eq.), THF (200 mL). n-BuLi (27.29 mL, 68.216 mmol, 1.3 eq.) was added drop wise for 1 hour at −78° C. (4S)-4-benzyl-1,3-oxazolidin-2-one (7.44 g, 41.979 mmol, 0.8 eq.) was added drop wise at −78° C. The resulting solution was stirred for 2 hours at −78° C. to rt. The reaction was then quenched by the addition of 200 mL of water. The resulting solution was extracted with 3×150 mL of EtOAc The resulting mixture was washed with brine (200 ml). The mixture was dried over anhydrous Na$_2$SO$_3$ and concentrated. The residue was purified on a silica gel column with EtOAc/PE (3/7). This resulted in 10.3 g (59.24%) of (S)-4-benzyl-3-(2-(2,3-difluorophenyl)acetyl)oxazolidin-2-one as yellow oil. LCMS (ES) [M+1]$^+$ m/z: 332.

Step 2

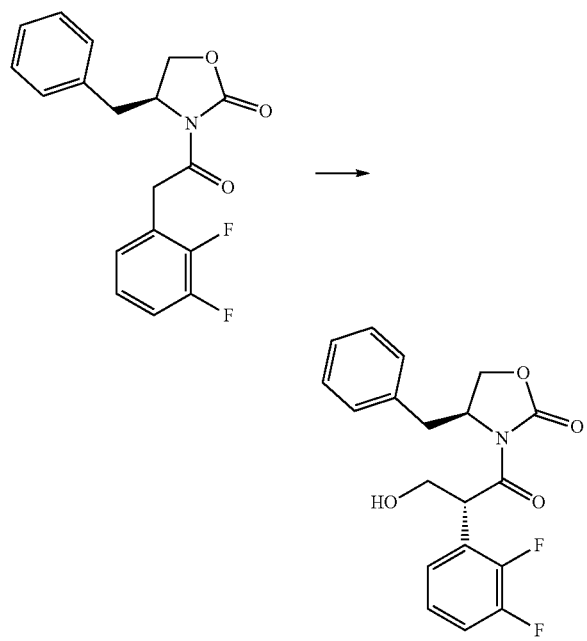

Into a 250-mL 3-necked round-bottom flask, to a stirred, cooled (0° C.) solution of (S)-4-benzyl-3-(2-(2,3-difluorophenyl)acetyl)oxazolidin-2-one (5.0 g, 15.091 mmol, 1 eq.) in DCM was added TiCl₄ (3.15 g, 16.6 mmol, 1.1 eq.) drop wise. The resulting yellow solution was stirred for ca. 5 min (0° C.) after which DIEA (2.24 g, 17.3 mmol, 1.15 eq.) was added drop wise. The resulting dark red-to-purple mixture was stirred for 1 h at 0° C., then 1,3,5-trioxane (1.50 g, 16.6 mmol, 1.1 eq.) and additional TiCl₄ (3.15 g, 16.6 mmol, 1.1 eq.) were added. The resulting mixture was stirred for an additional 4 hours at 0° C. and then quenched by the addition of saturated aqueous NH₄Cl (100 ml) (approximately an equal volume) and extracted with additional DCM (3×100 ml). The organic layer was washed with Sat. NaHCO₃ (200 ml), dried over anhydrous Na₂SO₄, and concentrated. This resulted is 6.1 g (crude) of (S)-4-benzyl-3-((S)-2-(2,3-difluorophenyl)-3-hydroxypropanoyl)oxazolidin-2-one as yellow oil. LCMS (ES) [M+1]⁺ m/z: 362.

Step 3

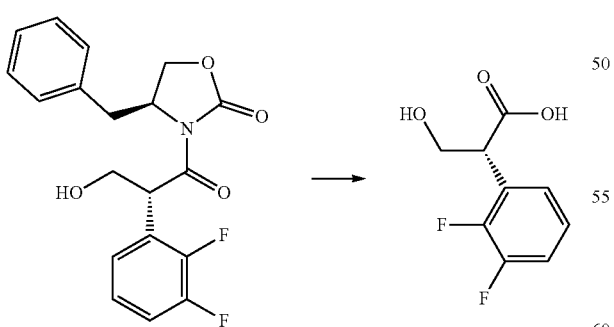

Into a 250-mL 3-necked round-bottom flask, was placed a mixture of (S)-4-benzyl-3-((R)-2-(2,3-difluorophenyl)-3-hydroxypropanoyl)oxazolidin-2-one (6.1 g, 16.8 mmol, 1 eq.), THF (60 mL), H₂O (15 mL), H₂O₂ (9.57 mL, 84.405 mmol, 5 eq.) and LiOH (0.81 g, 33.762 mmol, 2.0 eq.) at 0° C. The resulting solution was stirred for 2 hours at 0° C. The reaction was then quenched by the addition of sat. Na₂SO₃ (15 ml) and water (35 ml). The pH value of the solution was adjusted to 1 with 2M HCl. The resulting solution was extracted with DCM/MeOH (10/1) (3×100 mL), dried over anhydrous Na₂SO₃ and concentrated. The residue was purified by silica gel column chromatography, eluted with PE/THF (1:4) to afford (R)-2-(2,3-difluorophenyl)-3-hydroxypropanoic acid (2.3 g, 67.40%) as an off-white solid. LCMS (ES) [M+1]⁺ m/z: 201.

Step 4

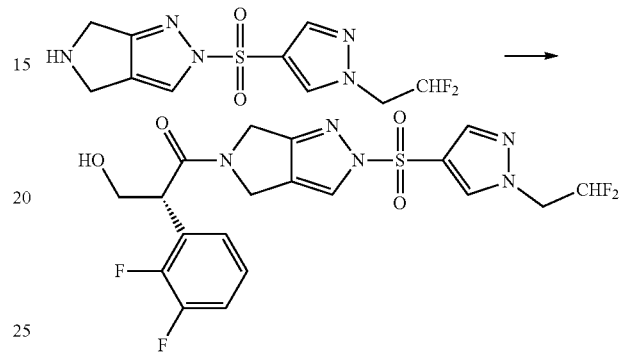

Into a 8-mL vial, was placed a mixture of (2R)-2-(2,3-difluorophenyl)-3-hydroxypropanoic acid (100 mg, 0.495 mmol, 1 eq.), DMF (2.00 mL), 1-(2,2-difluoroethyl)-4-{4H,5H,6H-pyrrolo[3,4-c]pyrazol-2-sulfonyl}pyrazole (150.03 mg, 0.495 mmol, 1.0 eq.), DIEA (191.80 mg, 1.485 mmol, 3.0 eq.), HATU (244.51 mg, 0.643 mmol, 1.3 eq.). The resulting solution was stirred for 2 hours at room temperature. The crude product was purified by Prep-HPLC using the following conditions (Prep-HPLC-001): Column, Sunfire Prep C18 OBD Column, 50*250 mm, 5 m 10 nm; mobile phase, Water (0.1% TFA) and ACN (20% PhaseB up to 55% in 12 min); Detector, uv. product was obtained. This resulted in 145.2 mg (60.22%) of (R)-1-(2-((1-(2,2-difluoroethyl)-1H-pyrazol-4-yl)sulfonyl)-2,6-dihydropyrrolo[3,4-c]pyrazol-5(4H)-yl)-2-(2,3-difluorophenyl)-3-hydroxypropan-1-one as a white solid. ¹H NMR (300 MHz, DMSO-d₆) δ 8.72 (s, 1H), 8.18 (s, 1H), 8.17 (s, 1H), 7.42-7.24 (m, 1H), 7.22-7.15 (m, 2H), 6.37 (tt, J=54.3, 3.5 Hz, 1H), 5.25-4.83 (m, 2H), 4.79-4.65 (m, 2H), 4.54-4.23 (m, 4H), 4.05-3.94 (m, 1H), 3.71-3.59 (m, 1H). LCMS (ES) [M+1]⁺ m/z: 488.

Example 1.54

Synthesis of (2S)-2-(2-chloro-3-fluorophenyl)-1-{2-[1-(2,2-difluoroethyl)pyrazol-4-ylsulfonyl]-4H,6H-pyrrolo[3,4-c]pyrazol-5-yl}-3-hydroxypropan-1-one (Compound 55)

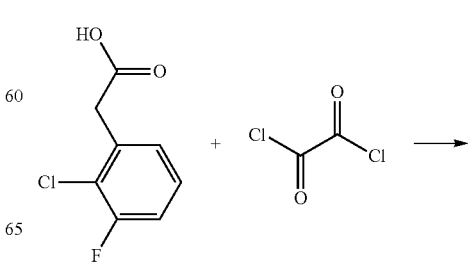

Step 1

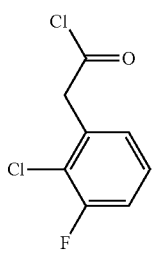

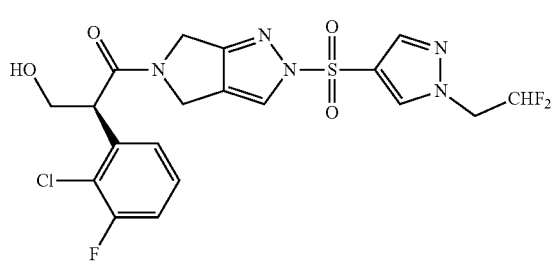 [SMILES: O=C([C@H](CO)c1cccc(F)c1Cl)N1Cc2cn(S(=O)(=O)c3cnn(CC(F)F)c3)nc2C1]

Into a 500 mL 3-necked round-bottom flask were added (2-chloro-3-fluorophenyl)acetic acid (30.00 g, 159.09 mmol, 1.00 eq.), DMF (2.00 mL) and DCM (300.00 mL). To the above mixture was added oxalyl chloride (30.29 g, 238.63 mmol, 1.50 eq.) drop wise at 0° C. The resulting mixture was stirred for additional 3 h at room temperature. The resulting mixture was concentrated under reduced pressure. This resulted in (2-chloro-3-fluorophenyl)acetyl chloride (31.00 g, crude) as yellow oil. LCMS (ES) [M−Cl+OH−1]⁺ m/z: 187.

Step 2

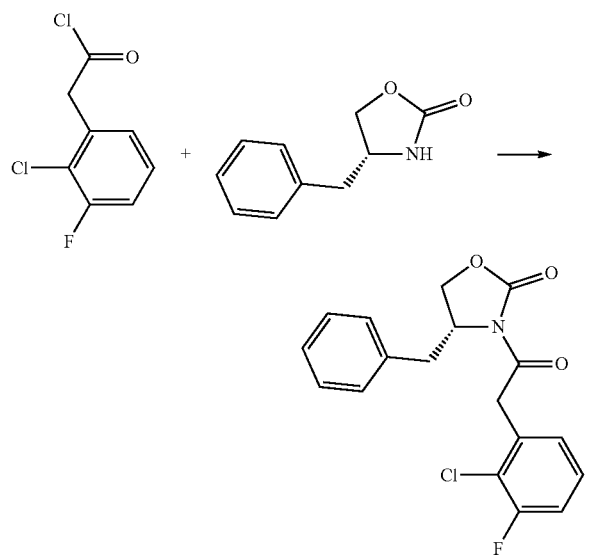

Into a 250 mL 3-necked round-bottom flask were added (4R)-4-benzyl-1,3-oxazolidin-2-one (10.70 g, 60.38 mmol, 1.00 eq.) and THF (150.00 mL). To the above mixture was added n-BuLi (2.5M) (31.40 mL, 78.50 mmol, 1.30 eq.) drop wise at −78° C. The resulting mixture was stirred for 1 h at −78° C. under nitrogen atmosphere. To the above mixture was added (2-chloro-3-fluorophenyl)acetyl chloride (15.00 g, 72.46 mmol, 1.20 eq.) in THF (20.00 mL) drop wise at −78° C. The resulting mixture was stirred for additional 1 h at −78° C. The reaction was quenched with sat. NH₄Cl (aq.). The resulting mixture was extracted with EtOAc (3×150 mL). The combined organic layers were dried over anhydrous Na₂SO₄. After filtration, the filtrate was concentrated under reduced pressure. The residue was purified by silica gel column chromatography, eluted with EA/PE (9%) to afford (4R)-4-benzyl-3-[2-(2-chloro-3-fluorophenyl)acetyl]-1,3-oxazolidin-2-one (8.00 g, 38.10%) as yellow oil. LCMS (ES) [M+1]⁺ m/z: 348.

Step 3

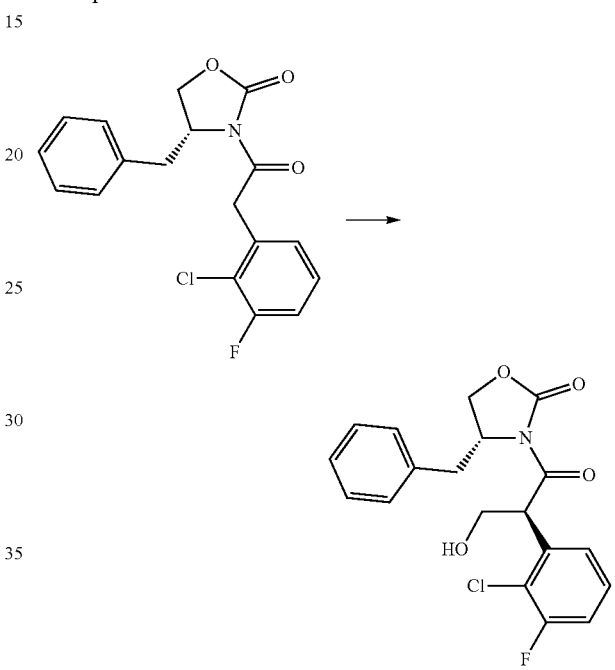

Into a 250 mL 3-necked round-bottom flask were added (4R)-4-benzyl-3-[2-(2-chloro-3-fluorophenyl)acetyl]-1,3-oxazolidin-2-one (8.00 g, 23.00 mmol, 1.00 eq.) and DCM (80.00 mL). A solution of TiCl₄ (2.77 mL, 25.30 mmol, 1.10 eq.) in DCM (1.00 mL) was added drop wise at 0° C. The resulting mixture was stirred for 5 min at 0° C. under nitrogen atmosphere. To the above mixture was added DIEA (3.42 g, 26.46 mmol, 1.15 eq.) drop wise at 0° C. The resulting mixture was stirred for additional 1 h at 0° C. A solution of trioxane (2.28 g, 25.30 mmol, 1.10 eq.) in DCM (5.00 mL) was added drop wise at 0° C. and treated for 10 min at 0° C. Then a mixture of TiCl₄ (2.77 mL, 25.30 mmol, 1.10 eq.) in DCM (1.00 mL) was added drop wise at 0° C. The resulting mixture was stirred for 2 h at 0° C. The reaction was quenched by the addition of sat. NH₄Cl (aq.) (80.00 mL). The resulting mixture was extracted with DCM (3×150 mL). The combined organic layers were washed with sat. NaHCO₃ (100.00 mL), dried over anhydrous Na₂SO₄. After filtration, the filtrate was concentrated under reduced pressure. This resulted in (4R)-4-benzyl-3-[(2S)-2-(2-chloro-3-fluorophenyl)-3-hydroxypropanoyl]-1,3-oxazolidin-2-one (8.20 g, crude) as yellow oil. LCMS (ES) [M+1]⁺ m/z: 378.

Step 4

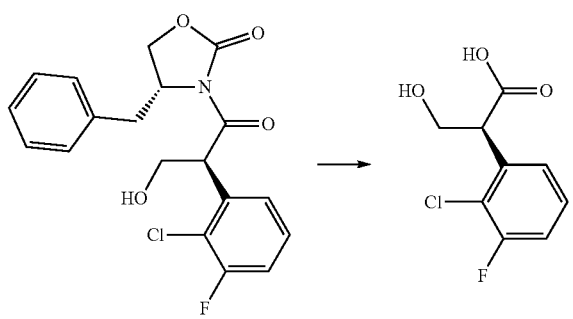 [SMILES: O=C1OC[C@@H](Cc2ccccc2)N1C(=O)[C@H](CO)c1cccc(F)c1Cl ; O=C(O)[C@H](CO)c1cccc(F)c1Cl]

Into a 250 mL 3-necked round-bottom flask were added (4R)-4-benzyl-3-[(2S)-2-(2-chloro-3-fluorophenyl)-3-hydroxypropanoyl]-1,3-oxazolidin-2-one (8.20 g, 21.71 mmol, 1.00 eq.) and THF (60.00 mL). To the above mixture was added $H_2O_2$ (30%) (3.70 mL, 108.74 mmol, 5.01 eq.) and LiOH (1.04 g, 43.41 mmol, 2.00 eq.) in $H_2O$ (15.00 mL) drop wise at 0° C. The resulting mixture was stirred for additional 1 h at 0° C. The reaction was quenched with sat. $Na_2SO_3$ (aq.). The aqueous layer was extracted with DCM (3×100 mL). The aqueous layer was collected and acidified to pH 2 with 2 M HCl. The resulting mixture was extracted with DCM/MeOH (10:1) (10×150 mL). The combined organic layers were dried over anhydrous $Na_2SO_4$. After filtration, the filtrate was concentrated under reduced pressure. The crude product was purified by Prep-HPLC using the following conditions: Column, XBridge Prep C18 OBD Column, 19 cm, 150 mm, 5 m; mobile phase, Water (0.1% FA) and CAN (5% Phase B up to 30% in 11 min); Detector, 254. This resulted in (2S)-2-(2-chloro-3-fluorophenyl)-3-hydroxypropanoic acid (3.30 g, 69.55%) as yellow oil. LCMS (ES) [M−1]$^+$ m/z: 217.

Step 5

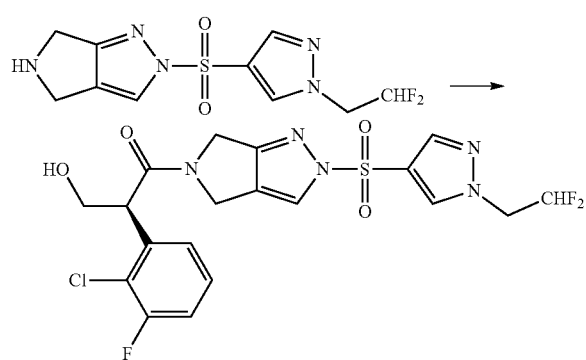

Into a 8 mL vial were added (2S)-2-(2-chloro-3-fluorophenyl)-3-hydroxypropanoic acid (100.00 mg, 0.46 mmol, 1.00 eq.), 1-(2,2-difluoroethyl)-4-{4H,5H,6H-pyrrolo[3,4-c]pyrazole-2-sulfonyl}pyrazole (110.99 mg, 0.37 mmol, 0.80 eq.), DMF (3.00 mL) and NMM (138.80 mg, 1.37 mmol, 3.00 eq.). To the above mixture was added HATU (208.72 mg, 0.55 mmol, 1.20 eq.) in portions at 0° C. The resulting mixture was stirred for additional 1 h at room temperature. The crude product was purified by Prep-HPLC using the following conditions: Column, Atlantis Prep T3 OBD Column, 19*150 mm 5 m; Mobile Phase A: Water (0.1% FA), Mobile Phase B: MeOH-HPLC; Flow rate: 20 mL/min; Gradient: 35% B to 70% B in 7 min; Wave Length: 220 nm. This resulted in (2S)-2-(2-chloro-3-fluorophenyl)-1-{2-[1-(2,2-difluoroethyl)pyrazol-4-ylsulfonyl]-4H,6H-pyrrolo[3,4-c]pyrazol-5-yl}-3-hydroxypropan-1-one (70.80 mg, 30.72%) as white solid. $^1$H NMR (300 MHz, DMSO-d$_6$) δ 8.72 (s, 1H), 8.19 (s, 1H), 8.12 (d, J=1.6 Hz, 1H), 7.44-7.24 (m, 3H), 6.42 (tt, J=54.4, 3.6 Hz, 1H), 5.06-4.95 (m, 1H), 4.94-4.84 (m, 1H), 4.72 (td, J=15.1, 3.6 Hz, 2H), 4.54-4.29 (m, 4H), 4.05-3.91 (m, 1H), 3.60 (dt, J=10.0, 5.1 Hz, 1H). LCMS (ES) [M+1]$^+$ m/z: 504.

Example 1.55

Synthesis of (2R)-2-(2-chloro-3-fluorophenyl)-1-{2-[1-(2,2-difluoroethyl)pyrazol-4-ylsulfonyl]-4H,6H-pyrrolo[3,4-c]pyrazol-5-yl}-3-hydroxypropan-1-one (Compound 56)

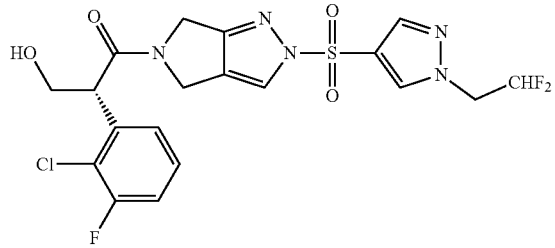 [SMILES: O=C([C@@H](CO)c1cccc(F)c1Cl)N1Cc2cn(S(=O)(=O)c3cnn(CC(F)F)c3)nc2C1]

The title compound was synthesized according to the procedures described in steps 2-5 for the synthesis of Compound 55 by reacting (2-chloro-3-fluorophenyl)acetyl chloride (step 1) with (4S)-4-benzyl-1,3-oxazolidin-2-one (10.70 g, 60.38 mmol, 1.00 eq.) on step 2. (2R)-2-(2-Chloro-3-fluorophenyl)-1-{2-[1-(2,2-difluoroethyl)pyrazol-4-ylsulfonyl]-4H,6H-pyrrolo[3,4-c]pyrazol-5-yl}-3-hydroxypropan-1-one as white solid. $^1$H NMR (300 MHz, DMSO-d$_6$) δ 8.72 (s, 1H), 8.19 (s, 1H), 8.12 (d, J=1.7 Hz, 1H), 7.44-7.23 (m, 3H), 6.65-6.18 (m, 1H), 5.00 (d, J=4.2 Hz, 1H), 4.92 (dd, J=22.0, 13.9 Hz, 1H), 4.72 (td, J=15.1, 3.6 Hz, 2H), 4.54-4.27 (m, 4H), 3.98 (d, J=6.0 Hz, 1H), 3.61 (dd, J=10.1, 5.2 Hz, 1H). LCMS (ES) [M−1]$^+$ m/z: 504.

Example 1.56

Synthesis of (2S)-2-(2-fluorophenyl)-3-hydroxy-1-[2-(1-isopropylpyrazol-4-ylsulfonyl)-4H,6H-pyrrolo[3,4-c]pyrazol-5-yl]propan-1-one (Compound 57)

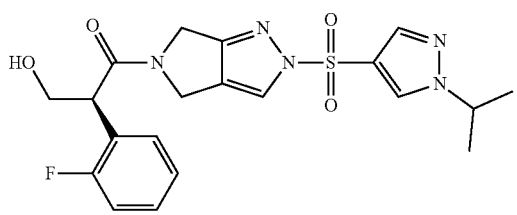 [SMILES: CC(C)n1cc(S(=O)(=O)n2cc3c(n2)CN(C(=O)[C@H](CO)c2ccccc2F)C3)cn1]

Step 1

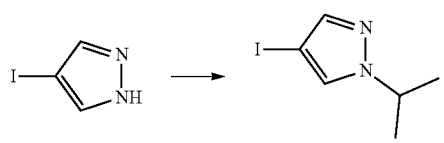

Into a 100 mL 3-necked round-bottom flask were added 4-iodopyrazole (5.0 g, 25.77 mmol, 1.00 eq.) and DMF (50 mL). To the above mixture was added NaH (60% in mineral oil) (1.13 g, 28.35 mmol, 1.10 eq.) in portions at 0° C. The resulting mixture was stirred for additional 0.5 h at the same temperature, followed by the addition of 2-iodopropane (5.70 g, 33.51 mmol, 1.30 eq.) drop wise at 0° C. The resulting mixture was stirred for additional 1 h at room temperature. The reaction was quenched with water (50 mL), extracted with EtOAc (3×50 mL). The combined organic layer was washed with brine (3×50 mL), dried over anhydrous Na$_2$SO$_4$. After filtration, the filtrate was concentrated under reduced pressure. The residue was purified by silica gel column chromatography, eluted with EA/PE (1:3) to afford 4-iodo-1-isopropylpyrazole (6.0 g, 98%) as a light yellow oil. LCMS (ES) [M+1]$^+$ m/z: 237.

Step 2

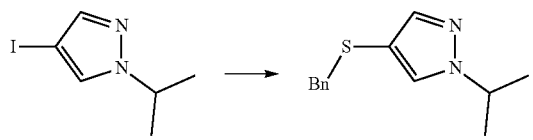

Into a 250 mL round-bottom flask were added 4-iodo-1-isopropylpyrazole (6.0 g, 25.41 mmol, 1.00 eq.) and toluene (60 mL), DIEA (9.86 g, 76.25 mmol, 3.00 eq.), Pd$_2$(dba)$_3$ (2.92 g, 5.08 mmol, 0.20 eq.), XantPhos (1.47 g, 2.54 mmol, 0.10 eq.), benzyl mercaptan (6.31 g, 50.83 mmol, 2.00 eq.). The resulting mixture was stirred for 12 h at 100° C. under nitrogen atmosphere. The resulting mixture was cooled to room temperature and concentrated under vacuum. The residue was purified by silica gel column chromatography, eluted with PE/EA (5:1) to afford 4-(benzylsulfanyl)-1-isopropylpyrazole (5.2 g, 88%) as a yellow oil. LCMS (ES) [M+1]$^+$ m/z: 233.

Step 3

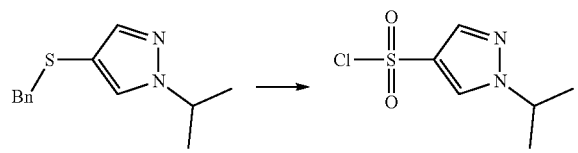 [SMILES: CC(C)n1cc(SCc2ccccc2)cn1 ; CC(C)n1cc(S(=O)(=O)Cl)cn1]

Into a 250 mL round-bottom flask were added 4-(benzylsulfanyl)-1-isopropylpyrazole (5.2 g, 22.38 mmol, 1.00 eq.), HOAc (90 mL), H$_2$O (10 mL), and NCS (8.97 g, 67.14 mmol, 3.00 eq.). The resulting mixture was stirred for 1 h at room temperature. The reaction mixture was concentrated under vacuum. The residue was purified by silica gel column chromatography, eluted with PE/EA (5:1) to afford 1-isopropylpyrazole-4-sulfonyl chloride (3.2 g, 69%) as a light yellow oil. LCMS (ES) [M−Cl+OH−1]$^-$ m/z: 189.

Step 4

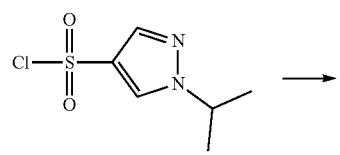

-continued

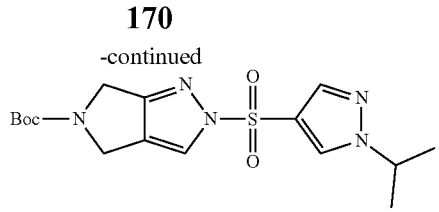

Into a 100 mL 3-necked round-bottom flask were added tert-butyl 2H,4H,6H-pyrrolo[3,4-c]pyrazole-5-carboxylate (3.21 g, 15.33 mmol, 1.00 eq.) and THF (30 mL). The reaction was cooled to 0° C., to the above mixture was added NaH (60% in mineral oil) (0.66 g, 16.87 mmol, 1.10 eq.) in portions. The resulting mixture was stirred for additional 0.5 h at 0° C. To the above mixture was added 1-isopropylpyrazole-4-sulfonyl chloride (3.2 g, 15.34 mmol, 1.00 eq.) in portions. The resulting mixture was stirred for additional 1 h at room temperature. The reaction was quenched with water (20 mL), extracted with EtOAc (3×50 mL), dried over anhydrous Na$_2$SO$_3$. Filtered and the filtrate was concentrated, the residue was purified by silica gel column chromatography, eluted with PE/EA (5:1) to afford crude product. The crude product was re-crystallized from EtOAc/hexane (1:10) to afford tert-butyl 2-(1-isopropylpyrazol-4-ylsulfonyl)-4H,6H-pyrrolo[3,4-c]pyrazole-5-carboxylate (400 mg, 7%) as a white solid. LCMS (ES) [M+1]$^+$ m/z: 382.

Step 5

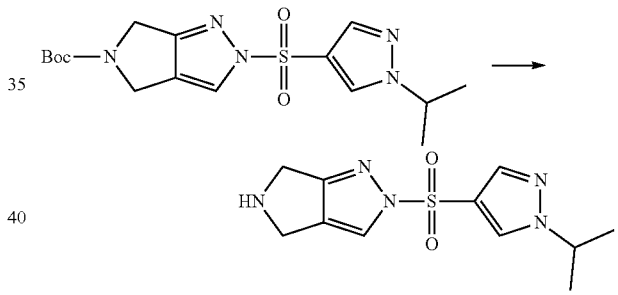

Into a 50 mL 3-necked round-bottom flask were added tert-butyl 2-(1-isopropylpyrazol-4-ylsulfonyl)-4H,6H-pyrrolo[3,4-c]pyrazole-5-carboxylate (400 mg, 1.04 mmol, 1.00 eq.) and DCM (10 mL), 2,6-lutidine (450 mg, 4.19 mmol, 4.00 eq.). The reaction mixture was cooled to 0° C., to the above mixture was added TMSOTf (700 mg, 3.14 mmol, 3.00 eq.) drop wise at 0° C. The resulting mixture was stirred for additional 1 h at room temperature. The reaction was quenched with water (20 mL), filtered, the filter cake was dried under infrared lamp for 4 h, to afford 1-isopropyl-4-{4H,5H,6H-pyrrolo[3,4-c]pyrazole-2-sulfonyl}pyrazole (270 mg, 92%) as a white solid. LCMS (ES) [M+1]$^+$ m/z: 282.

Step 6

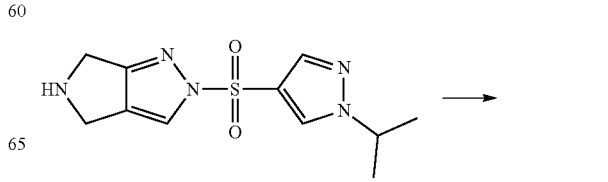

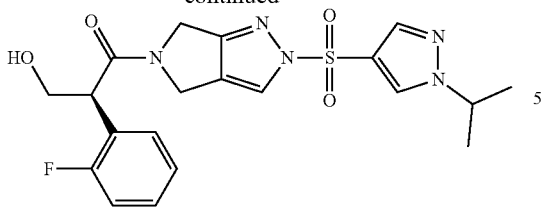

Into a 20 mL vial were added 1-isopropyl-4-{4H,5H,6H-pyrrolo[3,4-c]pyrazole-2-sulfonyl}pyrazole (270 mg, 0.96 mmol, 1.00 eq.) and DMF (3 mL), NM (291.22 mg, 2.88 mmol, 3 eq.), (2S)-2-(2-fluorophenyl)-3-hydroxypropanoic acid (176.75 mg, 0.96 mmol, 1 eq.). The reaction was cooled to 0 degrees C. To the above mixture was added HATU (438 mg, 1.15 mmol, 1.20 eq.) in portions. The resulting mixture was stirred for additional 1 h at 0° C. The crude product was purified by Prep-HPLC using the following conditions: SunFire Prep C18 OBD Column, 19*150 mm, 5 μm, 10 nm, mobile phase, water (0.1% FA) and CH$_3$CN (33% CH$_3$CN up to 70% in 7 min), Detector, UV 254 nm, to afford (2S)-2-(2-fluorophenyl)-3-hydroxy-1-[2-(1-isopropylpyrazol-4-ylsulfonyl)-4H,6H-pyrrolo[3,4-c]pyrazol-5-yl]propan-1-one (105.6 mg, 25%) as a white solid. $^1$H NMR (300 MHz, DMSO-d$_6$) δ 8.70 (s, 1H), 8.15 (d, J=2.5 Hz, 1H), 8.01 (d, J=1.0 Hz, 1H), 7.40 (t, J=7.5 Hz, 1H), 7.30 (dd, J=7.8, 5.9 Hz, 1H), 7.26-7.11 (m, 2H), 4.99-4.81 (m, 2H), 4.57 (dd, J=13.5, 6.8 Hz, 1H), 4.54-4.15 (m, 4H), 4.07-3.92 (m, 1H), 3.61 (dt, J=10.3, 5.4 Hz, 1H), 1.40 (d, J=6.6 Hz, 6H). LCMS (ES) [M+1]$^+$ m/z: 448.

Example 1.57

Synthesis of (S)-2-(2-fluorophenyl)-3-hydroxy-1-(2-((1-(3,3,3-trifluoropropyl)-1H-pyrazol-4-yl)sulfonyl)-2,6-dihydropyrrolo[3,4-c]pyrazol-5(4H)-yl)propan-1-one (Compound 58) and (R)-2-(2-fluorophenyl)-3-hydroxy-1-(2-((1-(3,3,3-trifluoropropyl)-1H-pyrazol-4-yl)sulfonyl)-2,6-dihydropyrrolo[3,4-c]pyrazol-5(4H)-yl)propan-1-one (Compound 59)

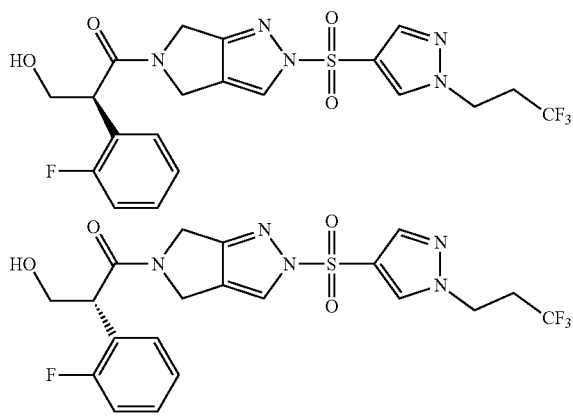

Step 1

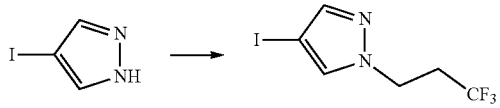

Into a 100-mL round-bottom flask, was placed 4-iodo-1H-pyrazole (2.0 g, 10.31 mmol, 1.00 eq.), 1,1,1-trifluoro-3-iodopropane (3.46 g, 15.46 mmol, 1.50 eq.), K$_2$CO$_3$ (2.84 g, 20.62 mmol, 2 eq.), DMF (30.00 mL). The resulting solution was stirred for 5 hr at room temperature. The resulting solution was extracted with EtOAc (3×50 mL) of and the organic layers combined and dried over anhydrous Na$_2$SO$_3$ and concentrated under vacuum. The residue was applied onto a silica gel column with THF/PE (1:4). This resulted in 1.4 g (46.82%) of 4-iodo-1-(3,3,3-trifluoropropyl)-1H-pyrazole as an off-white solid. LCMS (ES) [M+1]$^+$ m/z: 291.

Step 2

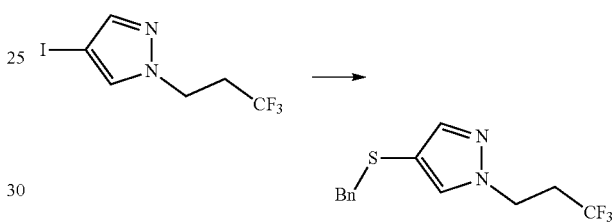

Into a 100-mL round-bottom flask, was placed 4-iodo-1-(3,3,3-trifluoropropyl)-1H-pyrazole (2.25 g, 7.77 mmol, 1.00 eq.), benzyl mercaptan (1.93 g, 15.53 mmol, 2.00 eq.), XantPhos (0.45 g, 0.77 mmol, 0.1 eq.), Pd$_2$(dba)$_3$ (1.42 g, 1.55 mmol, 0.2 eq.), DIEA (2.01 g, 15.54 mmol, 2 eq.), dioxane (30.00 mL). The resulting solution was stirred for 18 hours at 100 degrees C. The reaction mixture was cooled to room temperature. The residue was applied onto a silica gel column with THF/PE (1:3). This resulted in 1.5 g (67.87%) of 4-(benzylthio)-1-(3,3,3-trifluoropropyl)-1H-pyrazole as light yellow oil. LCMS (ES) [M+1]$^+$ m/z: 287.

Step 3

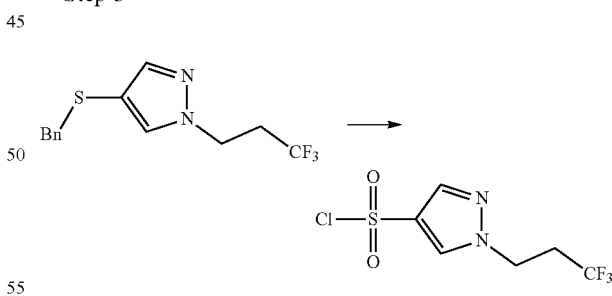

Into a 100-mL round-bottom flask, was placed 4-(benzylthio)-1-(3,3,3-trifluoropropyl)-1H-pyrazole (1.50 g, 5.24 mmol, 1.00 eq.), NCS (2.09 g, 15.72 mmol, 3.00 eq.), HOAc (27.00 mL), H$_2$O (3.00 mL). The resulting solution was stirred for 6 hr at room temperature. The resulting solution was extracted with DCM (3×30 mL) and the organic layers combined and dried over anhydrous Na$_2$SO$_3$ and concentrated under vacuum. The residue was applied onto a silica gel column with EtOAc/PE (1:3). This resulted in 800 mg (58.39%) of 1-(3,3,3-trifluoropropyl)-1H-pyrazole-4-sulfonyl chloride as light yellow oil.

Step 4

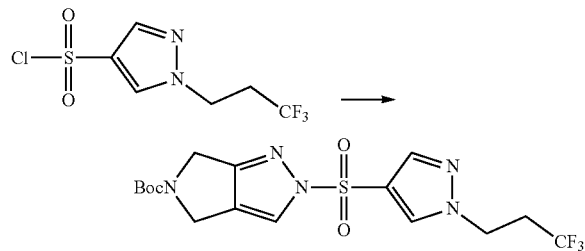

Into a 100-mL round-bottom flask, was placed tert-butyl 2H,4H,6H-pyrrolo[3,4-c]pyrazole-5-carboxylate (500.00 mg, 2.39 mmol, 1.0 eq.), NaH (143.54 mg, 1.50 eq.), THF (20.00 mL), 1-(3,3,3-trifluoropropyl)-1H-pyrazole-4-sulfonyl chloride (626.79 mg, 2.39 mmol, 1.00 eq.) was added portions, The resulting solution was stirred for 4 hours at room temperature. The reaction was then quenched by the addition of water. The resulting solution was extracted with DCM (3×30 mL) and the organic layers combined and dried over anhydrous Na$_2$SO$_3$ and concentrated under vacuum. The residue was applied onto a silica gel column with EtOAc/PE (1:3). This resulted in 750 mg (65.68%) of tert-butyl 2-((1-(3,3,3-trifluoropropyl)-1H-pyrazol-4-yl)sulfonyl)-2,6-dihydropyrrolo[3,4-c]pyrazole-5(4H)-carboxylate as an off-white solid. LCMS (ES) [M+1]$^+$ m/z: 436.

Step 5

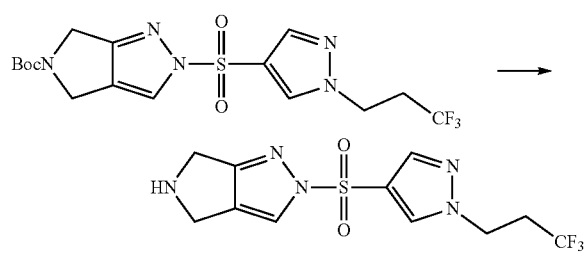

Into a 100-mL round-bottom flask, was placed tert-butyl 2-((1-(3,3,3-trifluoropropyl)-1H-pyrazol-4-yl)sulfonyl)-2,6-dihydropyrrolo[3,4-c]pyrazole-5(4H)-carboxylate (843 mg, 1.94 mmol, 1.00 eq.), TMSOTf (1.30 g, 5.849 mmol, 3.01 eq.), 2,6-Dimethylpyridine (834.07 mg, 7.784 mmol, 4.00 eq.). The resulting solution was stirred for 4 hours at room temperature. The reaction was then quenched by the addition of water (30 mL). The resulting mixture was concentrated under vacuum. The resulting mixture was washed with H$_2$O (5×30 mL). The solids were collected by filtration. This resulted in 330 mg (50.84%) of 2-((1-(3,3,3-trifluoropropyl)-1H-pyrazol-4-yl)sulfonyl)-2,4,5,6-tetrahydropyrrolo[3,4-c]pyrazole as a white solid. LCMS (ES) [M+1]$^+$ m/z: 336.

Step 6

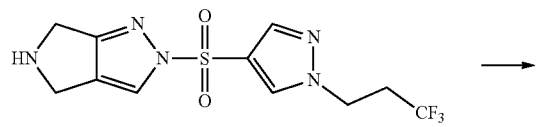

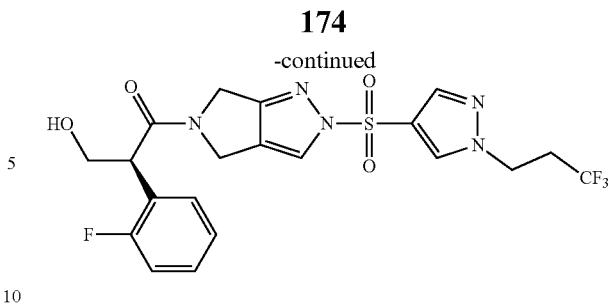

Into a 50-mL round-bottom flask, was placed 2-((1-(3,3,3-trifluoropropyl)-1H-pyrazol-4-yl)sulfonyl)-2,4,5,6-tetrahydropyrrolo[3,4-c]pyrazole (150.00 mg, 0.44 mmol, 1.00 eq.), (2S)-2-(2-fluorophenyl)-3-hydroxypropanoic acid (98.86 mg, 0.54 mmol, 1.20 eq.), HATU (255.22 mg, 0.67 mmol, 1.5 eq.), DIEA (115.52 mg, 0.895 mmol, 2 eq.), DMF (10.00 mL). The resulting solution was stirred for 4 hours at room temperature. The resulting solution was extracted with 3×30 mL of DCM and the organic layers combined and dried over anhydrous Na$_2$SO$_4$ and concentrated under vacuum. The crude product was purified by Prep-HPLC using the following conditions: Column: Sunfire Prep C18 OBD Column, 50*250 mm, 5 m 10 nm; Mobile Phase A: Water (0.1% FA), Mobile Phase B: ACN; Flow rate: 90 mL/min; Gradient: 15% B to 50% B in 12 min, 50% B; Wave Length: 220 nm; RT1 (12 min): This resulted in 140 mg (62.50%) of (S)-2-(2-fluorophenyl)-3-hydroxy-1-(2-((1-(3,3,3-trifluoropropyl)-1H-pyrazol-4-yl)sulfonyl)-2,6-dihydropyrrolo[3,4-c]pyrazol-5(4H)-yl)propan-1-one as a white solid. $^1$H NMR (300 MHz, DMSO-d$_6$) δ 8.75 (s, 1H), 8.15 (d, J=2.3 Hz, 1H), 8.06 (d, J=3.1 Hz, 1H), 7.45-7.35 (m, 1H), 7.33-7.28 (m, 1H), 7.25-7.11 (m, 2H), 4.95-4.82 (m, 2H), 4.52-4.23 (m, 6H), 4.04-3.95 (m, 1H), 3.65-3.57 (m, 1H), 2.98-2.84 (m, 2H). LCMS (ES) [M+1]$^+$ m/z: 502.

Step 7

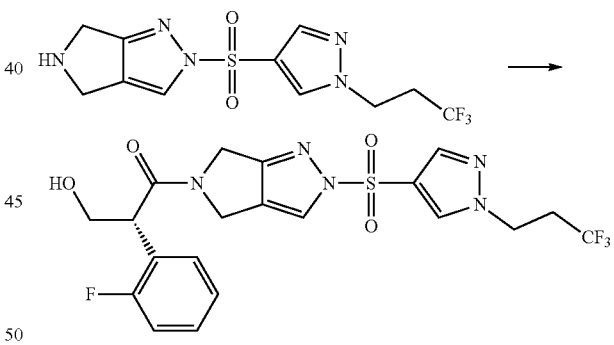

Into a 50-mL round-bottom flask, was placed 2-((1-(3,3,3-trifluoropropyl)-1H-pyrazol-4-yl)sulfonyl)-2,4,5,6-tetrahydropyrrolo[3,4-c]pyrazole (150.00 mg, 0.44 mmol, 1.00 equiv), (2R)-2-(2-fluorophenyl)-3-hydroxypropanoic acid (98.86 mg, 0.54 mmol, 1.20 equiv), HATU (255.22 mg, 0.67 mmol, 1.5 equiv), DIEA (115.52 mg, 0.895 mmol, 2 equiv), DMF (10.00 mL). The resulting solution was stirred for 4 hours at room temperature. The resulting solution was extracted with DCM (3×30 mL) and the organic layers combined and dried over anhydrous sodium sulfate and concentrated under vacuum. The crude product was purified by Prep-HPLC using the following conditions: Column: Sunfire Prep C18 OBD Column, 50*250 mm, 5 m 10 nm; Mobile Phase A: Water (0.1% FA), Mobile Phase B: ACN; Flow rate: 90 mL/min; Gradient: 15% B to 50% B in 15 min, 50% B; Wave Length: 220 nm; RT1 (15 min): This resulted in 120 mg (53.57%) of (R)-2-(2-fluorophenyl)-3-hydroxy-1-(2-((1-(3,3,3-trifluoropropyl)-1H-pyrazol-4-yl)sulfonyl)-2,6-dihydropyrrolo[3,4-c]pyrazol-5(4H)-yl)propan-1-one as a white solid. $^1$H NMR (300 MHz, DMSO-d$_6$) δ 8.74 (s, 1H), 8.14 (d, J=2.3 Hz, 1H), 8.05 (d, J=3.1 Hz, 1H), 7.45-7.35 (m, 1H), 7.33-7.28 (m, 1H), 7.25-7.11 (m, 2H), 4.95-4.82 (m, 2H), 4.52-4.23 (m, 6H), 4.04-3.95 (m, 1H), 3.65-3.57 (m, 1H), 2.98-2.84 (m, 2H). LCMS (ES) [M+1]$^+$ m/z: 502.

Example 1.58

Synthesis of (2S)-2-(2-fluorophenyl)-3-hydroxy-1-{2-[1-(2-methoxyethyl)pyrazol-4-ylsulfonyl]-4H,6H-pyrrolo[3,4-c]pyrazol-5-yl}propan-1-one (Compound 60) and (2R)-2-(2-fluorophenyl)-3-hydroxy-1-{2-[1-(2-methoxyethyl)pyrazol-4-ylsulfonyl]-4H,6H-pyrrolo[3,4-c]pyrazol-5-yl}propan-1-one (Compound 61)

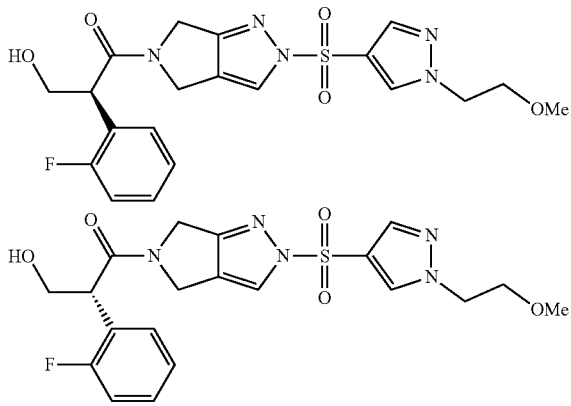

The title compounds were synthesized according to the procedures described in the synthesis of Compounds 58 and 59 Steps 1-7 using 2-bromoethyl methyl ether instead of 1,1,1-trifluoro-3-iodopropane in Step 1. (2R)-2-(2-fluorophenyl)-3-hydroxy-1-{2-[1-(2-methoxyethyl)pyrazol-4-ylsulfonyl]-4H,6H-pyrrolo[3,4-c]pyrazol-5-yl}propan-1-one was obtained as a white solid. $^1$H NMR (300 MHz, DMSO-d$_6$) δ 8.61 (s, 1H), 8.15 (s, 1H), 8.01 (s, 1H), 7.39 (dd, J=7.9 Hz, 7.9 Hz 1H), 7.34-7.26 (m, 1H), 7.18 (dd, J=9.0, 7.6 Hz, 2H), 4.97-4.80 (m, 2H), 4.50-4.37 (m, 2H), 4.36-4.23 (m, 4H), 3.99 (d, J=7.5 Hz, 1H), 3.68 (t, J=5.2 Hz, 2H), 3.65-3.51 (m, 1H), 3.18 (d, J=1.7 Hz, 3H). LCMS (ES) [M+1]$^+$ m/z: 464.

Similarly, (2S)-2-(2-fluorophenyl)-3-hydroxy-1-{2-[1-(2-methoxyethyl)pyrazol-4-ylsulfonyl]-4H,6H-pyrrolo[3,4-c]pyrazol-5-yl}propan-1-one was obtained as a white solid. $^1$H NMR (300 MHz, DMSO-d$_6$) δ 8.61 (s, 1H), 8.15 (s, 1H), 8.01 (s, 1H), 7.39 (dd, J=7.9 Hz, 7.9 Hz 1H), 7.34-7.26 (m, 1H), 7.18 (dd, J=9.0, 7.6 Hz, 2H), 4.97-4.80 (m, 2H), 4.50-4.37 (m, 2H), 4.36-4.23 (m, 4H), 3.99 (d, J=7.5 Hz, 1H), 3.68 (t, J=5.2 Hz, 2H), 3.65-3.51 (m, 1H), 3.18 (d, J=1.7 Hz, 3H). LCMS (ES) [M+1]$^+$ m/z: 464.

Example 1.59

Synthesis of (2S)-2-(2-fluorophenyl)-3-hydroxy-1-{2-[1-(2,2,2-trifluoroethyl)pyrazol-3-ylsulfonyl]-4H,6H-pyrrolo[3,4-c]pyrazol-5-yl}propan-1-one (Compound 62)

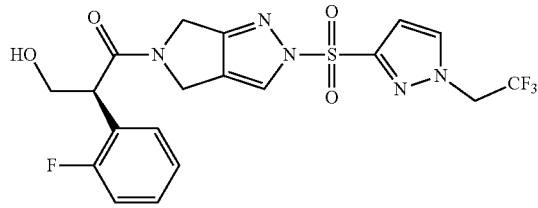 [SMILES: O=C([C@H](CO)c1ccccc1F)N1Cc2cn(S(=O)(=O)c3ccn(CC(F)(F)F)n3)nc2C1]

To a stirred solution of (2S)-2-(2-fluorophenyl)-3-hydroxypropanoic acid (55 mg, 0.30 mmol, 1.20 eq.), NMI (61 mg, 0.75 mmol, 3.00 eq.) and 3-{4H,5H,6H-pyrrolo[3,4-c]pyrazole-2-sulfonyl}-1-(2,2,2-trifluoroethyl)pyrazole (Step 5, Example 1.78), 80 mg, 0.25 mmol, 1.00 eq.) in CH$_3$CN (2 mL) were added TCFH (140 mg, 0.50 mmol, 2.00 eq.) in portions at room temperature under nitrogen atmosphere. The resulting mixture was stirred for 2 h at room temperature under nitrogen atmosphere. The reaction solution was purified by Prep-HPLC using the following conditions: C18 OBD Column, 50*250 mm, 5 μm, 10 nm, mobile phase, CH$_3$CN/H$_2$O (FA: 0.1%), from 5% to 48% in 12 min, Flow rate, 80 mL/min, Detector, UV 254 nm. The fraction of the target was freezing dried to afford (2S)-2-(2-fluorophenyl)-3-hydroxy-1-{2-[1-(2,2,2-trifluoroethyl)pyrazol-3-ylsulfonyl]-4H,6H-pyrrolo[3,4-c]pyrazol-5-yl}propan-1-one (93 mg, 76.6%) as a white solid. $^1$H NMR (300 MHz, DMSO-d$_6$) δ 8.23 (d, J=2.4 Hz, 1H), 8.14 (d, J=2.6 Hz, 1H), 7.40 (t, J=7.5 Hz, 1H), 7.35-7.26 (m, 1H), 7.25-7.12 (m, 2H), 7.02 (d, J=2.5 Hz, 1H), 5.45-5.26 (m, 2H), 5.01-4.80 (m, 2H), 4.61-4.39 (m, 2H), 4.39-4.19 (m, 2H), 4.11-3.89 (m, 1H), 3.80-3.47 (m, 1H). LCMS (ES) [M+1]$^+$ m/z: 488.

Example 1.60

Synthesis of (2S)-2-(2-chlorophenyl)-3-hydroxy-1-[2-[1-(2,2,2-trifluoroethyl)pyrazol-3-ylsulfonyl]-4H,6H-pyrrolo[3,4-c]pyrazol-5-yl]propan-1-one (Compound 63)

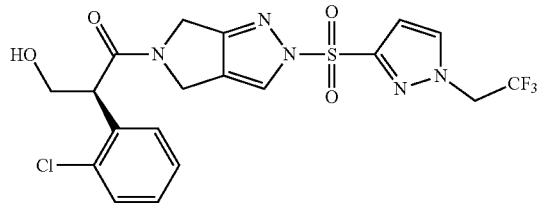 [SMILES: O=C([C@H](CO)c1ccccc1Cl)N1Cc2cn(S(=O)(=O)c3ccn(CC(F)(F)F)n3)nc2C1]

Into a 20-mL vial, was placed (2S)-2-(2-chlorophenyl)-3-hydroxypropanoic acid (80.00 mg, 0.39 mmol, 1.00 eq.), 3-[4H,5H,6H-pyrrolo[3,4-c]pyrazole-2-sulfonyl]-1-(2,2,2-trifluoroethyl)pyrazole (Step 5, Example 1.78), 128.11 mg, 0.39 mmol, 1.00 eq.), NMM (80.67 mg, 0.79 mmol, 2.00 eq.), DMF (5.00 mL). This was followed by the addition of HATU (181.95 mg, 0.49 mmol, 1.20 eq.), in portions at 0°

C. The resulting solution was stirred for 1 h at room temperature. The crude product (300 mg) was purified by Prep-HPLC using the following conditions: Column, Sunfire Prep C18 OBD Column, 50*250 mm 5 m 10 nm; mobile phase, Water (0.1% NH$_3$.H$_2$O) and ACN (15% PhaseB up to 70% in 15 min); Detector, 254. This resulted in 112 mg (55.74%) of (2S)-2-(2-chlorophenyl)-3-hydroxy-1-[2-[1-(2,2,2-trifluoroethyl)pyrazol-3-ylsulfonyl]-4H,6H-pyrrolo[3,4-c]pyrazol-5-yl]propan-1-one as white solid. $^1$H NMR (300 MHz, DMSO-d$_6$) δ 8.24 (s, 1H), 8.15 (d, J=2.6 Hz, 1H), 7.53-7.40 (m, 2H), 7.32 (q, J=5.6, 4.7 Hz, 2H), 7.03 (d, J=2.5 Hz, 1H), 5.33 (q, J=9.0 Hz, 2H), 4.98 (d, J=4.2 Hz, 1H), 4.98-4.83 (m, 1H), 4.41 (dtt, J=28.4, 13.4, 8.0 Hz, 4H), 3.97 (d, J=7.3 Hz, 1H), 3.58 (dq, J=10.0, 5.0 Hz, 1H). LCMS (ES) [M+1]$^+$ m/z: 504.

Example 1.61

Synthesis of 3-chloro-2-(3-{2-[1-(2,2-difluoroethyl)pyrazol-3-ylsulfonyl]-4H,6H-pyrrolo[3,4-c]pyrazole-5-carbonyl}oxetan-3-yl)pyridine (Compound 64)

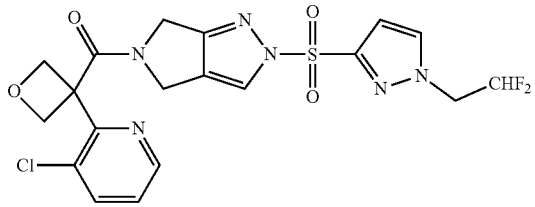 [SMILES: O=C(N1Cc2cn(S(=O)(=O)c3ccn(CC(F)F)n3)nc2C1)C1(c2ncccc2Cl)COC1]

Into a 20 mL vial were added 2-((1-(2,2-difluoroethyl)-1H-pyrazol-3-yl)sulfonyl)-2,4,5,6-tetrahydropyrrolo[3,4-c]pyrazole (170 mg, 0.56 mmol, 1.00 eq.) and DMF (3 mL), 3-(3-chloropyridin-2-yl)oxetane-3-carboxylic acid (120 mg, 0.56 mmol, 1.00 eq.), NMM (170 mg, 1.68 mmol, 3.00 eq.). The reaction was cooled to 0° C., to the above mixture was added HATU (256 mg, 0.67 mmol, 1.20 eq.) in portions. The resulting mixture was stirred for additional 1 h at room temperature. The reaction solution was purified by Prep-HPLC using the following conditions: Sunfire Prep C18 OBD Column, 50*250 mm, 5 μm, 10 nm, Mobile Phase A: water (0.1% FA), Mobile Phase B: CH$_3$CN, Flow rate: 90 mL/min, Gradient: 15% B to 50% B in 15 min, Wave Length: UV 220 nm. The fraction of the target was freezing dried to afford 3-chloro-2-(3-{2-[1-(2,2-difluoroethyl)pyrazol-3-ylsulfonyl]-4H,6H-pyrrolo[3,4-c]pyrazole-5-carbonyl}oxetan-3-yl)pyridine (104.1 mg, 37%) as a white solid. $^1$H NMR (300 MHz, DMSO-d$_6$) δ 8.70 (dq, J=4.7, 1.7 Hz, 1H), 8.28-7.95 (m, 1H), 8.22-7.80 (m, 2H), 7.49 (dtd, J=6.6, 4.8, 1.8 Hz, 1H), 6.96 (t, J=2.2 Hz, 1H), 6.73-6.03 (m, 1H), 5.18 (ddd, J=28.4, 6.2, 2.8 Hz, 4H), 4.77 (tt, J=15.3, 2.5 Hz, 2H), 4.74-4.34 (m, 2H), 3.71 (d, J=4.5 Hz, 2H). LCMS (ES) [M+1]$^+$ m/z: 499.

Example 1.62

Synthesis of (3-(3-chloropyridin-2-yl)oxetan-3-yl)(2-((1-(2,2,2-trifluoroethyl)-1H-pyrazol-3-yl)sulfonyl)-2,6-dihydropyrrolo[3,4-c]pyrazol-5(4H)-yl)methanone (Example 65)

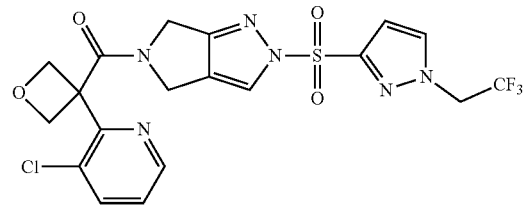 [SMILES: O=C(N1Cc2cn(S(=O)(=O)c3ccn(CC(F)(F)F)n3)nc2C1)C1(c2ncccc2Cl)COC1]

Into a 8-mL vail, was placed 2-((1-(2,2,2-trifluoroethyl)-1H-pyrazol-3-yl)sulfonyl)-2,4,5,6-tetrahydropyrrolo[3,4-c]pyrazole (161 mg, 0.50 mmol, 1.20 eq.), DMF (4.00 mL), 3-(3-chloropyridin-2-yl)oxetane-3-carboxylic acid (100 mg, 0.42 mmol, 1.00 eq.), NMI (107 mg, 1.25 mmol, 3.00 eq.). This was followed by the addition of TCFH (238 mg, 0.83 mmol, 2.00 eq.) with stirring at 0° C. After addition, the resulting solution was stirred for 1 h at 0° C. and was purified by Prep-HPLC using these conditions: Sunfire Prep C18 OBD Column, 50*250 mm, 5 μm, 10 nm, Mobile Phase A: water (0.1% FA), Mobile Phase B: CH$_3$CN, Flow rate: 90 mL/min, Gradient: from 20% B to 55% B in 12 min, Detector, UV 220 nm. This resulted in 118 mg of (3-(3-chloropyridin-2-yl)oxetan-3-yl)(2-((1-(2,2,2-trifluoroethyl)-1H-pyrazol-3-yl)sulfonyl)-2,6-dihydropyrrolo[3,4-c]pyrazol-5(4H)-yl)methanone as a white solid. $^1$H NMR (300 MHz, DMSO-d$_6$) δ 8.71-8.68 (m, 1H), 8.20-8.12 (m, 2H), 8.01-7.96 (m, 1H), 7.52 (dt, J=8.1, 5.1 Hz, 1H), 7.00 (d, J=2.7 Hz, 1H), 5.37 (q, J=9.0 Hz, 2H), 5.24 (dd, J=6.0, 3.9 Hz, 2H), 5.14 (d, J=6.0 Hz, 2H), 4.50 (d, J=6.0 Hz, 2H), 3.72 (d, J=4.8 Hz, 2H). LCMS (ES) [M+1]$^+$ m/z: 517.

Example 1.63

Synthesis of (2S)-3-hydroxy-1-{2-[4-methyl-1-(2,2,2-trifluoroethyl)pyrazol-3-ylsulfonyl]-4H,6H-pyrrolo[3,4-c]pyrazol-5-yl}-2-phenylpropan-1-one (Compound 66) and (2R)-3-hydroxy-1-{2-[4-methyl-1-(2,2,2-trifluoroethyl)pyrazol-3-ylsulfonyl]-4H,6H-pyrrolo[3,4-c]pyrazol-5-yl}-2-phenylpropan-1-one (Compound 67)

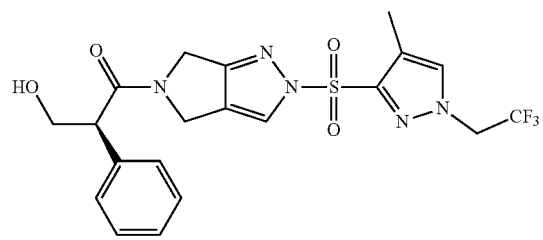

-continued

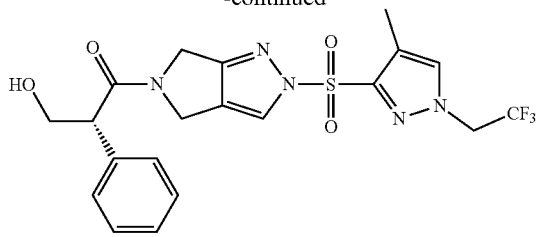

Step 1

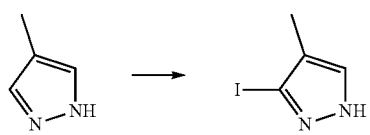

Into a 500 mL round-bottom flask were added fomepizole (20 g, 243.59 mmol, 1.00 eq.); DMF (200 mL) and NIS (57.54 g, 255.77 mmol, 1.05 eq.) at room temperature. The resulting mixture was stirred for 4 h at room temperature. The reaction was quenched with Water at room temperature. The resulting mixture was extracted with EtOAc (3×200 mL). The combined organic layers were washed with brine (3×200 mL), dried over anhydrous $Na_2SO_4$. After filtration, the filtrate was concentrated under reduced pressure. The residue was purified by silica gel column chromatography, eluted with PE/EA (5:1) to afford 3-iodo-4-methyl-1H-pyrazole (20 g, 39.47%) as a yellow oil. LCMS (ES) $[M+1]^+$ m/z: 209.

Step 2

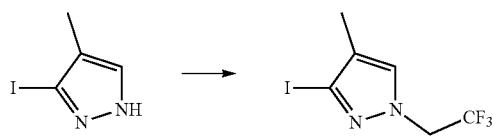

Into a 500 mL round-bottom flask were added 3-iodo-4-methyl-1H-pyrazole (10 g, 48.08 mmol, 1.00 eq.); DMF (150 mL); 2,2,2-trifluoroethyl trifluoromethanesulfonate (13.95 g, 60.10 mmol, 1.25 eq.) and $Cs_2CO_3$ (31.33 g, 96.15 mmol, 2 eq.) at room temperature. The resulting mixture was stirred for 3 h at room temperature. The reaction was quenched with Water at room temperature. The resulting mixture was extracted with EtOAc (3×200 mL). The combined organic layers were washed with brine (3×200 mL), dried over anhydrous $Na_2SO_4$. After filtration, the filtrate was concentrated under reduced pressure. The residue was purified by silica gel column chromatography, eluted with PE/EA (8:1) to afford 3-iodo-4-methyl-1-(2,2,2-trifluoroethyl)pyrazole (12 g, 86.06%) as a yellow oil. LCMS (ES) $[M+1]^+$ m/z: 291.

Step 3

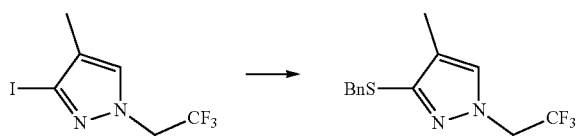

Into a 500 mL 3-necked round-bottom flask were added 3-iodo-4-methyl-1-(2,2,2-trifluoroethyl)pyrazole (11 g, 37.927 mmol, 1.00 eq.); DIEA (14.71 g, 113.781 mmol, 3 eq.); XantPhos (4.39 g, 7.585 mmol, 0.2 eq.) and $Pd_2(dba)_3 \cdot CHCl_3$ (3.93 g, 3.79 mmol, 0.1 eq.) at room temperature. To a stirred mixture was added benzyl mercaptan (14.13 g, 113.78 mmol, 3 eq.) drop wise at room temperature under nitrogen atmosphere. The resulting mixture was stirred for 16 h at 100° C. under nitrogen atmosphere. The resulting mixture was concentrated under reduced pressure. The residue was purified on a silica gel column, eluted with PE/EA (10:1) to afford 3-(benzylsulfanyl)-4-methyl-1-(2,2,2-trifluoroethyl)pyrazole (9 g, 82.88%) as an orange oil. LCMS (ES) $[M+1]^+$ m/z: 287.

Step 4

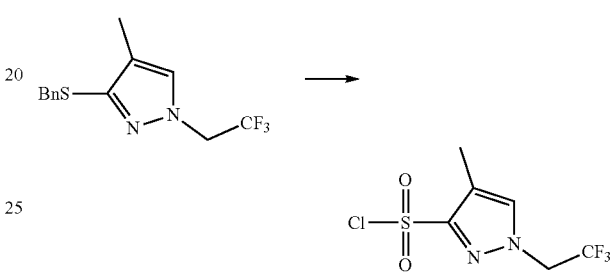

Into a 250 mL round-bottom flask were added 3-(benzylsulfanyl)-4-methyl-1-(2,2,2-trifluoroethyl)pyrazole (8.5 g, 29.69 mmol, 1.00 eq.); HOAc (77 mL); $H_2O$ (8.5 mL) and NCS (15.86 g, 118.75 mmol, 4 eq.) at 0° C. The resulting mixture was stirred for 2 h at room temperature. The resulting mixture was concentrated under reduced pressure. The residue was purified by silica gel column chromatography, eluted with PE/EA (8:1) to afford 4-methyl-1-(2,2,2-trifluoroethyl)pyrazole-3-sulfonyl chloride (7 g, 89.78%) as a yellow oil. LCMS (ES) $[M+1]^+$ m/z: 263.

Step 5

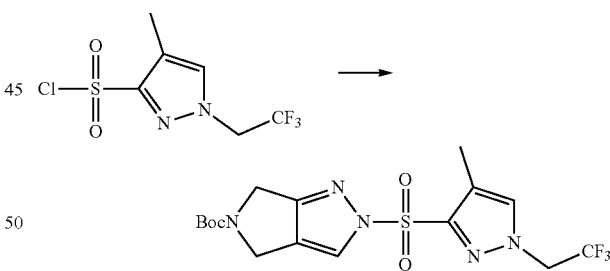

Into a 250 mL 3-necked round-bottom flask were added 4-methyl-1-(2,2,2-trifluoroethyl)pyrazole-3-sulfonyl chloride (8.53 g, 32.50 mmol, 1.0 eq.) and THF (100 mL) at room temperature. To the above mixture was added NaH (0.94 g, 39.00 mmol, 1.2 eq.) at 0 degrees C. The resulting mixture was stirred for additional 30 min at 0° C. To the above mixture was added tert-butyl 2H,4H,6H-pyrrolo[3,4-c]pyrazole-5-carboxylate (6.8 g, 32.50 mmol, 1.00 eq.) at 0° C. The resulting mixture was stirred for additional 2 h at room temperature. The reaction was quenched with Water at room temperature. The resulting mixture was extracted with EtOAc (3×150 ml). The combined organic layers were washed with brine (3×150 ml), dried over anhydrous $Na_2SO_4$. After filtration, the filtrate was concentrated under reduced pressure. The crude product was re-crystallized from hexane/EtOAc (5:1, 100 ml) to afford tert-butyl 2-[4-methyl-1-(2,2,2-trifluoroethyl)pyrazol-3-ylsulfonyl]-4H,6H-pyrrolo[3,4-c]pyrazole-5-carboxylate (9 g, 63.60%) as a light yellow solid. LCMS (ES) [M+1]+ m/z: 436.

Step 6

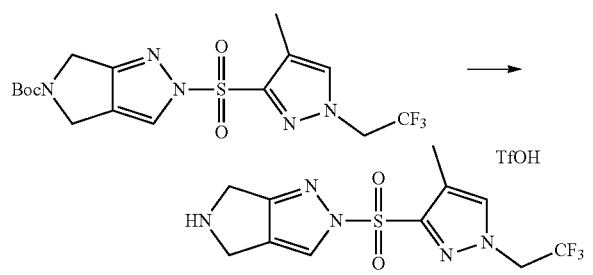

Into a 250 mL round-bottom flask were added tert-butyl 2-[4-methyl-1-(2,2,2-trifluoroethyl)pyrazol-3-ylsulfonyl]-4H,6H-pyrrolo[3,4-c]pyrazole-5-carboxylate (9 g, 20.67 mmol, 1.00 eq.); DCM (100 mL) and 2,6-Dimethylpyridine (8.86 g, 82.68 mmol, 4 eq.) at room temperature. To the above mixture was added TMSOTf (13.78 g, 62.01 mmol, 3 eq.) drop wise at 0° C. The resulting mixture was stirred for additional 3 h at room temperature. The reaction was quenched with MeOH at room temperature. The resulting mixture was concentrated under reduced pressure. The crude product was re-crystallized from hexane/EtOAc (1:1, 100 ml) to afford 4-methyl-3-{4H,5H,6H-pyrrolo[3,4-c]pyrazole-2-sulfonyl}-1-(2,2,2-trifluoroethyl)pyrazole; trifluoromethanesulfonic acid (9 g, 89.71%) as a white solid. LCMS (ES) [M+1]+ m/z: 336.

Step

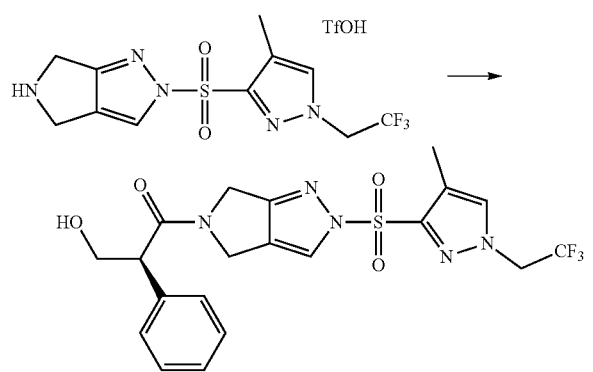

Into a 40 mL vial were added (S)-tropic acid (68 mg, 0.41 mmol, 1 eq.); DMF (5 mL); 4-methyl-3-{4H,5H,6H-pyrrolo[3,4-c]pyrazole-2-sulfonyl}-1-(2,2,2-trifluoroethyl)pyrazole; trifluoromethanesulfonic acid (200 mg, 0.41 mmol, 1.00 eq.) and NMM (83 mg, 0.82 mmol, 2 eq.) at room temperature. To the above mixture was added HATU (188 mg, 0.49 mmol, 1.2 eq.) at 0° C. The resulting mixture was stirred for additional 1 h at 0° C. The crude product was purified by Prep-HPLC using the following conditions (Prep-HPLC-003): Column, SunFire Prep C18 OBD Column, 19*150 mm, 5 m; mobile phase, Water (0.1% FA) and ACN (30% ACN up to 74% in 7 min). This resulted in (2S)-3-hydroxy-1-{2-[4-methyl-1-(2,2,2-trifluoroethyl)pyrazol-3-ylsulfonyl]-4H,6H-pyrrolo[3,4-c]pyrazol-5-yl}-2-phenylpropan-1-one (131 mg, 65.76%) as a white solid. 1H NMR (300 MHz, DMSO-d6) δ 8.22 (d, J=1.9 Hz, 1H), 7.94 (d, J=1.6 Hz, 1H), 7.40-7.20 (m, 5H), 5.26 (q, J=9.0 Hz, 2H), 4.96-4.76 (m, 2H), 4.56-4.26 (m, 3H), 4.07-3.92 (m, 2H), 3.61-3.45 (m, 1H), 2.20 (t, J=1.0 Hz, 3H). LCMS (ES) [M+1]+ m/z: 483.

Step 8

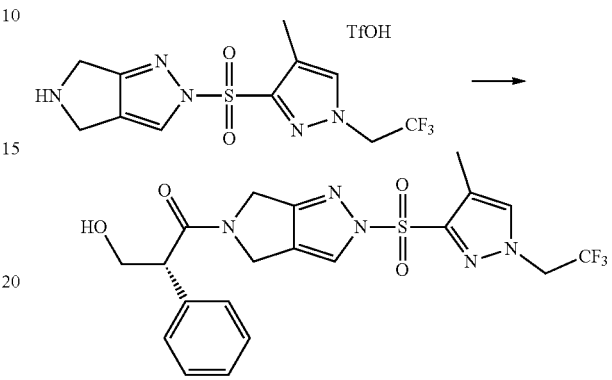

Into a 40 ml vial were added (R)-tropic acid (68 mg, 0.412 mmol, 1.0 eq.). DMF (5 ml) and NMM (83 mg, 0.82 mmol, 2 eq.) at room temperature. To the above mixture was added HATU (188 mg, 0.49 mmol, 1.2 eq.) at 0° C. The resulting mixture was stirred for additional 1 h at 0° C. The crude product was purified by Prep-HPLC using the following conditions (Prep-HPLC-003): Column, SunFire Prep C18 OBD Column, 19*150 mm, 5 m; mobile phase, Water (0.1% FA) and ACN (30% ACN up to 74% in 7 min); This resulted in (2R)-3-hydroxy-1-{2-[4-methyl-1-(2,2,2-trifluoroethyl)pyrazol-3-ylsulfonyl]-4H,6H-pyrrolo[3,4-c]pyrazol-5-yl}-2-phenylpropan-1-one (122.6 mg, 61.54%) as a white solid. 1H NMR (300 MHz, DMSO-d6) δ 8.22 (d, J=1.9 Hz, 1H), 7.94 (s, 1H), 7.40-7.19 (m, 5H), 5.26 (q, J=9.0 Hz, 2H), 4.96-4.76 (m, 2H), 4.56-4.26 (m, 3H), 4.07-3.92 (m, 2H), 3.59-3.49 (m, 1H), 2.20 (t, J=1.0 Hz, 3H). LCMS (ES) [M+1]+ m/z: 483.

Example 1.64

(2S)-2-(2-fluorophenyl)-3-hydroxy-1-{2-[4-methyl-1-(2,2,2-trifluoroethyl)pyrazol-3-ylsulfonyl]-4H,6H-pyrrolo[3,4-c]pyrazol-5-yl}propan-1-one (Compound 68) and (2R)-2-(2-fluorophenyl)-3-hydroxy-1-{2-[4-methyl-1-(2,2,2-trifluoroethyl)pyrazol-3-ylsulfonyl]-4H,6H-pyrrolo[3,4-c]pyrazol-5-yl}propan-1-one (Compound 69)

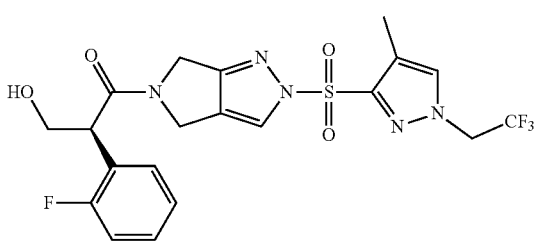

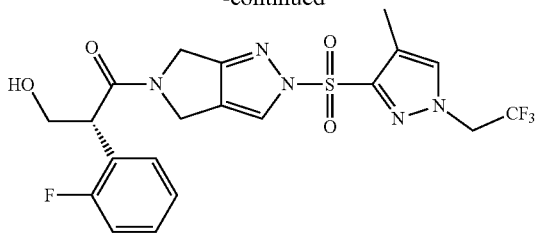

The title compounds were synthesized by reacting 4-methyl-3-{4H,5H,6H-pyrrolo[3,4-c]pyrazole-2-sulfonyl}-1-(2,2,2-trifluoroethyl)pyrazole Step 6, Example 1.63 with (2S)-2-(2-fluorophenyl)-3-hydroxypropanoic acid or (2R)-2-(2-fluorophenyl)-3-hydroxypropanoic acid, according to the procedure described in Step 7, Example 1.63 to give (2S)-2-(2-fluorophenyl)-3-hydroxy-1-{2-[4-methyl-1-(2,2,2-trifluoroethyl)pyrazol-3-ylsulfonyl]-4H,6H-pyrrolo[3,4-c]pyrazol-5-yl}propan-1-one (58.37%) as a white solid. $^1$H NMR (300 MHz, DMSO-$d_6$) δ 8.23 (d, J=1.6 Hz, 1H), 7.94 (s, 1H), 7.46-7.35 (m, 1H), 7.35-7.26 (m, 1H), 7.26-7.11 (m, 2H), 5.27 (q, J=9.0 Hz, 2H), 4.99-4.82 (m, 2H), 4.54-4.38 (m, 2H), 4.37-4.21 (m, 2H), 4.06-3.92 (m, 1H), 3.60 (dq, J=10.3, 5.3 Hz, 1H), 2.20 (d, J=1.0 Hz, 3H). LCMS (ES) [M+1]$^+$ m/z: 502.

(2R)-2-(2-Fluorophenyl)-3-hydroxy-1-{2-[4-methyl-1-(2,2,2-trifluoroethyl)pyrazol-3-ylsulfonyl]-4H,6H-pyrrolo[3,4-c]pyrazol-5-yl}propan-1-one (61.08%) was also isolated as a white solid. $^1$H NMR (300 MHz, DMSO-$d_6$) δ 8.23 (d, J=1.6 Hz, 1H), 7.94 (s, 1H), 7.46-7.34 (m, 1H), 7.38-7.25 (m, 1H), 7.31-7.11 (m, 2H), 5.27 (q, J=9.0 Hz, 2H), 4.99-4.82 (m, 2H), 4.57-4.37 (m, 2H), 4.37-4.21 (m, 2H), 4.07-3.92 (m, 1H), 3.60 (dq, J=10.5, 5.3 Hz, 1H), 2.20 (d, J=1.0 Hz, 3H). LCMS (ES) [M+1]$^+$ m/z: 502.

Example 1.65

Synthesis of (2S)-2-(2-chlorophenyl)-3-hydroxy-1-{2-[4-methyl-1-(2,2,2-trifluoroethyl)pyrazol-3-ylsulfonyl]-4H,6H-pyrrolo[3,4-c]pyrazol-5-yl}propan-1-one (compound 70) and (2R)-2-(2-chlorophenyl)-3-hydroxy-1-{2-[4-methyl-1-(2,2,2-trifluoroethyl)pyrazol-3-ylsulfonyl]-4H,6H-pyrrolo[3,4-c]pyrazol-5-yl}propan-1-one (Compound 71)

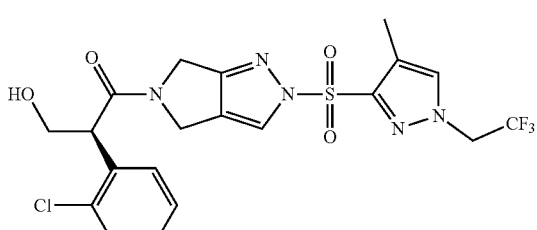

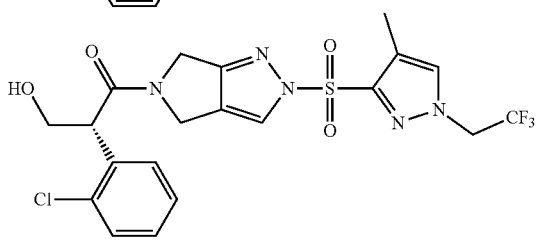

The title compounds were synthesized by reacting 4-methyl-3-{4H,5H,6H-pyrrolo[3,4-c]pyrazole-2-sulfonyl}-1-(2,2,2-trifluoroethyl)pyrazole Step 6, Example 1.63 with (2S)-2-(2-chlorophenyl)-3-hydroxypropanoic acid or (2R)-2-(2-chlorophenyl)-3-hydroxypropanoic acid, according to the procedure described in Step 7, Example 1.63, to give (2S)-2-(2-chlorophenyl)-3-hydroxy-1-{2-[4-methyl-1-(2,2,2-trifluoroethyl)pyrazol-3-ylsulfonyl]-4H,6H-pyrrolo[3,4-c]pyrazol-5-yl}propan-1-one (52.24%) as a white solid. $^1$H NMR (300 MHz, DMSO-$d_6$) δ 8.23 (s, 1H), 7.94 (s, 1H), 7.53-7.39 (m, 2H), 7.37-7.23 (m, 2H), 5.27 (q, J=9.0 Hz, 2H), 4.98 (s, 1H), 4.94-4.84 (m, 1H), 4.58-4.24 (m, 4H), 4.02-3.93 (m, 1H), 3.62-3.53 (m, 1H), 2.20 (s, 3H). LCMS (ES) [M+1]$^+$ m/z: 518. (2R)-2-(2-chlorophenyl)-3-hydroxy-1-{2-[4-methyl-1-(2,2,2-trifluoroethyl)pyrazol-3-ylsulfonyl]-4H,6H-pyrrolo[3,4-c]pyrazol-5-yl}propan-1-one was also isolated as a white solid (56.65%). $^1$H NMR (300 MHz, DMSO-$d_6$) δ 8.23 (s, 1H), 7.94 (s, 1H), 7.53-7.39 (m, 2H), 7.31 (ddt, J=6.3, 4.3, 2.1 Hz, 2H), 5.27 (q, J=9.0 Hz, 2H), 5.03-4.83 (m, 2H), 4.58-4.24 (m, 4H), 3.97 (q, J=7.8, 6.5 Hz, 1H), 3.57 (dq, J=10.1, 4.9 Hz, 1H), 2.20 (s, 3H). LCMS (ES) [M+1]$^+$ m/z: 518.

Example 1.66

Synthesis of (2S)-1-{2-[1-(2,2-difluoroethyl)pyrazol-3-ylsulfonyl]-4H,6H-pyrrolo[3,4-c]pyrazol-5-yl}-3-hydroxy-2-phenylpropan-1-one (compound 72)

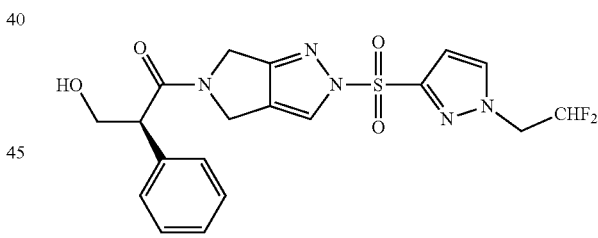

The title compound was synthesized from (S)-(2-fluorophenyl)(hydroxy)acetic acid (66 mg, 0.40 mmol, 1.00 eq.) and 1-(2,2-difluoroethyl)-3-{4H,5H,6H-pyrrolo[3,4-c]pyrazole-2-sulfonyl}pyrazole (Step 5, Example 1.16, 120 mg, 0.40 mmol, 1.00 eq.) following the procedure described on Step 5, Example 1.16. (2S)-1-{2-[1-(2,2-difluoroethyl)pyrazol-3-ylsulfonyl]-4H,6H-pyrrolo[3,4-c]pyrazol-5-yl}-3-hydroxy-2-phenylpropan-1-one was isolated as a white solid (87.3 mg, 48.87%). $^1$H NMR (400 MHz, DMSO-$d_6$) δ 8.21 (s, 1H), 8.06 (d, J=2.5 Hz, 1H), 7.42-7.18 (m, 5H), 6.97 (t, J=2.0 Hz, 1H), 6.39 (tt, J=54.6, 3.4 Hz, 1H), 5.02-4.65 (m, 4H), 4.54-4.28 (m, 3H), 4.03-3.96 (m, 2H), 3.58-3.50 (m, 1H). LCMS (ES) [M+1]$^+$ m/z: 452.

Example 1.67

Synthesis of (2S)-2-(2,3-difluorophenyl)-3-hydroxy-1-{2-[1-(2,2,2-trifluoroethyl)pyrazol-4-ylsulfonyl]-4H,6H-pyrrolo[3,4-c]pyrazol-5-yl}propan-1-one (Compound 73) and (2R)-2-(2,3-difluorophenyl)-3-hydroxy-1-{2-[1-(2,2,2-trifluoroethyl)pyrazol-4-ylsulfonyl]-4H,6H-pyrrolo[3,4-c]pyrazol-5-yl}propan-1-one (Compound 74)

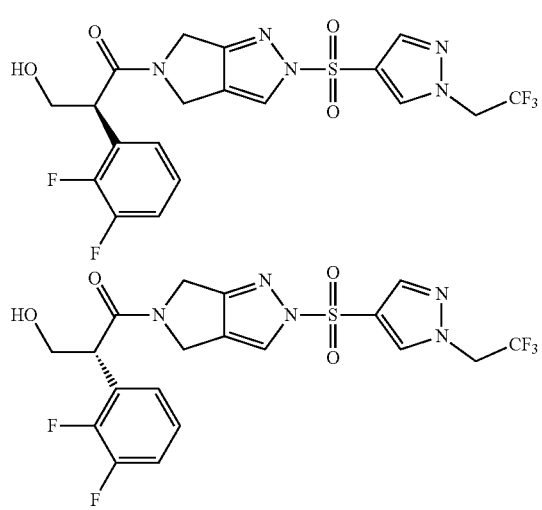

To a stirred mixture of 4-{4H,5H,6H-pyrrolo[3,4-c]pyrazole-2-sulfonyl}-1-(2,2,2-trifluoroethyl)pyrazole (200 mg, 0.623 mmol, 1.00 eq.) and (2S)-2-(2,3-difluorophenyl)-3-hydroxypropanoic acid (151.01 mg, 0.748 mmol, 1.2 eq.) in DMF was added T3P (297.11 mg, 0.934 mmol, 1.5 eq.) and DIEA (160.91 mg, 1.246 mmol, 2 eq.) drop wise at room temperature. The resulting mixture was extracted with $CH_2Cl_2$ (3×20 mL). The combined organic layers were dried over anhydrous $Na_2SO_4$. After filtration, the filtrate was concentrated under reduced pressure. The crude product was purified by Prep-HPLC using the following conditions (purified by Chiral-Prep-HPLC using the following conditions (Prep-HPLC-003): Column, SunFire Prep C18 OBD Col n, 19*150 mm, 5 μm 10 nm; mobile phase, Water (0.1% FA) and ACN (35% ACN up to 80% in 7 min) to afford (2S)-2-(2,3-difluorophenyl)-3-hydroxy-1-{2-[1-(2,2,2-trifluoroethyl)pyrazol-4-ylsulfonyl]-4H,6H-pyrrolo[3,4-c]pyrazol-5-yl}propan-1-one (58 mg, 18.43%) as a white solid. $^1$H NMR (400 MHz, DMSO-$d_6$) δ 8.81 (s, 1H), 8.22-8.16 (m, 2H), 7.33 (s, 1H), 7.24-7.16 (m, 2H), 5.25 (q, J=8.9 Hz, 2H), 4.91 (dd, J=27.3, 14.0 Hz, 2H), 4.55-4.23 (m, 4H), 3.99 (t, J=9.0 Hz, 1H), 3.63 (dd, J=10.5, 5.7 Hz, 1H). LCMS (ES) [M+1]$^+$ m/z: 506.

(2R)-2-(2,3-difluorophenyl)-3-hydroxy-1-{2-[1-(2,2,2-trifluoroethyl)pyrazol-4-ylsulfonyl]-4H,6H-pyrrolo[3,4-c]pyrazol-5-yl}propan-1-one was synthesize from (2R)-2-(2,3-difluorophenyl)-3-hydroxypropanoic acid using the same conditions described above and isolated as a white solid (94.2 mg, 29.94%). $^1$H NMR (400 MHz, DMSO-$d_6$) δ 8.81 (s, 1H), 8.23-8.16 (m, 2H), 7.33 (ddq, J=8.9, 6.6, 4.5, 3.6 Hz, 1H), 7.27-7.13 (m, 2H), 5.25 (q, J=8.9 Hz, 2H), 5.00-4.83 (m, 2H), 4.55-4.25 (m, 4H), 3.99 (dt, J=10.3, 6.6 Hz, 1H), 3.64 (dq, J=11.0, 5.6 Hz, 1H). LCMS (ES) [M+1]$^+$ m/z: 506.

Example 1.68

Synthesis of (3-(3-chloropyridin-2-yl)oxetan-3-yl)(2-((4-methyl-1-(2,2,2-trifluoroethyl)-1H-pyrazol-3-yl)sulfonyl)-2,6-dihydropyrrolo[3,4-c]pyrazol-5(4H)-yl)methanone (Compound 75)

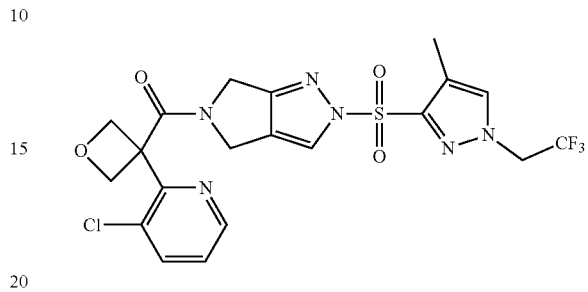

Into a 8-mL vail, was placed 2-((4-methyl-1-(2,2,2-trifluoroethyl)-1H-pyrazol-3-yl)sulfonyl)-2,4,5,6-tetrahydropyrrolo[3,4-c]pyrazole (285 mg, 0.85 mmol, 2.00 eq.), DMF (4.00 mL), sodium 3-(3-chloropyridin-2-yl)oxetane-3-carboxylate (Compound 8, Example 1.12, 100 mg, 0.43 mmol, 1.00 eq.), NMI (232 mg, 1.28 mmol, 3.00 eq.). This was followed by the addition of TCFH (238 mg, 0.85 mmol, 2.00 eq.) with stirring at 0° C. After addition, the resulting solution was stirred for 1 h at 0° C. The reaction solution was purified by Prep-HPLC using these conditions: Sunfire Prep C18 OBD Column, 50*250 mm, 5 m 10 nm, Mobile Phase A: water (0.1% FA), Mobile Phase B: $CH_3CN$, Flow rate: 90 mL/min, Gradient: from 25% B to 60% B in 12 min, Detector, UV 220 nm. The fraction of the target was freezing dried, this resulted in 80 mg of (3-(3-chloropyridin-2-yl)oxetan-3-yl)(2-((4-methyl-1-(2,2,2-trifluoroethyl)-1H-pyrazol-3-yl)sulfonyl)-2,6-dihydropyrrolo[3,4-c]pyrazol-5(4H)-yl)methanone as a white solid. $^1$H NMR (400 MHz, DMSO-$d_6$) δ 8.71-8.69 (m, 1H), 8.19 (d, J=28.4 Hz, 1H), 8.01-7.97 (m, 1H), 7.93 (t, J=1.2 Hz, 1H), 7.51-7.47 (m, 1H), 5.29-5.22 (m, 4H), 5.14 (d, J=6.0 Hz, 2H), 4.53 (d, J=10.8 Hz, 2H), 3.73 (d, J=13.6 Hz, 2H), 2.18 (d, J=3.2 Hz, 3H). LCMS (ES) [M+1]$^+$ m/z: 531.

Example 1.69

Synthesis of (2S)-1-{2-[1-(2,2-difluoroethyl)-4-methylpyrazol-3-ylsulfonyl]-4H,6H-pyrrolo[3,4-c]pyrazol-5-yl}-3-hydroxy-2-phenylpropan-1-one (Compound 76)

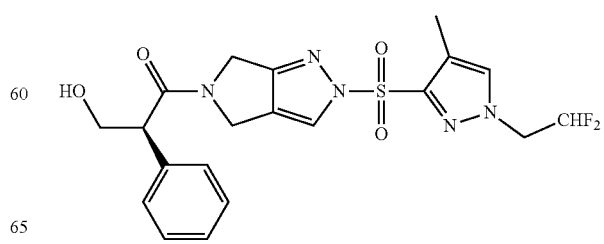

Step 1

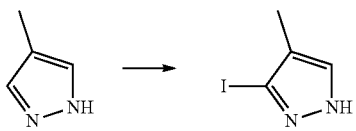

Into a 500 mL 3-necked round-bottom flask were added fomepizole (25.00 g, 304.49 mmol, 1.00 eq.) and DMF (370.00 mL). To the above mixture was added NIS (71.93 g, 319.71 mmol, 1.05 eq.) in portions at 0° C. The resulting mixture was stirred for additional 2 h at room temperature. The resulting mixture was diluted with water/ice (300 mL). The resulting mixture was extracted with EA (3×250 mL). The combined organic layers were washed with brine (3×300 mL), dried over anhydrous $Na_2SO_4$. After filtration, the filtrate was concentrated under reduced pressure. The residue was purified by silica gel column chromatography, eluted with EA/PE (11%) to afford 3-iodo-4-methyl-1H-pyrazole (18.00 g, 28.42%) as white solid. LCMS (ES) $[M+1]^+$ m/z: 209.

Step 2

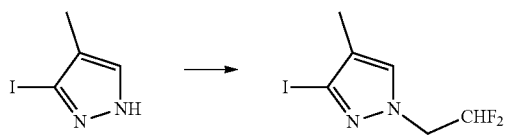

Into a 250 mL 3-necked round-bottom flask were added 3-iodo-4-methyl-1H-pyrazole (11.70 g, 56.25 mmol, 1.00 eq.) and DMF (120.00 mL). To the above mixture was added NaH (2.02 g, 84.37 mmol, 1.50 eq.) in portions at 0° C. The resulting mixture was stirred for 30 min at 0° C. under nitrogen atmosphere. To the above mixture was added 1,1-difluoro-2-iodoethane (16.20 g, 84.37 mmol, 1.50 eq.) drop wise at 0° C. The resulting solution was stirred for additional overnight at room temperature. The reaction was quenched with Water/Ice. The resulting mixture was extracted with EA (3×150 ml). The combined organic layers were washed with brine (3×200 ml), dried over anhydrous $Na_2SO_4$. After filtration, the filtrate was concentrated under reduced pressure. The residue was purified by silica gel column chromatography, eluted with EA/PE (4%). The crude product was purified by Prep-HPLC using the following conditions: Column, CHIRAL ART Cellulose-SB, 5*25 cm, 5 μm; Mobile Phase A: $CO_2$, Mobile Phase B: IPA; Flow rate: 160 mL/min; Gradient: isocratic 15% B; Column Temperature (° C.): 35; Back Pressure (bar): 100; Wave Length: 220 nm; $RT_1$ (min): 3.53; $RT_2$ (min): 4.38; Sample Solvent: IPA:ACN=1:1; Injection Volume: 2.5 mL. This resulted in 1-(2,2-difluoroethyl)-3-iodo-4-methylpyrazole (9.50 g, 62.08%) as colorless liquid. LCMS (ES) $[M+1]^+$ m/z: 273.

Step 3

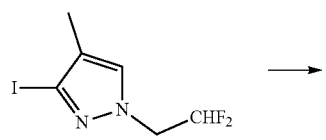

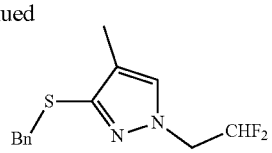

Into a 250 mL round-bottom flask were added 1-(2,2-difluoroethyl)-3-iodo-4-methylpyrazole (9.50 g, 34.922 mmol, 1.00 eq.), DIEA (13.54 g, 104.77 mmol, 3.00 eq.), XantPhos (4.04 g, 6.98 mmol, 0.20 eq.), $Pd_2(dba)_3$ (3.20 g, 3.49 mmol, 0.10 eq.), Toluene (100.00 mL) and benzyl mercaptan (8.67 g, 69.84 mmol, 2.00 eq.). The resulting mixture was stirred for overnight at 100° C. under nitrogen atmosphere. The mixture was allowed to cool down to room temperature. The resulting mixture was concentrated under reduced pressure. The residue was purified by silica gel column chromatography, eluted with EA/PE (2%) to afford 3-(benzylsulfanyl)-1-(2,2-difluoroethyl)-4-methylpyrazole (8.20 g, 87.51%) as yellow liquid. LCMS (ES) $[M+1]^+$ m/z: 269.

Step 4

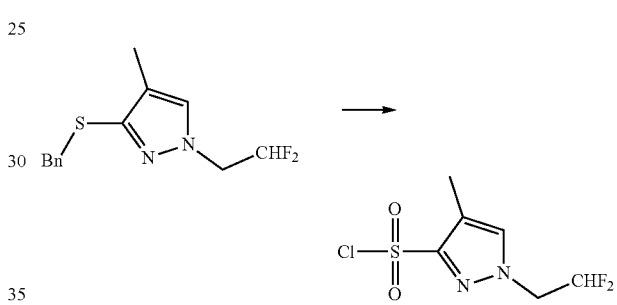

Into a 250 mL round-bottom flask were added 3-(benzylsulfanyl)-1-(2,2-difluoroethyl)-4-methylpyrazole (8.10 g, 30.19 mmol, 1.00 eq.), NCS (12.09 g, 90.56 mmol, 3.00 eq.), HOAc (90.00 mL) and $H_2O$ (10.00 mL). The resulting mixture was stirred for 1 h at room temperature. The resulting mixture was concentrated under reduced pressure. The residue was purified by silica gel column chromatography, eluted with EA/PE (13%) to afford 1-(2,2-difluoroethyl)-4-methylpyrazole-3-sulfonyl chloride (6.10 g, 82.60%) as light yellow liquid. LCMS (ES) $[M+1]^+$ m/z: 245.

Step 5

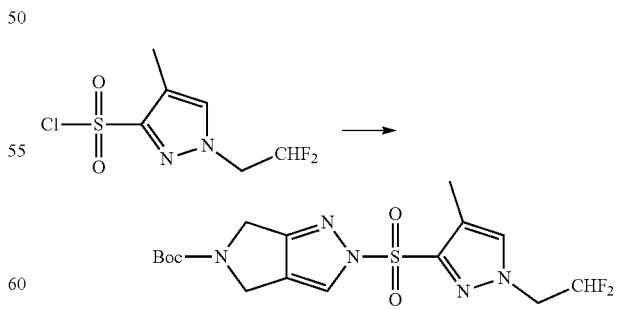

Into a 250 mL 3-necked round-bottom flask were added tert-butyl 2H,4H,6H-pyrrolo[3,4-c]pyrazole-5-carboxylate (4.67 g, 22.32 mmol, 1.00 eq.) and THF (70.00 mL). To a stirred solution was added NaH (0.80 g, 33.48 mmol, 1.50 eq.) in portions at 0° C. under nitrogen atmosphere. To the above mixture was added 1-(2,2-difluoroethyl)-4-methylpyrazole-3-sulfonyl chloride (6.01 g, 24.55 mmol, 1.10 eq.) in THF (20.00 mL) drop wise at 0° C. The resulting mixture was stirred for additional 2 h at room temperature. The reaction was quenched by the addition of HOAc (2 mL) at 0° C. The resulting mixture was diluted with sat. NH$_4$Cl (aq.) (50 mL). The aqueous layer was extracted with CH$_2$Cl$_2$ (3×100 mL) and the organic layers combined and dried over anhydrous Na$_2$SO$_3$ and concentrated. The residue was purified by silica gel column chromatography, eluted with THF/PE (25%). The crude product was purified by Prep-HPLC using the following conditions: Column, CHIRAL ART Amylose-C NEO, 3*25 cm, 5 μm; Mobile Phase A: CO$_2$, Mobile Phase B: MeOH-Preparative; Flow rate: 75 mL/min; Gradient: isocratic 15% B; Column Temperature: 35° C.; Back Pressure (bar): 100; Wave Length: 220 nm; RT$_1$ (min): 3.3; RT$_2$ (min): 4; Sample Solvent: MeOH-HPLC; Injection Volume: 2 mL. This resulted in tert-butyl 2-[1-(2,2-difluoroethyl)-4-methylpyrazol-3-ylsulfonyl]-4H,6H-pyrrolo[3,4-c]pyrazole-5-carboxylate (3.60 g, 38.64%) as off-white solid. LCMS (ES) [M+1]$^+$ m/z: 418.

Step 6

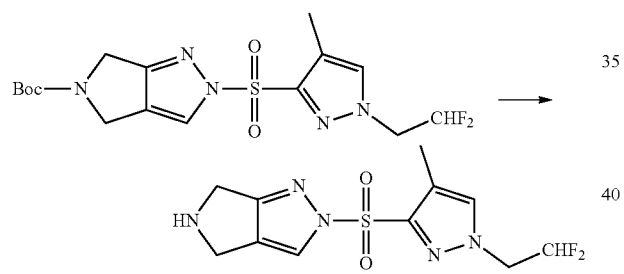

Into a 100 mL round-bottom flask were added tert-butyl 2-[1-(2,2-difluoroethyl)-4-methylpyrazol-3-ylsulfonyl]-4H,6H-pyrrolo[3,4-c]pyrazole-5-carboxylate (3.50 g, 8.39 mmol, 1.00 eq.), 2,6-lutidine (3.59 g, 33.54 mmol, 4.00 eq.) and DCM (30.00 mL). To the above mixture was added TMSOTf (5.59 g, 25.16 mmol, 3.00 eq.) drop wise at 0° C. The resulting mixture was stirred for additional 1 h at room temperature. The resulting mixture was concentrated under reduced pressure. The resulting mixture was filtered, the filter cake was washed with DCM (2×10 mL). The filter cake was concentrated under reduced pressure. This resulted in 1-(2,2-difluoroethyl)-4-methyl-3-{4H,5H,6H-pyrrolo[3,4-c]pyrazole-2-sulfonyl}pyrazole (2.20 g, 82.69%) as off-white solid. LCMS (ES) [M+1]$^+$ m/z: 318.

Step 7

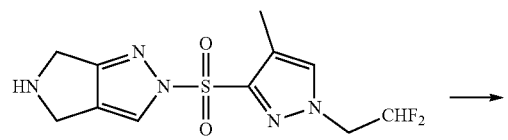

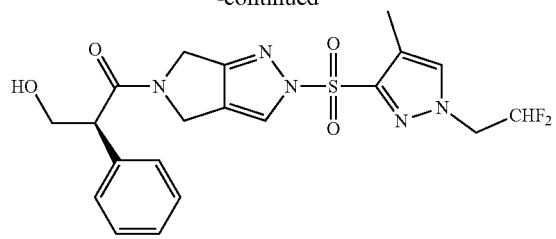

Into a 20 mL vial were added (S)-tropic acid (64.00 mg, 0.39 mmol, 1.00 eq.), 1-(2,2-difluoroethyl)-4-methyl-3-f{4H,5H,6H-pyrrolo[3,4-c]pyrazole-2-sulfonyl}pyrazole (134.43 mg, 0.42 mmol, 1.10 eq.), DMF (5.00 mL) and NMM (77.91 mg, 0.77 mmol, 2.00 eq.). To the above mixture was added HATU (175.73 mg, 0.46 mmol, 1.20 eq.) in portions at 0° C. The resulting mixture was stirred for additional 1 h at room temperature. The crude product was purified by Prep-HPLC using the following conditions: Column, Sunfire Prep C18 OBD Column, 50*250 mm 5 m 10 nm; mobile phase, Water (0.05% NH$_3$.H$_2$O) and ACN (15% Phase B up to 50% in 12 min); Detector, 254. This resulted in (2S)-1-{2-[1-(2,2-difluoroethyl)-4-methylpyrazol-3-ylsulfonyl]-4H,6H-pyrrolo[3,4-c]pyrazol-5-yl}-3-hydroxy-2-phenylpropan-1-one (134.80 mg, 75.19%) as white solid. $^1$H NMR (400 MHz, DMSO-d$_6$) δ 8.20 (d, J=1.9 Hz, 1H), 7.86 (s, 1H), 7.45-7.20 (m, 5H), 6.37 (tt, J=54.3, 3.5 Hz, 1H), 4.97-4.60 (m, 4H), 4.55-4.27 (m, 3H), 4.06-3.93 (m, 2H), 3.61-3.47 (m, 1H), 2.19 (s, 3H). LCMS (ES) [M+1]$^+$ m/z: 466.

Example 1.70

Synthesis of (2R)-1-{2-[1-(2,2-difluoroethyl)-4-methylpyrazol-3-ylsulfonyl]-4H,6H-pyrrolo[3,4-c]pyrazol-5-yl}-3-hydroxy-2-phenylpropan-1-one (Compound 77)

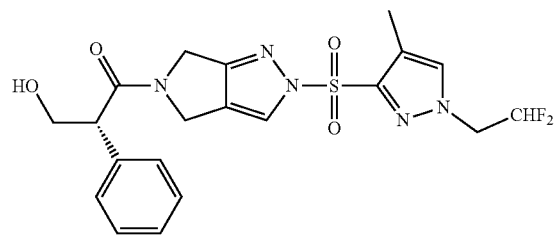 [SMILES: Cc1cn(CC(F)F)nc1S(=O)(=O)n1cc2c(n1)CN(C(=O)[C@@H](CO)c1ccccc1)C2]

The title compound was synthesized according to the procedure described in Step 7, for the synthesis of Compound 76 using (R)-tropic acid (64.00 mg, 0.39 mmol, 1.00 eq.) and 1-(2,2-difluoroethyl)-4-methyl-3-{4H,5H,6H-pyrrolo[3,4-c]pyrazole-2-sulfonyl}pyrazole (134.43 mg, 0.42 mmol, 1.10 eq.) to give (2R)-1-{2-[1-(2,2-difluoroethyl)-4-methylpyrazol-3-ylsulfonyl]-4H,6H-pyrrolo[3,4-c]pyrazol-5-yl}-3-hydroxy-2-phenylpropan-1-one (162.60 mg, 90.70%) as a white solid. $^1$H NMR (300 MHz, DMSO-d$_6$) δ 8.20 (d, J=1.8 Hz, 1H), 7.86 (s, 1H), 7.43-7.18 (m, 5H), 6.37 (tt, J=54.3, 3.5 Hz, 1H), 4.97-4.62 (m, 4H), 4.55-4.27 (m, 3H), 4.07-3.91 (m, 2H), 3.64-3.44 (m, 1H), 2.19 (s, 3H). LCMS (ES) [M+1]$^+$ m/z: 466.

Example 1.71

Synthesis of (2S)-1-{2-[1-(2,2-difluoroethyl)-4-methylpyrazol-3-ylsulfonyl]-4H,6H-pyrrolo[3,4-c]pyrazol-5-yl}-2-(2-fluorophenyl)-3-hydroxypropan-1-one (Compound 78)

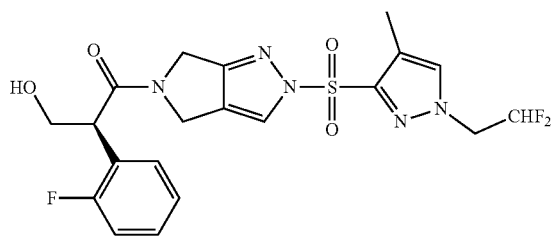 [SMILES: Cc1cn(CC(F)F)nc1S(=O)(=O)n1cc2c(n1)CN(C(=O)[C@H](CO)c1ccccc1F)C2]

The title compound was synthesized according to the procedure described in Step 7, for the synthesis of Compound 76 using (2S)-2-(2-fluorophenyl)-3-hydroxypropanoic acid (72.00 mg, 0.39 mmol, 1.00 eq.) and 1-(2,2-difluoroethyl)-4-methyl-3-{4H,5H,6H-pyrrolo[3,4-c]pyrazole-2-sulfonyl}pyrazole (136.46 mg, 0.43 mmol, 1.10 eq.) to give (2S)-1-{2-[1-(2,2-difluoroethyl)-4-methylpyrazol-3-ylsulfonyl]-4H,6H-pyrrolo[3,4-c]pyrazol-5-yl}-2-(2-fluorophenyl)-3-hydroxypropan-1-one (134.30 mg, 71.05%) as white solid. $^1$H NMR (300 MHz, DMSO-$d_6$) δ 8.21 (d, J=1.4 Hz, 1H), 7.87 (s, 1H), 7.40 (ddd, J=9.4, 6.7, 1.8 Hz, 1H), 7.31 (ddd, J=7.7, 5.2, 2.1 Hz, 1H), 7.25-7.11 (m, 2H), 6.37 (tt, J=54.3, 3.5 Hz, 1H), 5.02-4.83 (m, 2H), 4.71 (td, J=15.4, 3.5 Hz, 2H), 4.57-4.21 (m, 4H), 4.07-3.91 (m, 1H), 3.60 (dq, J=10.5, 5.3 Hz, 1H), 2.19 (s, 3H). LCMS (ES) [M+1]$^+$ m/z: 484.

Example 1.72

Synthesis of (2R)-1-{2-[1-(2,2-difluoroethyl)-4-methylpyrazol-3-ylsulfonyl]-4H,6H-pyrrolo[3,4-c]pyrazol-5-yl}-2-(2-fluorophenyl)-3-hydroxypropan-1-one (Compound 79)

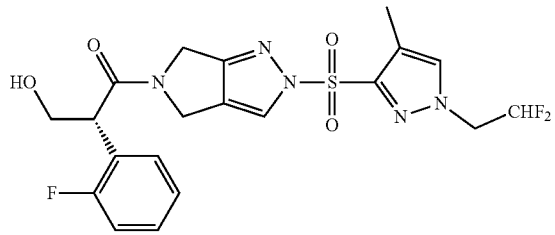 [SMILES: Cc1cn(CC(F)F)nc1S(=O)(=O)n1cc2c(n1)CN(C(=O)[C@@H](CO)c1ccccc1F)C2]

The title compound was synthesized according to the procedure described in Step 7, for the synthesis of Compound 76 using (2R)-2-(2-fluorophenyl)-3-hydroxypropanoic acid (72.00 mg, 0.39 mmol, 1.00 eq.) and 1-(2,2-difluoroethyl)-4-methyl-3-{4H,5H,6H-pyrrolo[3,4-c]pyrazole-2-sulfonyl}pyrazole (136.46 mg, 0.43 mmol, 1.10 eq.) to give (2R)-1-{2-[1-(2,2-difluoroethyl)-4-methylpyrazol-3-ylsulfonyl]-4H,6H-pyrrolo[3,4-c]pyrazol-5-yl}-2-(2-fluorophenyl)-3-hydroxypropan-1-one (134.90 mg, 71.37%) as white solid. $^1$H NMR (300 MHz, DMSO-$d_6$) δ 8.21 (s, 1H), 7.87 (s, 1H), 7.40 (t, J=7.5 Hz, 1H), 7.30 (dd, J=7.9, 5.7 Hz, 1H), 7.26-7.14 (m, 2H), 6.62-6.15 (m, 1H), 4.98-4.81 (m, 2H), 4.71 (td, J=15.4, 3.5 Hz, 2H), 4.56-4.38 (m, 2H), 4.36-4.21 (m, 2H), 4.08-3.93 (m, 1H), 3.68-3.54 (m, 1H), 2.19 (s, 3H). LCMS (ES) [M+1]$^+$ m/z: 484.

Example 1.73

Synthesis of (2S)-2-(2-chlorophenyl)-1-(2-{[1-(2,2-difluoroethyl)-4-methyl-1H-pyrazol-3-yl]sulfonyl}-2H,4H,5H,6H-pyrrolo[3,4-c]pyrazol-5-yl)-3-hydroxypropan-1-one (Compound 80)

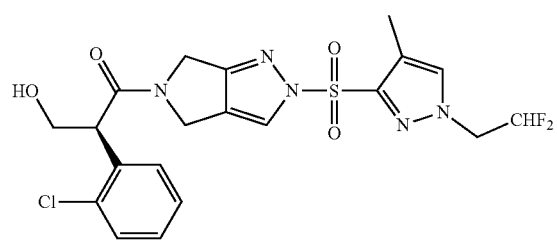

The title compound was synthesized according to the procedure described in Step 7, for the synthesis of Compound 76 using (2S)-2-(2-chlorophenyl)-3-hydroxypropanoic acid (90.00 mg, 0.45 mmol, 1.00 eq.) and 1-(2,2-difluoroethyl)-4-methyl-3-{4H,5H,6H-pyrrolo[3,4-c]pyrazole-2-sulfonyl}pyrazole (157 mg, 0.50 mmol, 1.10 eq.) to give (2S)-2-(2-chlorophenyl)-1-(2-{[1-(2,2-difluoroethyl)-4-methyl-1H-pyrazol-3-yl]sulfonyl}-2H,4H,5H,6H-pyrrolo[3,4-c]pyrazol-5-yl)-3-hydroxypropan-1-one (161 mg, 71.79%) as off-white solid. $^1$H NMR (300 MHz, DMSO-$d_6$) δ 8.22 (s, 1H), 7.87 (s, 1H), 7.53-7.39 (m, 2H), 7.30 (dtd, J=7.5, 6.0, 5.1, 3.7 Hz, 2H), 6.37 (tt, J=54.4, 3.5 Hz, 1H), 4.98 (t, J=4.6 Hz, 1H), 4.99-4.83 (m, 1H), 4.71 (td, J=15.4, 3.5 Hz, 2H), 4.58-4.39 (m, 2H), 4.39 (s, 1H), 4.31 (dd, J=13.9, 9.8 Hz, 1H), 4.02-3.92 (m, 1H), 3.57 (dq, J=10.0, 5.0 Hz, 1H), 2.19 (s, 3H). LCMS (ES) [M+1]$^+$ m/z: 500.

Example 1.74

Synthesis of (2R)-2-(2-chlorophenyl)-1-{2-[1-(2,2-difluoroethyl)-4-methylpyrazol-3-ylsulfonyl]-4H,6H-pyrrolo[3,4-c]pyrazol-5-yl}-3-hydroxypropan-1-one (Compound 81)

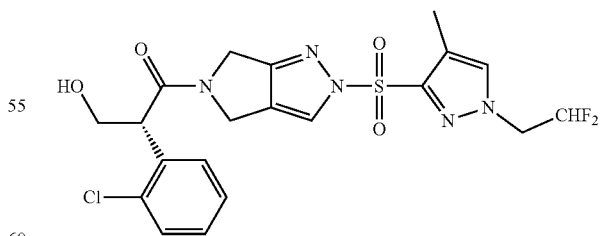

The title compound was synthesized according to the procedure described in Step 7, for the synthesis of Compound 76 using (2R)-2-(2-chlorophenyl)-3-hydroxypropanoic acid (90.00 mg, 0.45 mmol, 1.00 eq.) and 1-(2,2-difluoroethyl)-4-methyl-3-{4H,5H,6H-pyrrolo[3,4-c]pyrazole-2-sulfonyl}pyrazole (142.35 mg, 0.45 mmol, 1.00 eq.) to give (2R)-2-(2-chlorophenyl)-1-{2-[1-(2,2-difluoroethyl)-4-methylpyrazol-3-ylsulfonyl]-4H,6H-pyrrolo[3,4-c]pyrazol-5-yl}-3-hydroxypropan-1-one (122.6 mg, 54.67%) as off-white solid. ¹H NMR (300 MHz, DMSO-d₆) δ 8.21 (d, J=1.1 Hz, 1H), 7.87 (s, 1H), 7.46 (dddd, J=10.3, 9.1, 4.6, 2.8 Hz, 2H), 7.31 (ddt, J=6.2, 4.1, 2.1 Hz, 2H), 6.37 (tt, J=54.3, 3.5 Hz, 1H), 5.03-4.83 (m, 2H), 4.71 (td, J=15.4, 3.5 Hz, 2H), 4.58-4.24 (m, 4H), 4.02-3.91 (m, 1H), 3.57 (dq, J=9.8, 4.9 Hz, 1H), 2.19 (s, 3H). LCMS (ES) [M+1]⁺ m/z: 500.

Example 1.75

Synthesis of 3-chloro-2-(3-{2-[1-(2,2-difluoroethyl)-4-methylpyrazol-3-ylsulfonyl]-4H,6H-pyrrolo[3,4-c]pyrazole-5-carbonyl}oxetan-3-yl)pyridine (Compound 82)

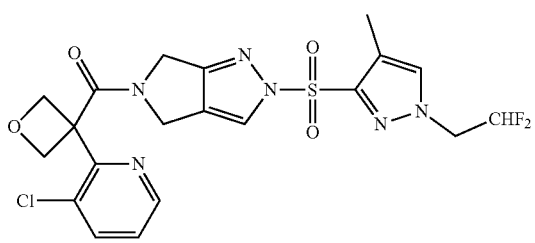 [SMILES: Cc1cn(CC(F)F)nc1S(=O)(=O)n1cc2c(n1)CN(C(=O)C1(c3ncccc3Cl)COC1)C2]

The title compound was synthesized according to the procedure described in Step 7, for the synthesis of Compound 76 using 1-(2,2-difluoroethyl)-4-methyl-3-{4H,5H,6H-pyrrolo[3,4-c]pyrazole-2-sulfonyl}pyrazole (130.00 mg, 0.41 mmol, 1.00 eq.) and sodium 3-(3-chloropyridin-2-yl)oxetane-3-carboxylate (96.52 mg, 0.41 mmol, 1.00 eq.) to give 3-chloro-2-(3-{2-[1-(2,2-difluoroethyl)-4-methylpyrazol-3-ylsulfonyl]-4H,6H-pyrrolo[3,4-c]pyrazole-5-carbonyl}oxetan-3-yl)pyridine (94.6 mg, 45.02%) as off-white solid. ¹H NMR (300 MHz, DMSO-d₆) δ 8.70 (dt, J=4.8, 1.5 Hz, 1H), 8.14 (d, J=21.2 Hz, 1H), 7.99 (ddd, J=8.1, 4.9, 1.5 Hz, 1H), 7.85 (s, 1H), 7.49 (dt, J=8.0, 4.7 Hz, 1H), 6.37 (tt, J=54.3, 3.5 Hz, 1H), 5.23 (dd, J=6.0, 2.8 Hz, 2H), 5.13 (d, J=6.1 Hz, 2H), 4.70 (td, J=15.4, 3.5 Hz, 2H), 4.51 (d, J=8.3 Hz, 2H), 3.71 (d, J=10.0 Hz, 2H), 2.17 (d, J=2.0 Hz, 3H). LCMS (ES) [M+1]⁺ m/z: 513.

Example 1.76

Synthesis of (2S)-3-hydroxy-2-phenyl-1-{2-[1-(2,2,2-trifluoroethyl)pyrazol-4-ylsulfonyl]-4H,6H-pyrrolo[3,4-c]pyrazol-5-yl}propan-1-one (Compound 83)

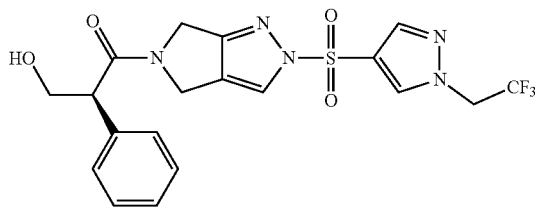 [SMILES: O=C([C@H](CO)c1ccccc1)N1Cc2cn(S(=O)(=O)c3cnn(CC(F)(F)F)c3)nc2C1]

Into a 50-mL round-bottom flask, was placed (S)-tropic acid (70 mg, 0.42 mmol, 1.00 eq.), DMF (5.00 mL), 4-{4H,5H,6H-pyrrolo[3,4-c]pyrazole-2-sulfonyl}-1-(2,2,2-trifluoroethyl)pyrazole (Intermediate I-10, 135 mg, 0.42 mmol, 1 eq.), NMM (85 mg, 0.84 mmol, 2 eq.). This was followed by the addition of HATU (192 mg, 0.51 mmol, 1.2 eq.) at 0° C. The resulting solution was stirred for 1 hr at 25° C. The crude product was purified by Prep-HPLC using the following conditions (Prep-HPLC-001): Column, Sunfire Prep C18 OBD Column, 50*250 mm, 5 m 10 nm; mobile phase, Water and ACN (15% PhaseB up to 50% in 15 min); Detector, uv. 254 nm. This resulted in (2S)-3-hydroxy-2-phenyl-1-{2-[1-(2,2,2-trifluoroethyl)pyrazol-4-ylsulfonyl]-4H,6H-pyrrolo[3,4-c]pyrazol-5-yl}propan-1-one (117 mg, 59.17%) as a white solid. ¹H NMR (300 MHz, DMSO-d₆) δ 8.78 (d, J=2.9 Hz, 1H), 8.17 (d, J=6.2 Hz, 2H), 7.39-7.27 (m, 4H), 7.24 (dt, J=8.6, 4.3 Hz, 1H), 5.23 (q, J=9.0 Hz, 2H), 5.01-4.71 (m, 2H), 4.53-4.27 (m, 3H), 4.02-3.88 (m, 2H), 3.57-3.50 (m, 1H). LCMS (ES) [M+1]⁺ m/z: 470.

Example 1.77

Synthesis of (2R)-3-hydroxy-2-phenyl-1-{2-[1-(2,2,2-trifluoroethyl)pyrazol-4-ylsulfonyl]-4H,6H-pyrrolo[3,4-c]pyrazol-5-yl}propan-1-one (Compound 84)

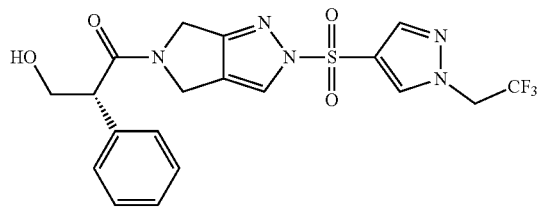 [SMILES: O=C([C@@H](CO)c1ccccc1)N1Cc2cn(S(=O)(=O)c3cnn(CC(F)(F)F)c3)nc2C1]

Into a 50-mL round-bottom flask, was placed (R)-tropic acid (60 mg, 0.36 mmol, 1.00 eq.), DMF (5.00 mL), 4-{4H,5H,6H-pyrrolo[3,4-c]pyrazole-2-sulfonyl}-1-(2,2,2-trifluoroethyl)pyrazole (Intermediate I-10, 116 mg, 0.36 mmol, 1 eq.), NMM (73 mg, 0.72 mmol, 2 eq.). This was followed by the addition of HATU (165 mg, 0.43 mmol, 1.2 eq.) at 0° C. The resulting solution was stirred for 1 hr at 25° C. The crude product was purified by Prep-HPLC using the following conditions (Prep-HPLC-001): Column, Sunfire Prep C18 OBD Column, 50*250 mm, 5 m 10 nm; mobile phase, Water and ACN (15% PhaseB up to 50% in 15 min); Detector, uv. 254 nm. This resulted in (2R)-3-hydroxy-2-phenyl-1-{2-[1-(2,2,2-trifluoroethyl)pyrazol-4-ylsulfonyl]-4H,6H-pyrrolo[3,4-c]pyrazol-5-yl}propan-1-one (106.4 mg, 62.77%) as a white solid. ¹H NMR (300 MHz, DMSO-d₆) δ 8.78 (d, J=2.9 Hz, 1H), 8.17 (d, J=6.2 Hz, 2H), 7.45-7.28 (m, 4H), 7.27-7.20 (m, 1H), 5.23 (qd, J=8.9, 2.2 Hz, 2H), 4.96-4.71 (m, 2H), 4.53-4.27 (m, 3H), 4.05-3.93 (m, 2H), 3.58-3.46 (m, 1H). LCMS (ES) [M+1]⁺ m/z: 470.

Example 1.78

Synthesis of (2R)-2-(2-fluorophenyl)-2-(2-hydroxyethoxy)-1-[2-[1-(2,2,2-trifluoroethyl)pyrazol-3-ylsulfonyl]-4H,6H-pyrrolo[3,4-c]pyrazol-5-yl]ethanone and (2S)-2-(2-fluorophenyl)-2-(2-hydroxyethoxy)-1-[2-[1-(2,2,2-trifluoroethyl)pyrazol-3-ylsulfonyl]-4H,6H-pyrrolo[3,4-c]pyrazol-5-yl]ethenone (Compounds 85 and 86)

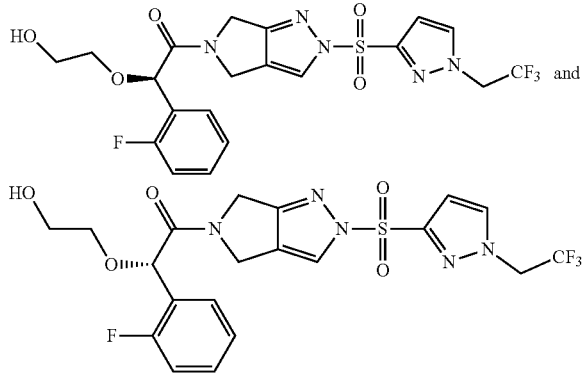

Step 1

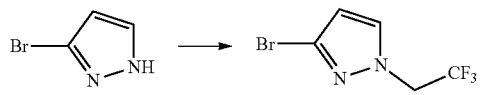 [SMILES: Brc1cc[nH]n1 ; FC(F)(F)Cn1ccc(Br)n1]

To a stirred solution of 3-bromo-1H-pyrazole (8.0 g, 54.43 mmol, 1.00 eq.) and K₂CO₃ (15.0 g, 108.86 mmol, 2.00 eq.) in DMF (160.00 mL) was added 2,2,2-trifluoroethyl trifluoromethanesulfonate (15.2 g, 65.32 mmol, 1.20 eq.) drop wise at 0° C. under nitrogen atmosphere. The resulting mixture was stirred for 6 h at room temperature under nitrogen atmosphere. The reaction was quenched with water (200 mL) at room temperature, extracted with EtOAc (3×200 mL). The combined organic layer was washed with water (200 mL), dried over anhydrous Na₂SO₄. After filtration, the filtrate was concentrated under reduced pressure. The residue was purified by silica gel column chromatography, eluted with PE/THF (10:1) to afford 3-bromo-1-(2,2,2-trifluoroethyl)pyrazole (8.1 g, 65%) as a yellow oil. LCMS (ES) [M+1]⁺ m/z: 229.

Step 2

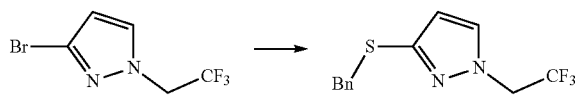 [SMILES: FC(F)(F)Cn1ccc(Br)n1 ; FC(F)(F)Cn1ccc(SCc2ccccc2)n1]

To a solution of 3-bromo-1-(2,2,2-trifluoroethyl)pyrazole (4.00 g, 17.47 mmol, 1.00 eq.) and DIEA (6.77 g, 52.40 mmol, 3.00 eq.) in toluene (80.00 mL) were added Xantphos (2.02 g, 3.49 mmol, 0.20 eq.), Pd₂(dba)₃ (1.60 g, 1.75 mmol, 0.10 eq.) and benzyl mercaptan (4.34 g, 34.93 mmol, 2.00 eq.). The mixture was stirred for 2 days at 110° C. under a nitrogen atmosphere. The resulting mixture was cooled to room temperature, concentrated under reduced pressure. The residue was purified by silica gel column chromatography, eluted with PE/EtOAc (4:1) to afford 3-(benzylsulfanyl)-1-(2,2,2-trifluoroethyl)pyrazole (2.8 g, 59%) as a yellow oil. LCMS (ES) [M+1]⁺ m/z: 273.

Step 3

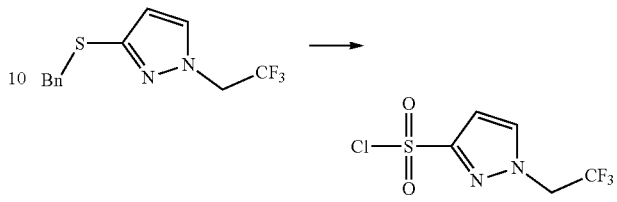

To a stirred solution of 3-(benzylsulfanyl)-1-(2,2,2-trifluoroethyl)pyrazole (5.00 g, 18.36 mmol, 1.00 eq.) in HOAc (45.00 mL) and H₂O (5.00 mL) was added NCS (7.36 g, 55.12 mmol, 3.00 eq.) in portions at 0° C. under air atmosphere. The resulting mixture was stirred for 1 h at room temperature under air atmosphere. The resulting mixture was concentrated under reduced pressure. The residue was purified by silica gel column chromatography, eluted with PE/EtOAc (4:1) to afford 1-(2,2,2-trifluoroethyl)pyrazole-3-sulfonyl chloride (4.1 g, 90%) as a yellow oil. LCMS (ES) [M+1]⁺ m/z: 249.

Step 4

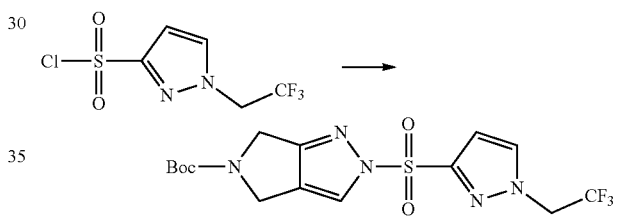

To a solution of tert-butyl 2H,4H,6H-pyrrolo[3,4-c]pyrazole-5-carboxylate (3.70 g, 17.70 mmol, 1.10 eq.) in THF (80.00 mL) was added sodium hydride (60% in mineral oil, 0.77 g, 32.18 mmol, 2.00 eq.) at 0° C. The mixture was stirred for 30 min. 1-(2,2,2-trifluoroethyl)pyrazole-3-sulfonyl chloride (4.00 g, 16.09 mmol, 1.00 eq.) in THF (20.00 mL) was added and the mixture was warmed to room temperature and stirred for 2 h. The reaction mixture was quenched by water (100 mL), extracted with EtOAc (3×100 mL). The combined organic layer was washed with water (100 mL), dried over anhydrous Na₂SO₄. After filtration, the filtrate was concentrated under reduced pressure. The residue was re-crystallized in mixed solvent PE/EA (10:1) to afford tert-butyl 2-[1-(2,2,2-trifluoroethyl)pyrazol-3-ylsulfonyl]-4H,6H-pyrrolo[3,4-c]pyrazole-5-carboxylate (5 g, 73.7%) as a white solid. LCMS (ES) [M+1]⁺ m/z: 422.

Step 5

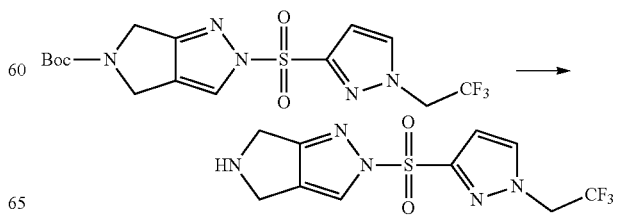

To a stirred solution of tert-butyl 2-[1-(2,2,2-trifluoroethyl)pyrazol-3-ylsulfonyl]-4H,6H-pyrrolo[3,4-c]pyrazole-5-carboxylate (4.50 g, 10.68 mmol, 1.00 eq.) and lutidine (4.58 g, 42.72 mmol, 4.00 eq.) in DCM (45 mL) was added TMSOTf (7.12 g, 32.04 mmol, 3.00 eq.) drop wise at 0° C. under nitrogen atmosphere. The resulting mixture was stirred for 1 h at 0° C. under nitrogen atmosphere. The reaction was quenched with water at room temperature. The precipitated solid was collected by filtration and dried under infrared light to afford 3-[4H,5H,6H-pyrrolo[3,4-c]pyrazole-2-sulfonyl]-1-(2,2,2-trifluoroethyl)pyrazole (2.2 g, 64%) as a white solid. LCMS (ES) [M+1]⁺ m/z: 322.

Step 6

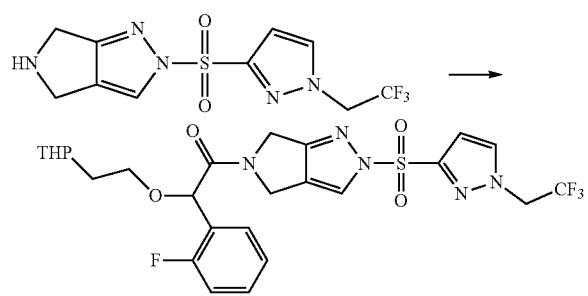

To a stirred solution of 3-[4H,5H,6H-pyrrolo[3,4-c]pyrazole-2-sulfonyl]-1-(2,2,2-trifluoroethyl)pyrazole (400 mg, 1.25 mmol, 1.00 eq.) and (2-fluorophenyl)[2-(oxan-2-yloxy)ethoxy]acetic acid (446 mg, 1.50 mmol, 1.20 eq.) in MeCN (8.00 mL) were added NMI (307 mg, 3.735 mmol, 3.00 eq.) and TCFH (699 mg, 2.50 mmol, 2.00 eq.) in portions at 0° C. under nitrogen atmosphere. The resulting mixture was stirred for 2 h at room temperature under nitrogen atmosphere. The reaction was quenched with water and extracted with EtOAc (3×20 mL). The combined organic layer was washed with water (1×20 mL), dried over anhydrous Na₂SO₄. After filtration, the filtrate was concentrated under reduced pressure. The residue was purified by silica gel column chromatography, eluted with PE/EtOAc (4:1) to afford 2-2-(2-fluorophenyl)-2-[2-(oxan-2-yl)ethoxy]-1-[2-[1-(2,2,2-trifluoroethyl)pyrazol-3-ylsulfonyl]-4H,6H-pyrrolo[3,4-c]pyrazol-5-yl]ethanone (520 mg, 71%) as a yellow solid. LCMS (ES) [M+1]⁺ m/z: 586.

Step 7

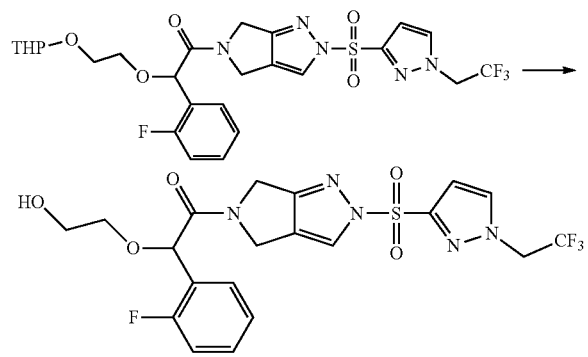

A solution of 2-2-(2-fluorophenyl)-2-[2-(oxan-2-yl)ethoxy]-1-[2-[1-(2,2,2-trifluoroethyl)pyrazol-3-ylsulfonyl]-4H,6H-pyrrolo[3,4-c]pyrazol-5-yl]ethanone (500 mg, 0.85 mmol, 1.00 eq.) and conc. HCl (0.10 mL) in MeOH (5.00 mL) was stirred for 2 h at room temperature under air atmosphere. The crude product was purified by Flash-Prep-HPLC using these conditions: C18 OBD Column, 50*250 mm, 5 μm, 10 nm, mobile phase, CH₃CN/H₂O (FA: 0.1%), from 5% to 52% in 12 min, Flow rate, 80 mL/min, Detector, UV 254 nm. The fraction of the target was freezing dried to afford 2-2-(2-fluorophenyl)-2-(2-hydroxyethoxy)-1-[2-[1-(2,2,2-trifluoroethyl)pyrazol-3-ylsulfonyl]-4H,6H-pyrrolo[3,4-c]pyrazol-5-yl]ethanone (310 mg, 70%) as a white solid.

Step 8

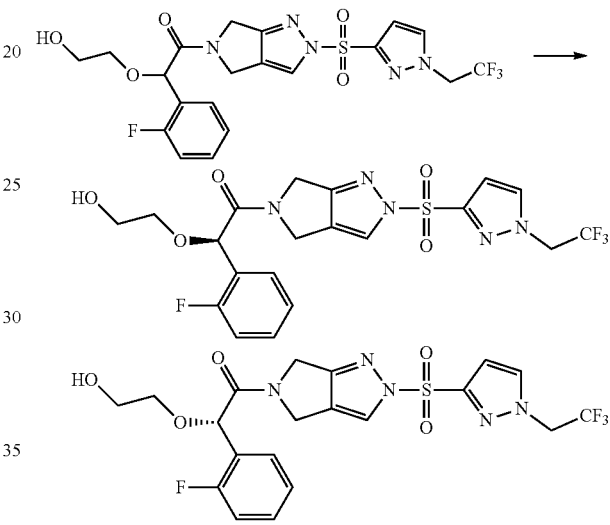

The racemic 2-2-(2-fluorophenyl)-2-(2-hydroxyethoxy)-1-[2-[1-(2,2,2-trifluoroethyl)pyrazol-3-ylsulfonyl]-4H,6H-pyrrolo[3,4-c]pyrazol-5-yl]ethanone (310 mg) was separated by SFC using the following conditions: CHIRALPAK IG, 3*25 cm, 5 μm, Mobile Phase A: CO₂ (1), Mobile Phase B: MeOH-Preparative, Flow rate: 80 mL/min, Gradient: isocratic 25% B. This resulted in two compounds. Stereoisomer 13: (91.2 mg, 20.6%, (Retention time 6.5 min) as a white solid. ¹H NMR (300 MHz, DMSO-d6) δ8.26 (d, J=2.5 Hz, 1H), 8.16 (s, 1H), 7.52-7.34 (m, 2H), 7.32-7.16 (m, 2H), 7.04 (d, J=2.3 Hz, 1H), 5.50 (d, J=9.9 Hz, 1H), 5.43-5.24 (m, 2H), 4.94 (dd, J=20.5, 14.5 Hz, 1H), 4.79-4.66 (m, 1H), 4.68-4.40 (m, 3H), 3.63-3.52 (m, 4H). LCMS (ES) [M+1]⁺ m/z: 518.

Stereoisomer 14: 98.3 mg, 22.3%, (Retention time 8.4 min) as a white solid. H NMR (300 MHz, DMSO-d6) δ 8.26 (d, J=2.5 Hz, 1H), 8.16 (s, 1H), 7.52-7.34 (m, 2H), 7.32-7.16 (m, 2H), 7.04 (d, J=2.3 Hz, 1H), 5.50 (d, J=9.9 Hz, 1H), 5.43-5.24 (m, 2H), 4.94 (dd, J=20.5, 14.5 Hz, 1H), 4.79-4.66 (m, 1H), 4.68-4.40 (m, 3H), 3.63-3.52 (m, 4H). LCMS (ES) [M+1]⁺ m/z: 518.

Example 1.79

Synthesis of (2S)-1-[2-[1-(2,2-difluoroethyl)-3,5-dimethylpyrazol-4-ylsulfonyl]-4H,6H-pyrrolo[3,4-c]pyrazol-5-yl]-3-hydroxy-2-phenylpropan-1-one (Compound 87)

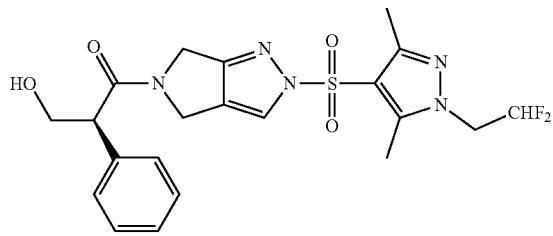 [SMILES: Cc1nn(CC(F)F)c(C)c1S(=O)(=O)n1cc2c(n1)CN(C(=O)[C@H](CO)c1ccccc1)C2]

Step 1

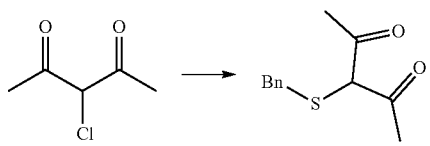

Into a 500-mL round-bottom flask, was placed 3-chloropentane-2,4-dione (15.00 g, 111.47 mmol, 1.00 eq.), benzyl mercaptan (13.85 g, 111.47 mmol, 1.00 eq.), NaHCO₃ (18.73 g, 222.95 mmol, 2.00 eq.), (CH₂OMe)₂ (200.00 mL). The resulting solution was stirred for 3 h at 90° C. in an oil bath. The resulting mixture was concentrated. The residue was purified on a silica gel column. This resulted in 13.80 g (55.7%) of 3-(benzylsulfanyl)pentane-2,4-dione as yellow solid. LCMS (ES) [M+1]⁺ m/z: 223.

Step 2

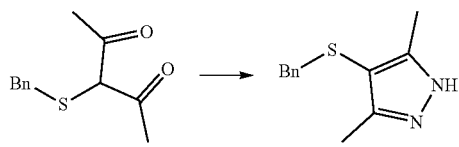

Into a 250-mL round-bottom flask, was placed 3-(benzylsulfanyl)pentane-2,4-dione (14.70 g, 66.13 mmol, 1.00 eq.), hydrazine hydrate (98%) (6.62 g, 132.24 mmol, 2.00 eq.), PTSA (1.14 g, 6.61 mmol, 0.10 eq.), EtOH (150.00 mL). The resulting solution was stirred for overnight at 80° C. in an oil bath. The resulting mixture was concentrated. The residue was applied onto a silica gel column with THF/PE (45%). This resulted in 13.30 g (92.13%) of 4-(benzylsulfanyl)-3,5-dimethyl-1H-pyrazole as light yellow solid. LCMS (ES) [M+1]⁺ m/z: 219.

Step 3

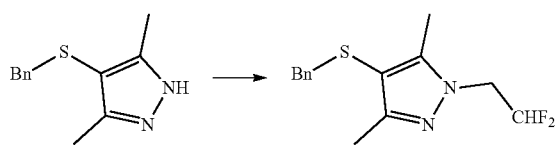 [SMILES: Cc1n[nH]c(C)c1SCc1ccccc1 ; Cc1nn(CC(F)F)c(C)c1SCc1ccccc1]

Into a 100-mL 3-necked round-bottom flask, was placed 4-(benzylsulfanyl)-3,5-dimethyl-1H-pyrazole (6.00 g, 27.48 mmol, 1.00 eq.), DMF (80.00 mL). This was followed by the addition of NaH (0.99 g, 41.22 mmol, 1.50 eq.), in portions at 0° C. The resulting solution was stirred for 0.5 h at room temperature. To this was added 1,1-difluoro-2-iodoethane (7.91 g, 41.21 mmol, 1.50 eq.) drop wise with stirring at 0° C. The resulting solution was stirred for 2 h at room temperature. The reaction was then quenched by the addition of water/ice. The resulting solution was extracted with EtOAc (3×100 mL) and the organic layers combined. The resulting solution was washed with brine (3×50 mL) and the organic layers combined and dried over anhydrous Na₂SO₃ and concentrated. The residue was applied onto a silica gel column with THF/PE (10%). This resulted in 6.00 g (77.32%) of 4-(benzylsulfanyl)-1-(2,2-difluoroethyl)-3,5-dimethylpyrazole as yellow liquid. LCMS (ES) [M+1]⁺ m/z: 283.

Step 4

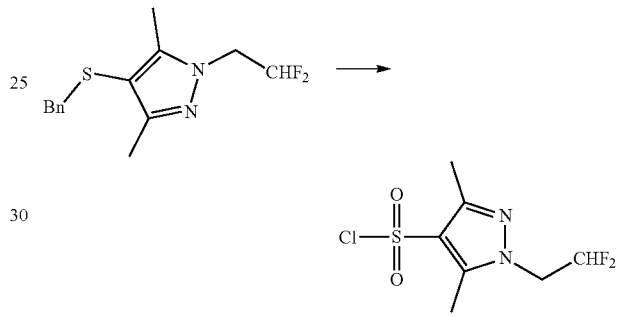

Into a 100-mL round-bottom flask, was placed 4-(benzylsulfanyl)-1-(2,2-difluoroethyl)-3,5-dimethylpyrazole (5.50 g, 19.48 mmol, 1.00 eq.), HOAc (63.00 mL), H₂O (7.00 mL). This was followed by the addition of NCS (7.80 g, 58.44 mmol, 3.00 eq.), in portions at 0° C. The resulting solution was stirred for 1 h at room temperature. The resulting mixture was concentrated. The residue was applied onto a silica gel column with THF/PE (5%). This resulted in 5.00 g (99.23%) of 1-(2,2-difluoroethyl)-3,5-dimethylpyrazole-4-sulfonyl chloride as yellow liquid. LCMS (ES) [M−Cl+OH−1]⁺ m/z: 239.

Step 5

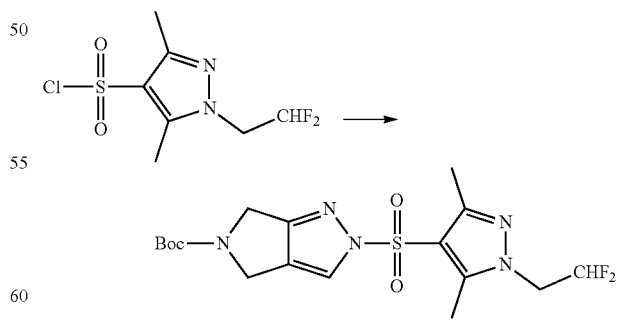

Into a 100-mL 3-necked round-bottom flask purged and maintained with an inert atmosphere of nitrogen, was placed tert-butyl 2H,4H,6H-pyrrolo[3,4-c]pyrazole-5-carboxylate (2.57 g, 12.28 mmol, 1.00 eq.), THF (60.00 mL). This was followed by the addition of NaH (0.44 g, 18.42 mmol, 1.50 eq.), in portions at 0° C. The resulting solution was stirred for 0.5 h at 0° C. To this was added a solution of 1-(2,2-difluoroethyl)-3,5-dimethylpyrazole-4-sulfonyl chloride (3.50 g, 13.53 mmol, 1.10 eq.) in THF (10.00 mL) drop wise with stirring at 0° C. The resulting solution was stirred for 2 h at 0° C. The reaction was then quenched by the addition of 4.00 mL of CH₃COOH. The resulting solution was diluted with 300 mL of sat. NH₄Cl (aq.). The resulting solution was extracted with DCM (3×200 mL) and the organic layers combined and dried over anhydrous Na₂SO₃ and concentrated. The crude product was purified by Flash-Prep-HPLC using the following conditions: Column, C18 silica gel; mobile phase, CH₃CN/H₂O (NH₃.H₂O 0.1%) =40% increasing to CH₃CN/H₂O (NH₃.H₂O 0.1%)=70% within 20 min; Detector, 220 nm. The crude product was purified by Prep-SFC using the following conditions (XA-Prep SFC150-1): Column: CHIRAL ART Amylose-C NEO, 3*25 cm, 5 μm; Mobile Phase A: CO₂, Mobile Phase B: MeOH-Preparative; Flow rate: 80 mL/min; Gradient: isocratic 15% B; Column Temperature (25° C.): 35; Back Pressure (bar): 100; Wave Length: 220 nm; RT₁ (min): 2.62; RT₂ (min): 3.20; Sample Solvent: MeOH-Preparative; Injection Volume: 2 mL. This resulted in 2.50 g (47.18%) of tert-butyl 2-[1-(2,2-difluoroethyl)-3,5-dimethylpyrazol-4-ylsulfonyl]-4H,6H-pyrrolo[3,4-c]pyrazole-5-carboxylate as white solid. LCMS (ES) [M+1]⁺ m/z: 432.

Step 6

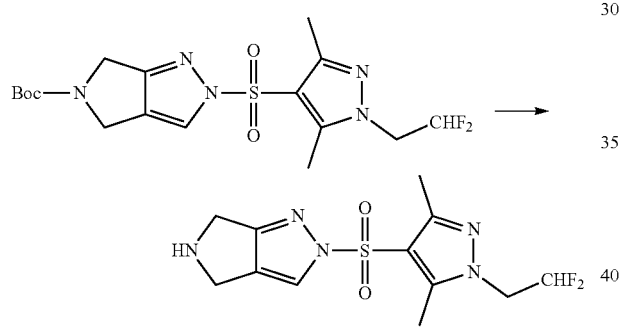

Into a 100-mL round-bottom flask, was placed tert-butyl 2-[1-(2,2-difluoroethyl)-3,5-dimethylpyrazol-4-ylsulfonyl]-4H,6H-pyrrolo[3,4-c]pyrazole-5-carboxylate (2.50 g, 5.80 mmol, 1.00 eq.), lutidine (2.48 g, 23.18 mmol, 4.00 eq.), DCM (30.00 mL). This was followed by the addition of trimethylsilyl triflate (3.86 g, 17.38 mmol, 3.00 eq.) drop wise with stirring at 0° C. The resulting solution was stirred for 2 h at 0° C. The reaction was then quenched by the addition of MeOH. The resulting mixture was concentrated. The residue was applied onto a silica gel column with THF/PE (83%). This resulted in 1.80 g (93.76%) of 1-(2,2-difluoroethyl)-3,5-dimethyl-4-[4H,5H,6H-pyrrolo[3,4-c]pyrazole-2-sulfonyl]pyrazole as yellow solid. LCMS (ES) [M+1]⁺ m/z: 332.

Step 7

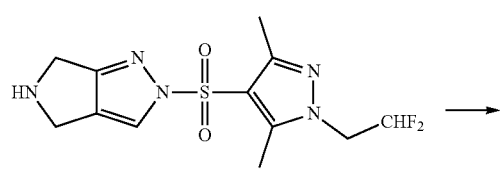

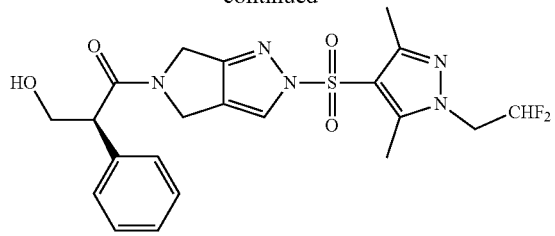

Into a 8-mL vial, was placed 1-(2,2-difluoroethyl)-3,5-dimethyl-4-[4H,5H,6H-pyrrolo[3,4-c]pyrazole-2-sulfonyl]pyrazole (280.24 mg, 0.85 mmol, 1.50 eq.), (S)-tropic acid (93.70 mg, 0.56 mmol, 1.00 eq.), DMF (2.00 mL), NMM (114.07 mg, 1.13 mmol, 2.00 eq.). This was followed by the addition of HATU (257.28 mg, 0.68 mmol, 1.20 eq.), in portions at 0° C. The resulting solution was stirred for 1 h at room temperature. The crude product (0.28 g) was purified by Prep-HPLC using the following conditions (Prep-HPLC-001): Column, Sunfire Prep C18 OBD Column, 50*250 mm, 5 μm 10 nm; mobile phase, Water (0.1% FA) and ACN (15% Phase B up to 50% in 12 min); Detector, uv. This resulted in 120.90 mg (41.90%) of (2S)-1-[2-[1-(2,2-difluoroethyl)-3,5-dimethylpyrazol-4-ylsulfonyl]-4H,6H-pyrrolo[3,4-c]pyrazol-5-yl]-3-hydroxy-2-phenylpropan-1-one as white solid. ¹H NMR (400 MHz, DMSO-d6) δ 8.22 (s, 1H), 7.37-7.23 (m, 5H), 6.37 (tt, J=54.4, 3.6 Hz, 1H), 4.94-4.77 (m, 2H), 4.61 (td, J=15.0, 3.5 Hz, 2H), 4.49-4.29 (m, 3H), 4.16-3.79 (m, 2H), 3.72-3.32 (m, 1H), 2.50 (s, 3H), 2.30 (s, 3H). LCMS (ES) [M+1]⁺ m/z: 480.

Example 1.80

Synthesis of (2R)-1-[2-[1-(2,2-difluoroethyl)-3,5-dimethylpyrazol-4-ylsulfonyl]-4H,6H-pyrrolo[3,4-c]pyrazol-5-yl]-3-hydroxy-2-phenylpropan-1-one (Compound 88)

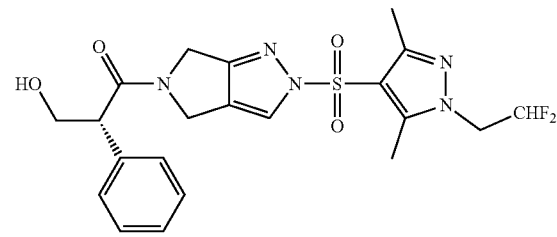 [SMILES: Cc1nn(CC(F)F)c(C)c1S(=O)(=O)n1cc2c(n1)CN(C(=O)[C@@H](CO)c1ccccc1)C2]

Into a 8-mL vial, was placed (R)-tropic acid (93.70 mg, 0.56 mmol, 1.00 eq.), 1-(2,2-difluoroethyl)-3,5-dimethyl-4-[4H,5H,6H-pyrrolo[3,4-c]pyrazole-2-sulfonyl]pyrazole (Step 6, synthesis of Compound 88), 280.24 mg, 0.85 mmol, 1.50 eq.), NMM (114.07 mg, 1.13 mmol, 2.00 eq.), DMF (2.00 mL). This was followed by the addition of HATU (257.28 mg, 0.68 mmol, 1.20 eq.), in portions at 0° C. The resulting solution was stirred for 1 h at room temperature. The crude product (0.28 g) was purified by Prep-HPLC using the following conditions: Column, Sunfire Prep C18 OBD Column, 50*250 mm, 5 μm 10 nm; mobile phase, Water (0.1% FA) and CH₃CN (15% Phase B up to 50% in 12 min); Detector, 220. This resulted in 135.30 mg (50.04%) of (2R)-1-{2-[1-(2,2-difluoroethyl)-3,5-dimethylpyrazol-4-ylsulfonyl]-4H,6H-pyrrolo[3,4-c]pyrazol-5-yl}-3-hydroxy- 2-phenylpropan-1-one as white solid. ¹H NMR (400 MHz, DMSO-d6) δ 8.22 (s, 1H), 7.37-7.23 (m, 5H), 6.59-6.17 (m, 1H), 4.94-4.77 (m, 2H), 4.61 (td, J=15.0, 3.5 Hz, 2H), 4.49-4.29 (m, 3H), 4.16-3.79 (m, 2H), 3.72-3.32 (m, 1H), 2.50 (s, 3H), 2.30 (s, 3H). LCMS (ES) [M+1]⁺ m/z: 480.

Example 1.81

Synthesis of (R)-1-(2-((1-(2,2-difluoroethyl)-5-methyl-1H-pyrazol-4-yl)sulfonyl)-2,6-dihydropyrrolo[3,4-c]pyrazol-5(4H)-yl)-3-hydroxy-2-phenyl-propan-1-one (Compound 89)

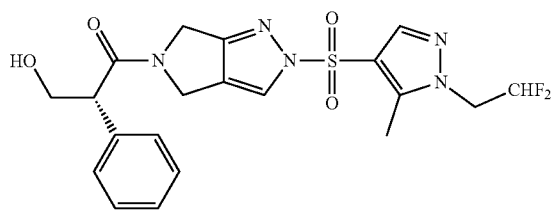 [SMILES: Cc1c(S(=O)(=O)n2cc3c(n2)CN(C(=O)[C@@H](CO)c2ccccc2)C3)cnn1CC(F)F]

Into a 20 mL vial were added 1-(2,2-difluoroethyl)-5-methyl-4-{4H,5H,6H-pyrrolo[3,4-c]pyrazole-2-sulfonyl}pyrazole (Step 5, Example 1.18, 120 mg, 0.38 mmol, 1.00 eq.) and DMF (3 mL), NMM (115 mg, 1.13 mmol, 3.00 eq.), (R)-tropic acid (63 mg, 0.38 mmol, 1.00 eq.). The reaction mixture was cooled to 0° C., HATU (173 mg, 0.45 mmol, 1.20 eq.) was added in one portion. The resulting mixture was stirred for additional 1 h at the same temperature. The reaction solution was purified by Prep-HPLC using the following conditions: Sunfire Prep C18 OBD Column, 50*250 mm, 5 μm, 10 nm, mobile phase, Water (0.1% FA) and CH₃CN (15% CH₃CN up to 50% in 12 min), Detector, UV 254 nm. The fraction of the target was freezing dried to afford (2R)-1-{2-[1-(2,2-difluoroethyl)-5-methylpyrazol-4-ylsulfonyl]-4H,6H-pyrrolo[3,4-c]pyrazol-5-yl}-3-hydroxy-2-phenylpropan-1-one (93.3 mg, 53%) as a white solid. ¹H NMR (300 MHz, DMSO-d6) δ 8.20 (s, 1H), 8.04 (s, 1H), 7.41-7.25 (m, 5H), 6.38 (tt, J=54.3, 3.4 Hz, 1H), 4.87 (dd, J=18.8, 14.1 Hz, 1H), 4.68 (td, J=15.1, 3.3 Hz, 2H), 4.55-4.36 (m, 2H), 4.36-4.26 (m, 1H), 3.99 (d, J=5.4 Hz, 2H), 3.59-3.46 (m, 1H). LCMS (ES) [M+1]⁺ m/z: 466.

Example 1.82

Synthesis of (2S)-2-(2-chlorophenyl)-1-{2-[1-(2-fluoroethyl)pyrazol-4-ylsulfonyl]-4H,6H-pyrrolo[3,4-c]pyrazol-5-yl}-3-hydroxypropan-1-one (Compound 90)

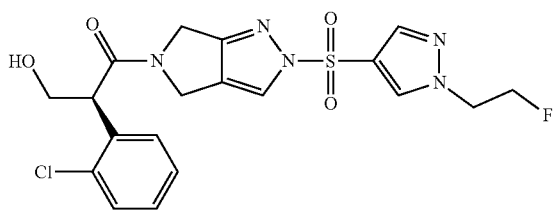 [SMILES: O=C([C@H](CO)c1ccccc1Cl)N1Cc2cn(S(=O)(=O)c3cnn(CCF)c3)nc2C1]

Into a 20 mL vial were added (2S)-2-(2-chlorophenyl)-3-hydroxypropanoic acid (90.00 mg, 0.45 mmol, 1.00 eq.), 1-(2-fluoroethyl)-4-{4H,5H,6H-pyrrolo[3,4-c]pyrazole-2-sulfonyl}pyrazole (Step 6, Example 1.9, 127.99 mg, 0.45 mmol, 1.00 eq.), DMF (5.00 mL) and NMM (136.13 mg, 1.35 mmol, 3.00 eq.) at room temperature. To a stirred solution was added HATU (204.69 mg, 0.54 mmol, 1.20 eq.) in portions at 0° C. The resulting mixture was stirred for 1 h at room temperature. The crude product was purified by Prep-HPLC using the following conditions: Column, XBridge Shield RP18 OBD Column, 19*150 mm, 5 μm; mobile phase, Water (10 mmol/L NH₄HCO₃+0.1% NH₃.H₂O) and ACN (27% ACN up to 60% in 11 min); Detector, 254. This resulted in (2S)-2-(2-chlorophenyl)-1-{2-[1-(2-fluoroethyl)pyrazol-4-ylsulfonyl]-4H,6H-pyrrolo[3,4-c]pyrazol-5-yl}-3-hydroxypropan-1-one (123.2 mg, 58.69%) as white solid. ¹HNMR (300 MHz, DMSO-d₆) δ 8.72 (s, 1H), 8.18 (s, 1H), 8.08 (d, J=1.8 Hz, 1H), 7.53-7.38 (m, 2H), 7.38-7.23 (m, 2H), 4.97 (s, 1H), 4.93-4.84 (m, 2H), 4.71 (t, J=4.7 Hz, 1H), 4.55 (t, J=4.7 Hz, 1H), 4.47 (q, J=4.8 Hz, 2H), 4.43-4.35 (m, 2H), 4.33-4.25 (m, 1H), 3.97 (t, J=9.3 Hz, 1H), 3.59-3.56 (m, 1H). LCMS (ES) [M+1]⁺ m/z: 468.

Example 1.83

Synthesis of (2R)-2-(2-chlorophenyl)-1-{2-[1-(2-fluoroethyl)pyrazol-4-ylsulfonyl]-4H,6H-pyrrolo[3,4-c]pyrazol-5-yl}-3-hydroxypropan-1-one (Compound 91)

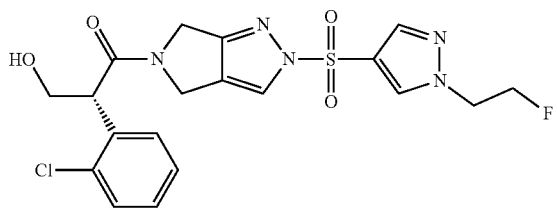 [SMILES: O=C([C@@H](CO)c1ccccc1Cl)N1Cc2cn(S(=O)(=O)c3cnn(CCF)c3)nc2C1]

Into a 20 mL vial were added (2R)-2-(2-chlorophenyl)-3-hydroxypropanoic acid (90.00 mg, 0.45 mmol, 1.00 eq.), 1-(2-fluoroethyl)-4-{4H,5H,6H-pyrrolo[3,4-c]pyrazole-2-sulfonyl}pyrazole (Step 6, Example 1.9, 127.99 mg, 0.45 mmol, 1 eq.), DMF (5.00 mL) and NMM (136.13 mg, 1.35 mmol, 3.00 eq.) at room temperature. To a stirred solution was added HATU (204.69 mg, 0.54 mmol, 1.20 eq.) in portions at 0° C. The resulting mixture was stirred for 1 h at room temperature. The crude product was purified by Prep-HPLC using the following conditions: Column, XBridge Shield RP18 OBD Column, 19*150 mm, 5 μm; mobile phase, Water (10 mmol/L NH₄HCO₃+0.1% NH₃.H₂O) and ACN (27% ACN up to 60% in 11 min); Detector, 254. This resulted in (2R)-2-(2-chlorophenyl)-1-{2-[1-(2-fluoroethyl)pyrazol-4-ylsulfonyl]-4H,6H-pyrrolo[3,4-c]pyrazol-5-yl}-3-hydroxypropan-1-one (142.7 mg, 67.98%) as white solid. ¹HNMR (300 MHz, DMSO-d₆) δ 8.72 (s, 1H), 8.21-8.12 (m, 1H), 8.08 (dd, J=1.8, 0.7 Hz, 1H), 7.53-7.39 (m, 2H), 7.38-7.23 (m, 2H), 5.00-4.82 (m, 3H), 4.71 (dd, J=5.2, 4.1 Hz, 1H), 4.66-4.24 (m, 6H), 3.98-3.96 (m, 1H), 3.59-3.56 (m, 1H). LCMS (ES) [M+1]⁺ m/z: 468.1.

Example 1.84

Synthesis of (S)-1-(2-((1-(2,2-difluoroethyl)-1H-pyrazol-4-yl)sulfonyl)-2,6-dihydropyrrolo[3,4-c]pyrazol-5(4H)-yl)-3-hydroxy-2-(2-(2-methoxyethoxy)phenyl)propan-1-one and (R)-1-(2-((1-(2,2-difluoroethyl)-1H-pyrazol-4-yl)sulfonyl)-2,6-dihydropyrrolo[3,4-c]pyrazol-5(4H)-yl)-3-hydroxy-2-(2-(2-methoxyethoxy)phenyl)propan-1-one (compounds 92 and 93)

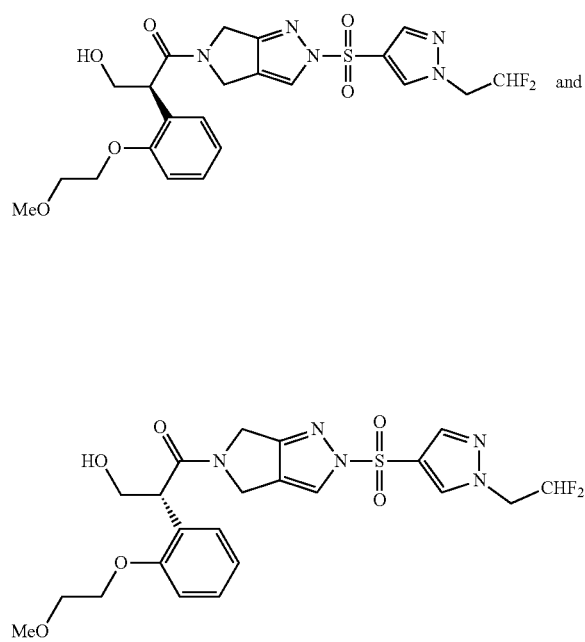

and

Step 1

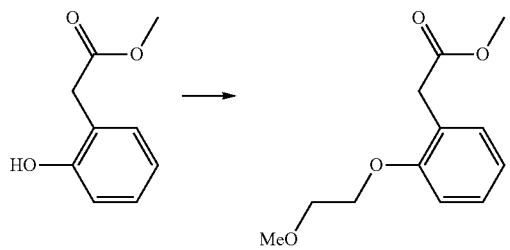 [SMILES: COC(=O)Cc1ccccc1O ; COCCOc1ccccc1CC(=O)OC]

Into a 250 mL round-bottom flask were added methyl 2-(2-hydroxyphenyl)acetate (5.0 g, 30.09 mmol, 1.00 equiv), acetone (50 mL), Cs$_2$CO$_3$ (12.7 g, 38.98 mmol, 1.30 equiv), 2-bromoethyl methyl ether (4.60 g, 33.10 mmol, 1.10 eq.) and NaI (0.45 g, 3.01 mmol, 0.10 eq.) at room temperature. The resulting mixture was stirred for 12 h at 50° C. The resulting mixture was concentrated under reduced pressure. The residue was purified by silica gel column chromatography, eluted with PE/THF (4:1) to afford methyl 2-(2-(2-methoxyethoxy)phenyl)acetate (1.55 g, 23%) as a yellow oil. GCMS m/z: 224.

Step 2

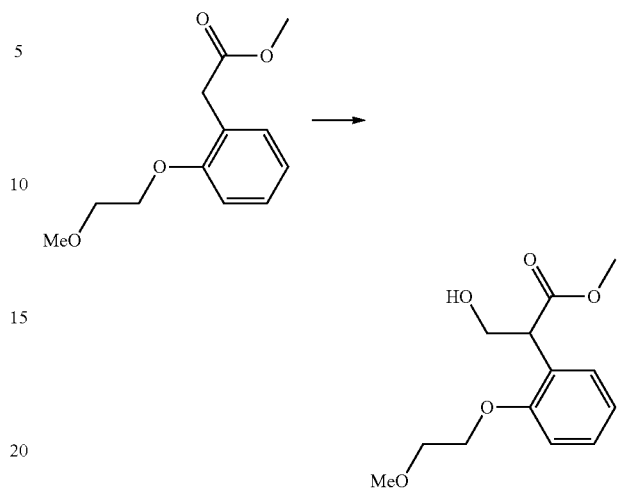

Into a 100 mL 3-necked round-bottom flask were added methyl 2-[2-(2-methoxyethoxy)phenyl]acetate (1.55 g, 6.91 mmol, 1.00 eq.) and DMF (30 mL) at room temperature. To the above mixture was added CH$_3$ONa (40 mg, 0.74 mmol, 0.11 eq.), (HCHO)$_n$ (0.21 g, 6.91 mmol, 1.0 eq.) at 0° C. The resulting mixture was stirred for 1 h at 0° C. The reaction was quenched with water (30 mL), extracted with EtOAc (2×60 mL). The combined organic phase was washed with brine (3×30 mL), dried over anhydrous Na$_2$SO$_3$. Filtered and the filtrate was concentrated under reduced pressure. The residue was purified by silica gel column chromatography, eluted with THF/PE (30%) to afford methyl 3-hydroxy-2-(2-(2-methoxyethoxy)phenyl)propanoate (681 mg, 39%) as a yellow oil. LCMS (ES) [M+1]$^+$ m/z: 255.

Step 3

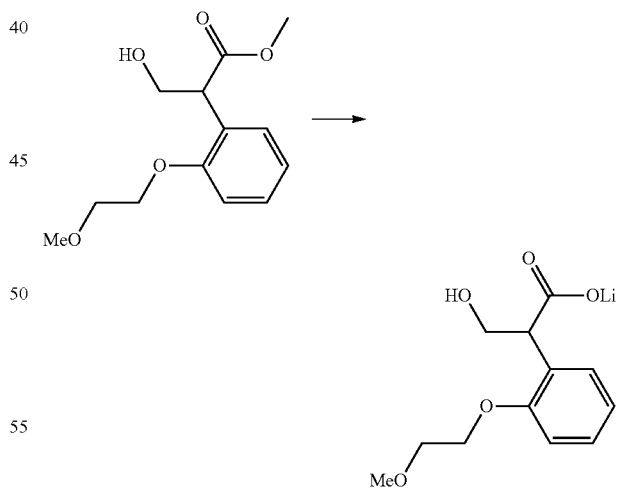

Into a 20 mL vial were added methyl 3-hydroxy-2-[2-(2-methoxyethoxy)phenyl]propanoate (681 mg, 2.68 mmol, 1.00 eq.), THF (5 mL), H$_2$O (5 mL) and LiOH (128 mg, 5.35 mmol, 2.00 eq.) at room temperature. The resulting mixture was stirred for 2 h at room temperature. The reaction solution was purified by reverse flash chromatography using the following conditions: C18-120 g, mobile phase, MeCN in water, 5% to 50% gradient in 10 min, flow rate, 70 mL/min, detector, UV 254 nm. The fraction of the target was freezing dried, this resulted in lithium 3-hydroxy-2-(2-(2-methoxyethoxy)phenyl)propanoate (440 mg, 67%) as a white solid. LCMS (ES) [M-Li+H+1]⁺ m/z: 241.

Step 4

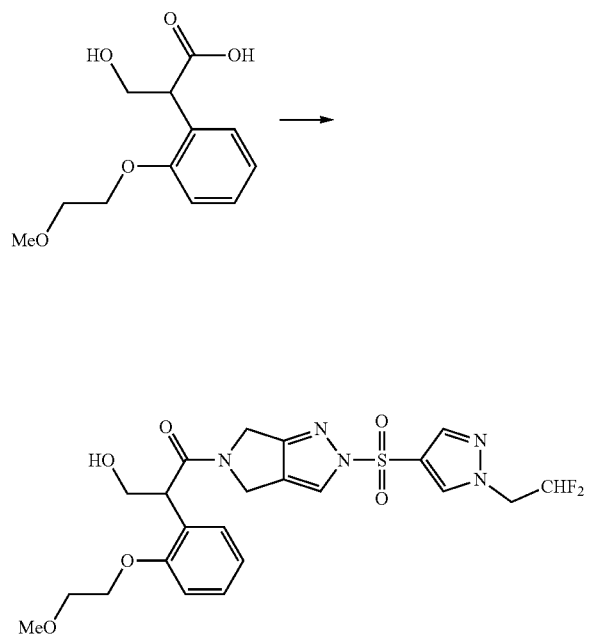

Into a 20 mL vial were added lithio 3-hydroxy-2-[2-(2 methoxyethoxy)phenyl]propanoate (202 mg, 0.82 mmol, 1.00 eq.), 1-(2,2-difluoroethyl)-4-{4H,5H,6H-pyrrolo[3,4-c]pyrazole-2-sulfonyl}pyrazole (324 mg, 1.07 mmol, 1.30 eq.), DMF (4 mL), DIEA (318 mg, 2.46 mmol, 3.00 eq.) and T₃P (50% in EA) (630 mg, 0.99 mmol, 1.20 eq.) at room temperature. The resulting mixture was stirred for 2 h at room temperature. The reaction solution was purified by Prep-HPLC using the following conditions: Sunfire Prep C18 OBD Column, 50*250 mm, 5 μm, 10 nm, mobile phase, water (0.1% FA) and CH₃CN (15% up to 50% in 15 min), Detector, UV 254 nm. This resulted in 1-(2-((1-(2,2-difluoroethyl)-1H-pyrazol-4-yl)sulfonyl)-2,6-dihydropyrrolo[3,4-c]pyrazol-5(4H)-yl)-3-hydroxy-2-(2-(2-methoxyethoxy)phenyl)propan-1-one (270 mg, 63%) as a white solid. LCMS (ES) [M+1]⁺ m/z: 526.

Step 5

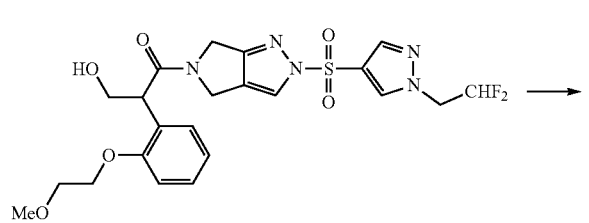

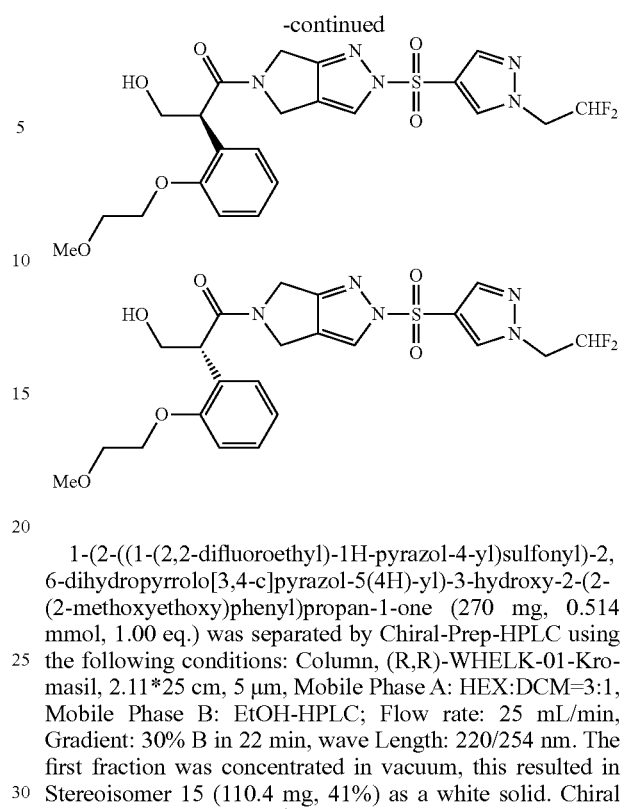

1-(2-((1-(2,2-difluoroethyl)-1H-pyrazol-4-yl)sulfonyl)-2,6-dihydropyrrolo[3,4-c]pyrazol-5(4H)-yl)-3-hydroxy-2-(2-(2-methoxyethoxy)phenyl)propan-1-one (270 mg, 0.514 mmol, 1.00 eq.) was separated by Chiral-Prep-HPLC using the following conditions: Column, (R,R)-WHELK-01-Kromasil, 2.11*25 cm, 5 μm, Mobile Phase A: HEX:DCM=3:1, Mobile Phase B: EtOH-HPLC; Flow rate: 25 mL/min, Gradient: 30% B in 22 min, wave Length: 220/254 nm. The first fraction was concentrated in vacuum, this resulted in Stereoisomer 15 (110.4 mg, 41%) as a white solid. Chiral HPLC, Rt: 1.628 Min. ¹HNMR (300 MHz, DMSO-d₆) δ 8.72 (s, 1H), 8.20 (d, J=8.7 Hz, 1H), 8.12 (d, J=2.0 Hz, 1H), 7.21 (ddd, J=8.9, 6.9, 1.5 Hz, 2H), 7.02-6.93 (m, 1H), 6.90 (dd, J=8.0, 6.9 Hz, 1H), 6.42 (tt, J=54.5, 3.5 Hz, 1H), 4.91-4.54 (m, 4H), 4.54-4.29 (m, 3H), 4.11 (q, J=4.8 Hz, 2H), 4.00 (td, J=9.6, 4.9 Hz, 1H), 3.75-3.51 (m, 3H), 3.17 (d, J=20.1 Hz, 3H). LCMS (ES) [M+1]⁺ m/z: 526.

The second fraction was concentrated in vacuum to give Stereoisomer 16 as a white solid (103.3 mg, 38%). Chiral HPLC, Rt: 2.006 Min. ¹HNMR (300 MHz, DMSO-d₆) δ8.72 (t, J=0.9 Hz, 1H), 8.20 (d, J=8.7 Hz, 1H), 8.14-8.09 (m, 1H), 7.28-7.15 (m, 2H), 7.02-6.94 (m, 1H), 6.90 (td, J=7.5, 1.1 Hz, 1H), 6.42 (tt, J=54.4, 3.6 Hz, 1H), 4.91-4.54 (m, 5H), 4.54-4.29 (m, 3H), 4.19-3.99 (m, 2H), 3.98 (dd, J=9.6, 4.9 Hz, 1H), 3.73-3.52 (m, 3H), 3.17 (d, J=20.0 Hz, 3H). LCMS (ES) [M+1]⁺ m/z: 526.

Example 1.85

Synthesis of (2S)-1-{2-[1-ethyl-3-(trifluoromethyl)pyrazol-4-ylsulfonyl]-4H,6H-pyrrolo[3,4-c]pyrazol-5-yl}-3-hydroxy-2-phenylpropan-1-one (Compound 94)

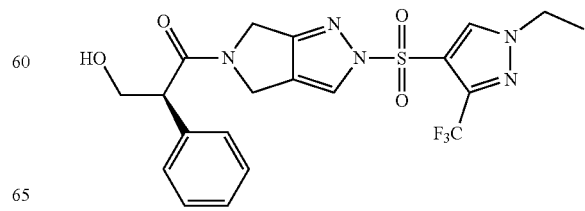

Step 1

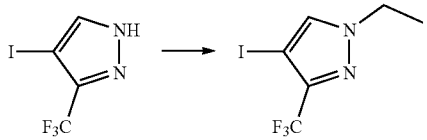

Into a 250 mL 3-necked round-bottom flask were added 4-iodo-3-(trifluoromethyl)-1H-pyrazole (10.0 g, 38.17 mmol, 1.00 eq.) and DMF (100 mL). The mixture was cooled to 0° C., followed by the addition of NaH (60% in mineral oil) (1.83 g, 45.80 mmol, 1.20 eq.) in portions at 0° C. The resulting mixture was stirred for additional 0.5 h at the same temperature. To the above mixture was added ethyl iodide (7.74 g, 49.62 mmol, 1.30 eq.) drop wise. The resulting mixture was stirred for additional 1 h at room temperature. The reaction was quenched with water (100 mL), extracted with EtOAc (3×200 mL). The combined organic layer was washed with brine (3×200 mL), dried over anhydrous $Na_2SO_4$. After filtration, the filtrate was concentrated under reduced pressure. The residue was purified by silica gel column chromatography, eluted with PE/EA (10:1) to afford 1-ethyl-4-iodo-3-(trifluoromethyl)pyrazole (8.7 g, 79%) as a light yellow oil. $^1$HNMR: (300 MHz, DMSO-$d_6$) δ 8.20 (d, J=1.2 Hz, 1H), 4.23 (q, J=7.2 Hz, 2H), 1.38 (t, J=7.2 Hz, 3H). LCMS (ES) [M+1]$^+$ m/z: 291.

Step 2

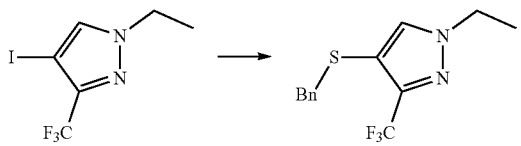 [SMILES: CCn1cc(I)c(C(F)(F)F)n1 ; CCn1cc(SCc2ccccc2)c(C(F)(F)F)n1]

Into a 250 mL round-bottom flask were added 1-ethyl-4-iodo-3-(trifluoromethyl)pyrazole (8.7 g, 29.99 mmol, 1.00 eq.) and toluene (90 mL), DIEA (11.63 g, 89.99 mmol, 3.0 eq.), $Pd_2(dba)_3$ (2.75 g, 3.00 mmol, 0.10 eq.), XantPhos (3.47 g, 5.99 mmol, 0.20 eq.), phenylmethanethiol (7.45 g, 59.99 mmol, 2.00 eq.). The resulting mixture was stirred for 12 at 100° C. under nitrogen atmosphere. The reaction mixture was cooled to room temperature and concentrated under vacuum. The residue was purified by silica gel column chromatography, eluted with PE/EA (5:1) to afford 4-(benzylsulfanyl)-1-ethyl-3-(trifluoromethyl)pyrazole (6.5 g, 76%) as a yellow oil. LCMS (ES) [M+1]$^+$ m/z: 287.

Step 3

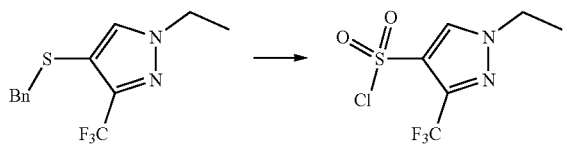 [SMILES: CCn1cc(SCc2ccccc2)c(C(F)(F)F)n1 ; CCn1cc(S(=O)(=O)Cl)c(C(F)(F)F)n1]

Into a 250 mL round-bottom flask were added 4-(benzylsulfanyl)-1-ethyl-3-(trifluoromethyl)pyrazole (6.5 g, 22.70 mmol, 1.00 eq.) and HOAc (90 mL), $H_2O$ (10 mL). The reaction was cooled to 0° C. To the above mixture was added NCS (9.09 g, 68.10 mmol, 3.00 eq.) in portions. The resulting mixture was stirred for additional 1 h at room temperature. The resulting mixture was concentrated under vacuum, the residue was purified by silica gel column chromatography, eluted with PE/EA (5:1) to afford 1-ethyl-3-(trifluoromethyl)pyrazole-4-sulfonyl chloride (1.6 g, 27%) as a yellow oil. LCMS (ES) [M−Cl+OH−1]$^-$ m/z: 243.

Step 4

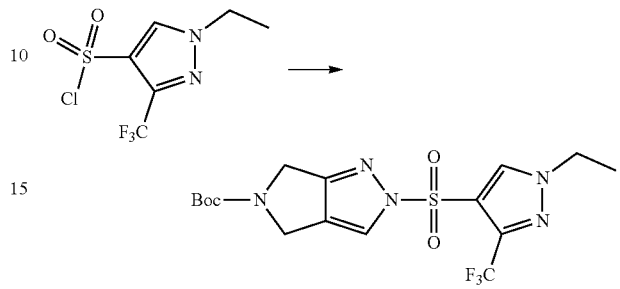

Into a 100 mL 3-necked round-bottom flask were added tert-butyl 2H,4H,6H-pyrrolo[3,4-c]pyrazole-5-carboxylate (981 mg, 4.68 mmol, 1.00 eq.) and DMF (20 mL). The reaction was cooled to 0° C., to the above mixture was added NaH (60% in mineral oil) (206 mg, 5.15 mmol, 1.10 eq.) in portions. The resulting mixture was stirred for additional 0.5 h at 0° C. To the above mixture was added 1-ethyl-3-(trifluoromethyl)pyrazole-4-sulfonyl chloride (1.60 g, 6.09 mmol, 1.30 eq.) drop wise. The resulting mixture was stirred for additional 1 h at room temperature. The reaction was quenched with water (30 mL), the resulting mixture was extracted with EtOAc (3×100 mL). The combined organic layer was washed with brine (3×100 mL), dried over anhydrous $Na_2SO_4$. After filtration, the filtrate was concentrated under reduced pressure. The residue was purified by silica gel column chromatography, eluted with PE/EA (2:1) to afford tert-butyl 2-[1-ethyl-3-(trifluoromethyl)pyrazol-4-ylsulfonyl]-4H,6H-pyrrolo[3,4-c]pyrazole-5-carboxylate (450 mg, 22%) as a white solid. LCMS (ES) [M+1]$^+$ m/z: 436.

Step 5

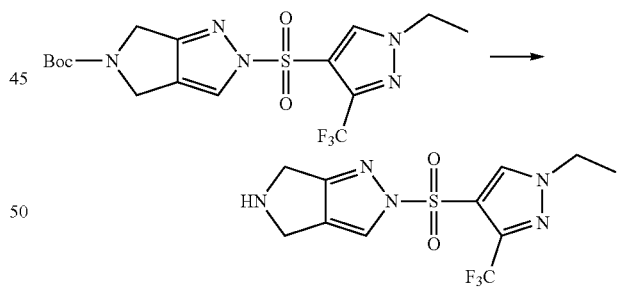

Into a 50 mL 3-necked round-bottom flask were added tert-butyl 2-[1-ethyl-3-(trifluoromethyl)pyrazol-4-ylsulfonyl]-4H,6H-pyrrolo[3,4-c]pyrazole-5-carboxylate (450 mg, 1.03 mmol, 1.00 eq.) and DCM (10 mL), 2,6-lutidine (443 mg, 4.13 mmol, 4.00 eq.). The reaction was cooled to 0° C. To the above mixture was added TMSOTf (690 mg, 3.09 mmol, 3.00 eq.) drop wise. The resulting mixture was stirred for additional 1 h at room temperature. The reaction was quenched with water (20 mL), extracted with dichloromethane (30 mL). The organic phase was concentrated under reduced pressure. The residue was purified by reverse flash chromatography using the following conditions: C18-12 g, mobile phase, $CH_3CN$ and water, 10% to 100% gradient in 10 min, detector, UV 254 nm. The fraction of the target was freezing dried to afford 1-ethyl-4-{4H,5H,6H-pyrrolo[3,4-c]pyrazole-2-sulfonyl}-3-(trifluoromethyl)pyrazole (340 mg, 98%) as a white solid. LCMS (ES) [M+1]$^+$ m/z: 336.

Step 6

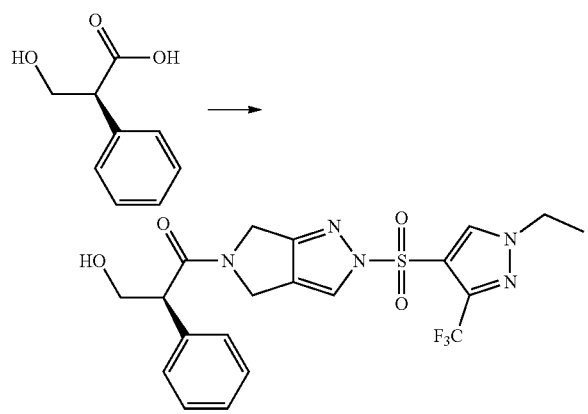

Into a 20 mL vial were added 1-ethyl-4-{4H,5H,6H-pyrrolo[3,4-c]pyrazole-2-sulfonyl}-3-(trifluoromethyl)pyrazole (151 mg, 0.45 mmol, 1.5 eq.) and DMF (3 mL), NMM (61 mg, 0.60 mmol, 2.00 eq.), (S)-tropic acid (50 mg, 0.30 mmol, 1.00 eq.). The reaction was cooled to 0° C., to the above mixture was added HATU (137 mg, 0.36 mmol, 1.20 eq.) in portions. The resulting mixture was stirred for additional 1 h at 0° C. The reaction solution was purified by Prep-HPLC using the following conditions: Sunfire Prep C18 OBD Column, 50*250 mm, 5 µm, 10 nm, mobile phase, water (0.1% FA) and CH$_3$CN (15% up to 50% in 12 min), Detector, UV 254 nm. The fraction of the target was freezing dried to afford (2S)-1-{2-[1-ethyl-3-(trifluoromethyl)pyrazol-4-ylsulfonyl]-4H,6H-pyrrolo[3,4-c]pyrazol-5-yl}-3-hydroxy-2-phenylpropan-1-one (107.4 mg, 74%) as a white solid. $^1$HNMR (300 MHz, DMSO-d$_6$) δ 8.96 (d, J=1.6 Hz, 1H), 8.16 (s, 1H), 7.42-7.21 (m, 5H), 4.98-4.79 (m, 2H), 4.57-4.26 (m, 5H), 4.02-3.96 (m, 2H), 3.54 (d, J=5.3 Hz, 1H), 1.40 (t, J=7.3 Hz, 3H). LCMS (ES) [M+1]$^+$ m/z: 484.

Example 1.86

Synthesis of (2R)-1-{2-[1-ethyl-3-(trifluoromethyl)pyrazol-4-ylsulfonyl]-4H,6H-pyrrolo[3,4-c]pyrazol-5-yl}-3-hydroxy-2-phenylpropan-1-one (Compound 95)

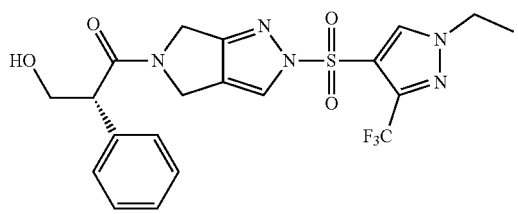 [SMILES: CCn1cc(S(=O)(=O)n2cc3c(n2)CN(C(=O)[C@@H](CO)c2ccccc2)C3)c(C(F)(F)F)n1]

The title compound was synthesized according to the procedure described on Step 6, synthesis of Compound 94 using (R)-tropic acid. (2R)-1-{2-[1-Ethyl-3-(trifluoromethyl)pyrazol-4-ylsulfonyl]-4H,6H-pyrrolo[3,4-c]pyrazol-5-yl}-3-hydroxy-2-phenylpropan-1-one was isolated as a white solid. $^1$HNMR (300 MHz, DMSO-d$_6$) δ 8.96 (d, J=1.6 Hz, 1H), 8.16 (s, 1H), 7.42-7.21 (m, 5H), 4.96-4.79 (m, 2H), 4.57-4.26 (m, 5H), 4.02-3.95 (m, 2H), 3.54 (d, J=5.3 Hz, 1H), 1.40 (t, J=7.3 Hz, 3H). LCMS (ES) [M+1]$^+$ m/z: 484.

Example 1.87

Synthesis of (2S)-1-(2-{[1-(2,2-difluoroethyl)-5-methyl-1H-pyrazol-4-yl]sulfonyl}-2H,4H,5H,6H-pyrrolo[3,4-c]pyrazol-5-yl)-3-hydroxy-2-phenylpropan-1-one (Compound 96)

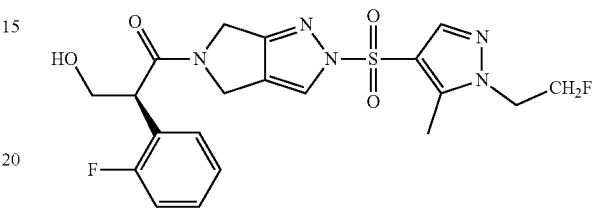

Into a 50-mL round-bottom flask, was placed (2S)-2-(2-fluorophenyl)-3-hydroxypropanoic acid (80 mg, 0.43 mmol, 1 eq.), DMF (5.00 mL), 1-(2-fluoroethyl)-5-methyl-4-{4H,5H,6H-pyrrolo[3,4-c]pyrazole-2-sulfonyl}pyrazole (Step 5, Example 1.18, 130 mg, 0.43 mmol, 1.00 eq.), NMM (88 mg, 0.87 mmol, 2 eq.). This was followed by the addition of HATU (198 mg, 0.52 mmol, 1.2 eq.) at 0° C. The resulting solution was stirred for 1 hr at RT. The crude product was purified by Prep-HPLC using the following conditions (Prep-HPLC-001): Column, Sunfire Prep C18 OBD Column, 50*250 mm, 5 m 10 nm; mobile phase, Water and ACN (15% Phase B up to 50% in 15 min); Detector, uv. 254 nm. This resulted in (2S)-1-{2-[1-(2-fluoroethyl)-5-methylpyrazol-4-ylsulfonyl]-4H,6H-pyrrolo[3,4-c]pyrazol-5-yl}-2-(2-fluorophenyl)-3-hydroxypropan-1-one (149.5 mg, 73.95%) as an off-white solid. $^1$HNMR (300 MHz, DMSO-d$_6$) δ 8.19 (d, J=2.7 Hz, 1H), 8.01 (s, 1H), 7.40 (t, J=7.6 Hz, 1H), 7.30 (t, J=7.0 Hz, 1H), 7.25-7.13 (m, 2H), 4.96-4.77 (m, 3H), 4.69 (t, J=4.8 Hz, 1H), 4.54-4.34 (m, 4H), 4.34-4.22 (m, 2H), 4.05-3.94 (m, 1H), 3.60 (dq, J=11.0, 5.8 Hz, 1H), 2.49 (d, J=2.0 Hz, 3H). LCMS (ES) [M+1]$^+$ m/z: 466.

Example 1.88

Synthesis of (2R)-1-{2-[1-(2-fluoroethyl)-5-methylpyrazol-4-ylsulfonyl]-4H,6H-pyrrolo[3,4-c]pyrazol-5-yl}-2-(2-fluorophenyl)-3-hydroxypropan-1-one (Compound 97)

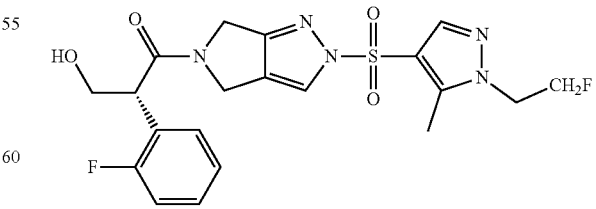

Into a 50-mL round-bottom flask, was placed (2R)-2-(2-fluorophenyl)-3-hydroxypropanoic acid (80 mg, 0.43 mmol, 1 eq.), DMF (5.00 mL), 1-(2-fluoroethyl)-5-methyl-4-{4H, 5H,6H-pyrrolo[3,4-c]pyrazole-2-sulfonyl}pyrazole (step 5, Example 1.18, 130 mg, 0.43 mmol, 1.00 eq.), NMM (88 mg, 0.87 mmol, 2 eq.). This was followed by the addition of HATU (198 mg, 0.52 mmol, 1.2 eq.) at 0° C. The resulting solution was stirred for 1 hr at RT. The crude product was purified by Prep-HPLC using the following conditions (Prep-HPLC-001): Column, Sunfire Prep C18 OBD Column, 50*250 mm, 5 m 10 nm; mobile phase, Water and ACN (15% PhaseB up to 50% in 15 min); Detector, uv. 254 nm. This resulted in (2R)-1-{2-[1-(2-fluoroethyl)-5-methylpyrazol-4-ylsulfonyl]-4H,6H-pyrrolo[3,4-c]pyrazol-5-yl}-2-(2-fluorophenyl)-3-hydroxypropan-1-one (121.6 mg, 60.15%) as a white solid. $^1$HNMR (400 MHz, DMSO-d$_6$) δ 8.19 (d, J=2.7 Hz, 1H), 8.01 (s, 1H), 7.40 (t, J=7.6 Hz, 1H), 7.30 (t, J=7.0 Hz, 1H), 7.25-7.13 (m, 2H), 4.96-4.77 (m, 3H), 4.69 (t, J=4.8 Hz, 1H), 4.54-4.34 (m, 4H), 4.34-4.22 (m, 2H), 4.05-3.94 (m, 1H), 3.60 (dq, J=11.0, 5.8 Hz, 1H), 2.49 (d, J=2.0 Hz, 3H). LCMS (ES) [M+1]$^+$ m/z: 466.

Example 1.89

Synthesis of (2S)-2-(2-chlorophenyl)-1-{2-[1-(2-fluoroethyl)-5-methylpyrazol-4-ylsulfonyl]-4H,6H-pyrrolo[3,4-c]pyrazol-5-yl}-3-hydroxypropan-1-one (Compound 98)

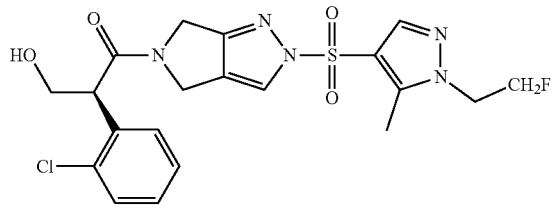

Into a 50-mL round-bottom flask, was placed (2S)-2-(2-chlorophenyl)-3-hydroxypropanoic acid (87 mg, 0.43 mmol, 1 eq.), DMF (5.00 mL), 1-(2-fluoroethyl)-5-methyl-4-{4H,5H,6H-pyrrolo[3,4-c]pyrazole-2-sulfonyl}pyrazole (Step 5, Example 1.18, 130 mg, 0.43 mmol, 1.00 eq.), NMM (88 mg, 0.87 mmol, 2 eq.). This was followed by the addition of HATU (198 mg, 0.52 mmol, 1.2 eq.) at 0° C. The resulting solution was stirred for 1 hr at 25° C. The crude product was purified by Prep-HPLC using the following conditions (Prep-HPLC-001): Column, Sunfire Prep C18 OBD Column, 50*250 mm, 5 m 10 nm; mobile phase, Water and ACN (15% Phase B up to 50% in 15 min); Detector, uv. 254 nm. This resulted in (2S)-2-(2-chlorophenyl)-1-{2-[1-(2-fluoroethyl)-5-methylpyrazol-4-ylsulfonyl]-4H,6H-pyrrolo[3,4-c]pyrazol-5-yl}-3-hydroxypropan-1-one (137.8 mg, 65.84%) as a white solid. $^1$H NMR (400 MHz, DMSO-d$_6$) δ8.20 (s, 1H), 8.01 (d, J=2.2 Hz, 1H), 7.53-7.48 (m, 2H), 7.36-7.25 (m, 2H), 4.99-4.78 (m, 3H), 4.69 (t, J=4.7 Hz, 1H), 4.55-4.35 (m, 5H), 4.30 (t, J=13.5 Hz, 1H), 4.02-3.91 (m, 1H), 3.57 (dq, J=10.5, 5.4 Hz, 1H), 2.49 (d, J=2.1 Hz, 3H). LCMS (ES) [M+1]$^+$ m/z: 482.

Example 1.90

Synthesis of (2R)-2-(2-chlorophenyl)-1-{2-[1-(2-fluoroethyl)-5-methylpyrazol-4-ylsulfonyl]-4H,6H-pyrrolo[3,4-c]pyrazol-5-yl}-3-hydroxypropan-1-one (Compound 99)

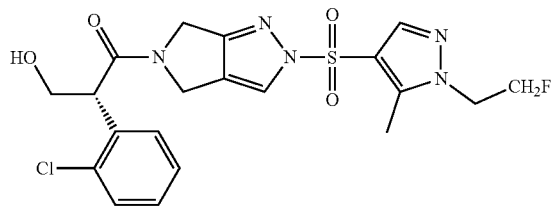

Similarly, (2R)-2-(2-chlorophenyl)-1-{2-[1-(2-fluoroethyl)-5-methylpyrazol-4-ylsulfonyl]-4H,6H-pyrrolo[3,4-c]pyrazol-5-yl}-3-hydroxypropan-1-one was obtained from (2R)-2-(2-chlorophenyl)-3-hydroxypropanoic acid under the same reaction conditions. $^1$H NMR (400 MHz, DMSO-d$_6$) δ 8.20 (s, 1H), 8.01 (d, J=2.2 Hz, 1H), 7.53-7.48 (m, 2H), 7.36-7.24 (m, 2H), 5.00-4.84 (m, 2H), 4.81 (t, J=4.7 Hz, 1H), 4.69 (t, J=4.7 Hz, 1H), 4.55-4.35 (m, 5H), 4.30 (t, J=13.4 Hz, 1H), 3.97 (qd, J=8.9, 2.9 Hz, 1H), 3.57 (dq, J=10.6, 5.4 Hz, 1H), 2.49 (d, J=2.0 Hz, 3H). LCMS (ES) [M+1]$^+$ m/z: 482.

Example 1.91

Synthesis of (R)-1-(2-((1-(2,2-difluoroethyl)-5-methyl-1H-pyrazol-4-yl)sulfonyl)-2,6 dihydropyrrolo[3,4-c]pyrazol-5(4H)-yl)-2-(2-fluorophenyl)-3-hydroxypropan-1-one (Compound 100)

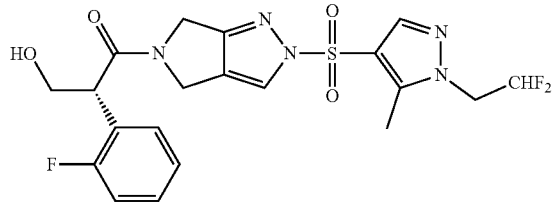 [SMILES: Cc1c(S(=O)(=O)n2cc3c(n2)CN(C(=O)[C@@H](CO)c2ccccc2F)C3)cnn1CC(F)F]

The title compound was made from (S)-2-(2-fluorophenyl)-3-hydroxypropanoic acid (50 mg, 0.27 mmol, 1.00 eq.), and 2-((1-(2,2-difluoroethyl)-5-methyl-1H-pyrazol-4-yl) sulfonyl)-2,4,5,6-tetrahydropyrrolo[3,4-c]pyrazole (Step 5, Example 1.18, 112 mg, 0.35 mmol, 1.30 eq.), following the procedure described on step 6, Example 1.18. The desired (R)-1-(2-((1-(2,2-difluoroethyl)-5-methyl-1H-pyrazol-4-yl) sulfonyl)-2,6-dihydropyrrolo[3,4-c]pyrazol-5(4H)-yl)-2-(2-fluorophenyl)-3-hydroxypropan-1-one was isolated as a white solid (37 mg). $^1$H NMR (300 MHz, DMSO-d$_6$) δ8.21 (d, J=2.4 Hz, 1H), 8.04 (s, 1H), 7.42-7.28 (m, 2H), 7.24-7.14 (m, 2H), 6.60 (tt, J=54.3, 3.3 Hz, 1H), 4.96-4.84 (m, 2H), 4.74 (td, J=15.3, 3.6 Hz, 2H), 4.53-4.40 (m, 2H), 4.35-4.24 (m 2H), 4.03-3.95 (m, 1H), 3.65-3.56 (m, 1H), 2.52 (s, 3H). LCMS (ES) [M+1]$^+$ m/z: 484.

Example 1.92

Synthesis of (2S)-2-(2-chlorophenyl)-1-{2-[1-(2,2-difluoroethyl)-5-methylpyrazol-4-ylsulfonyl]-4H,6H-pyrrolo[3,4-c]pyrazol-5-yl}-3-hydroxypropan-1-one (Compound 101)

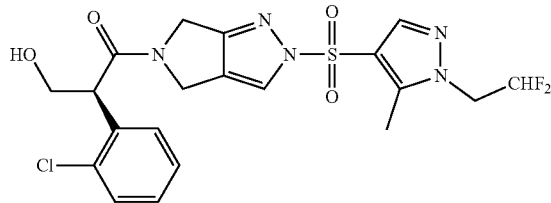 [SMILES: Cc1c(S(=O)(=O)n2cc3c(n2)CN(C(=O)[C@H](CO)c2ccccc2Cl)C3)cnn1CC(F)F]

Into a 20 mL vial were added (2S)-2-(2-chlorophenyl)-3-hydroxypropanoic acid (100 mg, 0.49 mmol, 1.00 eq.) and DMF (3 mL), NMM (101 mg, 0.99 mmol, 2.00 eq.), 1-(2,2-difluoroethyl)-5-methyl-4-{4H,5H,6H-pyrrolo[3,4-c]pyrazole-2-sulfonyl}pyrazole (Step 5, Example 1.18, 174 mg, 0.54 mmol, 1.10 eq.). The reaction was cooled to 0° C. To the above mixture was added HATU (228 mg, 0.59 mmol, 1.20 eq.) in portions. The resulting mixture was stirred for additional 1 h at 0° C. The reaction mixture was purified by Prep-HPLC using the following conditions: SunFire Prep C18 OBD Column, 19*150 mm, 5 μm, 10 nm, mobile phase, water (0.1% FA) and CH$_3$CN (35% up to 70% in 7 min), Detector, 254 nm UV) to afford (2S)-2-(2-chlorophenyl)-1-{2-[1-(2,2-difluoroethyl)-5-methylpyrazol-4-ylsulfonyl]-4H,6H-pyrrolo[3,4-c]pyrazol-5-yl}-3-hydroxypropan-1-one (83.4 mg, 33%) as a white solid. $^1$H NMR (400 MHz, DMSO-d$_6$) δ 8.21 (s, 1H), 8.05 (d, J=1.7 Hz, 1H), 7.66-7.10 (m, 4H), 6.40 (tt, J=54.3, 3.5 Hz, 1H), 5.03-4.81 (m, 2H), 4.68 (td, J=15.3, 3.5 Hz, 2H), 4.58-4.25 (m, 4H), 3.97 (s, 1H), 3.58 (s, 1H), 2.50 (d, J=1.8 Hz, 3H). LCMS (ES) [M+1]$^+$ m/z: 500.

Example 1.93

Synthesis of (2R)-2-(2-chlorophenyl)-1-{2-[1-(2,2-difluoroethyl)-5-methylpyrazol-4-ylsulfonyl]-4H,6H-pyrrolo[3,4-c]pyrazol-5-yl}-3-hydroxypropan-1-one (Compound 102)

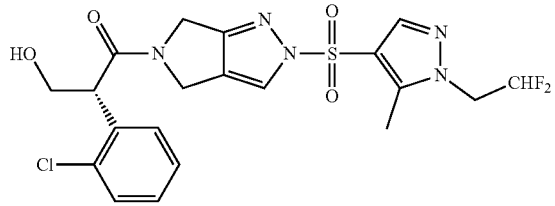 [SMILES: Cc1c(S(=O)(=O)n2cc3c(n2)CN(C(=O)[C@@H](CO)c2ccccc2Cl)C3)cnn1CC(F)F]

Into a 20 mL vial were added (2R)-2-(2-chlorophenyl)-3-hydroxypropanoic acid (60 mg, 0.29 mmol, 1.00 eq.) and DMF (3 mL), NMM (61 mg, 0.59 mmol, 2.00 eq.), 1-(2,2-difluoroethyl)-5-methyl-4-{4H,5H,6H-pyrrolo[3,4-c]pyrazole-2-sulfonyl}pyrazole (Step 5, Example 1.18, 105 mg, 0.32 mmol, 1.10 eq.). The reaction was cooled to 0° C. To the above mixture was added HATU (137 mg, 0.35 mmol, 1.20 eq.) in portions. The resulting mixture was stirred for additional 1 h at 0° C. The reaction mixture was purified by Prep-HPLC using the following conditions: SunFire Prep C18 OBD Column, 19*150 mm, 5 μm, 10 nm, mobile phase, water (0.1% FA) and CH$_3$CN (30% up to 70% in 7 min), Detector, UV 254 nm. The fraction of the target was freezing dried to afford (2R)-2-(2-chlorophenyl)-1-{2-[1-(2,2-difluoroethyl)-5-methylpyrazol-4-ylsulfonyl]-4H,6H-pyrrolo[3,4-c]pyrazol-5-yl}-3-hydroxypropan-1-one (38.8 mg, 26%) as a white solid. $^1$H NMR (300 MHz, DMSO-d$_6$) δ 8.21 (s, 1H), 8.05 (d, J=1.7 Hz, 1H), 7.66-7.10 (m, 4H), 6.40 (tt, J=54.3, 3.5 Hz, 1H), 5.03-4.81 (m, 2H), 4.68 (td, J=15.3, 3.5 Hz, 2H), 4.58-4.25 (m, 4H), 3.97 (s, 1H), 3.58 (s, 1H), 2.50 (d, J=1.8 Hz, 3H). LCMS (ES) [M+1]$^+$ m/z: 500.

Example 1.94

Synthesis of (2S)-1-{2-[1-(2,2-difluoroethyl)-5-methylpyrazol-4-ylsulfonyl]-4H,6H-pyrrolo[3,4-c]pyrazol-5-yl}-3-hydroxy-2-(2-methoxyphenyl)propan-1-one (Compound 103)

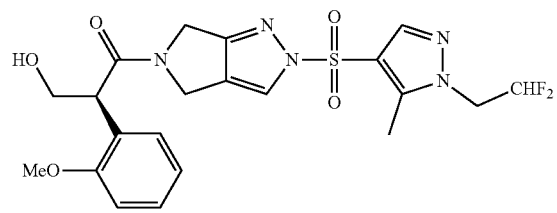 [SMILES: COc1ccccc1[C@@H](CO)C(=O)N1Cc2cn(S(=O)(=O)c3cnn(CC(F)F)c3C)nc2C1]

Step 1

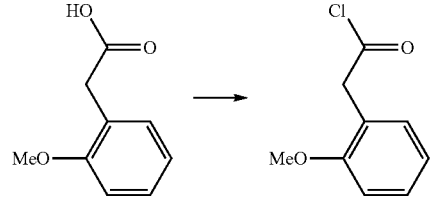 [SMILES: COc1ccccc1CC(=O)O ; COc1ccccc1CC(=O)Cl]

Into a 500 mL 3-necked round-bottom flask were added 2-(2-methoxyphenyl)acetic acid (30.00 g, 180.53 mmol, 1.00 eq.), DMF (2.00 mL) and DCM (300.00 mL). To the above mixture was added oxalyl chloride (34.37 g, 270.80 mmol, 1.50 eq.) drop wise at 0° C. The resulting mixture was stirred for additional 3 h at room temperature. The resulting mixture was concentrated under reduced pressure. This resulted in (2-methoxyphenyl)acetyl chloride (30.00 g, crude) as yellow oil.

Step 2

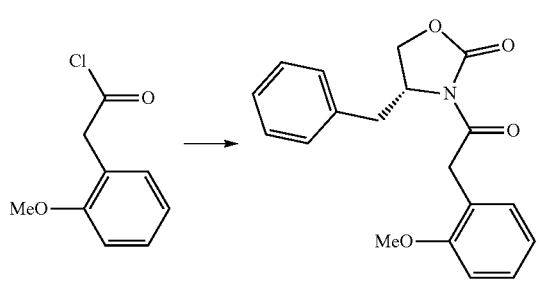 [SMILES: COc1ccccc1CC(=O)Cl ; COc1ccccc1CC(=O)N1C(=O)OC[C@H]1Cc1ccccc1]

Into a 250 mL 3-necked round-bottom flask were added (4R)-4-benzyl-1,3-oxazolidin-2-one (12.00 g, 67.72 mmol, 1.00 eq.) and THF (150.00 mL). To the above mixture was added n-BuLi (35.21 mL, 88.04 mmol, 1.30 eq.) drop wise at −78° C. under nitrogen atmosphere. The resulting mixture was stirred for additional 1 h at −78° C. To a stirred solution was added (2-methoxyphenyl)acetyl chloride (15.00 g, 81.263 mmol, 1.20 eq.) in THF drop wise at −78° C. The resulting mixture was stirred for additional 1 h at −78° C. to rt. The reaction was quenched by the addition of sat. NH$_4$Cl (aq.) (100 mL). The resulting mixture was extracted with EA (3×150 mL). The combined organic layers were dried over anhydrous Na$_2$SO$_4$. After filtration, the filtrate was concentrated under reduced pressure. The residue was purified by silica gel column chromatography, eluted with THF/PE (15%) to afford (4R)-4-benzyl-3-[2-(2-methoxyphenyl)acetyl]-1,3-oxazolidin-2-one (15.00 g, 68.08%) as white solid. LCMS (ES) [M+1]$^+$ m/z: 326.

Step 3

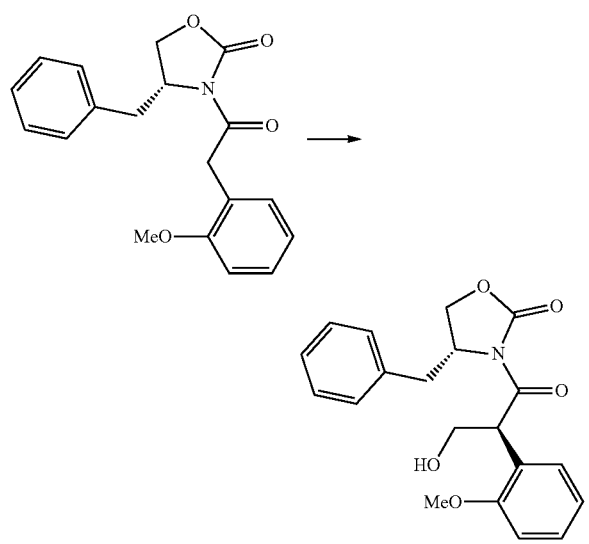

Into a 250 mL 3-necked round-bottom flask were added (4R)-4-benzyl-3-[2-(2-methoxyphenyl)acetyl]-1,3-oxazolidin-2-one (6.00 g, 18.44 mmol, 1.00 eq.) and DCM (60.00 mL). A solution of TiCl$_4$ (2.82 mL, 20.29 mmol, 1.10 eq.) in DCM (1.00 mL) was added drop wise at 0° C. The resulting mixture was stirred for 20 min at 0° C. under nitrogen atmosphere. To the above mixture was added DIEA (2.74 g, 21.21 mmol, 1.15 eq.) drop wise at 0° C. The resulting mixture was stirred for additional 1 h at 0° C. A solution of trioxane (1.83 g, 20.29 mmol, 1.10 eq.) in DCM was added drop wise at 0° C. and treated for 20 min at 0° C. Then a mixture of TiCl$_4$ (2.82 mL, 20.29 mmol, 1.10 eq.) in DCM (1.00 mL) was added drop wise at 0° C. The resulting mixture was stirred for 2 h at 0° C. The reaction was quenched by the addition of sat. NH$_4$Cl (aq.) (50 mL). The resulting mixture was extracted with DCM (3×100 mL). The combined organic layers were washed with sat. NaHCO$_3$ (aq.) (100 mL), dried over anhydrous Na$_2$SO$_4$. After filtration, the filtrate was concentrated under reduced pressure. This resulted in (4R)-4-benzyl-3-[(2S)-3-hydroxy-2-(2-methoxyphenyl)propanoyl]-1,3-oxazolidin-2-one (6.00 g, crude) as yellow oil. LCMS (ES) [M+1]$^+$ m/z: 356.

Step 4

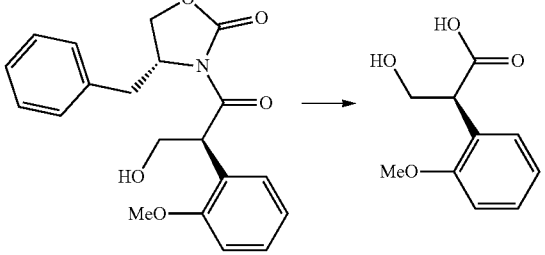

Into a 250 mL 3-necked round-bottom flask were added (4R)-4-benzyl-3-[(2S)-3-hydroxy-2-(2-methoxyphenyl)propanoyl]-1,3-oxazolidin-2-one (6.00 g, 16.88 mmol, 1.00 eq.) and THF (60.00 mL). To a stirred mixture were added H$_2$O$_2$ (30%) (1.97 mL, 84.42 mmol, 5.00 eq.) and LiOH (0.81 g, 33.77 mmol, 2.00 eq.) in H$_2$O (15.00 mL) drop wise at 0° C. The resulting mixture was stirred for additional 1 h at 0° C. The reaction was quenched with Na$_2$SO$_3$. The resulting mixture was extracted with DCM (3×100 mL). The combined aqueous layers were acidified to pH 3 with 2M HCl. The resulting mixture was extracted with DCM/MeOH (10:1) (10×100 mL). The combined organic layers were dried over anhydrous Na$_2$SO$_4$. After filtration, the filtrate was concentrated under reduced pressure. The crude product was purified by Prep-HPLC using the following conditions: Column, XBridge Prep C18 OBD Column, 19 cm, 150 mm, 5 um; mobile phase, Water (0.1% FA) and CAN (10% Phase B up to 30% in 20 min); Detector, 254. This resulted in (2S)-3-hydroxy-2-(2-methoxyphenyl)propanoic acid (1.20 g, 36.23%) as yellow oil. LCMS (ES) [M−1]$^+$ m/z: 195.

Step 5

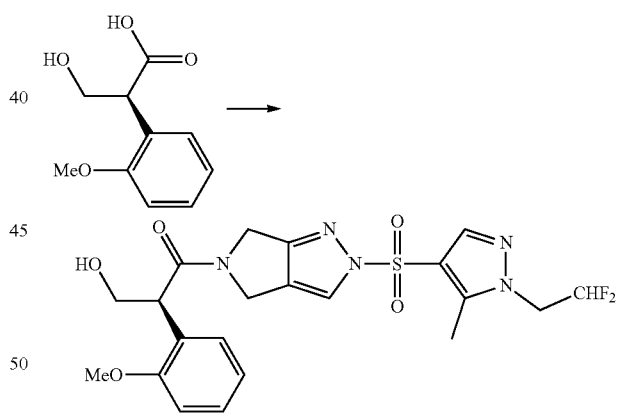

Into a 20 mL vial were added (2S)-3-hydroxy-2-(2-methoxyphenyl)propanoic acid (75.00 mg, 0.38 mmol, 1.00 eq.), 1-(2,2-difluoroethyl)-5-methyl-4-{4H,5H,6H-pyrrolo[3,4-c]pyrazole-2-sulfonyl}pyrazole (133.42 mg, 0.42 mmol, 1.10 eq.), DMF (5.00 mL) and NMM (77.33 mg, 0.76 mmol, 2.00 eq.). To the above mixture was added HATU (174.42 mg, 0.46 mmol, 1.20 eq.) drop wise at 0° C. The resulting mixture was stirred for additional 1 h at room temperature. The crude product was purified by Prep-HPLC using the following conditions: Column, Sunfire Prep C18 OBD Column, 50*250 mm Sum 10 nm; mobile phase, Water (0.1% NH$_3$.H$_2$O) and ACN (10% Phase B up to 55% in 15 min); Detector, 254. This resulted in (2S)-1-{2-[1-(2,2-difluoroethyl)-5-methylpyrazol-4-ylsulfonyl]-4H,6H-pyrrolo[3,4-c]pyrazol-5-yl}-3-hydroxy-2-(2-methoxyphenyl)
propan-1-one (90.90 mg, 47.99%) as white solid. $^1$HNMR
(300 MHz, DMSO-d6) δ 8.20 (d, J=5.0 Hz, 1H), 8.04 (d,
J=2.7 Hz, 1H), 7.29-7.19 (m, 2H), 7.01 (dd, J=8.2, 4.0 Hz,
1H), 6.89 (t, J=7.5 Hz, 1H), 6.40 (tt, J=54.3, 3.4 Hz, 1H),
4.90-4.75 (m, 2H), 4.68 (td, J=15.3, 3.4 Hz, 2H), 4.55-4.25
(m, 4H), 3.95 (td, J=9.5, 4.8 Hz, 1H), 3.84 (s, 3H), 3.48 (dtd,
J=10.0, 4.9, 2.8 Hz, 1H), 2.51 (s, 3H). LCMS (ES) [M+1]$^+$
m/z: 496.

Example 1.95

Synthesis of (2R)-1-{2-[1-(2,2-difluoroethyl)-5-methylpyrazol-4-ylsulfonyl]-4H,6H-pyrrolo[3,4-c]pyrazol-5-yl}-3-hydroxy-2-(2-methoxyphenyl)propan-1-one (Compound 104)

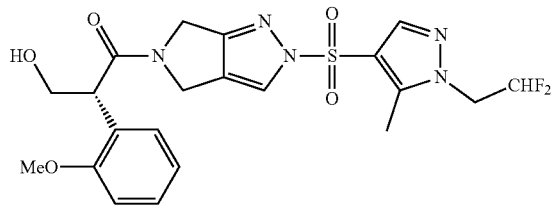 [SMILES: COc1ccccc1[C@H](CO)C(=O)N1Cc2cn(S(=O)(=O)c3cnn(CC(F)F)c3C)nc2C1]

The title compound was synthesized according the 5-step
procedure described in the synthesis of Compound 103
using (4S)-4-benzyl-1,3-oxazolidin-2-one in step 1. (2R)-1-
{2-[1-(2,2-difluoroethyl)-5-methylpyrazol-4-ylsulfonyl]-
4H,6H-pyrrolo[3,4-c]pyrazol-5-yl}-3-hydroxy-2-(2-
methoxyphenyl)propan-1-one was isolated as a white solid.
$^1$HNMR (400 MHz, DMSO-d$_6$) δ 8.20 (d, J=4.9 Hz, 1H),
8.04 (d, J=2.7 Hz, 1H), 7.30-7.16 (m, 2H), 7.01 (dd, J=8.1,
4.0 Hz, 1H), 6.89 (t, J=7.5 Hz, 1H), 6.40 (tt, J=54.4, 3.4 Hz,
1H), 4.89-4.75 (m, 2H), 4.68 (td, J=15.3, 3.4 Hz, 2H),
4.53-4.26 (m, 4H), 3.95 (tt, J=9.6, 6.1 Hz, 1H), 3.87 (s, 3H),
3.52-3.44 (m, 1H), 2.50 (s, 3H). LCMS (ES) [M+1]$^+$ m/z:
496.

Example 1.96

Synthesis of (S)-1-(2-((1-(2,2-difluoroethyl)-1H-pyrazol-4-yl)sulfonyl)-2,6-dihydropyrrolo[3,4-c]pyrazol-5(4H)-yl)-2-(2-ethylphenyl)-3-hydroxypropan-1-one (Compound 105)

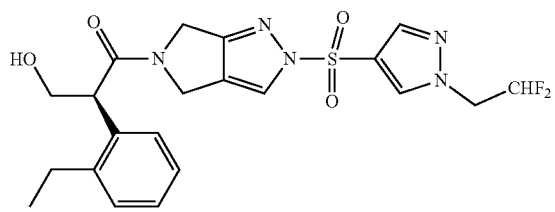 [SMILES: CCc1ccccc1[C@@H](CO)C(=O)N1Cc2cn(S(=O)(=O)c3cnn(CC(F)F)c3)nc2C1]

Step 1

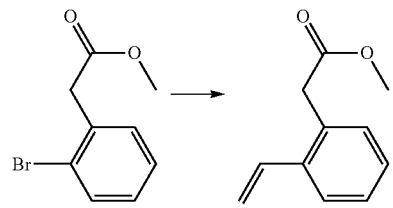

Into a 1000 mL round-bottom flask purged and maintained with an inert atmosphere of nitrogen, were added methyl 2-(2-bromophenyl)acetate (20.0 g, 87.308 mmol, 1.0 eq.), dioxane (400 mL), H$_2$O (60 mL), potassium vinyltrifluoroborate (17.42 g, 130.962 mmol, 1.5 eq.), Cs$_2$CO$_3$ (71.12 g, 218.270 mmol, 2.5 eq.) and Pd(dppf)Cl$_2$ (6.39 g, 8.731 mmol, 0.1 eq.) at room temperature. The resulting mixture was stirred for 16 overnight at 100° C. The resulting mixture was diluted with H$_2$O (400 ml). The resulting mixture was extracted with DCM (3×500 ml), dried over anhydrous Na$_2$SO$_4$. After filtration, the filtrate was concentrated under reduced pressure. The residue was purified by silica gel column chromatography, eluted with PE/EA (97/3) to afford methyl 2-(2-ethenylphenyl)acetate (11.13 g, 72.34%) as a yellow oil. LCMS (ES) [M+1]$^+$ m/z: 177.

Step 2

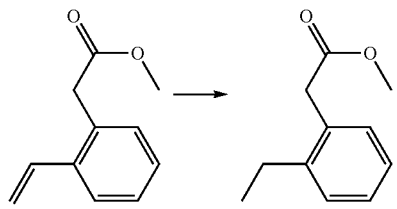

Into a 250 mL round-bottom flask containing methyl 2-(2-ethenylphenyl)acetate (11.0 g, 62.424 mmol, 1.0 eq.), MeOH (110 mL), Pd/C (1.1 g) was stirred for 16 overnight at room temperature at 1.5 atm of hydrogen. The resulting mixture was filtered; the filter cake was washed with MeOH (3×50 mL). The filtrate was concentrated under reduced pressure. This resulted in methyl 2-(2-ethylphenyl)acetate (10.0 g, 89.88%) as a transparent oil. LCMS (ES) [M+1]$^+$ m/z: 179.

Step 3

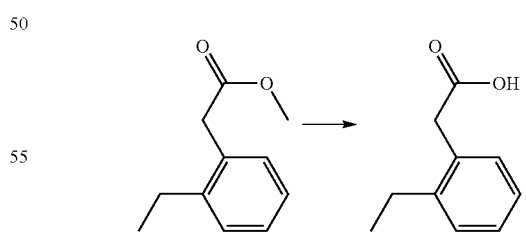

Into a 250 mL round-bottom flask were added methyl methyl 2-(2-ethylphenyl)acetate (11.0 g, 61.718 mmol, 1.0 eq.), MeOH (100 mL), H$_2$O (20 mL) and LiOH (2.96 g, 123.436 mmol, 2.0 eq.) at room temperature. The resulting mixture was stirred for 3 h at room temperature. The mixture was acidified to pH 4 with 2M HCl. The resulting mixture was extracted with DCM (3×100 mL), dried over anhydrous Na$_2$SO$_4$. After filtration, the filtrate was concentrated under Step 4

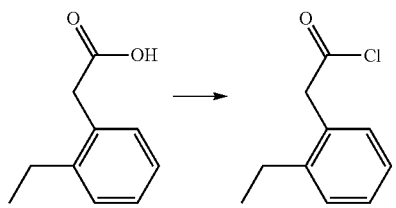

Into a 250 mL round-bottom flask and maintained with an inert atmosphere of nitrogen, were added (2-ethylphenyl)acetic acid (8.1 g, 49.329 mmol, 1.0 eq.), DCM (100 mL), chloro(hydroxy)acetyl chloride (19.08 g, 147.987 mmol, 3.0 eq.) at room temperature. The resulting mixture was stirred for 5 overnight at 50° C. The resulting mixture was concentrated under reduced pressure. This resulted in (2-ethylphenyl)acetyl chloride (9.0 g, 99.89%) as a colorless oil.

Step 5

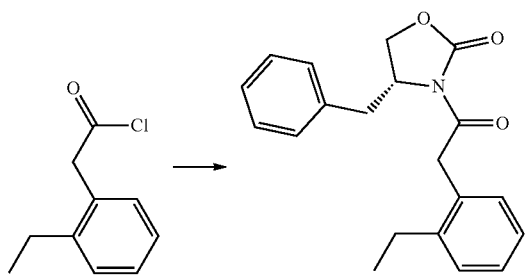 [SMILES: CCc1ccccc1CC(=O)Cl ; CCc1ccccc1CC(=O)N1C(=O)OC[C@H]1Cc1ccccc1]

Into a 250-mL 3-necked round-bottom flask purged and maintained with an inert atmosphere of nitrogen, was placed (4R)-4-benzyl-1,3-oxazolidin-2-one (3.93 g, 22.173 mmol, 0.9 eq.) and THF (135 mL) at −78 degrees C. n-BuLi (2.05 g, 32.028 mmol, 1.3 eq.) was added drop wise at −78° C. The resulting solution was stirred for 1 hours at −78° C. A solution of (2-ethylphenyl)acetyl chloride (4.5 g, 24.637 mmol, 1 eq.) in THF (10 mL) was added drop wise at −78° C. to room temperature and was stirred for 2 h. The reaction was then quenched by the addition of 100 mL of water. The resulting solution was extracted with EtOAc (3×100 mL). The resulting mixture was washed with 1×150 ml of brine. The mixture was dried over anhydrous Na$_2$SO$_3$ and concentrated. The residue was applied onto a silica gel column with EtOAc/PE (2/1). This resulted in (4R)-4-benzyl-3-[2-(2-ethylphenyl)acetyl]-1,3-oxazolidin-2-one (4.7 g, 58.99%) as a yellow oil. LCMS (ES) [M+1]⁻ m/z: 324.

Step 6

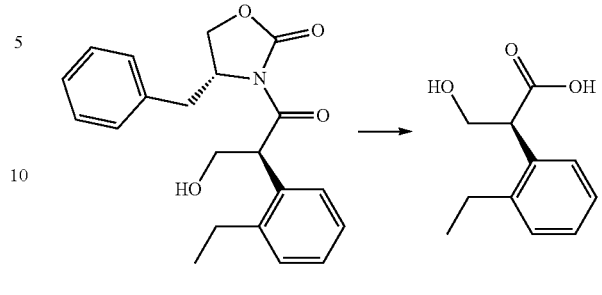

Into a 250-mL 3-necked round-bottom flask, was placed (4R)-4-benzyl-3-[(2S)-2-(2-ethylphenyl)-3-hydroxypropanoyl]-1,3-oxazolidin-2-one (4.6 g, 13.016 mmol, 1 eq.) and THF (60 mL, 780.960 mmol) at 0° C. To the above mixture was added H$_2$O$_2$ (30%) (2.21 g, 65.080 mmol, 5.0 eq.), LiOH.H$_2$O (0.62 g, 26.032 mmol, 2.0 eq.) at 0° C. The resulting mixture was stirred for additional 2 h at 0° C. The reaction was then quenched by the addition of sat. Na$_2$SO$_3$, H$_2$O (50 ml) and was extracted with DCM (3×100 mL). The pH was adjusted to 1 with 2M HCl. The resulting solution was extracted with DCM/MeOH (10/1) (10×100 mL), dried over anhydrous Na$_2$SO$_3$ and concentrated. The residue was purified by trituration with DCM/hexane (1/10). The resulting mixture was filtered; the filter cake was concentrated under reduced pressure. This resulted in (2S)-2-(2-ethylphenyl)-3-hydroxypropanoic acid (800 mg, 31.64%) as a white solid. LCMS (ES) [M−1]⁻ m/z: 193.

Step 7

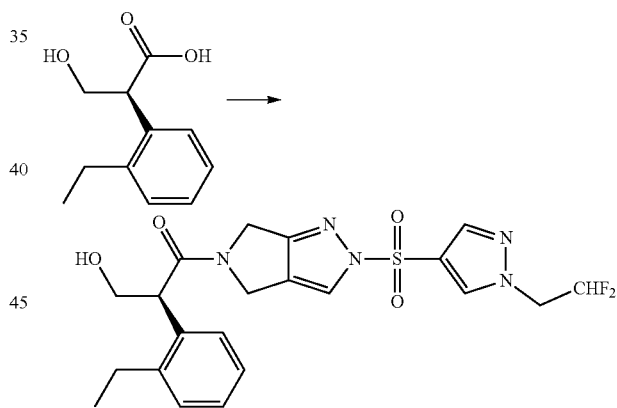

Into a 8 mL vial were added (2S)-2-(2-ethylphenyl)-3-hydroxypropanoic acid (100 mg, 0.515 mmol, 1 eq.) and DMF (2 mL). To the above mixture was added 1-(2,2-difluoroethyl)-4-{4H,5H,6H-pyrrolo[3,4-c]pyrazole-2-sulfonyl}pyrazole (234.22 mg, 0.772 mmol, 1.5 eq.), DIEA (199.63 mg, 1.545 mmol, 3.0 eq.) and HATU (254.49 mg, 0.670 mmol, 1.3 eq.). The resulting mixture was stirred for additional 1 h at room temperature. The crude product was purified by Prep-HPLC using the following conditions (SunFire Prep C18 OBD Column, 50×250 mm, 5um; mobile phase, phase A: H$_2$O (0.1% FA); phase B: CH$_3$CN (10% B up to 50% B in 12 min) to afford (2S)-1-{2-[1-(2,2-difluoroethyl)pyrazol-4-ylsulfonyl]-4H,6H-pyrrolo[3,4-c]pyrazol-5-yl}-2-(2-ethylphenyl)-3-hydroxypropan-1-one (150 mg, 60.76%) as a white solid. ¹HNMR (300 MHz, DMSO-d6) δ 8.70 (d, J=3.2 Hz, 1H), 8.16 (d, J=10.8 Hz, 1H), 8.10 (s, 1H), 7.29-7.14 (m, 3H), 7.12 (td, J=7.3, 1.8 Hz, 1H), 6.41 reduced pressure. This resulted in lithium (2-ethylphenyl)acetic acid (8.1 g, 79.93%) as a white solid. LCMS (ES) [M−1]m/z: 163.

(tt, J=55.5, 4.0 Hz, 1H), 4.90 (dd, J=25.3, 13.9 Hz, 1H), 4.79-4.62 (m, 2H), 4.58-4.34 (m, 2H), 4.22-4.08 (m, 1H), 4.09-3.89 (m, 2H), 3.44 (dd, J=10.3, 4.5 Hz, 1H), 2.79 (p, J=7.4 Hz, 2H), 1.24 (td, J=7.5, 3.0 Hz, 3H). LCMS (ES) [M+1]+ m/z 480. RT1 (min): 4.278.

Example 1.97

Synthesis of (R)-1-(2-((1-(2,2-difluoroethyl)-1H-pyrazol-4-yl)sulfonyl)-2,6-dihydropyrrolo[3,4-c]pyrazol-5(4H)-yl)-2-(2-ethylphenyl)-3-hydroxypropan-1-one (Compound 106)

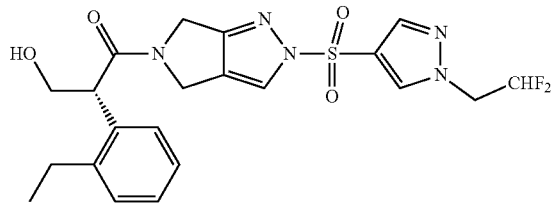 [SMILES: CCc1ccccc1[C@H](CO)C(=O)N1Cc2cn(S(=O)(=O)c3cnn(CC(F)F)c3)nc2C1]

The title compound was synthesized following the procedures reported in the synthesis of Compound 105, using (4S)-4-benzyl-1,3-oxazolidin-2-one in Step 5 instead of (4R)-4-benzyl-1,3-oxazolidin-2-one. ¹H NMR (400 MHz, DMSO-d6): δ 8.70 (d, J=3.2 Hz, 1H), 8.16 (d, J=10.8 Hz, 1H), 8.10 (s, 1H), 7.29-7.14 (m, 3H), 7.12 (td, J=7.3, 1.8 Hz, 1H), 6.41 (ddt, J=55.0, 52.2, 3.0 Hz, 1H), 4.90 (dd, J=25.3, 13.9 Hz, 1H), 4.71 (tt, J=15.0, 3.3 Hz, 2H), 4.58-4.34 (m, 2H), 4.22-4.08 (m, 1H), 4.09-3.89 (m, 2H), 3.44 (dd, J=10.3, 4.5 Hz, 1H), 2.89-2.71 (m, 2H), 1.24 (td, J=7.5, 3.0 Hz, 3H). LCMS (ES) [M+1]+ m/z: 480. RT1 (min): 3.049.

Example 1.98

Synthesis of (2S)-2-(2-chlorophenyl)-1-{2-[1-(2,2-difluoroethyl)-1,2,4-triazol-3-ylsulfonyl]-4H,6H-pyrrolo[3,4-c]pyrazol-5-yl}-3-hydroxypropan-1-one (Compound 107)

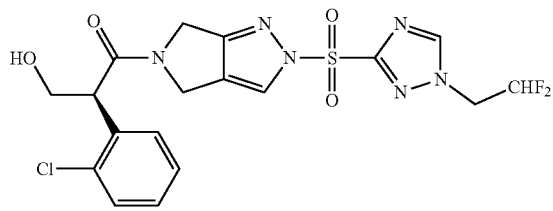 [SMILES: O=C([C@H](CO)c1ccccc1Cl)N1Cc2cn(S(=O)(=O)c3ncn(CC(F)F)n3)nc2C1]

Step 1

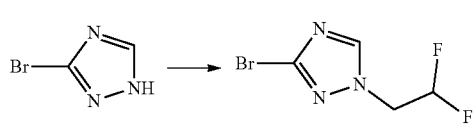 [SMILES: Brc1nc[nH]n1 ; FC(F)Cn1cnc(Br)n1]

Into a 500 mL round-bottom flask were added 3-bromo-1H-1,2,4-triazole (15.00 g, 101.38 mmol, 1.00 eq.), CH₃CN (200.00 mL), Cs₂CO₃ (66.06 g, 202.75 mmol, 2.00 eq.) and 2,2-difluoroethyl trifluoromethanesulfonate (26.05 g, 121.65 mmol, 1.20 eq.) at room temperature. The resulting mixture was stirred for 2 h at room temperature. The resulting mixture was filtered, the filter cake was washed with acetonitrile (3×100 mL). The filtrate was concentrated under reduced pressure. The residue was purified by silica gel column chromatography, eluted with THF/PE (10:100) to afford 3-bromo-1-(2,2-difluoroethyl)-1,2,4-triazole (10 g, 46.53%) as yellow oil. LCMS (ES) [M+1]+ m/z: 212.

Step 2

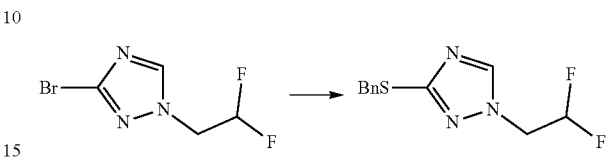

Into a 500 mL round-bottom flask were added 3-bromo-1-(2,2-difluoroethyl)-1,2,4-triazole (10.00 g, 47.17 mmol, 1.00 eq.), Toluene (150.00 mL), benzyl mercaptan (17.58 g, 141.51 mmol, 3.00 eq.), BINAP (5.87 g, 9.43 mmol, 0.20 eq.), DIEA (18.29 g, 141.51 mmol, 3.00 eq.) and Pd₂(dba)₃CHCl₃ (4.88 g, 4.72 mmol, 0.10 eq.) at room temperature. The resulting mixture was stirred for overnight at 100° C. under nitrogen atmosphere. The mixture was allowed to cool down to room temperature. The resulting mixture was concentrated under reduced pressure. The residue was purified by silica gel column chromatography, eluted with THF/PE (10:100) to afford 3-(benzylsulfanyl)-1-(2,2-difluoroethyl)-1,2,4-triazole (8 g, 66.43%) as yellow oil. LCMS (ES) [M+1]+ m/z: 256.

Step 3

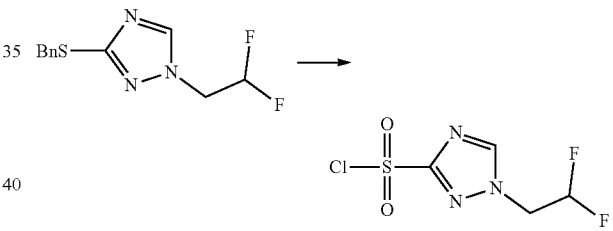

Into a 250 mL round-bottom flask were added 3-(benzylsulfanyl)-1-(2,2-difluoroethyl)-1,2,4-triazole (5.00 g, 19.59 mmol, 1.00 eq.), HOAc (54.00 mL), H₂O (6.00 mL) and NCS (7.85 g, 58.76 mmol, 3.00 eq.) at room temperature. The resulting mixture was stirred for 2 h at room temperature. The resulting mixture was concentrated under reduced pressure. The residue was purified by silica gel column chromatography, eluted with THF/PE (16:100) to afford 1-(2,2-difluoroethyl)-1,2,4-triazole-3-sulfonyl chloride (3.5 g, 77.16%) as white solid. LCMS (ES) [M−Cl+OH−1]− m/z: 212.

Step 4

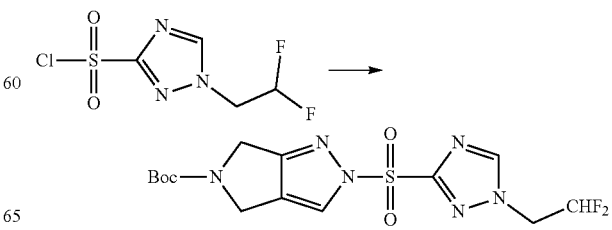

Into a 250 mL 3-necked round-bottom flask were added tert-butyl 2H,4H,6H-pyrrolo[3,4-c]pyrazole-5-carboxylate (2.50 g, 11.95 mmol, 1.00 eq.) and THF (40.00 mL) at room temperature. To a stirred solution was added NaH (0.43 g, 17.92 mmol, 1.50 eq.) in portions at 0° C. The resulting mixture was stirred for 0.5 h at 0° C. To a stirred solution was added 1-(2,2-difluoroethyl)-1,2,4-triazole-3-sulfonyl chloride (3.04 g, 13.14 mmol, 1.10 eq.) in portions at 0° C. The resulting mixture was stirred for 1 h at 0° C. The reaction was quenched by the addition of Water/Ice (50 mL) at 0° C. The resulting mixture was extracted with CH$_2$Cl$_2$ (3×50 mL). The combined organic layers were dried over anhydrous Na$_2$SO$_4$. After filtration, the filtrate was concentrated under reduced pressure. The precipitated solids were collected by filtration and washed with diethyl ether (3×30 mL). This resulted in tert-butyl 2-[1-(2,2-difluoroethyl)-1,2,4-triazol-3-ylsulfonyl]-4H,6H-pyrrolo[3,4-c]pyrazole-5-carboxylate (2 g, 41.40%) as white solid. LCMS (ES) [M+1]$^+$ m/z: 405.

Step 5

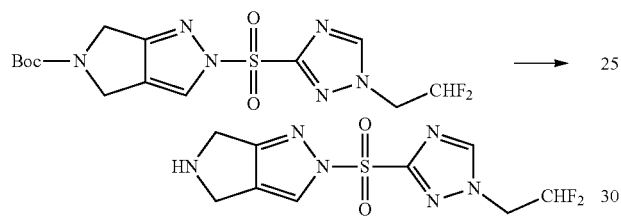

Into a 100 mL round-bottom flask were added tert-butyl 2-[1-(2,2-difluoroethyl)-1,2,4-triazol-3-ylsulfonyl]-4H,6H-pyrrolo[3,4-c]pyrazole-5-carboxylate (2.00 g, 4.95 mmol, 1.00 eq.), DCM (20.00 mL) and lutidine (2.12 g, 19.78 mmol, 4.00 eq.) at room temperature. To a stirred solution was added TMSOTf (3.30 g, 14.84 mmol, 3.00 eq.) drop wise at 0° C. The resulting mixture was stirred for 1 h at 0° C. The reaction was quenched with MeOH at 0° C. The resulting mixture was concentrated under reduced pressure. The crude product (4 g) was purified by Prep-HPLC using the following conditions: Column, XBridge Prep C18 OBD Column, 19 cm, 150 mm, 5 m; mobile phase, Water (0.05% FA) and CAN (5% Phase B up to 20% in 10 min); Detector, 254. This resulted in 1-(2,2-difluoroethyl)-3-{4H,5H,6H-pyrrolo[3,4-c]pyrazole-2-sulfonyl}-1,2,4-triazole (1.2 g, 79.74%) as yellow solid. LCMS (ES) [M−46+1]$^+$ m/z: 305.

Step 6

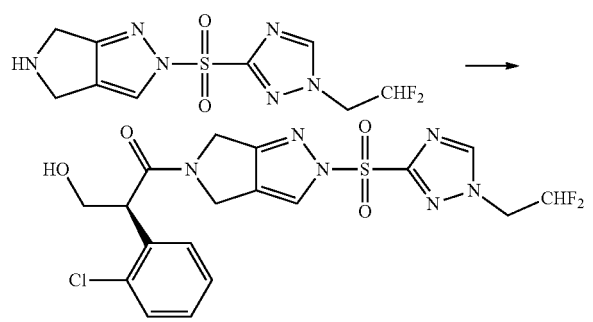

Into a 20 mL vial were added (2S)-2-(2-chlorophenyl)-3-hydroxypropanoic acid (90.00 mg, 0.45 mmol, 1.00 eq.), 1-(2,2-difluoroethyl)-3-{4H,5H,6H-pyrrolo[3,4-c]pyrazole-2-sulfonyl}-1,2,4-triazole (136.50 mg, 0.45 mmol, 1.00 eq.), DMF (5.00 mL) and NMM (136.13 mg, 1.35 mmol, 3.00 eq.) at room temperature. To a stirred solution was added HATU (204.69 mg, 0.54 mmol, 1.20 eq.) in portions at 0° C. The resulting mixture was stirred for 1 h at room temperature. The crude product was purified by Prep-HPLC using the following conditions: Column, XBridge Shield RP18 OBD Column, 19*150 mm, 5 μm; mobile phase, Water (10 mmol/L NH$_4$HCO$_3$+0.1% NH$_3$.H$_2$O) and ACN (15% ACN up to 70% in 9 min); Detector, 254. This resulted in (2S)-2-(2-chlorophenyl)-1-{2-[1-(2,2-difluoroethyl)-1,2,4-triazol-3-ylsulfonyl]-4H,6H-pyrrolo[3,4-c]pyrazol-5-yl}-3-hydroxypropan-1-one (130.3 mg, 59.66%) as white solid. $^1$H NMR (300 MHz, DMSO-d$_6$) δ 8.92 (s, 1H), 8.31 (s, 1H), 7.55-7.39 (m, 2H), 7.31 (tdd, J=8.1, 6.1, 3.2 Hz, 2H), 6.80-6.12 (m, 1H), 5.04-4.88 (m, 3H), 4.94-4.83 (m, 1H), 4.59-4.28 (m, 4H), 3.98 (dddd, J=10.9, 8.7, 5.9, 2.7 Hz, 1H), 3.59 (ddd, J=10.6, 5.4, 4.1 Hz, 1H). LCMS (ES) [M+1]$^+$ m/z: 487.

Example 1.99

Synthesis of (2R)-2-(2-chlorophenyl)-1-{2-[1-(2,2-difluoroethyl)-1,2,4-triazol-3-ylsulfonyl]-4H,6H-pyrrolo[3,4-c]pyrazol-5-yl}-3-hydroxypropan-1-one (Compound 108)

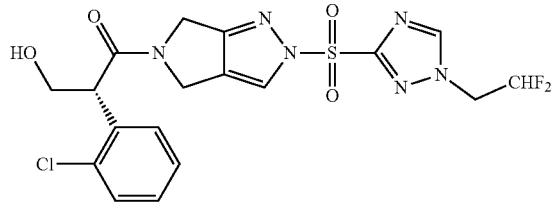 [SMILES: O=C([C@@H](CO)c1ccccc1Cl)N1Cc2cn(S(=O)(=O)c3ncn(CC(F)F)n3)nc2C1]

Into a 20 mL vial were added (2R)-2-(2-chlorophenyl)-3-hydroxypropanoic acid (90.00 mg, 0.45 mmol, 1.00 eq.), 1-(2,2-difluoroethyl)-3-{4H,5H,6H-pyrrolo[3,4-c]pyrazole-2-sulfonyl}-1,2,4-triazole (136.50 mg, 0.45 mmol, 1.00 eq.), DMF (5.00 mL) and NMM (136.13 mg, 1.35 mmol, 3.00 eq.) at room temperature. To a stirred solution was added HATU (204.69 mg, 0.54 mmol, 1.20 eq.) in portions at 0° C. The resulting mixture was stirred for 1 h at room temperature. The crude product was purified by Prep-HPLC using the following conditions: Column, XBridge Shield RP18 OBD Column, 19*150 mm, 5 μm; mobile phase, Water (10 mmol/L NH$_4$HCO$_3$+0.1% NH$_3$.H$_2$O) and ACN (15% ACN up to 70% in 9 min); Detector, 254. This resulted in (2R)-2-(2-chlorophenyl)-1-{2-[1-(2,2-difluoroethyl)-1,2,4-triazol-3-ylsulfonyl]-4H,6H-pyrrolo[3,4-c]pyrazol-5-yl}-3-hydroxypropan-1-one (124.4 mg, 56.95%) as white solid. $^1$H NMR (300 MHz, DMSO-d$_6$) δ 8.91 (s, 1H), 8.31 (d, J=1.4 Hz, 1H), 7.55-7.40 (m, 2H), 7.39-7.23 (m, 2H), 6.69-6.29 (m, 1H), 5.04-4.83 (m, 4H), 4.59-4.46 (m, 1H), 4.51-4.36 (m, 2H), 4.34 (dd, J=14.3, 6.6 Hz, 1H), 3.97 (ddq, J=10.5, 5.9, 2.7 Hz, 1H), 3.65-3.51 (m, 1H). LCMS (ES) [M+1]$^+$ m/z: 487.

Example 1.100

Synthesis of (S)-1-(2-((1-(2,2-difluoroethyl)-1H-pyrazol-4-yl)sulfonyl)-2,6-dihydropyrrolo[3,4-c]pyrazol-5(4H)-yl)-3-hydroxy-2-(2-(2-hydroxyethoxy)phenyl)propan-1-one and (R)-1-(2-((1-(2,2-difluoroethyl)-1H-pyrazol-4-yl)sulfonyl)-2,6-dihydropyrrolo[3,4-c]pyrazol-5(4H)-yl)-3-hydroxy-2-(2-(2-hydroxyethoxy)phenyl)propan-1-one (Compounds 109 and 110)

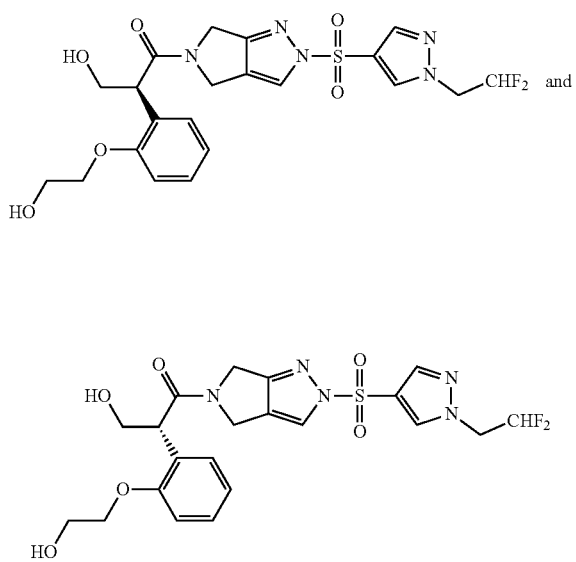

Step 1

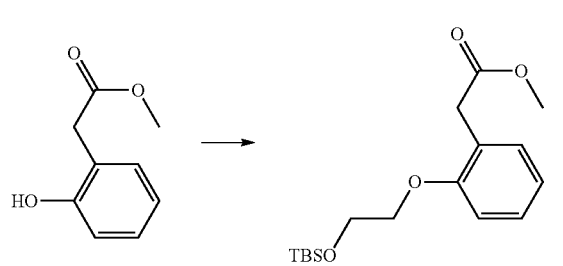 [SMILES: COC(=O)Cc1ccccc1O ; COC(=O)Cc1ccccc1OCCO[Si](C)(C)C(C)(C)C]

Into a 250 mL round-bottom flask were added methyl 2-(2-hydroxyphenyl)acetate (10 g, 60.177 mmol, 1 eq.), DMF (100 mL), K$_2$CO$_3$ (12.48 g, 90.266 mmol, 1.5 eq.), (2-bromoethoxy)(tert-butyl)dimethylsilane (21.59 g, 90.266 mmol, 1.5 eq.) and KI (5.0 g, 30.120 mmol, 0.50 eq.) at room temperature. The resulting mixture was stirred for 16 hs overnight at 70° C. The resulting mixture was concentrated under reduced pressure. The residue was purified by silica gel column chromatography, eluted with PE/EA (5/1) to afford methyl 2-(2-{2-[(tert-butyldimethylsilyl)oxy]ethoxy}phenyl)acetate (3.5 g, 17.92%) as a yellow oil. LCMS (ES) [M+1]$^+$ m/z: 325.

Step 2

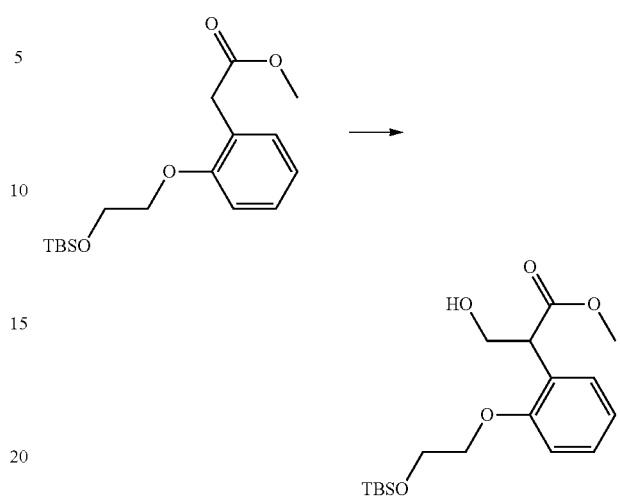

Into a 100 mL 3-necked round-bottom flask were added methyl 2-(2-{2-[(tert-butyldimethylsilyl)oxy]ethoxy}phenyl)acetate (1.5 g, 4.623 mmol, 1 eq.) and DMF (60 mL) at room temperature. To the above mixture was added NaOMe (0.02 g, 0.462 mmol, 0.1 eq.), (HCHO)n (0.14 g, 4.623 mmol, 1.0 eq.) at 0° C. The resulting mixture was stirred for additional 1 h at 0° C. The reaction was quenched with water. The resulting mixture was extracted with EtOAc and the organic layer was concentrated under reduced pressure. The residue was purified by silica gel column chromatography, eluted with EA/PE (1/4) to afford methyl 2-(2-{2-[(tert-butyldimethylsilyl)oxy]ethoxy}phenyl)-3-hydroxypropanoate (720 mg, 43.93%) as a yellow oil. LCMS (ES) [M+1]$^+$ m/z: 355.

Step 3

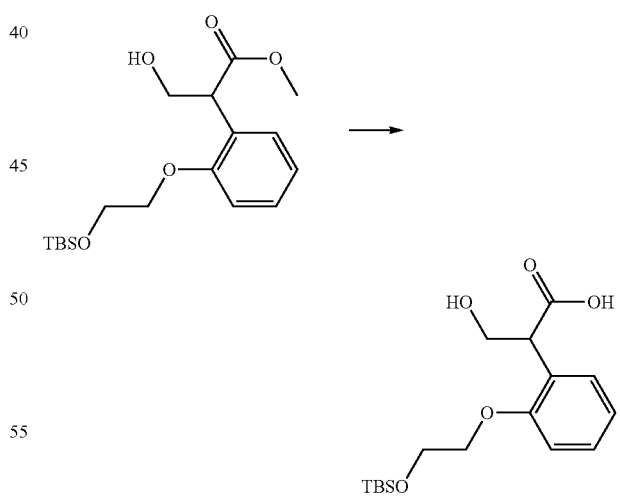

Into a 40 mL vial were added methyl 2-(2-{2-[(tert-butyldimethylsilyl)oxy]ethoxy}phenyl)-3-hydroxypropanoate (720 mg, 2.031 mmol, 1.0 eq.), THF (10 mL), H$_2$O (2.5 mL) and LiOH—H$_2$O (170.44 mg, 4.062 mmol, 2.0 eq.) at room temperature. The resulting mixture was stirred for 3 h at room temperature. The mixture was acidified to pH 4 with 2 M HCl. The resulting mixture was extracted with DCM (3×15 ml), dried over anhydrous Na$_2$SO$_4$. After filtration, the filtrate was concentrated under reduced pressure. This resulted in lithium 2-(2-{2-[(tert-butyldimethylsilyl)oxy]ethoxy}phenyl)-3-hydroxypropanoic acid (445 mg, 64.35%) as a white solid. LCMS (ES) [M−1]⁻ m/z: 339.

Step 4

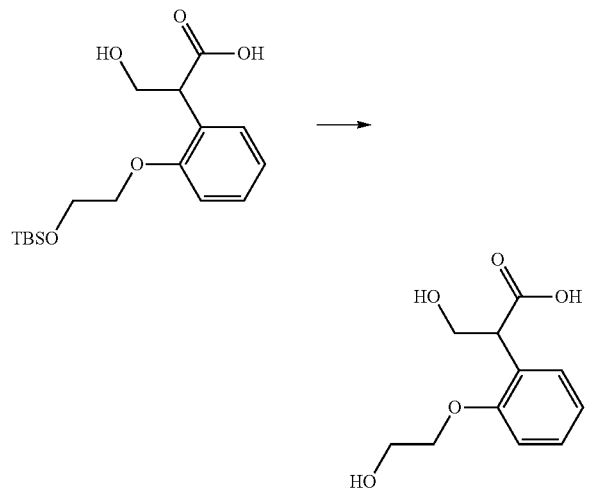

Into a 20 mL vial were added 2-(2-{2-[(tert-butyldimethylsilyl)oxy]ethoxy}phenyl)-3-hydroxypropanoic acid (400 mg, 1.175 mmol, 1 eq.), DCM (10 mL), TEA-3HF (1.893 g, 11.750 mmol, 10.0 eq.) and LiOH (128 mg, 5.345 mmol, 2.00 eq.) at room temperature. The resulting mixture was stirred for 4 h at room temperature. The resulting mixture was concentrated under reduced pressure. This resulted in lithium 3-hydroxy-2-[2-(2-hydroxyethoxy)phenyl]propanoic acid (320 mg crude) as a yellow oil. LCMS (ES) [M+1]⁺ m/z: 227.

Step 5

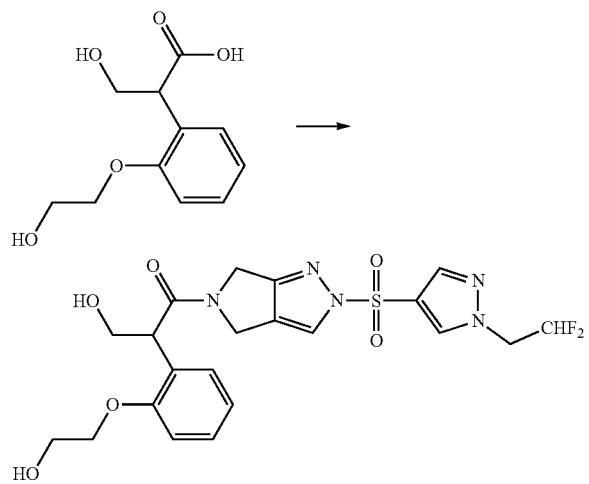

Into a 20 mL vial were added 3-hydroxy-2-[2-(2-hydroxyethoxy)phenyl]propanoic acid (300 mg, 1.326 mmol, 1.0 eq.), DMF (5 mL), 1-(2,2-difluoroethyl)-4-{4H,5H,6H-pyrrolo[3,4-c]pyrazole-2-sulfonyl}pyrazole (603.29 mg, 1.989 mmol, 1.5 eq.), DIEA (514.18 mg, 3.978 mmol, 3.0 eq.) and HATU (655.50 mg, 1.724 mmol, 1.3 eq.) at room temperature. The resulting mixture was stirred for 2 h at room temperature. The crude product was purified by Prep-HPLC using the following conditions (Prep-HPLC-001): Column, Sunfire Prep C18 OBD Column, 50*250 mm, 10 μm 10 nm; mobile phase, Water (0.1% FA) and ACN (20% ACN up to 55% in 12 min). This resulted in 1-{2-[1-(2,2-difluoroethyl)pyrazol-4-ylsulfonyl]-4H,6H-pyrrolo[3,4-c]pyrazol-5-yl}-3-hydroxy-2-[2-(2-hydroxyethoxy)phenyl]propan-1-one (250 mg, 36.86%) as a white solid. LCMS (ES) [M+1]⁺ m/z: 512.

Step 6

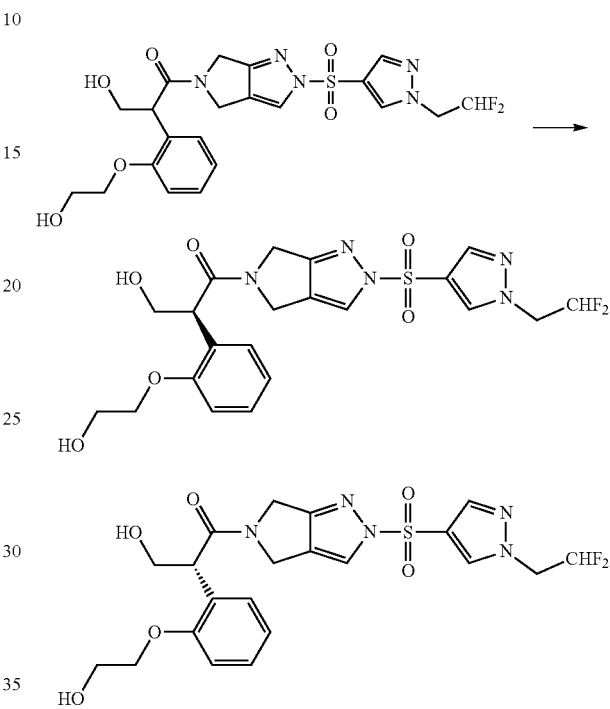

1-{2-[1-(2,2-difluoroethyl)pyrazol-4-ylsulfonyl]-4H,6H-pyrrolo[3,4-c]pyrazol-5-yl}-3-hydroxy-2-[2-(2-hydroxyethoxy)phenyl]propan-1-one (200 mg, 0.391 mmol, 1 eq.). Column: (R,R)-WHELK-01-Kromasil, 2.11*25 cm, 5 m; Mobile Phase A: Hex:DCM=3:1 (0.5% 2M NH3-MeOH)—HPLC, Mobile Phase B: EtOH—HPLC; Flow rate: 25 mL/min; Gradient: 20% B to 20% B in 25 min; Wave Length: 220/254 nm; RT1 (min): 15; RT2 (min): 17; Sample Solvent: EtOH-HPLC; Injection Volume: 0.5 mL; Number Of Runs: 24. This resulted in the isolation of two isomers: Stereoisomer 17 (100 mg, 50.00%) as an off white solid, RT1 (min): 6.050. ¹H NMR (300 MHz, DMSO-d6) δ 8.71 (d, J=1.9 Hz, 1H), 8.17 (d, J=5.6 Hz, 1H), 8.12 (t, J=0.9 Hz, 1H), 7.28-7.15 (m, 2H), 6.99 (d, J=8.2 Hz, 1H), 6.89 (t, J=7.4 Hz, 1H), 6.42 (tt, J=54.5, 3.6 Hz, 1H), 4.93-4.63 (m, 5H), 4.58-4.29 (m, 4H), 4.00 (ddd, J=19.1, 9.3, 5.5 Hz, 3H), 3.79-3.70 (m, 2H), 3.65-3.43 (m, 1H). LCMS (ES) [M+1]⁺ m/z: 512.

Stereoisomer 18 (100 mg, 50.00%) as an off white solid, RT1 (min): 6.889. ¹H NMR (300 MHz, DMSO-d6) δ 8.71 (d, J=1.9 Hz, 1H), 8.17 (d, J=5.6 Hz, 1H), 8.12 (t, J=0.9 Hz, 1H), 7.28-7.15 (m, 2H), 6.99 (d, J=8.2 Hz, 1H), 6.89 (t, J=7.4 Hz, 1H), 6.42 (tt, J=54.5, 3.6 Hz, 1H), 4.93-4.63 (m, 5H), 4.58-4.29 (m, 4H), 4.00 (ddd, J=19.1, 9.3, 5.5 Hz, 3H), 3.79-3.70 (m, 2H), 3.65-3.43 (m, 1H). LCMS (ES) [M+1]⁺ m/z: 512.

Example 1.101

Synthesis of (2S)-1-{2-[1-ethyl-5-(trifluoromethyl)pyrazol-4-ylsulfonyl]-4H,6H-pyrrolo[3,4-c]pyrazol-5-yl}-3-hydroxy-2-phenylpropan-1-one (Compound 111)

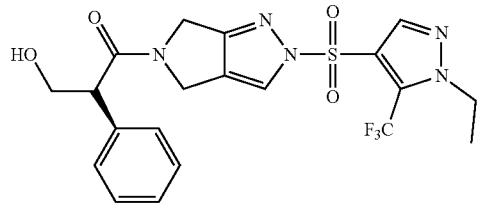

Step 1

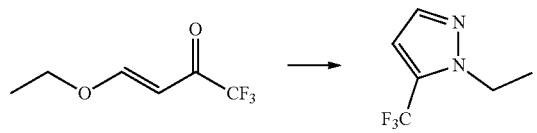

A solution of ethylhydrazine oxalic acid salt (23.22 g, 154.65 mmol, 1.30 eq.) in H₂O (105 mL) was stirred for 10 min at 60° C. under nitrogen atmosphere. A solution of (3E)-4-ethoxy-1,1,1-trifluorobut-3-en-2-one (20 g, 118.96 mmol, 1.00 eq.) in MeOH (150 mL) was added. The resulting mixture was stirred for 4 h at 60° C. The reaction mixture was cooled to room temperature, diluted with H₂O (500 mL), extracted with EtOEt (4×200 mL). The combined organic layer was washed with brine (500 mL), dried over anhydrous Na₂SO₄. After filtration, the filtrate was concentrated under reduced pressure. The crude product 1-ethyl-5-(trifluoromethyl)pyrazole (15 g) (regioisomer contained) was used to the next step directly without further purification. LCMS (ES) [M+1]⁺ m/z: 165.

Step 2

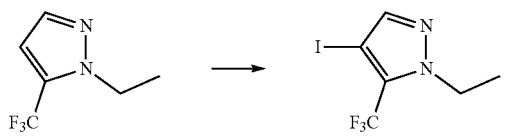

To a stirred solution of 1-ethyl-5-(trifluoromethyl)pyrazole (15 g, 91.39 mmol, 1.0 eq.) in AcOH (80 mL) were added a solution of NIS (24.67 g, 109.66 mmol, 1.2 eq.) in TFA (80 mL) drop wise at room temperature. The resulting mixture was stirred for 3 h at 80° C. The mixture was allowed to cool down to room temperature and quenched with NaHSO₃ (10%, 100 mL). The mixture was basified to pH 7 with 2 M NaOH, extracted with EtOEt (3×100 mL). The combined organic layer was washed with brine (300 mL), dried over anhydrous Na₂SO₄. After filtration, the filtrate was concentrated under reduced pressure. The residue was purified by silica gel column chromatography, eluted with PE/EA (10:1) to afford 1-ethyl-4-iodo-5-(trifluoromethyl)pyrazole (9.0 g, 33.9%) (the regioisomer was avoid) as a light yellow oil. ¹HNMR (300 MHz, DMSO-d₆) δ 7.79 (s, 1H), 4.33 (q, J=7.5 Hz, 2H), 1.36 (t, J=7.2 Hz, 3H). LCMS (ES) [M+1]⁺ m/z: 291.

Step 3

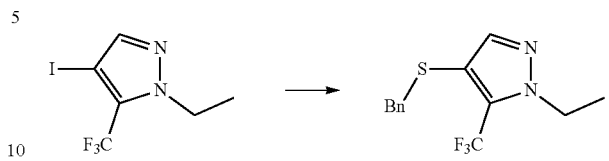

To a stirred mixture of 1-ethyl-4-iodo-5-(trifluoromethyl)pyrazolidine (9.0 g, 30.60 mmol, 1.0 eq.) and benzyl mercaptan (7.6 g, 61.21 mmol, 2.0 eq.) in toluene (150 mL) were added Pd₂(dba)₃ (2.8 g, 3.06 mmol, 0.1 eq.), XantPhos (3.5 g, 6.12 mmol, 0.2 eq.) and DIEA (11.8 g, 91.81 mmol, 3.0 eq.). The resulting mixture was stirred for 5 h at 80° C. under nitrogen atmosphere. The mixture was cooled down to room temperature and concentrated to remove the solvent. The residue was purified by silica gel column chromatography, eluted with PE/EA (50:1) to afford 4-(benzylsulfanyl)-1-ethyl-5-(trifluoromethyl)pyrazole (6.8 g, 77.6%) as a light yellow oil. LCMS (ES) [M+1]⁺ m/z: 287.

Step 4

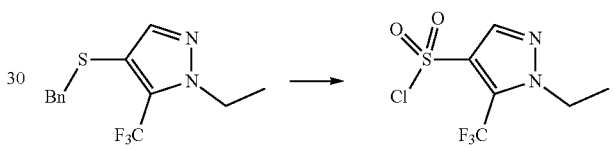

To a stirred solution of 4-(benzylsulfanyl)-1-ethyl-5-(trifluoromethyl)pyrazole (6.8 g, 23.75 mmol, 1.0 eq.) in AcOH (90 mL) and H₂O (10 mL) was added NCS (9.5 g, 71.25 mmol, 3.0 eq.) in portions at room temperature. The resulting mixture was stirred for 2 h at room temperature. The resulting mixture was concentrated, the residue was diluted with DCM (100 mL). The resulting mixture was filtered, the filter cake was washed with DCM (50 mL). The filtrate was concentrated under reduced pressure. The residue was purified by silica gel column chromatography, eluted with PE/THF (50:1) to afford 1-ethyl-5-(trifluoromethyl)pyrazole-4-sulfonyl chloride (6.0 g, 91.5%) as a colorless oil. LCMS (ES) [M−Cl+OH−1]⁺ m/z: 243.

Step 5

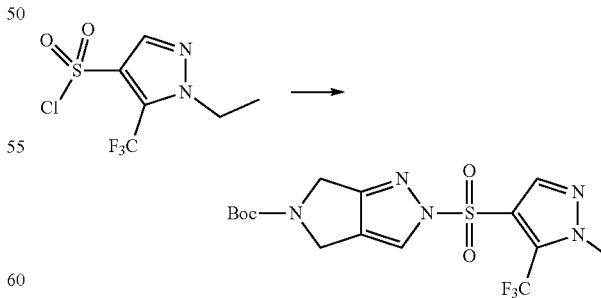

To a stirred solution of tert-butyl 2H,4H,6H-pyrrolo[3,4-c]pyrazole-5-carboxylate (3.6 g, 17.13 mmol, 1.0 eq.) in DMF (60 mL) was added NaH (60% in mineral oil) (1.0 g, 25.70 mmol, 1.5 eq.) in portions at 0° C. under nitrogen atmosphere. The resulting mixture was stirred for 30 min at 0° C. To the above mixture was added a solution of 1-ethyl-5-(trifluoromethyl)pyrazole-4-sulfonyl chloride (4.5 g, 17.13 mmol, 1.0 eq.) in DMF (10 mL) drop wise at 0° C. The resulting mixture was stirred for 2 h at the same temperature. The reaction was quenched with sat. NH₄Cl (aq.), extracted with EtOAc (3×50 mL). The combined organic layer was washed with brine (60 mL), dried over anhydrous Na₂SO₄. After filtration, the filtrate was concentrated under reduced pressure. The residue was purified by silica gel column chromatography, eluted with PE/EA (3:1) to afford the crude product. The crude product was further purified by trituration with mixed solvent PE/EA (3:1) (100 mL). This resulted in tert-butyl 2-[1-ethyl-5-(trifluoromethyl)pyrazol-4-ylsulfonyl]-4H,6H-pyrrolo[3,4-c]pyrazole-5-carboxylate (3.2 g, 42.8%) as a light yellow solid. LCMS (ES) [M+1]⁺ m/z: 436.

Step 6

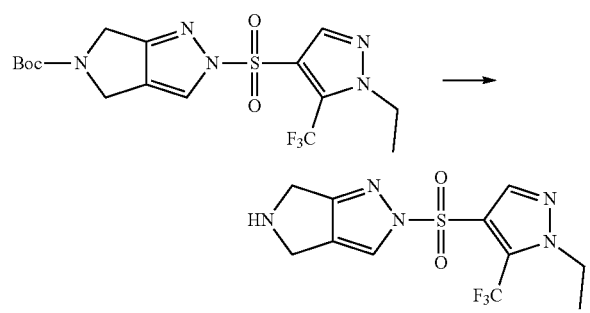

To a stirred solution of tert-butyl 2-[1-ethyl-5-(trifluoromethyl)pyrazol-4-ylsulfonyl]-4H,6H-pyrrolo[3,4-c]pyrazole-5-carboxylate (3.2 g, 7.34 mmol, 1.0 eq.) in DCM (50 mL) was added 2,6-dimethylpyridine (3.1 g, 29.39 mmol, 4.0 eq.). To the above mixture was added TMSOTf (4.9 g, 22.07 mmol, 3.0 eq.) drop wise at 0° C. The resulting mixture was stirred for 2 h at room temperature, diluted with H₂O (50 mL). The mixture was basified to pH 7 with saturated Na₂CO₃ (aq.). The resulting mixture was extracted with CH₂Cl₂ (3×30 mL). The combined organic layers were washed with brine (50 mL), dried over anhydrous Na₂SO₄. After filtration, the filtrate was concentrated under reduced pressure. The residue was purified by reverse flash chromatography using the following conditions: column, C18-120 g, mobile phase, CH₃CN in water, 10% to 50% gradient in 10 min, detector, UV 254 nm. This resulted in 1-ethyl-4-{4H,5H,6H-pyrrolo[3,4-c]pyrazole-2-sulfonyl}-5-(trifluoromethyl)pyrazole (2.0 g, 81.1%) as a white solid. LCMS (ES) [M+1]⁺ m/z: 336.

Step 7

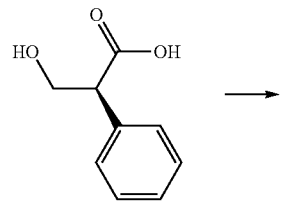

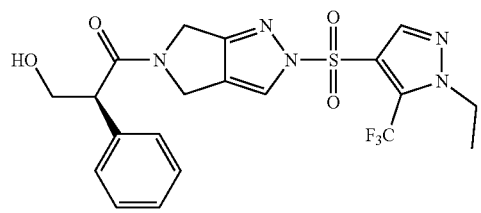

To a stirred solution of 1-ethyl-4-{4H,5H,6H-pyrrolo[3,4-c]pyrazole-2-sulfonyl}-5-(trifluoromethyl)pyrazole (220 mg, 0.65 mmol, 1.00 eq.) and (S)-tropic acid (109 mg, 0.65 mmol, 1.0 eq.) in DMF (5 mL) was added NMM (199 mg, 1.96 mmol, 3.0 eq.). To the above mixture was added HATU (299 mg, 0.78 mmol, 1.2 eq.) in portions at 0° C. The resulting mixture was stirred for 1 h at 0° C. The resulting mixture was diluted with H₂O (50 mL), extracted with EtOAc (3×20 mL). The combined organic layer was washed with brine (20 mL), dried over anhydrous Na₂SO₄. After filtration, the filtrate was concentrated under reduced pressure. The crude product was purified by Prep-HPLC using the following conditions: XBridge Prep C¹⁸ OBD Column, 19*150 mm, 5 um, mobile phase, water (0.1% FA) and CH₃CN (30% Phase B up to 40% in 7 min), Detector, UV 254 nm. This resulted in (2S)-1-{2-[1-ethyl-5-(trifluoromethyl)pyrazol-4-ylsulfonyl]-4H,6H-pyrrolo[3,4-c]pyrazol-5-yl}-3-hydroxy-2-phenylpropan-1-one (117.1 mg, 36.9%) as a white solid. ¹H NMR (300 MHz, DMSO-d₆) δ 8.24 (d, J=1.2 Hz, 1H), 8.20 (s, 1H), 7.42-7.20 (m, 5H), 4.90 (t, J=15.1 Hz, 1H), 4.57-4.29 (m, 5H), 4.07-3.93 (m, 2H), 3.61-3.46 (m, 1H), 1.39 (t, J=7.2 Hz, 3H). LCMS (ES) [M+1]⁺ m/z: 484.

Example 1.102

Synthesis of (2R)-1-{2-[1-ethyl-5-(trifluoromethyl)pyrazol-4-ylsulfonyl]-4H,6H-pyrrolo[3,4-c]pyrazol-5-yl}-3-hydroxy-2-phenylpropan-1-one (Compound 112)

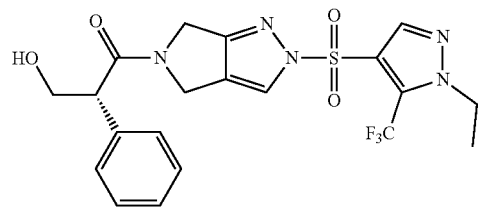 [SMILES: CCn1ncc(S(=O)(=O)n2cc3c(n2)CN(C(=O)[C@@H](CO)c2ccccc2)C3)c1C(F)(F)F]

The title compound was synthesized according to the procedure described in Step 7, in the synthesis of Compound 112 using (R)-tropic acid. (2R)-1-{2-[1-Ethyl-5-(trifluoromethyl)pyrazol-4-ylsulfonyl]-4H,6H-pyrrolo[3,4-c]pyrazol-5-yl}-3-hydroxy-2-phenylpropan-1-one was isolated as a white solid. ¹H NMR (300 MHz, DMSO-d₆) δ 8.24 (d, J=1.2 Hz, 1H), 8.20 (s, 1H), 7.42-7.17 (m, 5H), 4.90 (t, J=15.1 Hz, 1H), 4.57-4.29 (m, 5H), 4.07-3.93 (m, 2H), 3.60-3.46 (m, 1H), 1.39 (t, J=7.2 Hz, 3H). LCMS (ES) [M+1]⁺ m/z: 484.

Example 1.103

Synthesis of (2S)-3-hydroxy-1-(2-{[1-(oxolan-3-yl)-1H-pyrazol-4-yl]sulfonyl}-2H,4H,5H,6H-pyrrolo[3,4-c]pyrazol-5-yl)-2-phenylpropan-1-one (Compound 113)

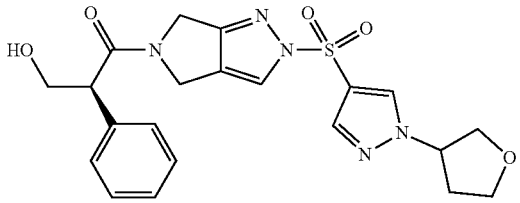 [SMILES: O=C([C@H](CO)c1ccccc1)N1Cc2cn(S(=O)(=O)c3cnn(C4CCOC4)c3)nc2C1]

The title compound was synthesized according the 3-step procedure described for Compound 15 using 1-(oxolan-3-yl)-1H-pyrazole-4-sulfonyl chloride instead of 2,4-dimethyl-1,3-thiazole-5-sulfonyl chloride in step 1. (2S)-3-Hydroxy-1-(2-{[1-(oxolan-3-yl)-1H-pyrazol-4-yl]sulfonyl}-2H,4H,5H,6H-pyrrolo[3,4-c]pyrazol-5-yl)-2-phenylpropan-1-on was isolated as a white solid. $^1$H NMR (400 MHz, DMSO-d6) δ 8.65 (dd, J=1.9, 0.7 Hz, 1H), 8.11 (q, J=1.1 Hz, 1H), 8.01 (d, J=0.7 Hz, 1H), 7.36-7.24 (m, 4H), 7.23-7.17 (m, 1H), 5.10-5.00 (m, 1H), 4.91-4.69 (m, 2H), 4.50-4.22 (m, 3H), 4.03-3.80 (m, 5H), 3.74 (td, J=8.3, 5.4 Hz, 1H), 3.56-3.41 (m, 1H), 2.39-2.27 (m, 1H), 2.22 (dddd, J=13.2, 8.3, 5.4, 3.6 Hz, 1H). LCMS (ES) [M+1]$^+$ m/z: 458.45.

Example 1.104

Synthesis of (2S)-1-{2-[1-(2,2-difluoroethyl)pyrazol-4-ylsulfonyl]-4H,6H-pyrrolo[3,4-c]pyrazol-5-yl}-2-(2,3-difluorophenyl)-3-hydroxypropan-1-one (Compound 114)

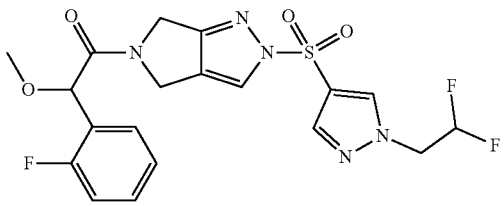 [SMILES: COC(C(=O)N1Cc2cn(S(=O)(=O)c3cnn(CC(F)F)c3)nc2C1)c1ccccc1F]

The title compound was made from 6-{2H,4H,5H,6H-pyrrolo[3,4-c]pyrazole-2-sulfonyl}-1,3-benzothiazole (Intermediate I-7, 100.00 mg; 0.33 mmol; 1.00 eq.) and 2-(2-fluorophenyl)-2-methoxyacetic acid (60.72 mg; 0.33 mmol; 1.00 eq.) following a procedure similar to that of step 6 for the synthesis of Compound 5, Example 1.9. The crude product was taken in DMSO and purified on a reverse phase silica gel with a gradient elution 0-80% MeCN in water. The fractions containing the product were combined and freeze dried to give 1-(2-{[1-(2,2-difluoroethyl)-1H-pyrazol-4-yl]sulfonyl}-2H,4H,5H,6H-pyrrolo[3,4-c]pyrazol-5-yl)-2-(2-fluorophenyl)-2-methoxyethan-1-one as a white solid (66 mg, 43%). $^1$H NMR (400 MHz, DMSO-d6) δ 8.80-8.62 (m, 1H), 8.21-8.11 (m, 1H), 7.45-7.32 (m, 2H), 7.28-7.12 (m, 2H), 6.56-6.21 (m, 1H), 5.34-5.27 (m, 1H), 4.91-4.59 (m, 4H), 4.50-4.22 (m, 2H). LCMS (ES) [M+1]$^+$ m/z: 470.2.

Example 1.105

Synthesis of 1-(2-{[1-(2,2-difluoroethyl)-1H-pyrazol-4-yl]sulfonyl}-2H,4H,5H,6H-pyrrolo[3,4-c]pyrazol-5-yl)-2-(3-fluoropyridin-2-yl)-2-methoxyethan-1-one (Compound 115)

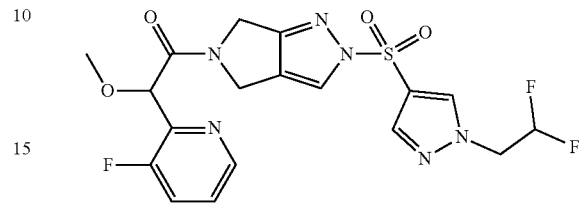

The title compound was made from 6-{2H,4H,5H,6H-pyrrolo[3,4-c]pyrazole-2-sulfonyl}-1,3-benzothiazole (Intermediate I-7, 60.00 mg; 0.20 mmol; 1.00 eq.) and lithium 2-(3-fluoropyridin-2-yl)-2-methoxyacetate (37.80 mg; 0.20 mmol; 1.00 eq.) following a procedure similar to that for the synthesis of Compound 1, Example 1.5. The crude product was taken in DMSO and purified on a reverse phase silica gel with a gradient elution 0-80% MeCN in water. The fractions containing the product were combined and freeze dried to give 1-(2-{[1-(2,2-difluoroethyl)-1H-pyrazol-4-yl]sulfonyl}-2H,4H,5H,6H-pyrrolo[3,4-c]pyrazol-5-yl)-2-(3-fluoropyridin-2-yl)-2-methoxyethan-1-one as a white solid (13 mg, 43%). $^1$H NMR (400 MHz, DMSO-d6) δ 8.69 (dd, J=2.2, 0.7 Hz, 1H), 8.36 (ddt, J=4.5, 3.0, 1.5 Hz, 1H), 8.14 (dd, J=18.0, 1.2 Hz, 1H), 8.09 (d, J=0.7 Hz, 1H), 7.74 (dddd, J=10.1, 8.4, 4.7, 1.3 Hz, 1H), 7.47 (dtd, J=8.5, 4.4, 3.2 Hz, 1H), 6.39 (tt, J=54.4, 3.6 Hz, 1H), 5.35 (d, J=9.6 Hz, 1H), 4.84 (dd, J=19.4, 14.4 Hz, 1H), 4.69 (td, J=15.1, 3.5 Hz, 2H), 4.57-4.37 (m, 2H), 4.27 (dd, J=38.4, 14.4 Hz, 1H), 3.35 (d, J=3.0 Hz, 3H). LCMS (ES) [M+1]$^+$ m/z 471.

Example 1.106

Synthesis of (2S)-1-(2-{[1-(difluoromethyl)-1H-pyrazol-4-yl]sulfonyl}-2H,4H,5H,6H-pyrrolo[3,4-c]pyrazol-5-yl)-3-hydroxy-2-phenylpropan-1-one (Compound 116)

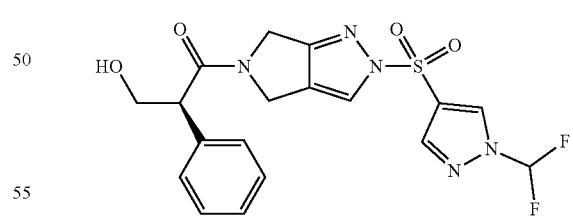

The title compound was synthesized according to the procedure described on Steps 1-3 for Compound 15 using 1-(difluoromethyl)-1H-pyrazole-4-sulfonyl chloride in step 1 instead of 2,4-dimethyl-1,3-thiazole-5-sulfonyl chloride. (2S)-1-(2-{[1-(Difluoromethyl)-1H-pyrazol-4-yl]sulfonyl}-2H,4H,5H,6H-pyrrolo[3,4-c]pyrazol-5-yl)-3-hydroxy-2-phenylpropan-1-one was isolated as a white solid. $^1$H NMR (400 MHz, DMSO-d6) δ 9.17 (dd, J=1.6, 0.7 Hz, 1H), 8.31 (s, 1H), 8.16 (q, J=1.3 Hz, 1H), 7.80 (d, J=1.7 Hz, 1H), 7.36-7.25 (m, 4H), 7.24-7.17 (m, 1H), 4.94-4.72 (m, 2H), 4.51-4.22 (m, 3H), 4.00-3.91 (m, 2H), 3.54-3.43 (m, 1H). LCMS (ES) [M+1]⁺ m/z 438.04.

Example 1.107

Synthesis of (2S)-3-hydroxy-2-phenyl-1-(2-{[5-(trifluoromethyl)thiophen-3-yl]sulfonyl}-2H,4H,5H,6H-pyrrolo[3,4-c]pyrazol-5-yl)propan-1-one (Compound 117)

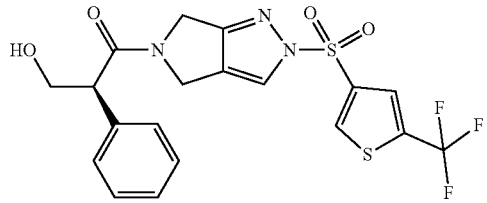 [SMILES: O=C([C@H](CO)c1ccccc1)N1Cc2cn(S(=O)(=O)c3csc(C(F)(F)F)c3)nc2C1]

The title compound was synthesized according the 3-step procedure described for Compound 15 using 5-(trifluoromethyl)thiophene-3-sulfonyl chloride instead of 2,4-dimethyl-1,3-thiazole-5-sulfonyl chloride in step 1. (2S)-3-hydroxy-2-phenyl-1-(2-{[5-(trifluoromethyl)thiophen-3-yl]sulfonyl}-2H,4H,5H,6H-pyrrolo[3,4-c]pyrazol-5-yl)propan-1-one as a white solid. ¹HNMR (400 MHz, DMSO-d₆) δ 8.89 (dd, J=1.7, 0.9 Hz, 1H), 8.23 (p, J=1.6 Hz, 1H), 8.13 (t, J=1.4 Hz, 1H), 7.37-7.24 (m, 4H), 7.24-7.17 (m, 1H), 4.96-4.74 (m, 2H), 4.54-4.21 (m, 3H), 4.04-3.88 (m, 2H), 3.56-3.42 (m, 1H). LCMS (ES) [M+1]⁺ m/z: 471.95.

Example 1.108

Synthesis of (2S)-3-hydroxy-2-phenyl-1-(2-{[5-(trifluoromethyl)-1H-pyrrol-3-yl]sulfonyl}-2H,4H,5H,6H-pyrrolo[3,4-c]pyrazol-5-yl)propan-1-one (Compound 118)

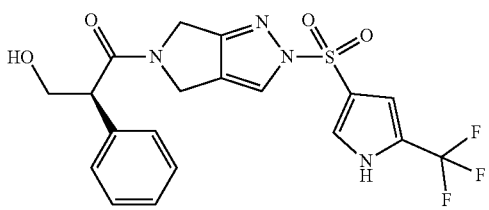 [SMILES: O=C([C@H](CO)c1ccccc1)N1Cc2cn(S(=O)(=O)c3c[nH]c(C(F)(F)F)c3)nc2C1]

The title compound was synthesized according the 3-step procedure described for Compound 15 using 5-(trifluoromethyl)-1H-pyrrole-3-sulfonyl chloride in step 1. (2S)-3-hydroxy-2-phenyl-1-(2-{[5-(trifluoromethyl)-1H-pyrrol-3-yl]sulfonyl}-2H,4H,5H,6H-pyrrolo[3,4-c]pyrazol-5-yl)propan-1-one as a white solid. LCMS (ES) [M+1]⁺ m/z: 455.12.

Example 1.109

Synthesis of (2S)-1-{2-[(2-ethoxy-1,3-thiazol-5-yl)sulfonyl]-2H,4H,5H,6H-pyrrolo[3,4-c]pyrazol-5-yl}-3-hydroxy-2-phenylpropan-1-one (Compound 119)

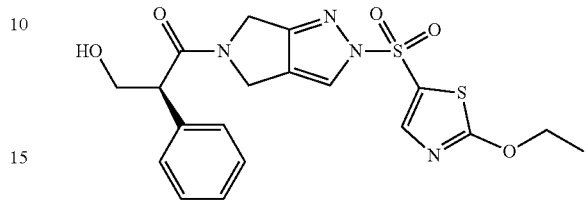

The title compound was synthesized according the 3-step procedure described for Compound 15 using 2-ethoxy-1,3-thiazole-5-sulfonyl chloride instead of 2,4-dimethyl-1,3-thiazole-5-sulfonyl chloride in step 1. (2S)-1-{2-[(2-Ethoxy-1,3-thiazol-5-yl)sulfonyl]-2H,4H,5H,6H-pyrrolo[3,4-c]pyrazol-5-yl}-3-hydroxy-2-phenylpropan-1-one as a white solid. ¹HNMR (400 MHz, DMSO-d6) δ 8.16 (d, J=1.3 Hz, 1H), 8.09 (s, 1H), 7.36-7.25 (m, 4H), 7.23-7.18 (m, 1H), 4.94-4.81 (m, 1H), 4.81-4.71 (m, 1H), 4.53-4.23 (m, 5H), 3.95 (s, 2H), 1.32 (t, J=7.0 Hz, 3H). LCMS (ES) [M+1]⁺ m/z: 449.12.

Example 1.110

Synthesis of (2S)-1-{2-[1-(2,2-difluoroethyl)pyrazol-4-ylsulfonyl]-4H,6H-pyrrolo[3,4-c]pyrazol-5-yl}-3-hydroxy-2-(2-methoxyphenyl)propan-1-one (Compound 120)

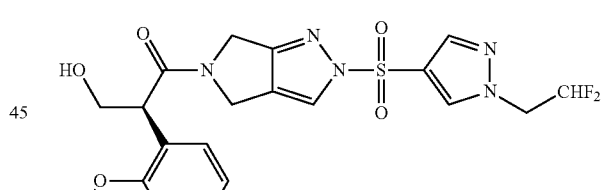

The title compound was synthesized from (2S)-3-hydroxy-2-(2-methoxyphenyl)propanoic acid (90.00 mg, 0.46 mmol, 1.00 eq.) and 1-(2,2-difluoroethyl)-4-{4H,5H,6H-pyrrolo[3,4-c]pyrazole-2-sulfonyl}pyrazole (Intermediate-7, 139.12 mg, 0.46 moml, 1.00 eq.) following the procedure described for the synthesis of compound 4, example 1.8. (2S)-1-{2-[1-(2,2-difluoroethyl)pyrazol-4-ylsulfonyl]-4H,6H-pyrrolo[3,4-c]pyrazol-5-yl}-3-hydroxy-2-(2-methoxyphenyl)propan-1-one was obtained as white solid (125.8 mg, 56.96%). ¹HNMR (300 MHz, DMSO-d6) δ 8.71 (t, J=1.0 Hz, 1H), 8.18 (d, J=2.3 Hz, 1H), 8.14-8.08 (m, 1H), 7.29-7.16 (m, 2H), 7.06-6.97 (m, 1H), 6.89 (td, J=7.5, 1.1 Hz, 1H), 6.42 (tt, J=54.4, 3.6 Hz, 1H), 4.91-4.64 (m, 4H), 4.53-4.24 (m, 4H), 3.95 (ddd, J=15.3, 9.8, 5.7 Hz, 1H), 3.84 (s, 3H), 3.48 (ddd, J=10.1, 5.0, 3.4 Hz, 1H). LCMS (ES) [M+1]⁺ m/z: 482.

Example 1.111

Synthesis of (2R)-1-{2-[1-(2,2-difluoroethyl)pyrazol-4-ylsulfonyl]-4H,6H-pyrrolo[3,4-c]pyrazol-5-yl}-3-hydroxy-2-(2-methoxyphenyl)propan-1-one (Compound 121)

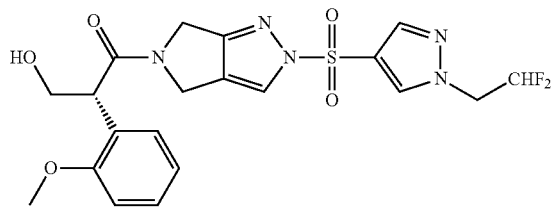 [SMILES: COc1ccccc1[C@H](CO)C(=O)N1Cc2cn(S(=O)(=O)c3cnn(CC(F)F)c3)nc2C1]

The title compound was synthesized from (2R)-3-hydroxy-2-(2-methoxyphenyl)propanoic acid (80.00 mg, 0.41 mmol, 1.00 eq.) and 1-(2,2-difluoroethyl)-4-{4H,5H,6H-pyrrolo[3,4-c]pyrazole-2-sulfonyl}pyrazole (Intermediate-7, 123.66 mg, 0.41 mmol, 1.00 eq.), following the procedure described for the synthesis of compound 4, example 1.8. (2R)-1-{2-[1-(2,2-difluoroethyl)pyrazol-4-ylsulfonyl]-4H,6H-pyrrolo[3,4-c]pyrazol-5-yl}-3-hydroxy-2-(2-methoxyphenyl)propan-1-one (109.7 mg, 55.88%) as white solid. $^1$HNMR (300 MHz, DMSO-d6) δ 8.75-8.68 (m, 1H), 8.18 (d, J=2.3 Hz, 1H), 8.12 (d, J=1.7 Hz, 1H), 7.30-7.16 (m, 2H), 7.06-6.96 (m, 1H), 6.89 (td, J=7.5, 1.1 Hz, 1H), 6.42 (tt, J=54.4, 3.6 Hz, 1H), 4.91-4.63 (m, 4H), 4.55-4.25 (m, 4H), 3.95 (tt, J=9.8, 5.7 Hz, 1H), 3.84 (s, 3H), 3.54-3.42 (m, 1H). LCMS (ES) [M+1]$^+$ m/z: 482.

Example 1.112

Synthesis of (2R)-1-(2-{[1-(2,2-difluoroethyl)-1H-pyrazol-4-yl]sulfonyl}-2H,4H,5H,6H-pyrrolo[3,4-c]pyrazol-5-yl)-3-hydroxy-2-phenylpropan-1-one (Compound 122)

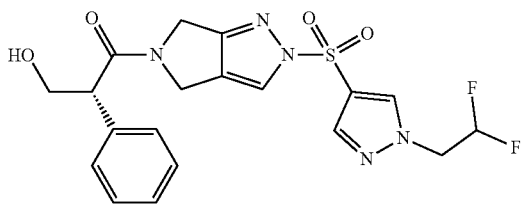 [SMILES: O=C([C@@H](CO)c1ccccc1)N1Cc2cn(S(=O)(=O)c3cnn(CC(F)F)c3)nc2C1]

The title compound was synthesized from (2R)-3-hydroxy-2-phenylpropanoic acid (175.94 mg; 1.06 mmol; 1.20 eq.) and 1-(2,2-difluoroethyl)-4-{2H,4H,5H,6H-pyrrolo[3,4-c]pyrazole-2-sulfonyl}-1H-pyrazole (Intermediate I-7, (400.00 mg; 0.88 mmol; 1.00 eq.) according to the procedures described in Example 1.6. (2R)-1-(2-{[1-(2,2-Difluoroethyl)-1H-pyrazol-4-yl]sulfonyl}-2H,4H,5H,6H-pyrrolo[3,4-c]pyrazol-5-yl)-3-hydroxy-2-phenylpropan-1-one was obtained as a white solid. $^1$H NMR (300 MHz, DMSO-d$_6$) δ 8.66 (dd, J=2.5, 0.7 Hz, 1H), 8.13 (d, J=1.0 Hz, 1H), 8.07 (d, J=0.8 Hz, 1H), 7.39-7.13 (m, 5H), 6.37 (tt, J=54.4, 3.6 Hz, 1H), 4.93-4.74 (m, 2H), 4.67 (tdd, J=15.2, 3.6, 1.5 Hz, 2H), 4.49-4.23 (m, 3H), 4.00-3.91 (m, 2H), 3.54-3.43 (m, 1H). LCMS (ES) [M+1]$^+$ m/z: 452.12.

BIOLOGICAL EXAMPLES

Example 2.1

Pyruvate Kinase Activation Methods

Protein Production and Purification

Human pyruvate kinase R (PKR), residues 14-574, and human pyruvate kinase M2, residues 1-531, were cloned into expression plasmids and obtained from ATUM Bio (Newark, Calif.). Proteins were translated as fusions with 6×-His,8×-Arg, and SUMO at the N-terminus. A third construct of human PKR was truncated, residues 50-574, and similarly cloned for use in crystallography experiments. All proteins were cloned, expressed in E. coli, and purified using similar protocols. Cells were grown at 30° C. in Luria-Bertani broth supplemented with 0.4% glucose to OD600=0.8 and induced with 0.4 mM IPTG at 16° C. for 18 hours. Cells were harvested by centrifugation, resuspended in 50 mM potassium phosphate pH 8.0, 500 mM NaCl, 25 mM imidazole pH 8.0, and 3 mM β-mercaptoethanol. Cells were lysed using a LM20 microfluidizer from Microfluidics (Westwood, Mass.). The crude lysate was immediately supplemented with 0.2 mM phenylmethylsulfonyl fluoride (PMSF) and centrifuged at 20,000 g for 20 minutes. The soluble fraction was subsequently incubated with 2 mL Ni-NTA (GE Healthcare) per 1,000 ODs for 1 hour at 4° C. Following incubation with the Ni-NTA resin, lysate was removed by pelleting resin at 2,500 g for 3 minutes and washed 3 times with 9 bed volumes of 50 mM potassium phosphate pH 8.0, 500 mM NaCl, 25 mM imidazole, and 3 mM β-mercaptoethanol. Following the batch wash Ni-NTA resin was loaded onto a gravity column and His-tagged protein was eluted with 6 bed volumes of 10 mM Tris/HCl pH 8.0, 200 mM NaCl, 500 mM imidazole, and 3 mM β-mercaptoethanol. Eluted protein was dialyzed overnight against 10 mM Tris/HCl pH 8.0, 200 mM NaCl, and 1 mM DTT and the 6×-His-8×-Arg-SUMO-tag was cleaved using a 20:1 molar ratio of protein: 3C protease. The protein was purified by anion exchange chromatography on a HiTrapQ or MonoQ 10/100 GL column (GE Healthcare) via a linear NaCl gradient and twice by size exclusion chromatography using a Superdex S200 26/60 column (GE Healthcare) run in 10 mM Tris/HCl pH 8.0, 200 mM NaCl, 10 mM MgCl$_2$, 1 mM DTT. Proteins were concentrated to ~12 mg/mL for crystallization and flash frozen for storage.

Example 2.2

Biochemical assay for Activation of Pyruvate Kinase R

Activation of pyruvate kinase R (PKR) and pyruvate kinase M2 (PKM2) were measured using a luminescence based measurement of ATP generation and the Kinase-Glo luminescent kinase reagent kit. 0.1 nM of PKR or PKM2 was incubated for 1 hour with 0.3 mM ADP, 1% DMSO, compound or 2 mM FBP in Assay Buffer mix (500 mM Tris/HCl pH 7.5, 500 mM NaCl, 50 mM MgCl$_2$, BSA, and 2 mM DTT, in a total reaction volume of 30 uL. After one hour PEP was added to the reaction at a final concentration of 0.1 mM and incubated for another hour at room temperature. 30 uL of KinaseGlo reagent was added and the reaction was incubated for 15 minutes. Endpoint luminescence data was measured using an EnVision plate reader (PerkinElmer). The assay results are provided in Table 2.

TABLE 2

| Compd No. From Table 1 | PKR AC$_{50}$ (nM) | PKR % activation[a] |
|---|---|---|
| 1 | 5.4 | 97 |
| 2 | 4.7 | 110 |
| 3 | 7.1 | 108 |
| 4 | 22 | 62 |
| 5 | 2.7 | 88 |
| 6 | 11 | 86 |
| 7 | 17 | 102 |
| 8 | 5.7 | 103 |
| 9 | 3 | 126 |
| 10 | 116 | 112 |
| 11 | 5.7 | 92 |
| 12 | 6.9 | 121 |
| 13 | 7 | 133 |
| 14 | 7.1 | 129 |
| 15 | 44 | 15 |
| 16 | 1000 | 55 |
| 17 | 53 | 23 |
| 18 | 72 | 70 |
| 19 | 19 | 67 |
| 20 | 720 | 7 |
| 21 | 16 | 65 |
| 22 | 1000 | 0 |
| 23 | 8.6 | 30 |
| 24 | 64 | 93 |
| 25 | 22 | 73 |
| 26 | 11 | 51 |
| 27 | 570 | 0 |
| 28 | 3400 | 85 |
| 29 | 420 | 86 |
| 30 | 46 | 119 |
| 31 | 3600 | 45 |
| 32 | 40 | 114 |
| 33 | 450 | 89 |
| 34 | 930 | 102 |
| 35 | 130 | 125 |
| 36 | 23 | 85 |
| 37 | 960 | 126 |
| 38 | 1800 | 121 |
| 39 | 120 | 90 |
| 40 | 81 | 53 |
| 41 | 3400 | 40 |
| 42 | 2100 | 102 |
| 43 | 29 | 108 |
| 44 | 110 | 53 |
| 45 | 1300 | 53 |
| 46 | 150 | 191 |
| 47 | 10 | 108 |
| 48 | 580 | 111 |
| 49 | 71 | 113 |
| 50 | 82 | 89 |
| 51 | 140 | 112 |
| 52 | 24 | 93 |
| 53 | 5.2 | 100 |
| 54 | 260 | 108 |
| 55 | 5.1 | 98 |
| 56 | 170 | 122 |
| 57 | 6.7 | 50 |
| 58 | 30 | 59 |
| 59 | 1600 | 55 |
| 60 | 28 | 74 |
| 61 | 3000 | 49 |
| 62 | 70 | 60 |
| 63 | 50 | 85 |
| 64 | 12 | 100 |
| 65 | 110 | 42 |
| 66 | 120 | 0 |
| 67 | 100000 | 0 |
| 68 | 2100 | 9 |
| 69 | 15 | 4 |
| 70 | 82 | 36 |
| 71 | 3900 | 30 |
| 72 | 9.6 | 98 |
| 73 | 17 | 66 |
| 74 | 440 | 72 |
| 75 | 0.51 | 3 |
| 76 | 3800 | 3 |
| 77 | 0.51 | 16 |
| 78 | 7.1 | 32 |
| 79 | 550 | 33 |
| 80 | 8.9 | 73 |
| 81 | 500 | 62 |
| 82 | 8.3 | 19 |
| 83 | 15 | 69 |
| 84 | 2500 | 73 |
| 85 | >10000 | 103 |
| 86 | 1.1 | 0 |
| 87 | 10000 | 59 |
| 88 | 680 | 0 |
| 89 | 1200 | 105 |
| 90 | 5.7 | 131 |
| 91 | 91 | 164 |
| 92 | 10000 | 0 |
| 93 | 120 | 180 |
| 94 | 34 | 18 |
| 95 | 2900 | 15 |
| 96 | 6.4 | 93 |
| 97 | 550 | 102 |
| 98 | 9.1 | 117 |
| 99 | 410 | 100 |
| 100 | 380 | 126 |
| 101 | 8.5 | 123 |
| 102 | 690 | 126 |
| 103 | 26 | 101 |
| 104 | 560 | 121 |
| 105 | 74 | 67 |
| 106 | 210 | 189 |
| 107 | 53 | 89 |
| 108 | 3300 | 62 |
| 109 | 26 | 63 |
| 110 | 37 | 146 |
| 111 | 1600 | 42 |
| 112 | 3100 | 174 |
| 113 | 24 | 47 |
| 114 | 320 | 134 |
| 115 | 2100 | 96 |
| 116 | 34 | 53 |
| 117 | 22 | 35 |
| 118 | 160 | 13 |
| 119 | 54 | 58 |
| 120 | 16 | 102 |
| 121 | 98 | 166 |
| 122 | 240 | 120 |
| 123 | >10000 | 123 |

[a]The maximal activation level achieved with each compound relative to the activation level achieved by the literature compound AG-348 @ 10 μM.

Example 2.3

Cell Based Assay for Activation of Pyruvate Kinase M2 in Lung Carcinoma Cell Line H1299 cells were seeded in 96-well plates at 2,000 cells/well (100 uL). Treated plates were incubated overnight at 37° C. with 5% $CO_2$. Compounds were diluted in complete media and added to cells in the presence of 1% DMSO. Cells were incubated with compound for 90 minutes at 37° C. and 5% $CO_2$ before washing three times with PBS to remove residual compound and then lysed in lysis buffer (Cell Signaling). Cell lysate was analyzed using the NADH coupled assay described below with a reaction mixture of 180 uM NADH, 2 mM ADP, 0.5 units of LDH and 0.5 mM of PEP. PKM2 activity was measured at steady state using a coupled enzyme activation system based on NADH consumption. PKM2 produces pyruvate and the coupled system uses lactate dehydrogenase (LDH) to reduce pyruvate to lactate with the concomitant oxidation of NADH to $NAD^+$. Conversion of NADH to $NAD^+$ was monitored using a SPECTROstar Nano plate reader (BMG Labtech) at a wavelength of 340 nm and subtraction of background absorbance measured at 750 nm. The change in NADH absorbance after PEP addition was monitored and slope obtained by subtracting baseline at 750 nm followed by least squares fitting to a simple linear regression model. A 10-point curve was generated to calculate the $AC_{50}$ values by fitting the rates of NADH consumption against increasing concentration of compound.

Efforts have been made to ensure accuracy with respect to numbers used (e.g., amounts, temperature, etc.) but some experimental errors and deviations should be accounted for.

One skilled in the art will recognize many methods and materials similar or equivalent to those described herein, which could be used in the practicing the subject matter described herein. The present disclosure is in no way limited to just the methods and materials described.

Unless defined otherwise, technical and scientific terms used herein have the same meaning as commonly understood by one of ordinary skill in the art to which this subject matter belongs, and are consistent with: Singleton et al (1994) Dictionary of Microbiology and Molecular Biology, 2nd Ed., J. Wiley & Sons, New York, N.Y.; and Janeway, C., Travers, P., Walport, M., Shlomchik (2001) Immunobiology, 5th Ed., Garland Publishing, New York.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller rangers is also encompassed, subject to any specifically excluded limit in the stated range. Where the stated range includes one or both of the limits, ranges excluding either or both of those included limits are also included.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:
1. A compound selected from the group consisting of

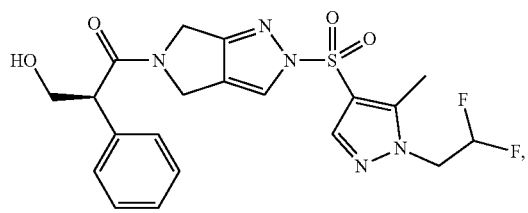

-continued

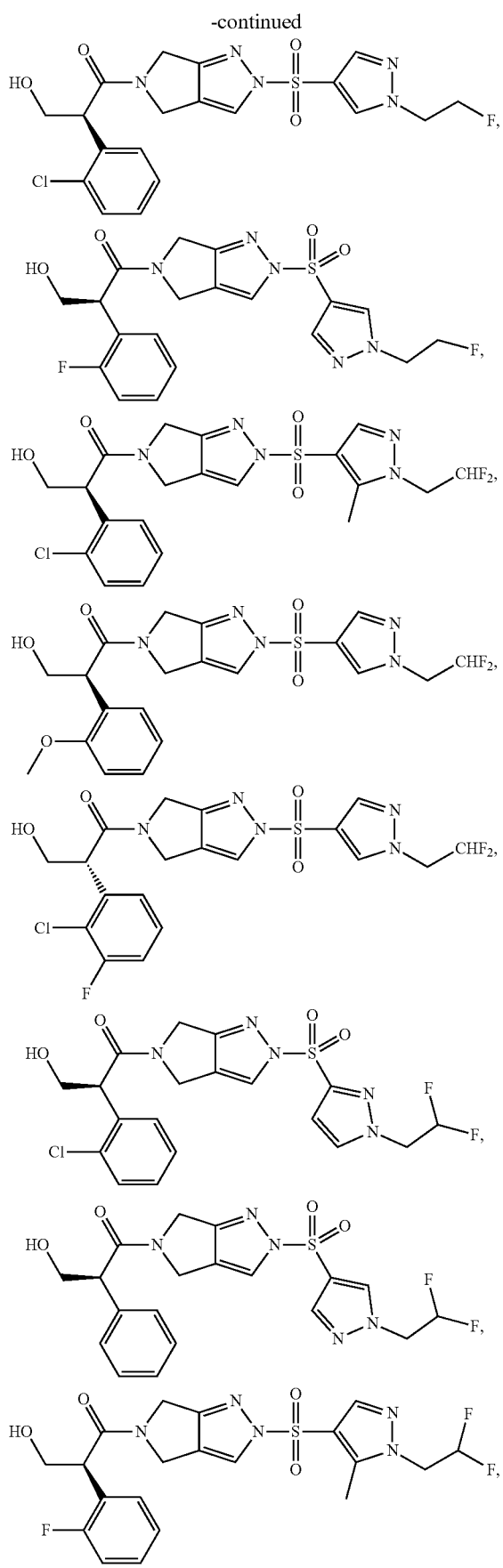

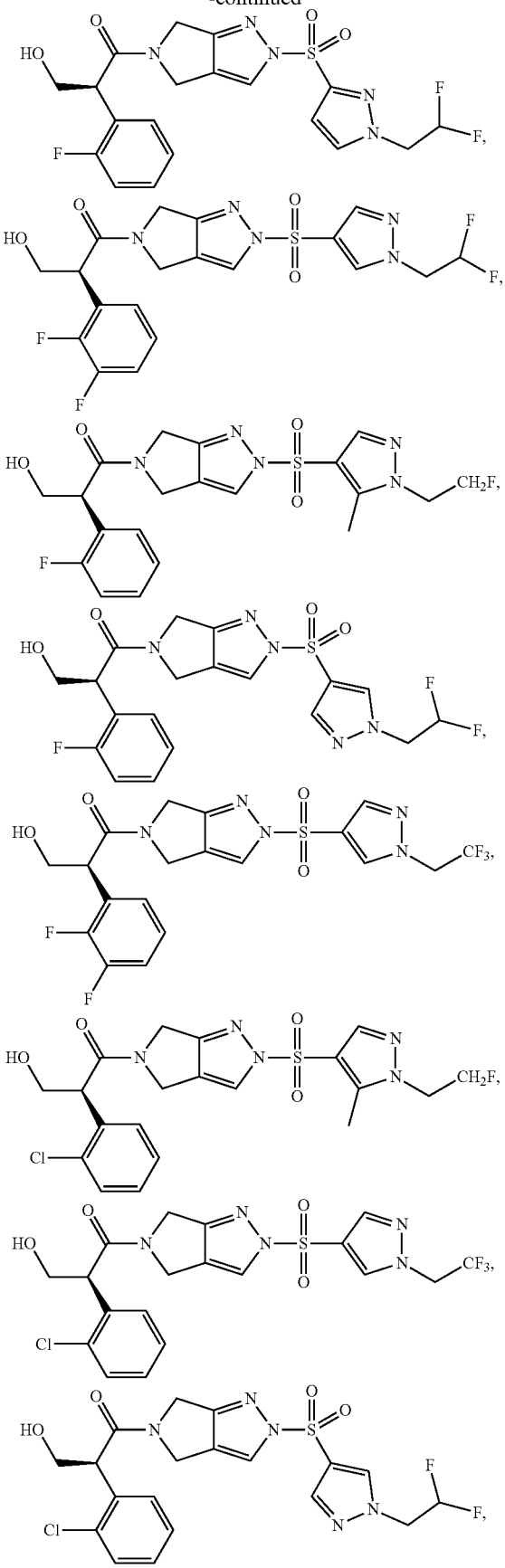
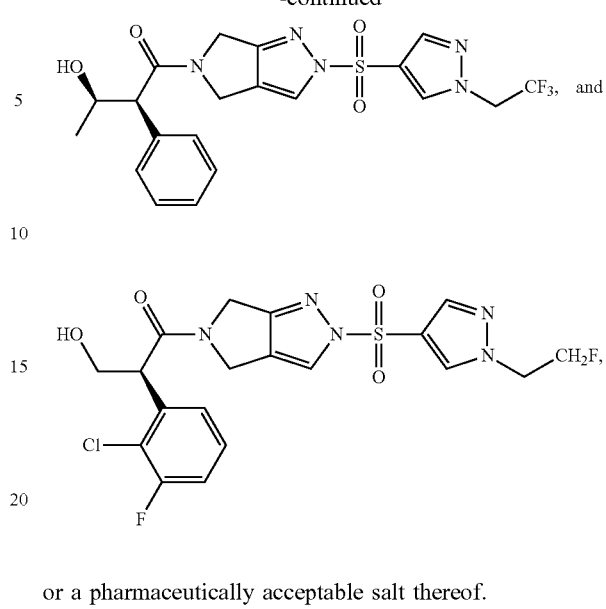
or a pharmaceutically acceptable salt thereof.
2. The compound of claim 1, wherein the compound is
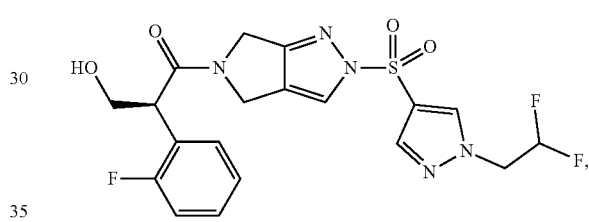
or a pharmaceutically acceptable salt thereof.
3. The compound of claim 1, wherein the compound is
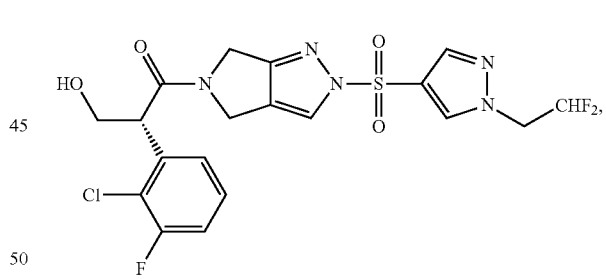
or a pharmaceutically acceptable salt thereof.
4. The compound of claim 1, wherein the compound is
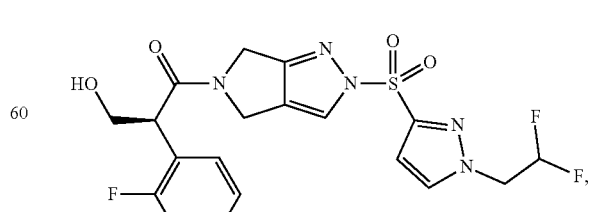
or a pharmaceutically acceptable salt thereof.

5. The compound of claim 1, wherein the compound is

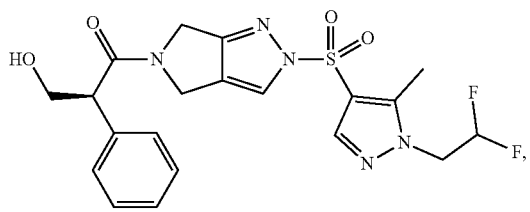 [SMILES: Cc1c(S(=O)(=O)n2cc3c(n2)CN(C(=O)[C@H](CO)c2ccccc2)C3)cnn1CC(F)F]

or a pharmaceutically acceptable salt thereof.

6. The compound of claim 1, wherein the compound is

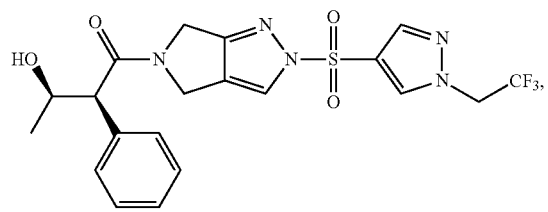 [SMILES: C[C@@H](O)[C@@H](C(=O)N1Cc2cn(S(=O)(=O)c3cnn(CC(F)(F)F)c3)nc2C1)c1ccccc1]

or a pharmaceutically acceptable salt thereof.

7. The compound of claim 1, wherein the compound is

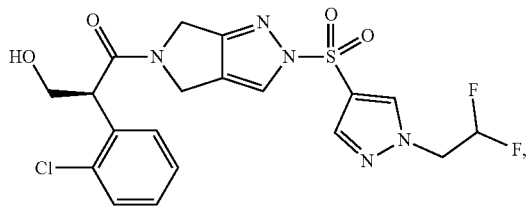 [SMILES: O=C([C@H](CO)c1ccccc1Cl)N1Cc2cn(S(=O)(=O)c3cnn(CC(F)F)c3)nc2C1]

or a pharmaceutically acceptable salt thereof.

8. The compound of claim 1, wherein the compound is

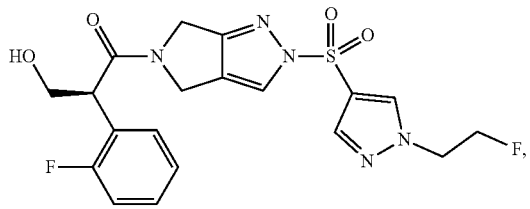 [SMILES: O=C([C@H](CO)c1ccccc1F)N1Cc2cn(S(=O)(=O)c3cnn(CCF)c3)nc2C1]

or a pharmaceutically acceptable salt thereof.

9. The compound of claim 1, wherein the compound is

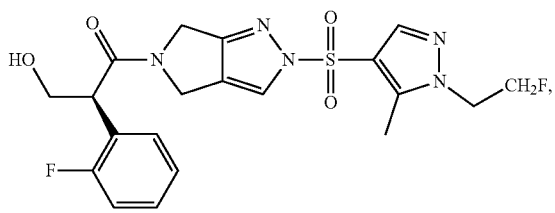

or a pharmaceutically acceptable salt thereof.

10. The compound of claim 1, wherein the compound is

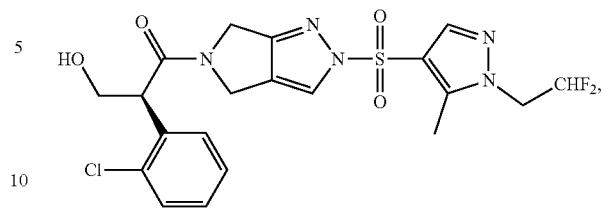

or a pharmaceutically acceptable salt thereof.

11. The compound of claim 1, wherein the compound is

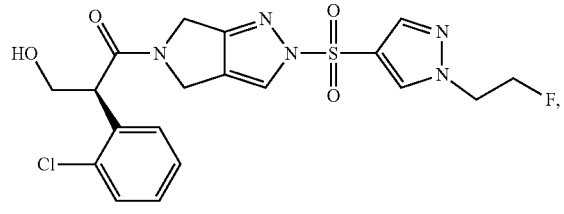 [SMILES: O=C([C@H](CO)c1ccccc1Cl)N1Cc2cn(S(=O)(=O)c3cnn(CCF)c3)nc2C1]

or a pharmaceutically acceptable salt thereof.

12. The compound of claim 1, wherein the compound is

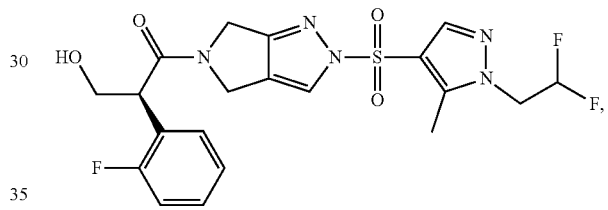

or a pharmaceutically acceptable salt thereof.

13. The compound of claim 1, wherein the compound is

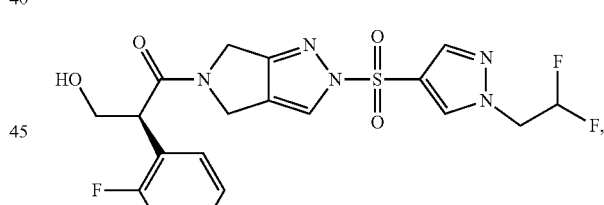

or a pharmaceutically acceptable salt thereof.

14. The compound of claim 1, wherein the compound is

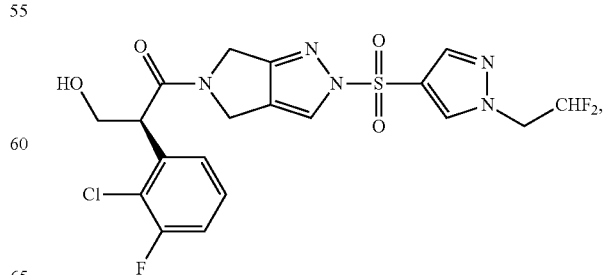

or a pharmaceutically acceptable salt thereof.

15. The compound of claim 1, wherein the compound is

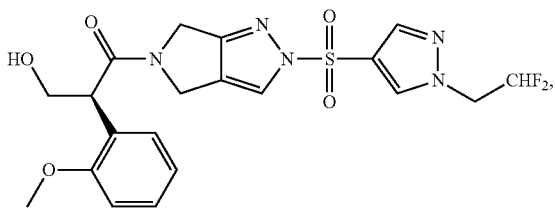 [SMILES: COc1ccccc1[C@@H](CO)C(=O)N1Cc2cn(S(=O)(=O)c3cnn(CC(F)F)c3)nc2C1]

or a pharmaceutically acceptable salt thereof.

16. The compound of claim 1, wherein the compound is

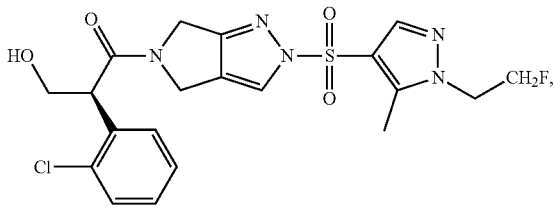

or a pharmaceutically acceptable salt thereof.

17. The compound of claim 1, wherein the compound is

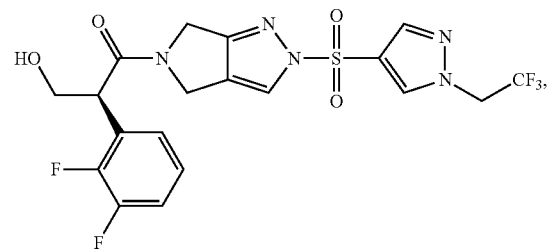 [SMILES: O=C([C@H](CO)c1cccc(F)c1F)N1Cc2cn(S(=O)(=O)c3cnn(CC(F)(F)F)c3)nc2C1]

or a pharmaceutically acceptable salt thereof.

18. The compound of claim 1, wherein the compound is

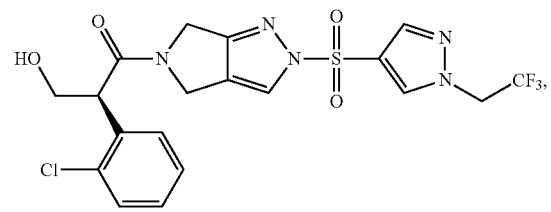 [SMILES: O=C([C@H](CO)c1ccccc1Cl)N1Cc2cn(S(=O)(=O)c3cnn(CC(F)(F)F)c3)nc2C1]

or a pharmaceutically acceptable salt thereof.

19. The compound of claim 1, wherein the compound is

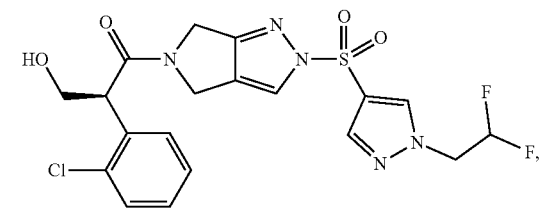 [SMILES: O=C([C@H](CO)c1ccccc1Cl)N1Cc2cn(S(=O)(=O)c3cnn(CC(F)F)c3)nc2C1]

or a pharmaceutically acceptable salt thereof.

20. A pharmaceutical composition comprising a compound of claim 1, or a pharmaceutically acceptable salt thereof, and a pharmaceutically acceptable excipient.

21. A method for activating pyruvate kinase (PK) in a subject, wherein the method comprises administering to the subject in need thereof a therapeutically effective amount of a compound of claim 1, or a pharmaceutically acceptable salt thereof;
wherein the pyruvate kinase (PK) is selected from the group consisting of pyruvate kinase from erythrocytes and/or red blood cells (PKR) and pyruvate kinase M2 (PKM2).

22. A method for treating a subject afflicted with a disease associated with decreased activity of pyruvate kinase from erythrocytes and/or red blood cells (PKR) and/or pyruvate kinase M2 (PKM2), wherein the method comprises administering to the subject in need thereof a therapeutically effective amount of a compound of claim 1, or a pharmaceutically acceptable salt thereof;
wherein the disease associated with decreased activity of pyruvate kinase from erythrocytes and/or red blood cells (PKR) and/or pyruvate kinase M2 (PKM2) is selected from the group consisting of hemolytic anemia, sickle cell disease, and thalassemia.

23. The method of claim 22, wherein the hemolytic anemia is acquired hemolytic anemia or hereditary, non-spherocytic hemolytic anemia.

24. The method of claim 22, wherein the disease associated with decreased activity of pyruvate kinase from erythrocytes and/or red blood cells (PKR) and/or pyruvate kinase M2 (PKM2) is selected from the group consisting of sickle cell disease and thalassemia.

25. The method of claim 24, wherein the thalassemia is beta-thalassemia.

26. A compound having the structure:

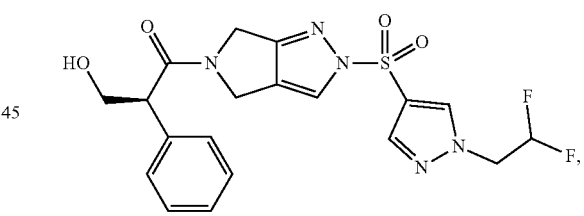

or a pharmaceutically acceptable salt thereof.

27. A pharmaceutical composition comprising the compound of claim 26, or a pharmaceutically acceptable salt thereof, and a pharmaceutically acceptable excipient.

28. A method for treating a subject afflicted with a disease associated with decreased activity of pyruvate kinase from erythrocytes and/or red blood cells (PKR) and/or pyruvate kinase M2 (PKM2), wherein the method comprises administering to the subject in need thereof a therapeutically effective amount of a compound of claim 26, or a pharmaceutically acceptable salt thereof;
wherein the disease associated with decreased activity of pyruvate kinase from erythrocytes and/or red blood cells (PKR) and/or pyruvate kinase M2 (PKM2) is selected from the group consisting of hemolytic anemia, sickle cell disease, and thalassemia.

29. A compound having the structure:

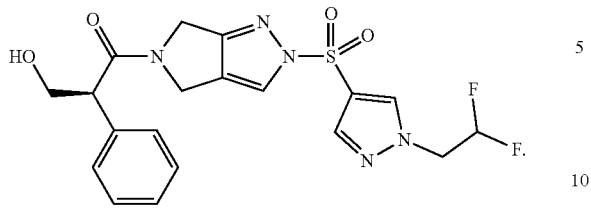

30. A pharmaceutical composition comprising the compound of claim 29 and a pharmaceutically acceptable excipient.

31. A method for treating a subject afflicted with a disease associated with decreased activity of pyruvate kinase from erythrocytes and/or red blood cells (PKR) and/or pyruvate kinase M2 (PKM2), wherein the method comprises administering to the subject in need thereof a therapeutically effective amount of a compound of claim 29;
   wherein the disease associated with decreased activity of pyruvate kinase from erythrocytes and/or red blood cells (PKR) and/or pyruvate kinase M2 (PKM2) is selected from the group consisting of hemolytic anemia, sickle cell disease, and thalassemia.

* * * * *